(12) United States Patent (10) Patent No.: US 7,037,678 B2
Kumagai et al. (45) Date of Patent: May 2, 2006

(54) CLASPIN PROTEINS AND METHODS OF USE THEREOF

(75) Inventors: Akiko Kumagai, Altadena, CA (US); William G. Dunphy, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 255 days.

(21) Appl. No.: 09/982,091

(22) Filed: Oct. 17, 2001

(65) Prior Publication Data

US 2002/0151030 A1 Oct. 17, 2002

Related U.S. Application Data

(60) Provisional application No. 60/241,246, filed on Oct. 17, 2000.

(51) Int. Cl.
*C12P 21/02* (2006.01)
*C07H 21/04* (2006.01)
*C12N 1/00* (2006.01)
*C12N 5/10* (2006.01)
*C12N 15/00* (2006.01)

(52) U.S. Cl. ............... 435/69.1; 435/252.3; 435/254.2; 435/320.1; 435/325; 435/419; 536/23.5

(58) Field of Classification Search ............... 536/23.5, 536/24.31; 435/320.1, 325, 69.1, 69.3

See application file for complete search history.

(56) References Cited

FOREIGN PATENT DOCUMENTS

| WO | WO 99/28470 | * | 6/1999 |
| WO | WO 01/60860 A2 | * | 8/2001 |

OTHER PUBLICATIONS

Accession No. AL354864 (Apr. 4, 2001) available at http://www.ncbi.nih.gov/entrez/.*
Accession No. AP001261 (May 31, 2000) available at http://www.ncbi.nih.gov/entrez/n.*
Accession No. G30470 (1996), available at http://www.ncbi.nih.gov/entrez/.*
U.S. Appl. No. 60/183,319.*
U.S. Appl. No. 60/189,862.*
U.S. Appl. No. 60/207,454.*
U.S. Appl. No. 60/211,314.*
U.S. Appl. No. 60/219,007.*
U.S. Appl. No. 60/255,281.*
Kumagai, et al., "Claspin, A Novel Protein Required for the Activation of Chk1 during DNA Replication Checkpoint Response in Xenopous Egg Extracts," *Molecular Cell*, v.6 (4)839-849, Oct. 2000.
Database GenEmbl on STIC, USPTO, (Arlington, VA, USA), GenBank Accession AF297867, Kumagai, et al., "Claspin, A Novel Protein Required for the Activation of Chk1 during DNA Replication Checkpoint Response in Xenopous Egg Extracts," *Molecular Cell*, v.6(4)839-849, Oct. 2000.
Kumagai, et al., "The Xenopus Chk1 Protein Kinase Mediates a Caffeine-sensitive Pathway of Checkpoint Control in Cell-free Extracts," *J. Cell Biol.*, v. 142(6), 1559-1569, Sep. 1998.
Guo, et al., "Requirement for Atr in Phosphorylation of Chk1 and Cell Cycle Regulation in Response to DNA Replication Blocks and UV-damaged DNA in Xenopus Egg Extracts," *Genes and Dev.*, v. 14, 2745-2756, 2000.

* cited by examiner

*Primary Examiner*—Daniel M. Sullivan
(74) *Attorney, Agent, or Firm*—DLA Piper Rudnick Gray Cary US LLP

(57) ABSTRACT

Claspin proteins and nucleotides encoding Claspin proteins are provided. Also provided is a method for identifying a compound that modulates cell cycle progression. A method is further provided for modulating cell cycle progression.

8 Claims, 32 Drawing Sheets

SEQ ID NO:1  Xenopus Claspin nucleotide sequence (AF297867)

```
ACGCATAGGGCGCGAATTCCAAGGCGGCAGTAGTGAGGATTGGCGGGAGCTGTCATCACCG
GGTAGCACCATGGCCGCGCTTTGCGAAGAAGAGCAGGTATTTTGGAACCAGAAGACATCA
GTCTGAAAATTGTGGAGACTGATTCTGACAGTGGTCAAGGCAGCTGTGAAATGGCTGATCA
GAATAAATTATTGGGTTGTGTGGAGGATAAAGATACAGATGATGAAATCTTGGTTCGTAAA
AAATCTAAAAGAAGGAAGTATTGGTGGATAGTGACAGTGACGAAGAATTGGAAATGCGTA
ATTTTGCAGATAATGTAAAGGGGCACTCTGATAATGAGGAGAATGAGGAGACTATGTCTGC
TTATAGAGAAAAACCAAGAAGATCCGTTCAGCTGTATTGGACAGTGACAATAGTGATCAT
GAGCTTGATGTTCAAATAAGTACAAGTCAAAATGCAGCTGAAATACCTGAGTCAGAACATG
ATAGCTTGGAGAAGGAAACTCATACTGTGAAGCCTAAAACAAGCAAGTCCTTGAAAAAACA
AACTGACACTAATAAAGAGGAAATCGTGAAGAATAAATCAAAGCGCAAAATTCCGAAAGAG
AAGATTAAAAGGAGGACAAAACAGAAGTCAAAAGCAGTTGCTGAAGCTAGGCCAAATTTAA
ATGACAGTGGCTGCTTACTCACAGATGGAGATCTTTTTGACAATGGGGTGGAAAATGAGAT
GGATTCTAATGAAGAAGAGGATTCTCTTGAAGCTATCCGGGCAAAAATGAAAAGCAAACTG
AATAGTCATTCTGCTGAAAATTTTGAAGACTTTGAACTTGATACTGAAGGCAATCAAGAAT
CCCCAGAAAAAGAAAGGAACGAAAAGCTGCGCGACTTGGTAAAGAAGCCATGAAACAAAT
GCACAGTGAGACCCAAAGACTAATACGTGAATCTTCTGTATCTTTACCATATCATCTACCT
GAACCAAAAACAATCCATGATTTTTTCAAAAGGCGTCCAAGGCCTCTTTGTCAAGGAAATG
CAATGCAGCTTATAAAGTCAACAAAATACCAGCCCTGCACTGAAGAGAAAAAAAAACCCAA
TGAGGAAATATGTGCTGAAGTTCCAGAGTTTGATTATGTTTCAAAGGAAGATTTAGAAATC
AGTCCAGAGCAACCTTTACTAAATACTCAGTGTTCACATGCTGCAGTCCTATGTGTTGTGC
AAAATGATGCTCGGACTGAGGGGTTAAGTAAATCCACAGAGGCAGTTGTGACTGGTCAAAT
GAATGACCATGAGGATGCTTTCAGTGATTCAAACATTGTTCATGAACAAGAAACAGTTGGA
TTAATAACCGTAACTGAAACCTTTCAGACACCCTTTATTCCCCAACCAGAGAGCGTAGTAT
GTGAACAAATCCAGAATGATGTAGTAGAGATGCAACGTATGCCTGAACAACCCACGCATAA
ACCCAAGTTATCCAAGCTTGAAAAGCTGAAAGCTCTTGGAGTGGACTTGTCTATAAAACCT
CGCCTTTGCCCTGATGATGGTTCTTTTGTCAACTTGGATGAACCAAAGCCGAATAAAGAAT
TTGAAGCTTTGAAGGAGCGTTTCCTGAAGCACACTCTGCAAAAGTCCAAACCCAGAACTGA
GCGGAAAGTCAATCTTAATATTATCCGCAAGGAGACCACTGCTGATGGAAAAGAAGAACTA
AAAGCAGACGTTGTGCCAATAGTTATGGCTACAGAAAAACCAGACAAGAGCATTTATCAAA
AGCCAGGTGAGAAGCTGCAGGTATTGAAAGTCAAACTGCAGGAAGCAATGAAAATCCGTCG
CAGTGAGGAGCGCCTGAAGCGGCAAGCCTTGTATAAGCTTGACAATGAAGATGGCTTTGAA
GATGATGAAGAGGAGGAAGAAATGACAGAGGAGTCTGAAGATGATGGGGATGGAAATGCTG
AGACTGCAGATTATCCTGGAGGGGAAGATGAGGAAGAGGTTGGTGATGCTGAAGATGACAA
TGATGAGGATGATACTGTAAATGATAGATTGTTGGGAAATGTGCCTGAAATTGTTATCCCA
CTGCCGAGACCAGTAACTACTGATTCTAGCCTCATGCTGTTCAAGGACAATTCTTCAAAGC
TAGGAGATTCGCTACCTGATGAAAGTGGATGCAAGAGAAGCAGCAGGCTAGAATATGAAGA
AGACTCCCTGTTGCCACAATTAAAAGAAAACAGCCATAATAGTAGCTTTGAACTTATTAGT
TCAATGATACCATCATACCAGCCATGTAATAAAACAACTCGAGTTGTGATCAACTCCAATA
ACCTTGGCTTTCGCTCACCATCTCCGGTTCATTTCAAAACAAGTTTTCTCAGCTCTGCATC
AAAGAGTTCTGGCAAGATGTCTGAACCATCCCTTCCCGTGGAAGACTCACAGGATCTATAT
AATGCTTCCCCAGAGCCCAAAGCCTCATATCTCTGTGCTGGAAGAAACTCTCAATTTCAAT
```

FIGURE 1A

```
TTTCGTTGGAGGATGACACCCAGAGCCAACTGCTTGATGCTGATGGGTTTCTGAATGTTGG
TCGCCATAAATCTAGCTCTGCCAAACACAGGCTAGCTTTGGATACAATGGACGAGAATGCT
ATGGATGCCAATATGGATGAACTACTAGACCTTTGCTCAGGACAGTTCAAAGAATCTCTTT
CAGGCACATCACAGGCAGCTGAAAGTGATGCTAAGAAACAACCAATGGATGAATTGCTTGA
ATTGTGTTCTGGCAAATTTGTATCTCAAGCTGACTGCTCCACACAAGATTCTTCTGCTTCA
GCTAAGGACCGTTCTACAGCTGTAAAAAAGGACATTTCTGATGAAGTGGCAACGGTTTCAA
GTTCATTCCTTACTGAGAGAGAACAGGAAGAAGATGAGGAAGAAGAATTTGGTGAATTCAA
GCTCTTACCCTGTGATGATTCGGAGAGCGAAAACGAAGAACAAAATGAAGAGGAAGAAGAA
GAAGAGGATGCTAAGGATGATGAAGATGAGGAAGAAATTTTGCAGAAGCAGCAAAAGAGAA
AATTGAGGCTGAATGACTTCATGGAAGATGAAGCCGAATTGTCTGGAAGTGATGTAGGTAG
CGGAGATGAGTATGAAGGAGATGATGATGAGTATGAGGAAGAAGCCATAGATGAAGATCTC
CCATCTGATGAGGAACTGCAGGATCAAGTCAATAAAATTCATATGAAAGTTACCATGGATG
AAGACCAGCGACAGCTTCGTTTCTATCAGGAGCGGTACCTGGCTGATGGGGATCTCCATAG
TGACGGACCAGGGAGAACAAGAAAGTTCAGATGGAAACATCTTGATGATGCCTCACAGGTG
GACATGTTCCGCCGAGACTCTGAATTGGAAGAGGTGGACGGAGAGAATGAGGAAACTGAGG
AAACCGAACTTAAATGGAGGAAAGAGCGGTTCGAAAGGGAACAATGGCTGCGAGAACAGCC
ACAAGGTAGTAGAGATAACAATGAGGAGGAGGAGGAGGATATTGGAGAAGACAGCCAGTTT
ATGAAATTGGCAAAGAAGGTCACTGCAAAAGCCCTACAGAGAAAAGTGAGTACAGAGACTA
ATGAACCAAAGAAACCTGGGCCTAGAAATCCATATGAAGTGATCAGGCCTTTCAGCCTCCC
CAAGTTGCGTACTGGTTCGCTGTTAAGCAAACCAAAAGAAGTTTTACAGAAGCTGGCAGCT
GTGTCAGACCTGAATCCAAATGCACCTCGAAACTCAAGAAACTTTGTCTTCCAAACTGTCT
CACCCGGAAAGAAAGAAGAAACTACAGACAAGCCAAGATCAAAGGTACGAAAGAATATAGC
TGTTGCCATGCCTTCCCCTAAACGTTTTAAAAGGGACAGCACCCCTACTGTTAAAAGCCGC
AGTATATTTCAGTTGTTGGAGTAGGTTTCTGCGAATATTCCACTAAATCAGTAATTTGTTT
TTGTGTCCTAGTTACAGCAAATTCTATATTTTAATGTAGCTGTGCTTACATGCTACAGTTC
TCGCTTTACTGAAATTTGTCAGATACTTGAACTAAGTGTTTTTCATCATGAAATTAGTTGT
GCTGCATGTTATTCATACAGAGGCATGTGAAATACACTGTGTATTTCTATTGCCTTGTGTC
AAATGTTCTACACTTGTTTTGTTCAAAATTACACAAACCGTATCACCTAATGTAAATCTAC
CTCATAGAGATACAGATACCCTACAAAAATACAGTAATTTTGTTTACAACCACCCATATAT
TTTGTACTTTGCATTCTTATTCTATTCTCTAAATGTACTCCATTTACAAGTGCTGATTTAT
AAAGGGGCATTGTACCTATTTGTTCAACACAAGTTCAATTACGTCATGTGCTGAACATGCT
CTCCCCCCCATCTTAAAATATGTTTTTCTTATGAATTGCATTAAACAGGGCAAACACTGAA
ACTATAAGTTTATGGGAGTGCTGGTAAAAACAACAACCTATTAGTGCTTTATAATATAAAA
AATTAGGTTATTATATGGATTGTTTTAATTAAAACAATAAGCAGAACAAATTTAAAACAA
GTCCTATTTATTTTGCTCATGTTAAATAAAAGTGTATATATCCATATACTACCCGTTTAAA
CTGTGTAATGAATGTGTTTCTTGTAATATATTTTATTGTACATTGTTATAAATGTTTGTGA
GATTTGTTAATAAATACATTTTTTAAAAAAAAAAAAAAAAAAAAAAAAAAAAAAA
```

FIGURE 1B

SEQ ID NO:2: Xenopus Claspin amino acid sequence

```
MAALCEEEQVFLEPEDISLKIVETDSDSGQGSCEMADQNKLLGCVEDKDTDDEILVRKKSK
KKEVLVDSDSDEELEMRNFADNVKGHSDNEENEETMSAYREKPRKIRSAVLDSDNSDHELD
VQISTSQNAAEIPESEHDSLEKETHTVKPKTSKSLKKQTDTNKEEIVKNKSKRKIPKEKIK
RRTKQKSKAVAEARPNLNDSGCLLTDGDLFDNGVENEMDSNEEEDSLEAIRAKMKSKLNSH
SAENFEDFELDTEGNQESPEKRKERKAARLGKEAMKQMHSETQRLIRESSVSLPYHLPEPK
TIHDFFKRRPRPLCQGNAMQLIKSTKYQPCTEEKKKPNEEICAEVPEFDYVSKEDLEISPE
QPLLNTQCSHAAVLCVVQNDARTEGLSKSTEAVVTGQMNDHEDAFSDSNIVHEQETVGLIT
VTETFQTPFIPQPESVVCEQIQNDVVEMQRMPEQPTHKPKLSKLEKLKALGVDLSIKPRLC
PDDGSFVNLDEPKPNKEFEALKERFLKHTLQKSKPRTERKVNLNIIRKETTADGKEELKAD
VVPIVMATEKPDKSIYQKPGEKLQVLKVKLQEAMKIRRSEERLKRQALYKLDNEDGFEDDE
EEEEMTEESEDDGDGNAETADYPGGEDEEEVGDAEDDNDEDDTVNDRLLGNVPEIVIPLPR
PVTTDSSLMLFKDNSSKLGDSLPDESGCKRSSRLEYEEDSLLPQLKENSHNSSFELISSMI
PSYQPCNKTTRVVINSNNLGFRSPSPVHFKTSFLSSASKSSGKMSEPSLPVEDSQDLYNAS
PEPKASYLCAGRNSQFQFSLEDDTQSQLLDADGFLNVGRHKSSSAKHRLALDTMDENAMDA
NMDELLDLCSGQFKESLSGTSQAAESDAKKQPMDELLELCSGKFVSQADCSTQDSSASAKD
RSTAVKKDISDEVATVSSSFLTEREQEEDEEEEFGEFKLLPCDDSESENEEQNEEEEEEED
AKDDEDEEEILQKQQKRKLRLNDFMEDEAELSGSDVGSGDEYEGDDDEYEEEAIDEDLPSD
EELQDQVNKIHMKVTMDEDQRQLRFYQERYLADGDLHSDGPGRTRKFRWKHLDDASQVDMF
RRDSELEEVDGENEETEETELKWRKERFEREQWLREQPQGSRDNNEEEEEDIGEDSQFMKL
AKKVTAKALQRKVSTETNEPKKPGPRNPYEVIRPFSLPKLRTGSLLSKPKEVLQKLAAVSD
LNPNAPRNSRNFVFQTVSPGKKEETTDKPRSKVRKNIAVAMPSPKRFKRDSTPTVKSRSIF
QLLE
```

FIGURE 1C

SEQ ID NO:3
Human Claspin nucleotide sequence AF297866

```
GACGGCGGGAGCCGCTGCTCTCCGGCTGAGGGAATCAGAGACAGCTCCGTCCCTAGTGGAG
CGCAGGGGAGGCAGAAGTCATGACAGGCGAGGTGGGTTCTGAGGTTCACCTAGAAATCAAT
GACCCAAACGTCATTTCACAAGAGGAAGCAGATAGTCCTTCAGATAGTGGACAGGGCAGCT
ATGAAACAATTGGACCCTTGAGTGAAGGAGATTCAGATGAAGAGATATTTGTAAGTAAGAA
GTTGAAAAACAGGAAGGTTCTACAAGACAGTGATTCCGAAACAGAGGACACAAATGCCTCT
CCAGAGAAAACTACCTATGACAGTGCCGAGGAGGAAAATAAAGAGAATTTATATGCTGGGA
AAAATACAAAAATCAAAAGGATTTACAAAACTGTGGCAGACAGTGATGAAAGTTACATGGA
AAAGTCTTTGTATCAGGAAAATCTTGAAGCGCAAGTGAAACCTTGCTTAGAGCTGAGTCTT
CAGTCTGGAAACTCTACAGACTTTACCACTGACAGAAAGAGTTCCAAAAAGCACATACATG
ATAAAGAAGGAACTGCAGGAAAAGCAAAAGTAAAATCAAAAGAAGACTTGAGAAAGAGGA
GAGAAAAATGGAAAAAATTAGACAGCTAAAAAGAAGGAAACAAAAAACCAGGAAGATGAT
GTAGAACAGCCATTTAATGACAGTGGCTGTCTTCTTGTGGATAAAGACCTTTTTGAAACTG
GGTTGGAGGATGAAAATAACTCTCCATTGGAAGATGAAGAGTCATTAGAATCAATAAGAGC
AGCTGTAAAAAACAAAGTAAAAAAGCACAAGAAAAAGAACCATCTTTGGAGAGTGGGGTC
CATTCATTTGAGGAAGGAAGTGAGTTATCAAAAGGAACCACGAGGAAGGAAAGAAAGGCAG
CCAGATTAAGTAAAGAAGCATTAAAACAACTGCATAGTGAGACTCAGCGCCTTATTCGAGA
GTCTGCACTGAACCTTCCATATCATATGCCTGAGAATAAAACCATTCATGATTTCTTCAAA
CGTAAACCCCGGCCCACTTGCCACGGAAATGCCATGGCACTATTGAAGTCATCTAAATATC
AGTCAAGCCATCACAAAGAAATCATAGACACTGCAAATACTACTGAAATGAACAGTGATCA
CCATAGTAAAGGTTCTGAGCAGACAACAGGTGCAGAAAATGAAGTGGAAACTAATGCACTC
CCTGTAGTTTCAAAGGAAACCCAGATCATTACTGGATCAGATGAGTCTTGCAGGAAGGATT
TGGTAAAAAATGAAGAGCTAGAAATTCAGGAGAAACAGAAGCAGAGTGACATTAGACCTTC
ACCTGGGGACAGCTCAGTGTTGCAACAGGAATCCAACTTCCTCGGGAACAATCACAGTGAG
GAATGTCAGGTTGGAGGGCTTGTAGCATTTGAACCTCATGCCCTGGAGGGTGAAGGCCCCC
AAAATCCAGAAGAAACAGATGAGAAAGTGGAAGAGCCTGAGCAGCAAAATAAATCATCAGC
AGTTGGGCCACCTGAAAAAGTGAGACGGTTTACTCTGGATAGACTTAAGCAACTGGGAGTA
GATGTTTCCATTAAACCACGGCTAGGTGCTGATGAAGATTCCTTTGTGATACTTGAACCTG
AAACCAACAGAGAACTGGAAGCCTTGAAGCAGCGTTTCTGGAAGCATGCTAATCCAGCAGC
CAAACCCAGGGCTGGTCAGACAGTGAATGTGAACGTCATAGTGAAAGACATGGGCACTGAT
GGAAAGGAAGAGCTAAAAGCAGATGTGGTACCTGTGACTTTAGCACCTAAGAAGTTGGATG
GAGCAAGCCACACAAACCAGGTGAAAAGCTTCAGGTGTTAAAAGCTAAACTGCAAGAAGC
AATGAAACTCCGAAGGTTTGAGGAGCGCCAGAAGCGCCAAGCACTGTTTAAATTAGATAAT
GAAGATGGGTCTGAGGAAGAGGAGGAGGAAGAGGAAGAAATGACAGATGAGTCTGAGGAAG
ATGGAGAAGAGAAGGTAGAGAAAGAAGAGAAAGAGGAAGAACTAGAGGAAGAGGAGGGGAA
AGAAGAGGAGGAGGAAGAAGAAGGAAATCAGGAGACTGCAGAATTCCTTCTTAGTAGTGAA
GAAATAGAAACAAAGATGAAAAGAAATGGATAAAGAAATAATGATGGCAGTAGTGAAA
TTGGCAAGGCAGTTGGCTTCCTCTCTGTTCCCAAGTCTCTCTCATCAGATTCTACTTTACT
TCTGTTTAAGGACAGCTCTTCCAAGATGGGTTACTCTCCTACTGAAGAAAATCAGAAACA
GATGAAAACTCAGGCAAGCAGCCTAGCAAACTGGATGAGGATGATTCATGTTCATTGCTAA
CAAAGGAGAGCAGCCACAATAGCAGCTTTGAGCTGATTGGCTCCACGATTCCATCCTATCA
```

FIGURE 2A

```
GCCTTGCAACAGACAAACAGGCCGTGGGACCAGTTTTTTCCCTACAGCAGGAGGATTCAGA
TCTCCTTCCCCTGGGCTATTTCGAGCCAGTTTGGTCAGCTCAGCTTCTAAGAGTTCAGGGA
AACTGTCTGAGCCTTCACTTCCCATAGAGGATTCCAGGATCTGTATAACGCCTCCCCAGA
GCCTAAGACACTTTTCCTAGGAGCAGGAGACTTCCAGTTCTGTTTAGAAGATGACACTCAG
AGCCAACTGTTGGATGCAGATGGGTTCTTAAATGTTAGAAACCACAGGAATCAGTACCAAG
CTTTGAAGCCTCGATTGCCATTGGCCAGTATGGATGAGAATGCCATGGATGCCAACATGGA
TGAGCTGTTGGATTTGTGTACTGGAAAGTTCACATCTCAGGCTGAAAAACATCTACCCAGG
AAGAGTGACAAGAAAGAGAACATGGAGGAACTTCTGAACCTTTGTTCAGGAAAATTCACTT
CTCAGGATGCCTCCACTCCAGCCTCATCAGAGTTAAATAAACAGGAGAAGGAGAGCAGCAT
GGGTGATCCAATGGAAGAAGCACTTGCTCTTTGCTCAGGCTCTTTTCCCACAGACAAGGAA
GAGGAAGACGAGGAGGAGGAATTTGGAGACTTTCGGCTTGTTTCAAATGATAATGAGTTTG
ATAGTGATGAGGATGAACACAGTGACTCTGGTAATGATCTGGCACTGGAAGACCATGAAGA
TGATGATGAAGAAGAACTCCTGAAGCGATCTGAGAAGTTGAAAAGGCAAATGAGGTTGAGG
AAATACCTGGAGGATGAGGCAGAGGTGTCAGGAAGTGATGTGGGAAGCGAAGATGAGTATG
ATGGGAAGAAATTGATGAATATGAAGAGGACGTAATTGATGAAGTACTTCCTTCTGATGA
GGAACTGCAGAGTCAAATCAAGAAAATACACATGAAAACTATGTTGGATGATGATAAGCGA
CAGCTACGTTTATACCAAGAGAGGTACCTTGCTGATGGGGATCTGCACAGCGATGGTCCTG
GGCGAATGAGGAAGTTTCGATGGAAAAACATAGATGATGCTTCCCAGATGGACTTGTTCCA
CAGAGACTCTGATGATGATCAGACTGAAGAACAGCTTGATGAGTCAGAAGCCAGGTGGAGG
AAGGAGCGAATTGAACGAGAGCAGTGGCTTCGGGACATGGCACAGCAGGGGAAAATTACAG
CTGAAGAAGAAGAAGAAATTGGGGAGGACAGTCAGTTTATGATACTGGCCAAGAAAGTTAC
AGCCAAAGCACTGCAGAAGAATGCCAGTCGCCCTATGGTTATTCAGGAATCAAAGTCTTTG
CTCAGAAATCCTTTTGAAGCCATCAGACCAGGAAGTGCTCAACAGGTGAAGACAGGCTCAC
TGCTAAACCAGCCCAAAGCTGTGCTTCAGAAACTGGCTGCTCTCTCTGACCATAACCCCAG
TGCTCCTCGAAATTCAAGAAACTTTGTCTTTCATACACTTTCTCCTGTCAAGGCTGAGGCG
GCAAAGGAATCGTCTAAGTCTCAGAAGATCCCAGAGAAGGACTCTGACTGGCTCACCTGGA
GTGGAGCTCCTATCCCTGGATTCTTCAGGCTTTCATTTGACCCACATGGTTAAGCTGGGAG
AGACAGAGTCCAAAGAGAGGCGGAGAAGGGCTATTCTGGGCAGAACAAACAATTGATGACT
TTATGGCTCTGTGGTCTGGGCAGAACTGCATAACCCTAGATCACCAAAGCTGAGAGCCTTT
AGGAGTGAGGATTTGGGCCGGGCATGGTGGCTCACGCCTGTAATCCCAGCACTTTGGGAGG
CCGAGGTGGGTGGATCACAAGGTCAGGAGATCAAGACCAACCTGACCAACATGGTGAGGCC
CCATCTCTACTAAAAATACAAAAATTAGCTGACGTGATGCATGCACCTGTAATCCCAGCTA
CTCGGGAGGCTGAGGCGGGAGAATCGCTTGAACCCGGGAGGTTGGAGGTTGCGGTGGGCCG
AGATTGCGCCACTGCACTCCAGCCTGGGCGACAGAGCGGGACTCCATCTCAAAAAAAAAA
AAAAAAAGTGAGGATTTGGGTCACCCCAGGCTGAAGGCCAGGGGAACCTGAATGATAAGGG
AAGGGAAAACTTAGGCCACAGTCTGATTAGAAATGGGGCTGAATTCCACCCTGTTTTTCCT
TTACTGGAGATTCAATTTGAATTACTCTGCCTCCTTCTTATTCCTTTTCCCTTTTAAAAA
GTCATCATAATCATAAAAATTTCTTTTCCAAAAAAAAAAAAAAAAAAAAAAAAAAAA
```

FIGURE 2B

SEQ ID NO:4
Human Claspin amino acid sequence

```
MTGEVGSEVHLEINDPNVISQEEADSPSDSGQGSYETIGPLSEGDSDEEIFVSKKLKNRKV
LQDSDSETEDTNASPEKTTYDSAEEENKENLYAGKNTKIKRIYKTVADSDESYMEKSLYQE
NLEAQVKPCLELSLQSGNSTDFTTDRKSSKKHIHDKEGTAGKAKVKSKRRLEKEERKMEKI
RQLKKKETKNQEDDVEQPFNDSGCLLVDKDLFETGLEDENNSPLEDEESLESIRAAVKNKV
KKHKKKEPSLESGVHSFEEGSELSKGTTRKERKAARLSKEALKQLHSETQRLIRESALNLP
YHMPENKTIHDFFKRKPRPTCHGNAMALLKSSKYQSSHHKEIIDTANTTEMNSDHHSKGSE
QTTGAENEVETNALPVVSKETQIITGSDESCRKDLVKNEELEIQEKQKQSDIRPSPGDSSV
LQQESNFLGNNHSEECQVGGLVAFEPHALEGEGPQNPEETDEKVEEPEQQNKSSAVGPPEK
VRRFTLDRLKQLGVDVSIKPRLGADEDSFVILEPETNRELEALKQRFWKHANPAAKPRAGQ
TVNVNVIVKDMGTDGKEELKADVVPVTLAPKKLDGASHTKPGEKLQVLKAKLQEAMKLRRF
EERQKRQALFKLDNEDGSEEEEEEEEMTDESEEDGEEKVEKEEKEEELEEEEGKEEEEEE
EGNQETAEFLLSSEEIETKDEKEMDKENNDGSSEIGKAVGFLSVPKSLSSDSTLLLFKDSS
SKMGYSPTEEKSETDENSGKQPSKLDEDDSCSLLTKESSHNSSFELIGSTIPSYQPCNRQT
GRGTSFFPTAGGFRSPSPGLFRASLVSSASKSSGKLSEPSLPIEDSQDLYNASPEPKTLFL
GAGDFQFCLEDDTQSQLLDADGFLNVRNHRNQYQALKPRLPLASMDENAMDANMDELLDLC
TGKFTSQAEKHLPRKSDKKENMEELLNLCSGKFTSQDASTPASSELNKQEKESSMGDPMEE
ALALCSGSFPTDKEEEDEEEEFGDFRLVSNDNEFDSDEDEHSDSGNDLALEDHEDDDEEEL
LKRSEKLKRQMRLRKYLEDEAEVSGSDVGSEDEYDGEEIDEYEEDVIDEVLPSDEELQSQI
KKIHMKTMLDDDKRQLRLYQERYLADGDLHSDGPGRMRKFRWKNIDDASQMDLFHRDSDDD
QTEEQLDESEARWRKERIEREQWLRDMAQQGKITAEEEEIGEDSQFMILAKKVTAKALQK
NASRPMVIQESKSLLRNPFEAIRPGSAQQVKTGSLLNQPKAVLQKLAALSDHNPSAPRNSR
NFVFHTLSPVKAEAAKESSKSQKIPEKDSDWLTWSGAPIPGFFRLSFDPHG
```

FIGURE 2C

Human_Claspin_Genomic Sequence Length: 58837   Type: N

```
   1  AAGCAGGTAG TTTTAAACTT TACTCCAGAG GAATAGCAGT ACTAAAAATG
  51  TAACATGGTA ATCTTCCTCA ATTTGCAGAA AAAGAAATAA AAGACATAAT
 101  TCAGTCAATT ATCTTCCTCC AAACTTTCTT AAGCCTTTGG TTTCTGCTTT
 151  TGTCTGCCAA GGAGCACAAT ATAAATAGAG CACTTTTAGA ACTGGCTGAG
 201  CATGTTAAGT TCCATGGCTG ATTTTTTCCC AGACTTGTAA TGTCAGAATT
 251  GCTTTTTAAA TATTTTTTTG TGATATAATA ATATATCCTA CTAGTTAAAA
 301  TGTTTCCGCA TTCAAATGAC CAGATTAACA GCATCAGTAC TGCAAAATGC
 351  TTCCTATGAA GTGCTATACT TTCGGGTGCC CTACTCATTA ACCTATTTG
 401  AGAATCATGA TCTCATCCAG TGTTTTCTAG TTACAAAAAA GAACAAGTTT
 451  CTTTTCTTTT TTTGAAATGG AGTCTTGCTC TGTCACCCAG GCTGGAGTGC
 501  AGTGGTGCAC GATCTCAGCT CACCACAATC TCCGCCTCCC AGGTTCAAGC
 551  AATTCTCCTG CCTCAGCCTC CCAAGTAGCT GGGACTACAG GTGCCCGCCA
 601  CCACGCCCGG CTAATTTTTG TGTTTTAGT AGAGTCAGGG TTTCACCATG
 651  TTGGCCAGGC TGGTCTCAAA CTCCTGGCCT CAAGTGATCT GACTGCCTCA
 701  GCCTCCCAAA ATTCTGGGAT TACAGGCATG ACCCACTGCA CCCAACCTCC
 751  AAAAAAGAAC ACATTTCTGA GAAACTAAAT TAGTTACCTA AGTTTATGAA
 801  GCCCTCTATG GGACAGGTTC AGACTAATCC CTGTAAAGTG AGCACTCCAG
 851  ATGTTTCCTT TGTTGCCATT TATCAACTTG ATAAACAAGG ATTGTTGGAT
 901  GACTACAACA ATGAAGGGAC AGAGAGGTCA AGGTGATTCA CAGGTTTCTA
 951  AACTGGTGAG TGGATATGGT TCCACTCACC AAAATTGAGA ATACAGGTTG
1001  CTAATTCTAA ATACAGACTC ACTTATCTT GGCACAAGTT AATGTGTAAA
1051  ATAAAAGTTT CCTGGGGATG GGAGGAGTAT GAAGTTGTTG CTTAATGGGC
1101  ATAGAGTTTC AGTTTGCAA GATGAAAGGA GTTCTAGGCC AGGCCCGTTG
1151  GGTCACACCT GTAATCCCAG CGCTTTGGGA GGCCGAGGTG CATGGGTCAC
1201  TTGAGGTCAG GAGTTCAAGA CTAGCCTGGC CAACATGGTG AAACCCCGTC
1251  TCTCCTAAGA ATACATACAA AAAAGTAGCC AGGCGTGGTG GCAGGTGCCT
1301  GTAATCCCAG CTACTTGGGA GGCTGAGGCA GGAGAATTGC TTGAACCCGG
1351  GAGGCAGAGG TTGCAGTGAG CCAAGATAGC ACCATTGCAT TCCAGCCTAG
1401  GCAACAAGAG CAAAACTCCA TTTCAAAAAA AAAAAGAAG AGAAAAAGAA
1451  AAGAATTCTG AAGATTGGTA GATTGGTTAC ATAACAATTT GAATGTACTT
1501  CTGAACTGCA TACTTTAAAA TGGTTAAGAT GGTAAATTTC ATGTTATATA
1551  TGTTTTACCA CAATAAAAAT TGAATGAAAG GTTTTCCTTT CCTAGCTTAC
1601  CCATGTCCAC CCATTGTTCA AATTGGAGCT TTCTCTCTTA GCTTCTGTGA
1651  TGAGTGAAAA GGTGCTCCCC AAAGATATTT TAAAATACTA ATATAAGGAA
1701  TATTATTTCA CTCATTCATT TTCAGAGGGA GCTCAAGAAG TTGTCAAGTG
1751  AATGAATTAA TTAGTTCAAC AAATATTTAT CAGTTTTCCT ACCTTGAACC
1801  TGGGATGTTC TAAGTCCTTT GTTCTCAAAG TGTGGTCTCC AGATCAGCAA
1851  CACTAGCATC ACCAGGGAAT TGTTAGTAA TATACATTCC TGTGGGGCAC
1901  GGTGGTTCAT GCCCGTAATC CCAGCACTTT GCGAGGCCGA GATGTGCAGG
1951  TTGCTTGAGT CCAGGAGTTT GAGACCAGCT TGGGCAACAT GGTGACACCC
2001  CGTCTCTACA AAATAAAAAA TTAGCTGGGC ATGGTGGTGC ACACCTGTAG
2051  TCCCAGCCAC TTGGGAGGCT GAGGTGGAAG GGTTGCTTGA GCCTGGGAGG
2101  TTGAGGCTGC AGTGAGCTGT GATCATGCCA CTGCACTCAG GGAGAAAAAG
2151  AAAAAAGGA AGAAAGAAG TATACATCTC TGGACCCCAC TTCAGACATA
2201  CTGAATCAGA AACTTTGGCA CTAGGACCCA ACAATAGCTG TTTTTACCAG
2251  CCTTTCAGAT TATTCTGATG CATGCTCAAG TTTAAGAAAG ACAATTCTAG
2301  GTTGCAATGA TACAGAGGCC AAGAAACAA AACGCCTGTT CTCTTGGAGC
2351  AACAACAGAC AAATAGATAT AAATAAAATT TCAGGCAAAG GAAAGTGTTA
2401  TCAGGGAAAC CAGCATAGGA TAAGGAGGCA GAACACAGAG GATGCTCAGG
2451  CAGGGTCTTT CTGAGGGGTA TGAGCTCTGA AGTCACATAG AGTCTGAAAA
2501  TTGGCTCCAC CAGTTTCTAG CCTTTTAAAA GTCTGGTTTC CTCATCTTCT
2551  AAGAAAGAGA TAATAATATT ACAAGTTTAC TCTGAAGATT AAATAAGATA
```

FIGURE 7A

```
2601 ACACTTATAA AATCCTTGCA ACTGTTTCTG CCACTGAGTA AGGCTTCAAT
2651 AAACGTTAGC CCTCCATATA TGATGGGGAG TGCCATAGAT GTATACCTGG
2701 GAATCGTTGA TGTAGAAATT AATAGTAAAT GGATGAAAAG GTGGATAAAC
2751 CAAGACACAA AAAGAGAAGA GGATGGATGA TGGGCTCTTG TTGGTGGGGA
2801 CAGAAGTGGA TTGAGAGATG GTGGGGAAGT AAAGAAATGA AGATGTGGAG
2851 AGGGAGCTTT TTTCTGAACC CAGCTAAAGG TGGAAACTTG GAAGAGGAGG
2901 CCAGTGGATT GGGTGAAGAA CCAACCATTT GGTATACCTG TGACTGAGGA
2951 GGTTCTCAGG ATGCAGGACT TTTAGTGCTA AAACTAGGAA AGTCCTGGGC
3001 AAGCTGGGCC AAGCTGGCCA CACTGGCAGT GGATATGACC ATGGAGGGTG
3051 AAGTGAGCAA TAAATACTCT GACCTTTCTT TCCTGGTGGC CTCTCATCTC
3101 CTTACAGTAA CCTTATAAGG TGTCTTTACA GGGGCCTGAC CCAACCAGAA
3151 GGGCAAGGGA GCTGGGATAA TACAGTCTAG AGAGGTCAGC CTTGCCTTGA
3201 CACACACCAG GGTAAAGGAA GGACAGAGAA TTGACCTGGA GAGGCAAAAA
3251 ATAATGGCCA GCACAGTGGC AAAACTGGGA TTAGAATTGT CTGGGATAGG
3301 CCAGGTGCGG TGACTCACAC CTGTAATCCC AGCACTTTGG GAGGCTGAGA
3351 CGGGCGGATC ACGAGGTCAG GAGTTCAAGA TCAGCCTGGC CAAAATGGTG
3401 AAATCTTGTC TCTACTAAAG TTACAAAAAA TTATCTGAGC GTGGTGGCAC
3451 ATGCCTATAA TCCTAGCTAC TCAGGAGGCT GAGGCAGGAG AATCGCTTGA
3501 ACCCGGGAGG CGGAGGTTGC AGTGAGCCGA GATCACGCCA TTGCACCCAG
3551 CCATGGTGAC AGGGAGAGAC TCTGTCTCAA CAAAAAAAAA AAAAAAAAA
3601 AAAGAACTGT GTCTGGGATA AACCTGATTT CAGAGCTTCA ATTCTTTTTC
3651 CAGCCTTGTT TAAAGGTAGA ATGCCCTCTA GGAGTGATGA GTGCTTTCTA
3701 CATCCTCAAA TTAACTCTAC AGAGAATTAT AAAGATTATC CAACCATATT
3751 CTTTGGTATC TGAGCAGCCC ACAAAACTTT TTTCTTTAGA GACAAGGTCT
3801 CCCTCTATCG CCTACGCTGA AGTGCAGTGG TGCGATCATA ACTCACTCTA
3851 ACCTCAAACT CCTGGACTCA AGCCATCCTC CCACCTCGGC CTCCCAAAGC
3901 GTTGAGATTA CAAGCGTGAG CCATGGAGCC CGGCCCTCTT TAAAAAATAA
3951 AAGTGGGCCG GGCACAGTGG CTCACGCCTG TGAGGGGTAT GAGGCCTCCC
4001 AGCACTTTGG GAGGCCGAGG CGAGGATCAT TTGAGATCAG GAGTTCGAGA
4051 CCAGCCTGGC CAACATGGTG AAACCCCGTC TCTACTAAAA ATACAAAAAT
4101 TAGCCAGGGG TTGGTGGCGG GTGCCTGTAA TCCTAGCTAC TCAGGAGGCT
4151 GAGGCACGAG AATCGCTTGA ACCCGGGAGG CGGAGGTTGC AGTGAGCCGA
4201 GATCGCGCCA CTGCATTTCA TCCTGGCTAA CAGAGGGAGA CTCCATCTCA
4251 AAAAAAAAAA AAGTGTGTGT GTATACACAT ACATGTGTAT GTGTATATAT
4301 GTGTATGTAT ATATGTGTGT ACATATGTGT GTGTGTGTGT ATATATATAT
4351 ATATATATAT ATATATATAT ATATATATAT ATTCAGTGGT AAGTGTCATG
4401 TACAAGAGGC ACACAGGATC TAGCTGCTCC AGAAATGAAG TCAGTGGAGA
4451 AAATCCCCAC GGGAACCTTG GAATTCCTCT AAAAAGTTCA GGTACAGGAC
4501 ACTCCCAGGT GCCCAGGAAC CGTTTCCCAG CTCACTTCCC CCCGAAAGAC
4551 TCACCCCTCC AATCGCACTC GATGCTTTGG CAAGTGTCAA AGGTCAAAGA
4601 CCACGGCTCG CCTGGTACCG ACTGCCCCGC CCCCGTGCAC CTCCAGCTCC
4651 CCCAGGCTCC GCTACCAGCA GCTGCGACCC GCCAACTCAG CCTGGGTAAT
4701 AGGAGATTGG GCGGCCAGAG GCGCTGCGTG ATTGGTGGGT CGGAAGGGGG
4751 CGGGGACTCG CTGGAAAGCC CCTCTGGAT TGGTGCAAAC CATCTGGGTG
4801 GGACCTCCAC TCTGGCTGGG CGGGAAAGCA AGAACAGCAC TGCTGGGCTG
4851 GAGACGGCGG GAGCCGCTGC TCTCCGGCTG AGGGAATCAG AGACAGCTCC
4901 GTCCCTAGTG GAGCGCAGGG GAGGCAGAAG TCATGACAGG CGAGGTGGGT
4951 TCTGAGGTGA GTTTATGCAC ACGCCCCCA CGGGGGCTTA GAAGGCCGGG
5001 CACCGAGAGG TTAGGTGGGG CCGGGGTAGA CCCCGCTGAC CCGAGGCGCC
5051 CGGGCGGGAG GACTGCGGCT CCCGGCGTTC GCCGCGCCGG CTCCCGCGGC
5101 CTCGAGACTC GGCCGGGATG GGTTCCGACC GGGCATCCCG TCCCGCCGCC
5151 GGGCTTCCCG CGCTTCGGGC TCCGTGGCCG GAGAGCTCCA GGTCTCTGCG
5201 GCGCGCACTG CCGGCAGCCC AGCCCCTCTT CAGCCGGTTC CTGCCGCCAG
5251 CCCTCCCCTT TGGCGCGTTT CCTGTCGCGG AAGCTCCTCC CCTCAGGGTG
```

FIGURE 7B

```
5301  CTCTGAAAGC CGGGAGGCTC TAGCCGAACC CGGCCGCAGC GGTGCGGGGG
5351  GATTCTCCGC AGAGAGAGGG CGAGCGAGGG TGTTAGGGAG TTCCACACTG
5401  GGCCTGGGAG GGGCCCTGGA GGTCATCGCG CGCAGGCCCT TTGCGTTTTC
5451  CGACCGGGCC CCGAGTGGGG AAGTCACCGC TGGGGCTCCT GGCTGGTGGC
5501  TGGCAGCTCC CTGGCGAAAT TGGGCATAGA AAACAGATGT TCCAGAGCT
5551  GTGTCCTTTC TGGGCCGGAT TCGGGCAAGG CACTCCCGCC TTAGGAGCAA
5601  AATTTAAAGG GGCGCCAAAA CCCTCAATCA AACTCATATT TTAATGCAAT
5651  ATTTTAAAA AACCAAATT AATGCAAAAA CTTTTTATGA TTTGATATTG
5701  AACAAAATAT CAGACGTTTA AACAAAGACG AGATCCGACC AGTCATTTGC
5751  ACGACCTTGC CTCAATCACC TCACCCTAAT TCCATCCCTG TTTCCAATAA
5801  ACTTTATTTA CAAAAGCGGG CATATTATTT ACCTCATGAG CTGTAGATTA
5851  TTGATTTAAT TTTTAAAAA ATATTGCATT AATGTTATTC ATTTTGATTA
5901  CTGAATTTTT TGAGACCTCA CCCCACCCTG TTACTGGCCC TGCCCTTTGA
5951  CGTTGCTGCA AATTGCCTAG AAGATAATCG TCATTCAAAG CAGCCCTATT
6001  CCTTGAGCTG TCTGGTTACC TAAATTCGGT TTCCACACTC ACAAACAGAA
6051  GTAATAGTTT TACTGCTTTG GATTGTTGAG AGGATCATCA GTGCATACAT
6101  ATTAATTCTC AGCAATCCCA GCACTTCGGG AGGCTAAGGC CGGCAGATTG
6151  CTTGAGCTCA AGAGTTCGAA ACCAGCCTGC ATAGAAAACA TGGCAAAACC
6201  CCGCCTCTAC AAAAAAAAA AAATTAGCCG GGCGTCGCCT GTGGTCCCAG
6251  CTACTCGGTC CCAGCTACTC GGGTGGCTGA GGTGAGAGAA TCCTTTGGGC
6301  CTGGGAGGTC AAGGCTGCAG TGAGCCATGA TCCTGCCACT GCACTCCAGC
6351  CTAGGTGACA GAGTGAGACA CTGTATCAAA AAAAAAAAA ATTTGTACCT
6401  TGCATTCAAA TCAATTTAAT AATTTTTTT TTTTGAGAC GGAGTCTCGC
6451  TCTGTTGCCC AGACTGGAGT GCAGTGGCAC AATCTCGGCT CACTGCAACT
6501  TCTGTCTCCT GGATTCAAGC GATTCTCCTG CCCCAGCCTC CTGAGCAGCT
6551  GGGACTACAG GCACACACCA CCACGCCCAG CTAATTTTTG TATTTTTAGT
6601  AGATACGGGG TTTTACTGTA TTGGCCAGGC TAGTCTCGAA CTCCTGACCT
6651  TGTGATCCAC CCACCTCGGC CTCCCAAAGT GCTGGGATTA CAGGCGTGAG
6701  CCACCATGCC TGACCAATTT AATAATTTTT TGAGAAACCA CTCAGCTGAG
6751  GCCTTGTGCC CTGTTACATT ACTGATGTTC ATATTTCTCC CTTTATTAAT
6801  AAGTTGATTC AGAGCCCTGA GAACACTAAG GAGGTAGACT TGGCATCTAG
6851  GGTTAGCTTT AAGGTCACTA ACTGATCAAG TCACCTAACA CACCCCTCCT
6901  CCTTAGGTTT TTATTTGCGA CTTTTTAAAC TGTCTTATTT AGAAATTTTC
6951  AAACCTATAC AACCGTAGAA AGGATGGTAT AATGAACCCA TCACCTTACT
7001  TCAACTACAG TTTGAATATC TCTCGTCTGA AATGCTTGGG ACCAGAAGCG
7051  TTTTGAATTT CAGATTCATT TTGGATTTTG GAATATTCGC ATACACATAA
7101  TGAGATATCT TGGGGGAGGG ACCCAAGTCT AAACATGAAA TTCAGTTATA
7151  TTTCATATAT ACCTTACACA CATAGTCTGA AGGTAATTTT ATACAGCATT
7201  TTAAATAAT TTCGTGCATG AAGCAAAGGT TTTACTGCAG CTCATCATAT
7251  GAGGTCAGGT GTGGAATTTT CATCTAGTGG CATCATGTCA GTGCTCAAAT
7301  ATTTTGGAAT TGGGAGCATT TCAGATTTTC AGGTTAGAGA TGTTCAACCT
7351  GTATTTCAA GTCATGGCCA ATCTTGTTTT ATTCATACAG CTACCCATTT
7401  TTCCTCTCAC AGGATTATTT GGAAGAAAAT CCAAGATATC ATATTATTTG
7451  AACCACAAAG ATTTAGTGT GCATATCTAA CAAACAAGAG CTTTCCAAAA
7501  ATAGATACTA CGATATTATT ACCACACCTA AGAAGTATCT AGTCAGTGTT
7551  CAGATTTCTT TGACTCAGAG ATATTTCATT TATTTTTATA TGCCACTTTA
7601  GCATAATTAT TTACATTTTT AGTTTTTTGA ATCATCATCC GAAGTTGGCA
7651  TTTTGTAATT GTTTATATTA TATATGTGTA TATATGCATA TATGTATGTA
7701  TTTTAAGATA TACATACATA TATAAAGCAT ACATTTATGT ATATAGAAAT
7751  ATACAGGGCC GGTTGTGGTG GCTTACGCTT GTAATTCCAG CATTTTGGGA
7801  GGCTGAGGCA GGCGGATCAC CTGAGGTCAA AGTTCGAGA CCAGCCTGGC
7851  TAACATTGTG AAACCCCGTT TCTACAAAAA ATTAGCCGGG CATGGTGGCA
7901  CGCACCTGTA ATCCCAGCTA CTCGGGAGGC TGAGGCTGGA GAATCGCTTG
7951  AACCCAGGAG GCGGAGGTTG TAGGGAGCCA AGATCGTGCC ATTGCACTCC
```

FIGURE 7C

```
 8001  AGCTTGGGCA ATAAGAGCGA AACTCCGTCT CAAAAAAAGA AAAAAGGAAA
 8051  TATACATATA GCCGGGCGTG GTGGCTCACG TCTGTAATCC CACCACTTTG
 8101  GGAGGCTGAG GCGGGCGGAT CACCTGAGGT CAGGAGTTGG AGACCAGCCT
 8151  GACTAACATG GAGAAACCCC ATCTCTACTA AAAATACAAA ATTAGCCAGA
 8201  CGTGGTGACA CATGCCTGTA ATCCCAGCTA CTCGGGAGGC TGAGGCAGGA
 8251  GAATCGCTTG AACCTGGGAG GCAGAGGTTG CGGTGAGCCG AGATCGCGCC
 8301  GTTGCGCTCC ATCCTGGGCG ACAACGGCAA AACTCCATCT CAAAAAAAAA
 8351  GAAATATACA CATAGCATAT AGAAATATAC ATACATATAT AAATATATAG
 8401  AAATATACAT ACGTACACAC ATATATACAT TCACTTATGT GTTAACTTTC
 8451  TTTATAGGTT TCTCTCCCTC TCTTTTTTTT TTCTTTGCAA TATATTGTTA
 8501  AAGAAACCGG CCGGGTGCAG TGGCTCATAC CTGTAATCCC AGCATTTGG
 8551  GAGGCCGAGG TGGGCGGATC ACCTGAGGTC AGGAGTTTGC AACCGGCCTG
 8601  GCCAGCATGG TGAAACCTTG TCTCTATTAA AATAGAAAAA ATTAGCTGGG
 8651  TGTGTTGATG TGCGCCTGTA ATCCCAGCTA CTCAGGAGGC TGAGGCAGGA
 8701  GAATCGCTTG AACCCAGGAG GCAGAGGTTG CAGTGAGCCG AGATTGCACC
 8751  ACTGCACTCC AGCCTGGGTG ACAGAGCGAG ATTCTATCTC AAAAAAAAAA
 8801  AAAAAAAGA GAGAGAGAGA GAAAGAAACC ACCCAGTTTG ACTTGTAGAA
 8851  TTTCCCACGT CTAGATTGCA TATCTGTGGT ATTATTCAAC ATGTTCCCCT
 8901  ATTCCCTCTA TTTCCTATAA CTTGCTAGTT AGATCTAGAG ACTTGATAGG
 8951  ATTCAAATTT GATTGTTCTG TCAGGAATAC TTTATGGCTA GTATTGGGTA
 9001  CTTCTATTAG GCAGCACATA ATGTCTGGTT GTTTCTCTTT TGGTGATGTT
 9051  AGCAGCCATT AATGATAATT GCCTAGGTCT GTTATTTAAT TGAGGGTTGA
 9101  TAAAATTGTG ATAATCTAAT TCTATCATTT ATTAATTCAT TAGGATATTT
 9151  CTCTAAATAG AAACTTCCCC TCATCAATTG TATGGATATA TTGGGGAACA
 9201  GTTCACACAG AAAAGGCATA ATAAATGCTT GATTCTTTTC ATTTTTTTTT
 9251  TTACCGTTAC TAAAAGAGTT GGTTCTGTTA GCATCCTTCA AAGGTGAAAA
 9301  ATGAACTTTT GTTTGTTTGT TGTCCAGTAA TTCTAAATGT CATCCCTTCA
 9351  AGGAACCATT GTATTTGGTT CTTTCCTTAG TTCAGGTTGA TGATCCCACG
 9401  ATGATTTGTG TGTCATTATG TACTTGGAGC TTTCGGTCAC CTGCTGGTTG
 9451  ATATAAAGTA TATTGTCATT TTCTAGGTTC ACCTAGAAAT CAATGACCCA
 9501  AACGTCATTT CACAAGAGGA AGCAGATAGT CCTTCAGATA GTGGACAGGG
 9551  CAGCTATGAA ACAATTGGAC CCTTGAGTGA AGGAGGTTTG TAATAGTACT
 9601  TTTATTTTTA GGAATAGGTT GCGGGAGCCT CAGTTGTAAG TAGATTGGAT
 9651  TGATTTCATT ATTCTCTTGA TTTATTACAT TATTAATGCC CCATCCTTAT
 9701  TGTTTGTTTT ATTATAAAAG CAAAATAACA GTGCTTGTAC CTTTTTGAAA
 9751  CTATGTTATA TTGTTAATG TCTAATAGCT ACCATATTGC CTGGTTAATT
 9801  GCATTCATCC TATAATAAAA GGAATTTTAA CACCTGCCGG AGGTTAGAAC
 9851  AACTTTACAC ATTGTAAATA TACGTAAAAT TACATTTCCC AGTAAGAGAC
 9901  ATTTTTCCCA GGGAAAATGT TTTTCAAAAT GTATTTTTAG ATTTGCTTTG
 9951  CTACAATCAG TTCTTAACAG TAGTCACGTA ATTTCACAAT GTTATATATC
10001  ACTTGTATAA AAATATATTT TTGAGGAGTA GTGGGACTAG GAGGAAGATC
10051  AAATGATGGT ATAATTAAAA GAAATTGTT TCCTCCAGAT TCAGATGAAG
10101  AGATATTTGT AAGTAAGAAG TTGAAAAACA GGAAGGTTCT ACAAGACAGT
10151  GATTCCGAAA CAGAGGACAC AAATGCCTCT CCAGAGAAAA CTACCTATGA
10201  CAGTGCCGAG GAGGAAAATA AAGAGAATTT ATATGCTGGG AAAAATACAA
10251  AAATCAAAAG GATTACAAA ACTGTGGCAG ACAGTGATGA AAGTTACATG
10301  GAAAAGTCTT TGTATCAGGA AAATCTTGAA GCGCAAGTGA AACCTTGCTT
10351  AGAGCTGAGT CTTCAGTCTG GAAACTCTAC AGACTTTACC ACTGACAGAA
10401  AGAGTTCCAA AAAGCACATA CATGATAAAG AAGGAACTGC AGGAAAAGCA
10451  AAAGTAAAAT CAAAAGAAG ACTTGAGAAA GAGGAGAGAA AAATGGAAAA
10501  AATTAGACAG CTAAAAAAGA AGGAAACAAA AAACCAGGTA CATTTTAAAG
10551  AATAATTTGC TATTGCTTGG GTAGGTTAAC ATTTTAGAAA AGGTTGCTGT
10601  TAGTACTTGA GGTTGTTTCT GCTCTCTGAC TATTGCTTTG AATTGACTAT
10651  TTTGTGTTGA GAATTATTCT CAATAGGTAT GTGATTTAAA ACTAACTGGT
```

FIGURE 7D

```
10701  CTTGGCCAGG TGCAGTGGTG CATACGTCTA ATCCCAGCAC TTTGGGAGGC
10751  TGAGGCCAGA GGGTCACTTA AGCCCAGGAG TTCGAGAACA GCCTAGGCAA
10801  CAGAGTGAGA TCCCATCTCT ACAAAAAATT TAAAAATTAG TTGGGTGTGG
10851  TGGCCGTAGT CCCAGCTGTA GTCCCAACTA CTTGGGAGGG TGAGGTGGGA
10901  GAATCACTTG AGCCCAGGAA GTCGAGGCTG CAATGAAGCT GTAATTGTAC
10951  CACTGCATTC CAGCCTGGAT GACAGAGTGA GACCCTGTCT CAAAAAAAAA
11001  AAAAACAAAA ACCAAAAAAA CAAAACTTAT TGGTCTTATT CTATTTTGGG
11051  TATGCAGAGG ACATTTCCAA ATAAATGGGT TTCTGATTTT CTTTATGAGC
11101  ACATGGAGTA ATTCTTTGCT GTCTCTGAGC TGATGAAAAT TAACTGAAAG
11151  AAGGCTTTTT TATGCATCTA TCAGTCAGTA GTCTTGTTTG CTAACTAGAA
11201  AAACCATCCT CAAATTTATA AACTAGTTGC TTAACAAGTA TTTTACTTCA
11251  AAAAAATATT TACTGTTTAT TAAGTTAGTT TTAGACAGTT GCATAAAATC
11301  ACAACTTGGA CTTCAAAGGA TACATGTGAG TTAGAAACCA GTAAGAATGT
11351  TCTAGATTTT ATATGCTTGT CTGTTGATGA AACATGGGCT TTTTCTGGCC
11401  TGATCCAAAT TGCCATATGA TGTTGTGAAA TACTGGATTT TTAAATGATT
11451  GGATTATGCT TTTTGTTTAT GTATTACTTA GGAAGATGAT GTAGAACAGC
11501  CATTTAATGA CAGTGGCTGT CTTCTTGTGG ATAAAGACCT TTTTGAAACT
11551  GGGTTGGAGG ATGAAAATAA CTCTCCATTG GAAGATGAAG AGTCATTAGA
11601  ATCAATAAGA GCAGCTGTAA AAAACAAAGT AAAAAAGCAC AAGGCAAGTA
11651  AAGCATGATT GCAATAAGAG TTAATCAACT GCTTCTGACC TTTGCTATAT
11701  TTTTAATTTA CTGTTGGAAC CTTAATTTTT TTTTTAACTG AAGAAAAACT
11751  TGTGTCAGTT GACTTAAGTG TTTCAGCTGT TAATTTTGGA GACTTGCAGT
11801  ACAAGTGATA GACATGCTAA CTTCTTTGGA AACTAGTGTT TTGTTATTAC
11851  CCTTTTAGGA ATGCTGAAAA AAAAAACCAC TAAGATATTT GATGGTGTAG
11901  TAAGATGCAG GTAAATAATA GGGAAGAGAT GTAAATTTTG CAATCCTATA
11951  GCCTTTGAGA AATGAACCCT ATAGGGTTTC AGGAAGGGTA TCAAAGAGAG
12001  GCATCAGTCA AAACATTGTT GTCCCGAGTG TTTGGAAGCA TAATTTTTCT
12051  TCCTAAGATT TTTTTTTAGC TTCCTGCGAG TTATTATCCC TCTTTAGGGA
12101  AAGATGTAAG CAGAGGTAAA AGAAATAAGG GTCCAGACTC CATCTGAGGT
12151  ATCTGTTTTC TAAGCATAAT AGGATGCTGT GTGTTTAATA ATTTCTAGTT
12201  GATGATTATT GATTTATTAA TGTAGCATGA TGTGGTGTTG GACTACAAAA
12251  GTAGTCTTCA GCTAAAGCAT CCTCTTATTT GAATTTCGTT TTTGTCCTAA
12301  TCAACCTGCC ATTTCTTTTA GAAAAAAGAA CCATCTTTGG AGAGTGGGGT
12351  CCATTCATTT GAGGAAGGAA GTGAGTTATC AAAAGGAACC ACGAGGAAGG
12401  TGAGGTAGAG CCCTGTATAT TAGTCACACT GATCTCTTTA CACAGGAGAT
12451  TATAGATTTC TTAGGGATAA ATATTTTATT TTGTCTATCA TATTTTTCTG
12501  TTACCCATCA TATTGCTTTG TACATAGTAG GAACAAAATA TGGATTGGAT
12551  TGAACAAATT CTCTGAGACT TGGGAATAAA TGAATTCCTT GAGTTTATAC
12601  TGCATTTGGG CTTACTCATG CTTACTATTT CCTTTCCTCT TTTCTTGGAG
12651  AGAGCAAACT CTTGAGTGAT GAATATCTAT CTTTCTGGAT ATTCATATAA
12701  TTAATGTAGT CTCACTTCTT GTTTTCTTTA AGGAAAGAAA GGCAGCCAGA
12751  TTAAGTAAAG AAGCATTAAA ACAACTGCAT AGTGAGACTC AGCGCCTTAT
12801  TCGAGGTAAT GCAACCCAGT AAACTTTGAG GCAAAATCAC AACATTTCTT
12851  TGTAAGCTCA ACTTGGATGT TGGGGACTTT TATTTTTTA ACACTTCTAA
12901  TGTGAACTCA GGTTATAATA TTAAGTTTAG AATTGATCTT GGTGAAAGGC
12951  CATTGTTCTA AAGCCCTTGG AACATTAGTA TAAACTGAAG AAATTTTCAG
13001  AACTGTAGTG CAGGTAAGGA GGAAATTTTT TAATGGTTGT CTATGGACTG
13051  ATTGTGTCAG GATTCTTTGG AGAGGTAGTA ATCCCTCCCT ATTTGCAGTT
13101  TTGGTTACCT GTGTCAGCCA TGGTCCATGG AACTTAAAAA TATCATCCCT
13151  TTGTCCAGAG TATCACGCTG TATACATTAC CTGCCTGTTA GTCCGTTAGT
13201  AGCCCTCTCA GTTATCAGAT CAAAAAAACA CTGCATGGTT TAGTACCATC
13251  TGCAGTTTCA GGCATCCACT GCAGGTCTTG GAATGTGTCT GTCTGGATAA
13301  GCGGGGACTA CTGTATATAA ATGTTTAGGT CCCACAGAGA TTCTGATTCA
13351  GTAGATTCGA AATGGGATCC AAGAATCTGT ATTTCTAAAA AACTTCCTGG
```

FIGURE 7E

```
13401  ATCATTTTGA TTTCACATCT AGGTTTAAAA GCCACTGGTC TTCAGGGAGC
13451  TTTTTTGTAC TTAGCTCCTC TGCCTTTGTT AAAGGGGAGT TTTCTATTTC
13501  TAGTGATGGC TTTGGTTATT ATGTTTAGTT AACTGAATAT GAAGTGACAT
13551  TTCAGAATAT ACAGTATATA TATTTGCTTG TTTTATTCCA TTTTATAGAG
13601  TCTGCACTGA ACCTTCCATA TCATATGCCT GAGAATAAAA CCATTCATGA
13651  TTTCTTCAAA CGTAAACCCC GGCCCACTTG CCACGGAAAT GCCATGGCAC
13701  TATTGAAGTA AGAACCCTCT TTCCTTATTA TAATTTTCAT GAACATTTAG
13751  TTTTGTAGCA AACATCTGGC ATAAAAGTT CAGATTTCTC ACTCCCTTAA
13801  AACTGATTTA ACTGATATAT ACTAAGGGAT GAGAATGTTT CACATTTAGG
13851  ATAATTTTCA ACTCCAGCTC AATTTCTCTT CTCTAGGTCA TCTAAATATC
13901  AGTCAAGCCA TCACAAAGAA ATCATAGACA CTGCAAATAC TACTGAAATG
13951  AACAGTGATC ACCATAGTAA AGGTTCTGAG CAGACAACAG GTGCAGAAAA
14001  TGAAGTGGAA ACTAATGCAC TCCCTGTAGT TTCAAAGGAA ACCCAGATCA
14051  TTACTGGATC AGATGAGTCT TGCAGGAAGG ATTTGGTAAA AAATGAAGAG
14101  CTAGAAATTC AGGAGAAACA GAAGCAGAGT GACATTAGAC CTTCACCTGG
14151  GGACAGCTCA GTGTTGCAAC AGGAATCCAA CTTCCTCGGG AACAATCACA
14201  GTGAGGAATG TCAGGTTGGA GGGCTTGTAG CATTTGAACC TCATGCCCTG
14251  GAGGGTGAAG GCCCCCAAAA TCCAGAAGAA ACAGATGAGA AAGTGGAAGA
14301  GCCTGAGCAG CAAAATAAAT CATCAGCAGT TGGGCCACCT GAAAAGTGA
14351  GACGGTTTAC TCTGGATAGA CTTAAGCAAC TGGGAGTAGA TGTTTCCATT
14401  AAACCACGGC TAGGTGCTGA TGAAGATTCC TTTGTGATAC TTGAACCTGA
14451  AACCAACAGA GGTAATCCTT TACATTGTGG GGAGCCTCCC TGGAGTGATT
14501  ATCCTGGTAG CTTTTGATTA TTGACTACTG TCGAGGACAG AGAACACAGG
14551  AGGAACCAAT AACCACTTTG ATCTTATCCT GCAGTTGTTC CAGATATGGG
14601  CAGAGTCTTT TTTAGAGAAA TTTGGCAGGG TATCAGAATG ATCTAAGCCA
14651  TGTTTAAAAT GGAAGTCTGT TGGCTGGGTG CGGTGGCTTA CGCCTGTAAT
14701  CCCAGCACTT TGGGAGGCCA AGGCGGGCAG ATCACGAGGT CAGGAGTTTG
14751  AGACTAGCCT GGCCAATACA GTGAAACCCC GTCTGTACTA AAAATACAAA
14801  AATTAGCCGG GCATGGTGGC ACGCATCTGT AGTCCTAGCT ACTCGGGAGG
14851  CTGGGGCAGG AGAATTACTT GAACCCAGAA GGCAGAGGTT GCAGTGAGCC
14901  GAGACTGCAC CATTGCACTC CAGCCGGGT GAGAGAGCGA GACTCTGTCT
14951  CAAAAAAAAA AAAAAAAAAA AAAGGTTGTT GATAGTTAAT ATAAAAAGA
15001  GGTACATTGC TACTGTGTTA TGGTATTTAG GAATTTATTA TTTCTGCCTT
15051  TCCAATCTGA AATTAAGTTT TTTCTGTAAT CCTGAGTCAA ATCTTAAGAC
15101  ATTGATGAAA ACATCATTTA GTTTTTTACT GCTAAAGAGA AACATTTTGG
15151  TTCACTTAAA TTATCTGTGA AACCGAATTT CTTTTGTTTT CACTCATTCA
15201  ACAAATATTA AAGTATCTAC TATGAGTAAG TTGCTGTGGG GCATACCAAG
15251  ATAAATCTGA CATTTAAGGT ATACTTAAGA TGCTTTTACT CTAATGGGCG
15301  AGATAAGAAG TATGCAAATA AGAAGTACAA AGGAGAAAAT GGTAAATGAT
15351  GTCTTTGATA ATGAATATGT CATTGATAAT TGGAAAATAA ATAACATGAA
15401  GAAAAAGGAA AAGTATTTTC TTAAAGAACA TTTAGAATAA AGTACTGTGG
15451  GAATTCAGAG AAGCATAAAT TTCTTCCAAT GAATAGTTAA AAGACAGCCT
15501  GAAGAATAGG TGGATTAATT ACTTGTTCAC TGCCTTCCCT TTATACTGTG
15551  AGTTGGTATC TTCTGCCTTG TTCCCTACTC TATCCCTAGT GCTTCCTCAG
15601  TGGACGACAC ATTGTAGGCA CTTGTATTTA TCAAATGAAT GAATGATCCC
15651  TCAACACTGA ACTCAAGTAT TACCACATTG AATAAATTTC CTGACTCTTA
15701  GATAGAGCTG GATGCTCCCC ACTCTGCCTT GAGGCAGTAT GGAATGGTGG
15751  TTAAGAGCTT AGACTTTGTA GCAAGACCAG GATTTGAATC TGAACTAGCA
15801  TAGTAATTGT TTAACATTGT ATACGCCATT TGACCTCTTC AAGCATCTTT
15851  TGTTTAAAAA AGAGAAGAAA GCCAGACACA GTGGTGCACA CCTGTAGTTC
15901  CAGCTACTCG GGAGGCTGAG GCACAAGAGG GTCACTTGAA CCCAGGAGTT
15951  TAAGGCCATC CTGGGCAGCA TATGAAATCC TGTCTCAAAA AAAAAAAAA
16001  AGAAAAAGAA AAAAGCACTA TATGACTTGT GGGCTATGGT GAAGATTTGT
```

FIGURE 7F

```
16051  TGAAATAATG CATGCAAATG GATAGTATAA ACAAGCACTC AAAAAGTTGT
16101  TGCTGCTTCT ACTATTATTA GTGAAATGGT TCACATCAAG ACTTTTTTTT
16151  TTTGAGACGG GCTTTCACTT GCTCTTGCCA CCTAGGCTGG AGTGCAATGC
16201  TGCGATCTCG GCTCACTGCA ACCTCCGCCT CCTGGGTTCA AGCAATTCTT
16251  CTGCCTCAGG CTCTCAAGTA GCTGGGATTA CAGGTACCCG CCACCACACC
16301  CAGCTAATTT TTGTATTTTT AGTAGAGACA GGGTTTCACC ATGTTGGCCA
16351  GGCTGGTCTC AAACTCCTGA CCTTAGGTGA TCTGCCTGCC TCAGCCTCCC
16401  AAAGTGCTGG GATTACAGGT GTGAGCCACT ACACTCAGCC AAGACTCTTT
16451  CATTAAACCA AGCATAGTCA GTGGCTTATG CCTGTAATTC TAGCACTTTA
16501  GGAGGCTGAG GTGGGAGGAT TGCTTGAGCC CAGGAGGTCA AGCTGCAGT
16551  GAGTTGTGAG CTGAAATTGC ACTCCTGCAC TCCAGTCTGG GAGACAGAAC
16601  GAGACCCTGT CTCATAAAAA AAAAAAAAC ACAAAAAAAT TATCTTTCAT
16651  TAAACATCTT ATTGTTGGCA GGTGCTATGT CAGTGACTAT ATCTGGTGTG
16701  TAAAATATGC TCAGTGAGTC TGTTAATTGA ATGGGTTGAC TTTGGAGATG
16751  GAGAGGATAG AAAGAGCACC TTGTCTCATT AAAACAAAAA GAAAACAAA
16801  ACACACACAA AAAGATTCT GTTTCATTAA ACAGCTTATT GTTGGCAAGT
16851  GCTATGTCAG CCACTGTATC TGGTGTGTAA AATATGCTTA GTGAGTCTGA
16901  TAATTGAATG GGTTGACTTT GGAGATGGAG AGAAGGACAG AAAGAACTCT
16951  GCATGGTGGT GCGTATTGGG AAGATGTGAA AGTCACTTTG ACCAGGGCTG
17001  GAGGTTCAGG TGGCAGAGTT GTATAACAGA ACTAGCATAG CTCCATTAGC
17051  AAAGAAGCAT GAGAATAAGC TGTTGTCCGG AACACTGAGG GAAAGTTTTT
17101  GTTATATGGG ACTAAAAGTT ACCTAAACAG TCCTAGACTG ATAGGAAAGG
17151  GAGAAACATT TTTTGAGTAC CAACTATATT AGACACTGGT ACATTCTTTG
17201  TTAGTTGTCT TTCTTAATTC TCACAGTGCC AGGTATTATT TTGCAAAATG
17251  AAGAGACTGA GGCTCAGAGA GGTTAGGTAA TTTTTCCAGC ATTATACTTG
17301  GCTTATAAAG GGACCTACAC AGTGGCTGGC ATATAATGAG CACTTATTTT
17351  TTAACTTGGA ACATGTTTTC CTTTAGAAAT AATTGACACG AAATTTGGGT
17401  TTCCAGACCA GCCATAATAT ACATGAAGTT AGAATCAACA TTCATTCATT
17451  CATTCATGCA ATAAACTTTT ATTTAGCACT GTGTTGGGTG CTGTGTATAC
17501  ACGTAAAACA CTCCCTGCTC TCAAAGAAAT TGAAGTGTAA TAGGAGTGAT
17551  AGACAGGCAA ACAGACCATT ACAATACTGG ATGGTAAGTG CTGCGATCAA
17601  GGTATATAAT TGAGGGTGCA TTGGGAACCT AGAGGAAGGG TACCTTACTT
17651  GGAGCCTAGA AGTCAGGGAA GTTTCTGAAA TGAGCTCAGT AGAGATACCA
17701  AGGCAGAGAG GTGAGGGAGG GCTTTTTTGG TGGAGGGGTT GGACCTGCAG
17751  ATGTCAGAGA CAATGGAAAG CACAGGGTGA TCTCCCTGGC TGAAGTGAAG
17801  ATAGCAAGGA CATTGGTGAT CAGAGCCCAG ATCATTCAGG GTTTTTATGC
17851  CATGCTAGGA GCTTGGACTT TAGCTCTTTG TAAGTAGAGG ACCACTGAAA
17901  GGTTTTCAGC AAAGGAAATG TTCAATCAGA TACTCACTTT AGGAAGTTAA
17951  ATCTGGTAGC TGTTGTGGTG GATGCATTGG AAGGGGTTAA GAGTAAAAAC
18001  AGTGGGAACA GCTCAGTTTC TTTACCTCAT ATAGAATAAG GTTTCCATGA
18051  GAAAATGCAT GTAAATTTAA ATTTTGTGAT GTCAGAAATA CATTATTTCT
18101  GTTGCTTGCA ATAGCATATG GAATAATCCC TGCCTCTAAT TCCTCTACTT
18151  TCTGGACAAG AGCAATGTGA ATGAGAACAG TTCTTATGCT GCTGATAGAG
18201  ATAAGCTAGG AAAGAGACTT TTCACTTAAG AGAGGAGATG AGAGGTGATG
18251  GAGGATGAGA GGTGATGGAC TAATAGAGAT GAATGGAGGT AGAGGAACTT
18301  GAACAGGGGT TTTAGGATGA AGACAGTGAT GGTTGCATCA TGTAATAAAG
18351  GCCAAAGAAA GTGGTTGCTC CAATGGGTTG GGGGAGGAAG AGCTTTGAGG
18401  ATCCTAGCTT TCTCCAGTTA TGAATGAAGA TACCTCTTGC CTGACTACTA
18451  TTTTAAGTCC CAGGTAATCT TCCCACCCAA CCATTTCTCT TACCCTAGTG
18501  GCACCCATAA TAACCTGCCT ATTTCTGTTC CCTTTTCCCT GCTACCACCT
18551  GTTGCTTTCA GCTTTACTGA ACCACTGCAA AATAGGAGGC AGACTTACAG
18601  CTTGTCTCTC TACTCTTTTG TTTGCAATGT AAACATACCA TCCTTTAGAG
18651  TTGGGTTTTT GCTGCTAATA ATGTTGGGGT TCAGGATAA AAAGATTTCC
18701  TTCATTTTTC TCTTTTTCTA GTAAGACCGT CTAGAGGAAA AAAACACATC
```

FIGURE 7G

```
18751  TAGATGCTAG  TCACAAAAAC  ACCGAAGTAT  GATTTGAGTG  CATTTTAGAA
18801  AATTAGTCAA  GTTTCATGCC  TATAGTCCCA  GCACTTTGGG  AGACTAAGGT
18851  GGGAAGTTCG  CTTTGAGGCC  AGGTGTTTGA  GACCAGCTTG  GGCAACATAG
18901  CGAGTTCCTG  TCTTTACAAA  AAATAACAAA  GCCAGATGTG  GTGACATGCA
18951  CCTGTAGTCC  TAGCTACTTG  GGAGGGTGAG  GTAGGAGGAA  TGCTTAAACC
19001  CAGGAGGTCA  AGGTTGCAGT  GAGCTGTGAT  CGCACCACTG  CACTCCAGCC
19051  TGAGCAACAG  AGCAAGACCC  TGTCTCTAAA  AAGACAAATG  AAAAGTGGCT
19101  GGGCACAATG  GCTCACACCT  GTAACCCTAG  CACTTTGGGA  GGCTGAGGAG
19151  GGTGGATCAT  TTCAGTCCAG  GAGTTCAAGA  CCAGCCTGGA  CAACATGGCA
19201  AAACCGGTCT  CTACAAAAAA  TACAAAAATC  GGCCAGTCGC  AGTGGCTCAC
19251  TCCTGTAATC  TCAGCACTTT  GGGAGGCCGA  GGTGGGTGGA  TCATCTGAGA
19301  TCAGGAGTTC  AAGACCAGCC  TGGCCAACAT  GGTGAAACCC  CATCTCTACT
19351  AAAAATAAAA  ATAAAAAAAT  TAGCTGGGTG  TGGTGACGCA  TGCCTGTAAT
19401  CCCAGCTTCT  AGGGAGGCTG  AGGCAGGAGA  ATTGCTTGAA  CCCAGGAGGT
19451  GGAGGTTACA  GTGAGCCGAG  ATCATGCCAC  TGCACTTTGG  CCTGGGCAAC
19501  AGAGTGAGAC  TCCGTCTCAA  AAAAAAAAA   AAAAAATTAG  CTGGATATGG
19551  TGGTACATGC  CTATAGTCCT  GGCTATCTCA  GGAGGCTGAG  GTGAGAGGAT
19601  CACCTCTAAG  CTTGGGGAGA  TTGAGGCTAC  AGTGAGAGCC  AAGATTGCAC
19651  CACTGCACTC  CAGCCTGGGC  GACAAAGCGA  GACTCCATTT  AAAAATAAAC
19701  CATTTTATCA  TGGACGAGAA  GGCCGCCTGA  AAATATCCAG  TGTGCATCAA
19751  CTCCAAAGGA  ACTTTCTCCT  TAAAACTGCC  AGCTCTCATC  ACAGATTCCA
19801  TTATGATATG  AAGTGTTAAG  CAGAGTGAGT  AGGGATTGGT  TCCAGGTAAC
19851  AGCTAGCTGA  GGGAGAAGGA  AATTCTAAGA  TATTGCAGTG  GGGAAGAGGG
19901  GTAAGTTTAT  ATCACTATTG  GATTGCTGAA  CTTACTGTTC  CCAGTATATA
19951  TATATTTCCG  TTTGTATACA  AGTTGAGCAT  GTGGTACTGG  GGCTGCAGTA
20001  TTTTCTTTCT  CATTGTACCA  ATTGTACTAG  TGTAACAGTT  TTCACCAAAA
20051  AACTTTTTAC  AGTCCTGCTG  CTTAGTTATA  TCACTGACTG  GATTGTCATT
20101  TTATTTTCCC  TTCTTGAAAA  AAATTGACTT  TGCCTATATT  TAGTAAGATT
20151  GCCAATAATG  AAACATTCAA  AATAGGGAAT  TTGATCCCAG  CACTTTGGGA
20201  GGCCAAGGTG  GGCTGATCAT  TTGAGGTCAG  GAGTTCGAGA  CCAGCCTGGC
20251  TAACATGGTG  AAACCCTGTC  TCTACTAAAA  ATACAAAAAA  ATTAGCTGGG
20301  CATGGTGGTG  CTCACCTGTA  ACCTCAGCTA  CTCAGGAGAC  TGAGGCAGGA
20351  GAATCGCTTG  AACCCTGGAG  ATGGAGGTTG  CAGTGAGCTG  AGATCACATC
20401  ACTGCACTCC  AGCCTGGGCA  ATAGAGTGAG  ACTGCATCTC  AAAACAAAAA
20451  CAAAAAACAG  CAATAACAAA  TAGGGAATTT  TAAAAGGAGA  CCAAAACCCA
20501  TGAAAAATTA  AGCCCTTGAA  TAGATGAGAT  TATAATCTTT  TTTCCTACCA
20551  GTTTAATACT  TTTAAAGAAT  TTTTAAAGAA  TGTTCAAAAG  AATTGCACAT
20601  ATTTAGAAAT  TTCAGGTATA  AATTTCTGTC  TGATTTTTTA  AAGTCTGATT
20651  TTTGAAACGT  TGAGGAAGAA  CAGTTGTGGC  AGTCAATTAG  TTTGGGTTAA
20701  GTTGTATGAA  TTTGACTCAG  GAGTTAGTAG  CAAGGGGTTT  TTGGTTTCTC
20751  TGTGTATGTG  TGGTTTCCCT  CATAATTGTT  GAGCTAAAAA  AAACTTAGCT
20801  TATAAGTCTT  AAAGGAAAGA  GTTTTGAGCA  TGGCAAACTG  ACACACTGGT
20851  TGGCGTTTGG  GTTTAGAACT  GGAAGCCTTG  AAGCAGCGTT  TCTGGAAGCA
20901  TGCTAATCCA  GCAGCCAAAC  CCAGGGCTGG  TCAGACAGTG  AATGTGAACG
20951  TCATAGTGAA  AGACATGGGC  ACTGATGGAA  AGGAAGAGCT  AAAAGCAGAT
21001  GTGGTACCTG  TGACTTTAGC  ACCTAAGAAG  TTGGATGGAG  CAAGCCACAC
21051  AAAACCAGGT  ATTTGAGCCC  ACAGGTTTTG  TTTTTGCTT   TTTGCTTTGT
21101  ATTCTAACAG  ATCTTCAAGG  CTATTGAAAA  CCTTATAATG  AAAAGTTATA
21151  GAATCTTTTT  CCTTGGAGGC  TTTGCAGAGC  AGTATCTCTG  GCATGATTCA
21201  CGTGTAGCAC  ACCTAGAGGT  GTGGGGTGGA  CAAGCTGGCT  TTATTTTTT
21251  TTTAGATATC  ATTTGTCTTA  TTATAAAAAA  CCCCATTATA  GACAAATATA
21301  TAGAATAAAT  GAAAACTTA   ATCTTCTATC  AGAGACAGGT  TCTATAACCA
21351  TATCGTGTAT  CCTTTTAAAC  TCTCTTCTTT  GCACATATGT  ATATGTAATT
21401  TAAACAAAAA  CAGGCTGGGT  GCAGTGGCAC  ATGCCTGTAA  TCCTAGCACT
```

FIGURE 7H

```
21451  TTGGAAGGAC AAGGCAGGAG GATCTGTTGA GCTCAGGAGT TGGAGACCAG
21501  CCTGGGCAAC ATAGTGAGCC CTCATCTCTA CCAAAAAAAA AAAATTATCC
21551  AGGCATGGTG GCCTGCACCT GTGGCCCCAG ATACTTGGGA GGCTGAGACA
21601  GGAGGATCAT TTGAGCCAGG AGGTTGAGGT TGTAATGAGT CATGATTGTG
21651  GCACTGCACT CCAGCCTAGG CGAGAGAGTG AGACCCTGTC TCAAAACAAA
21701  AAACCCAAAA CAAAACAACC CACCTATAAT GTGATCATAA CATGCATTCT
21751  GCTTTGTGTT TTAGAAATGT ATTAAGGACA GCTCTCACCC CTCCCTTGAA
21801  ATCACAAGTA ATATATCACA TGGAAAACAG TTTTAAACAC TGAAAAAAGG
21851  TATCAAATGA AAAACTAGTC TTCCCAAAGA TAACTATTAA CAATTTCTTG
21901  TATGTCTTTA TAGGAGTATT TTTATCCATA TACCGTATTT TGTGAATGTG
21951  TGTGACATTG AACATTTACT CCCTGTCAGG CATTGCTCTA GGTGCTTTAT
22001  ATGTTTTATC TCATTTAATC CTTACAACCC TATGAGGTAA ATAACATTAG
22051  TATCCTTATT TTGTATATGA AGAAACTGAT ATGCAGAGCA CTTAAGACAC
22101  TTGCTCAAGT TTACACAGCT AATAAATGGT AGGACCAGTA GTCTAATCCA
22151  GACCACCTAA CTCCAGAGCT CAGATCTACT TTATATTGCT TTGAGGCTT
22201  TTTTTTTTTT TTTTTTTTT CCTCTAAGAC AGAGTCCTGC ACTGTCACCC
22251  TGGCTGGAGT GCAATGGCAC GATCTTAGCT CACTGCAACC TCTACCTCCT
22301  GGGTTCAAGT GATTCTCCTG CCTCAGCCTC CCGAATAGCT GGGATTACAG
22351  GTGCCTGCCA CCATGCCTGG CTAATTTTTG TATTTTAGT AGAGATGAAG
22401  TTTCGCTATG TTGGCCAGGC TGGTCTCGAA CTCCTGACCT CGTGATCTGC
22451  CCACCTTGGC CCCGCAAAGT GCTGGGATTA CAGGCGTGAG TCACTGCGCC
22501  CGGCCTTGAG GCTTTTTTA AAATGGCTGC ATAATATTCC ATTGAATGAA
22551  TACAACATGA CTCATTAAAC CATACTCGTA TTGACAGATG TCTTGTTTGT
22601  TCCAGTTGTT GCTATTGCAT ACAGTGTTAT ATTATAGTGC CAGATATATG
22651  GTGGTATATT AGATGAAAAT TCCTTACAGT GGAATTGTCA TGATATATAT
22701  CACATTTTGA TATATATCAT CCAGTTGTCT TTCAGAATGG TTGTACCACT
22751  CTGAATCACA GTGTATGAGT TCCTGTTTCC TCTCAATAGG TATTATCAAA
22801  CCTTCTAATT TTTGCCAGGC TAACATGTCG AAAATGTATC TCGTTATTTT
22851  GATTTGTAGC TCTTCAATTA GAAGTGAGAT TAAGCATTAC TTTTAATTTA
22901  TTAACAATAT ATGTTTATTT TCGTGAACT GCCAGTTCAT ATCATTAGCT
22951  CATTTTACTC GAGTCGTTTC TCTTTTTCTT TAATATAGGT AAATTTATCA
23001  ATGTTTTTCT TCATGGCTTT TGAGCCACAG ACTTGAAGCT CTACTCCCTA
23051  CCCACCTTTT CTCTCTTTTG AACAATTATT TTATAATCCC TGAGTAGTAT
23101  ACTATCTAGG GTGCAGAAGT TCTCTTTGAT ACTTCAATTC ATAATAATAC
23151  TCTTGTGTTC AAATAACAAA AAAGCCCAGA ATACTAGAGT CTCAGATTTT
23201  CCTTTTGGGA TGTGACTAGA ATATTTCTGG AGTTGCCTAA AATGCATACC
23251  TAATTATTGT ATTATGTCTA AAGCATTTCT ACATATTTCT GTTCAGGTGA
23301  AAAGCTTCAG GTGTTAAAAG CTAAACTGCA AGAAGCAATG AAACTCCGAA
23351  GGTTTGAGGA GCGCCAGAAG CGCCAAGCAC TGTTTAAATT AGATAATGAA
23401  GATGGGTTTG AGGAAGAGGA GGAGGAAGAG GAAGAAATGA CAGATGAGTC
23451  TGAGGAAGAT GGAGAAGAGA AGGTAGAGAA AGAAGAGAAA GAGGAAGAAC
23501  TAGAGGAAGA GGAGGAGAAA GAAGAGGAGG AGGAAGAAGA AGGAAATCAG
23551  GAGGTTTCTG GCAATTACGT TGTTTTGTTA CCTTGTCATG GTGAATATGA
23601  GAGAAAAAGT CAGACTTGAA AAAGAGTATA ATAAGCATGT TCAATTGTAT
23651  AAGAGGTTTT AGGGGCATGA TGAGGGTAAC TACCTCATAT ATCCCTAAAT
23701  CTTAGGAACT TCAGTTCTGT CAGTACCACT GAATATCTGT AGATCATCAT
23751  TATATATCTG AATACAGATA TTCAGTGGTA CTGACAGAAT ACCATTGCCT
23801  GGGCTTCCAC CTGTTTATAT ATTTTAATAT AATAATGCTA ATATTAAAAA
23851  TGGCTTTGTA TTCGTAGGAA ATTTTATCTT TGTTGTTTAT TTAGGTTTCT
23901  CTAGCAGATT AAAAGCAGT CCTAACCTTG GCTAGATTGA GGCCTGGAGT
23951  AAATTCTTAG GGAGGTAGAG GCCTTTCTGA GTTATTTTCG TTCTTTGTAG
24001  AAGAAGGCAT TTGTAGAAGG GCCTCTTGCC CTTGTTCCGT AGTACTGTTT
24051  TCTGCCTAGG GAAAACAGGT GATGATACGA TTGTTAAGTA TTAAAAAACT
24101  TTCCTTTTTG GGCCGGGCAG GGTGGCTCAT GCCTGTAATC CTAGCACTTT
```

```
24151  GGAAGGCTGA GGTAGGTGGA TCACCTGAGG TCAGGAGTTT GAGAACAGCC
24201  TAGCCAACAT CGTGAAAATC CATCTCTACT AAAAATACAA AAATTAGCTG
24251  TGTGTGGTGG CACACACCTG TAATCCCAGC TACTCAGGCA GGAGAATTGC
24301  TTGAACTTGG GCAGTGAAGG TTGCAGTGAG CCAAGATTGT GCCACTATAC
24351  TCTAGCCTGA GCGACAGAGC AAGACTGCAT CTCAAAAAAA GAAAAAAAAA
24401  AAAAAACTTT CCTTTTTGTA TGCTGGGATC ACTTTATTTT ATTTTATTTT
24451  ATTTATTTAT TTAAATTTTT TTGAGATGAG GTCTCACTA TGTTGACCAG
24501  ACTGGTCTCG AACTCCTGGC CTCAAGTGAT CCTCCCATCG TTGTGGCCTC
24551  CCAAAGTGCT GGGATTACAG GCATGAGCCA CCATGCCCAG CAACTTGAGT
24601  TATTATTTAA TTTTGGGTAA AGGAGAAAGA AAGCAATGGC TGAGCTATAC
24651  AGCCTGTCTC AGTCTGTGCT TGGTTTGAGA TCAGTAGTCA GCCTGCAATC
24701  TTAGACTGAT TAATTAACCT CTTACTGCCT CAATAAAATG ATAATCCAGT
24751  CGTCCTTTAT AATCTTAGCA ATTTCGGGAG GGTAGAAGGT AAAAAAAAAA
24801  AATAGAAAAA AGTTCTAGAA GTGTCAGGGA AAATTATGTT GATAATGGTC
24851  ATATGGAACT TCCTTCAAGT TTACCTTTTT GAATTTAAGA TGTGATCTGT
24901  AACCAATCAG CCATATTTCA GGCTACCAGT GTATTTGCTT TTAAATGTTT
24951  TGACTTGTAT TTTTTGTTTT GTGGTGGCCT GATTGGTAAA GACTGCAGAA
25001  TTCCTTCTTA GTAGTGAAGA AATAGAAACA AAAGATGAAA AAGAAATGGA
25051  TAAAGAAAAT AATGATGGCA GTAGTGAAAT TGGCAAGGCA GTTGGCTTCC
25101  TCTCTGTTCC CAAGTCTCTC TCATCAGATT CTACTTTACT TCTGTTTAAG
25151  GACAGCTCTT CCAAGATGGG GTAAGTGATT CTCTCTAAGA AAACTTAAAA
25201  TTGCCTTGGA TTTGCCCCTC CTGTAAAAAC TAGGAACAGA TACTGAACCA
25251  ATTTACTTTC TTATTTTGCA GTTACTTTCC TACTGAAGAA AAATCAGAAA
25301  CAGATGAAAA CTCAGGCAAG CAGCCTAGCA AACTGGGTAA GTAGTGATTC
25351  TTGTGCAGAA CTTAACATTT CTTTTGTCCC TCAGCTTTGA TATTTAAGGA
25401  CTGCAGTACG GTAAGTTTCC ATGTTTTTAA ATCTGGTCAC TTCCCAGTTT
25451  CATATGTAGC TATGAAAAGG GTTTATGAAT TAGAATATTT TTCTTGGTCT
25501  ATTTTTTGCA GTTTATTTAT AGTAGACCAT GGTACATAAT GTCCTTAGTG
25551  AATGTGTGTT GATTGAGTGA GCAATGAAAT GTTTCTGTAT GTAGATCAAA
25601  GGAAGACGTA TAATTGATTG ACAATGAAG AGTGTGATCA TAGGCATTAG
25651  GAAGGATAAG AGAAAGAAGA GAACTTTCGG CCAGGCGCAG TGACTCACGC
25701  CTGTAATCCC AGCACTTTGG GAGGCTGAGG CAGGCGGATC ATGAGGTCAG
25751  GAGATCGAGA CCAGCCTGGC TAACATGGTG AAACCCTGTC TCTACTAAAA
25801  ATATAAAAAA TTAGCCAGGT GTGGTGGCAC GCGCCTGTAG TCCCAGCTAC
25851  TTGGGAGGGT GAGGCAGGAG AATCGCTTGA ACCTGGGAGG CGGAGGTTGC
25901  AGTGAGCCGA ATTCACGCCA CTACACTCCA GCTGGGGTGA CAGAGCGAGA
25951  CTGTCTCAAA AAAAAAAAAA AAAAAAAAAA AAGAACTTTC AAGTGTCACT
26001  TAGCTCAGAG TAATAAGCCC TGATTATATA ATGCTATCTT AGTACTGTAA
26051  TTTACCTTTA ACTAATGTT TTGGAACATA TAACTTGAGG GGTTGCCTA
26101  TGAATTTTAT CTGACAGTTT CATCCTCAAC TCTTTTTCCT AAACAAATCC
26151  ACCTTATTTC TGTAATCATG TGCTTAAAAG GTGTTTCTCT TTCTTTAGAT
26201  GAGGATGATT CATGTTCATT GCTAACAAAG GAGAGCAGCC ACAATAGCAG
26251  CTTTGAGCTG ATTGGCTCCA CGATTCCATC CTATCAGCCT TGCAACAGAC
26301  AAACAGGCCG TGGGACCAGT TTTTTCCCTA CAGCAGGAGG ATTCAGATCT
26351  CCTTCCCCTG GGCTATTTCG AGCCAGTTTG GTCAGCTCAG CTTCTAAGGT
26401  AAGATGGTAA TGGTTTTTCT AATCTCCTCC TCTCTTTGCT TCCCACATTG
26451  CTAAATAAAG TTTGTCCCAG CCAACCAACT CCCACCACGT TGGTACTGAG
26501  CTTATGTGTG TTCAGTTTAA AAAATCCACC CCCTTTGTGT ATTAAAAACA
26551  AGCTTCATCC AGTATTCTTA CTTTCTTGGA GGTATTTTTC TTTATGCTTC
26601  TCATGGCTGT GTATTGTCCC CCTCAACTAC AATTTCCTGA GAGTAGCTTA
26651  AATATTGCAA ATAGCAACTT TTGTGGTTGT CATGACAATG ACTGACATTT
26701  GTAAAATGTT TTGTTATTGT TTGTTTTTGT TTGTGTGCCA GAGTTCAGGG
26751  AAACTGTCTG AGCCTTCACT TCCCATAGAG GATTCCCAGG ATCTGTATAA
26801  CGCCTCCCCA GAGCCTAAGA CACTTTTCCT AGGAGCAGGA GACTTCCAGT
26851  TCTGTTTAGA AGATGACACT CAGAGCCAAC TGTTGGATGC AGATGGGTAG
```

FIGURE 7J

```
26901  GTAGTTTTGT GTTTCTGTGG GCGGGAATGG TGCTGGGTAC TGCTTAATTT
26951  TGTTTAAAAA TAAGTGAGCT TCTGTCACTC CATCTGTGCT TTCTCTTCTG
27001  AGAAAGAGAA GGTGTACAGA CCATTAGTAT TACATTCTAT AAGTTTGAAC
27051  AAAGTCTGTC CAGAAAATAA ACATAAATAG CTCTTGCTAA CATTCTGGTC
27101  CTTCAATTTC TGTCTTATTT GAAATGCATA GATCTTGTAT TGTAAGGTCA
27151  TCAAATTTCC CTGTATCCAT CCTGCTATGT TATTATTGTT GGGTAAGGTT
27201  GAGAATTCAC AGACTGGTGG CACATTACAG GACATAATGC CAAGCCCTGC
27251  TCTAGCATCA TCTGAAGCTA AAAGTTATCC TTTACACTTT ACCTTCTGAG
27301  TAACATTTTA TTCTTTCACA AAACTTTTCC CTCCCTCTTT AGATTAACAC
27351  AAGCCTAAAG TTTGAATCTT TTGCTTTCTG GTTTGAGATT CAGCTTTTAA
27401  CTGGTGTAGG AAATGAATTC AGAGGTTTTT CACCCCCTAC TTTGCCATTT
27451  CTCTGAGGAA TTTTTTTTA TTTTTTTTTT TGAGGCAGAG TCTTGCTCTG
27501  TCGCCCAGGC TGGAGTGCAG TGGCGCGATC TCGGCTCACT GCAAGCTCCA
27551  CCTCCTGGGT TCACGCCCTT CTCCTGCCTC AGCCTCCCGA ATAGCTGGGA
27601  CTACAGGCGC CCACCACCAC GCCCGGCTAA TTTTTTGTAT TTTTAGTAGA
27651  GACGGGGTTT CACCATGTTA GCCAGGATGG TCTTGATCTC CTGACCTCGT
27701  GATCCGCCCG CCTCGGCCTC CCGAAGTGCT GGGATTACAG GCGTGAGCTA
27751  CCGCACCCGG CCCTCTCTGA GGAATTTTTT ACACTATTCG TTGTGCTCAT
27801  TGGTTCTTAG GTTCTTAAAT GTTAGAAACC ACAGGAATCA GTACCAAGCT
27851  TTGAAGCCTC GATTGCCATT GGCCAGTATG GATGAGAATG CCATGGATGC
27901  CAACATGGAT GAGCTGTTGG ATTTGTGTAC TGGAAAGTTC ACATCTCAGG
27951  CTGAAAAACA TCTACCCAGG AAGAGTGACA AGAAAGAGAA CATGGAGGAA
28001  CTTCTGAACC TTTGTTCAGG AAAATTCACT TCTCAGGGTA AATATCCAAC
28051  CGAGAGTATC AAGCTTACCA CACCCAAGTA TCAGTGCCCT TGAAAAGAAT
28101  TCCCTGGGCG GGTGGGGTGG CTCATGCCTG TAATCCTAGA ACTTTGGGAG
28151  GCTAAGTTGG ATGGATCGCT TGAGCTCAGA AGTTTGAGAC CAGCCTGGGC
28201  AACATGGCAA ATCCCCATCT CTACGAAAAA AAAAAAAAAA ATTAGCCAGG
28251  CATGGTGGCA CGTGCCTGTG GTCCTAGCTA CTTGGGAGGC TGAGGTGGGA
28301  GGATCTCTTG AGCCTGGGAG ATGAAGGTTG CAGTGAGCTG AGATCACACC
28351  AGTGCACTCC AGCCTGGGTG GCAGAGACCC TGCATAAAAA TAGAAAAAAA
28401  GAAAGAAAGA AAAGAAGCCC CTTACCCTCA GGTGAAAAGT TCACAGAAAA
28451  CAGGGCTGTG ATGGAATCTG TGTATAAACT GAATTCACTG CTTAGTGCCC
28501  TGATATTTAG AACTCTTACT TTCTTAGAGT GGTAAAGTAT CAACTTAAGA
28551  CTACTTTAGG CCGGGCGCAG TGGCTCACGC CTGTAATCCC AGCACTTTGG
28601  GAGGCCAAGG CGGGGGATTT CCTGAGCTCA GGAGTTCGCC ACCAGCCTGG
28651  GCAGCACGGT GAAACCCCGT CTCTACTAAA ATACAAAAAA TTATCTGGGC
28701  ATGGTGGCCC GTGCCTGTAA TCGCAGCTAC TTGGGAGGCT GAGACAGGAG
28751  AACTGCTTGA ACCCCGGAGG TGGAGGTTGC AGTGAGCCGA GATTGTGCCA
28801  CTGCACTCCA GCCTGGGCAA CAGAGAGAGA CTGTCTCAAA AAAAAAGTCT
28851  TGAAAAAAAA AAAGACTGCT TTAGCTTTGC CCATATATCA TTTATGATTA
28901  ATGTATGTAC AAAGTTTAGA ACAGTGTCTG ATGTATAATA AATTTCATAT
28951  AAATGTTAAC TTACTTCCTG TTCCCTGCCC CCAATACACA CAACTGCTAG
29001  ATCGAACATA AGCTCTATGA GACCTGGGAT AGTGGTTTGT TCATTACTGT
29051  ATCCCTGGTG GCCTGGCACA TATGGCACAT AGTAAGCACT AAATAAGGAT
29101  TTGTTGAATG AATAGATGGT AGGCTCTTCT TGGCAAGCTT ACCTTAGAAC
29151  TGTATCGAGC TGGCATGACT TTAGATGGCT GGGAAAAGAG TATAAAGCTA
29201  TCATTCCTTG GTGACACATC TTTTCCTTGT TGTGATGTAG ATGCCTCCAC
29251  TCCAGCCTCA TCAGAGTTAA ATAAACAGGA GAAGGAGAGC AGCATGGGTG
29301  ATCCAATGGA AGAAGCACTT GCTCTTTGCT CAGGCTCTTT TCCCACAGAC
29351  AAGTAAGTCT CAGATTGCTG GAATTTGGG AAGGCCTGGC CTTTTGATAA
29401  AATCAAAATA ACTGATCATC TTAAGGGCTT TGCACCTTTT CTGAGAATCT
29451  TGCAGTGGAT TTGAGTCTCA TATATGCCTA GTAAGCAAAT TATAATGCTT
29501  TGGTGGAGAA CAGGGTAAAA AAGGCAAGAA TATGAAAGCT ATTTAATATC
29551  ATTAATAGAG AAATGCCAAT CAAAACCATA GTGAGACACC CATTAAGATG
```

FIGURE 7K

```
29601  ACTTTTATCA GAAAAACCCC AAGAGTGTTA GTGAGAATGT GGAGAAATTG
29651  GAAACCTTGT GTACTATTGG TGAGAATGTA AAATAGTGCA GCTGCCAGGG
29701  AAAGTATGAT GGCTCCTCAA AAATTAAAAA TAGAGGCCAG GCACGGTGGA
29751  TCATCTGAGG TCAGGAGTTC GAGACCAGCC TGACCAACAT GGTGAAACCC
29801  CGTCTCTACT AAATACAAAA AATTAGCTGG GCATGGTGGC GCATGCCTGT
29851  AATCCCAGCT ACTTGGGAGG CTGAGGCAGG AGAATTGCTT GAACCCGGGA
29901  GGCAGAGGTT GTAGTGAGCC GAGATCATGC CATTGCACTC CAACCTGGGC
29951  AACAAGAACA AAACTCCGTC TCAAAATAAA TAAATAAAAA TAGAATGACC
30001  ATATGATCCA GCAATTTCAC TTCTTAGTCT GTACCCCAAA AAAGTGAAAG
30051  CAGGACTTGA ACAGATATTT GCACCCCCAT GTTCAAAGCA GCATTATTCA
30101  CAGTAAGTAG TCAAACATG AAAGCGACCT ATGTTTATTG CAAATGAAT
30151  GGGTAAACAA AATGCGGTAT ATATGCAAAG GAATATTCAA CTTAAAATGG
30201  AAATTCTGGC TGGGCATGGT GGCTCACACG TGTAATCCCA ACACTTTGGG
30251  TGGCTGAGGT GGGCGCATCA CTTGAGCTCA GGAGTTTGAG ACCAGCCTGG
30301  ATAATATGGC AAAACCCCAT CCCTATAAAA AAAATACTAA AATTAGCTAG
30351  GCGTGTGCCG GCAGTACCAG CTATTCAGGG GGCTGAGGTG GGAGAATTGC
30401  TTGAGCCTGG GAGGTCAATG CTGCATTGAG CCATGATTGT GCCACTGCAC
30451  TCTGGGCATC AGAGCAAGAC CCTGTCTCAA AAAAAAAGAA GTTCTGACAC
30501  TTGCTACAAC ATGGATGAAC CTTAGAATGT TATGCTAAAA GAAATAAGCC
30551  AGTCACCAAA AGACAAATAC TGTATGAGTC CACTTACATG AGATACTTAG
30601  AGTAGTCAAA TGCATAGAGA CAGAAGGTAG AATGGTGGTT GCCAGAGACT
30651  GAGGTTATAA GGAAATGGAG AGTGTAATGG GTATAGAGTT TTAGTTTTGC
30701  AAGCTGAAAA GAGTTCTGGA GATTGCTTAA CAATATGAAT GTACTTAACA
30751  CTACAGAACT ATAGAAAGAT CGTTAAAAAG GCAAATTTTA TATTATGTGT
30801  ATTTTACCAC AATTGAAAAT TTAAAAAATT TTCTTCCTGT TTATTGAAGA
30851  GATTATTGGT GATAATAAAA GTTTTAAATT TGGCTGGGCG AGGTGGCTCA
30901  TACCTATAAT CCCAGTACTT TGGGAGCCCA AGGCAAGCAG ATTGCTTGAA
30951  TCCAGAAATT CAAGATGAAC CTGGGCAACA TGGTGAAATC TGTCTCTACA
31001  AAAATACAAA AATTAGCTGA ACATGGTGGC TTGTATCTCT AGTCCCAGCT
31051  ACTCAGGAGG CTGATGTGGG AGGATCACTT GAGCCCTGGA GGTGGAGGTT
31101  ACAGTGAGCT GAGATGGTGC CACTGTATTC CAGGTGGTGT AAGAGACCAA
31151  GACTGTCTCA GAGAAAAAAA AAAATTAAC ACACACAAAA TTTTTTTTAA
31201  TTCATAACTT GGCTGACTAC TTGTAGTTTG CTTTCAACAA CTTATTTATT
31251  GATTCATTGA TTTACATTTT AGGGAAGAGG AAGACGAGGA GGAGGAATTT
31301  GGAGACTTTC GGCTTGTTTC AAATGATAAT GAGTTTGATA GTGATGAGGT
31351  GAGTATGAAG GGAACAAAGT AATCATAACT GAGCTCCATG TATTGCTGCC
31401  CTCAAGTGTT TTTTTCCCCT CAGTTCTTGA GAATTCTAAG TTTGGCATCT
31451  TATCAGAAAC AATTTCCTAG AATGAGGTAT TGGGCAGAT GTTTATAAAT
31501  CCTTTTTTCA TTGAGGACGC ATTTTATTCT GCTTAATTTG GATATGATGC
31551  TGATTTGTA GGATGAACAC AGTGACTCTG GTAATGATCT GGCACTGGAA
31601  GACCATGAAG ATGATGATGA AGAAGAACTC CTGAAGCGAT CTGAGAAGTT
31651  GAAAAGGCAA ATGTACGTGT TATTAATATG TCCATTCCTT CAGGTGTATT
31701  TAAAATTTGG TCACTAGGCC AGGCATGGTG GCTTGCGCCT GTAATCCCAT
31751  CATTTTGGGA GGCTGAAGCA GGCGGATCAC CTGAGGTCAG GAGTTCAAGA
31801  CCAGCCTGGT CTTGGTGACA CAGGTCAAGA GATCGAGACC ATCCTGACAA
31851  ACATGGTGAA ACCCTGTCTC TACTAAAAAA TATAAAATT AGCCAGATGT
31901  GATGACAGGT GCCTGTAGTC CCAGCTACTC AGGAAGCTGA GGCAGGGAGA
31951  ATCGCTTGCA CCCAGGAGGT GGAGGTTGCA GTGAGCCGAG ATCGCACCAC
32001  TGCATTTCAG CCTGGGTGAC AGAGCGAGAC TCTGTCTCAA AAAAAAAAA
32051  AAAAAAAAG TTGATCACTT AATATGTCCT GTGTGCTAAT AACTGTGCTT
32101  TACAGGCATT AACATATTAT CTTATGCCAG GCACAGTGGC TCACGCCTGT
32151  AATCCCAGCA CTTTGGGAGG CCAAGGCAGG CATATTACTT GAGGTCAGGA
32201  GTTTGAGACC AGCGTGACCA ACATGGTGAA ACCCTCTCTA CTAAAAATAC
32251  AAAATACAAA ATAAAATACA AAAATTAGCC AGGCATGGTT CTGGGCGCCT
```

FIGURE 7L

```
32301  GTAGTGCCAG CTACTTGGGA GGCTGAGGCA GGAGAATTGC TTGAATATGG
32351  GAGGCGGAGG TTGCAGTGAG CCAAGATTGC CCCACTGCAC TCCAGCCTGG
32401  GTGATAGAGC AAGACTCCAT CTCAAAAAAA TTATCTTATG AGTGGGTACT
32451  ATTATTCTCC TCATTTTACA GTTGAAGGAA CTGAGCCTCA GAAAGATTAA
32501  ATTTACCCAA GATCACATAG CTAGAAGGCA GCAGAGGCTG GATTCAACTT
32551  AGATTAGGTG AAATCTCCCC TAACAGTCAG TTAATAGTTT GCCACTTTTT
32601  AACTTAAATC CTCCTGCCTC AGCTTCCCAA GTAGCTGGGA CAACAGGCAT
32651  GTGCCACCAC ACCTGGCTAA TTCTTTCTAT TTTTGTAGA GATGGGGCCT
32701  TGCTTTGTTC CCAGGCTGGT CTTAAACTGT TGGCCTCAAG TGATCCTCCT
32751  GCCTCTGCTT CCCAAAGTCT GGGATTACAG GCATGAGCCA CCAGGCCCAG
32801  CTTTTTTTTT TTTTTTTTTT TTTTTTTTTG AGACGGAGTC TCGCTCTGTC
32851  GCCCAGGCTG GAGGGCAGTG GCATGATCTC GGCTCACTGC AACCTCCGCC
32901  TCCCGGGTTC AAAGCGATTC TCCTGCTTCA GCCTCCTGAG TAGCTGGGAA
32951  TATAGGCACG TGCCACCACA CCCAGCTAAT TTTTGTATAT TTAGTAGAGA
33001  CGGGGTTTCA CCATGTTGGT CAGGATGGTC TCGATCTCTT GACCTCACGA
33051  TCCACCCGCC TTGGCCTTCC AACATGCTGG GATTACAGGC GTGAGCCACC
33101  CCACCTGGCC GGCCCAACTC ATTTTTTTGA TATGCTGTTC TGGTCATGAA
33151  AGTAAAATAT TTATTTTAGG ATATTTAAAA GAATACAAAC TGGGTGCAGT
33201  GGCCCACGCC TATAATCTCA GCACTTTGGG AAGCTGAGGC GGGTGGATCA
33251  CCTGAGGTCA GGAGTTCGAG ACCAGCCTGG CCAACATGGC GAGACCCCGT
33301  CTCTACTAAA AATACAAAAT TAGCCAAGCG TGATGGCCAG TGCCTGTAAT
33351  CCCAGCTACT CAGGAGGCAA AGCTGGAGAA TCGCTTGAAC CGGGAGGTGG
33401  AGGGTGCAGT GAGCTGAGAT TGTGCCATTG CATTCCAGCC TGGGCGACGA
33451  GAGAAACTCC ATTCTCCCCG ACCCCGCAA AAAAGAATA CAGAAAGATA
33501  TAAATAAAAA CTTATCCATG TCCACCATCC AGGATATAAA TGAAAGTTAG
33551  TTTGTTCCCC TTAATCTTTT TTATGCATAT ATTTTTATAT AGTTGAGATT
33601  TGTACAATCT TTCTATATGT ATAATTTTGC ATCTTTTTTT TTCTACTTAG
33651  CATATCCAGA AACATTTTCC TATGATGTTA AAAAAGTTT TATAAAGATA
33701  ATTCTAATAG GTATTTAATA TTATATTGTA TGTGAATGAT TTGGAATTCA
33751  CATATAGGAC ATCATATTGA TCCCTATTAG ATTTATATGG TTGCTTTTAT
33801  CCCATCATTT CATTCTATTA AGATTCACTT TGGGTTCTAA TTTATCACCT
33851  ATCAAATTAA CTCTCATACA GCTTAGGTT ATCCATAGAT TTTTCTAAGG
33901  TAGTGGTTCT TCTCTGCAGA GCTCTTTGTT CAAATAAAAT CTTTTAAAGA
33951  ATGACAGATA AAGTTGAAC TGTTCAAAGA TGGTAAGTGG GAAGTTTGGG
34001  AAACTTAGTG ACTAGTGGCC TCTGAAGGAA TTTTCCAGGA ACTCTAGGAT
34051  TTAGAACAAC TTAGCTTTAA GAAAATACAG TATAGGCTGG GCGTGGTGGC
34101  TCATGCCTGT AATCCCAGCA CTTTGGGAGG CTGAGATGGA CAGATCCCCT
34151  GAGGTCAGGA GTTCAAGACC ACCCTGGCCA ACATGGTGAA ACCCTATCTC
34201  TACTAAAAAA ACAAAATTA GCCAGGCATG GTGGCACGCA CCTGTAATCC
34251  CAGCTACTCG GGAGGTTGAG GCATGAGAAT CACTTGAACC CAGGAGGTGG
34301  AGGTTGCAGT GAGCCGAGAT GGCATCTCTG CACTCCAGCC TAGGCGACAG
34351  AGCGACACTT CATCTCAAAA AAAAAAAAA AGAGAAAATA CAGTATAGGT
34401  CTTCGATAAA AATCAGTTTT CAGAAAGCCA CCAAACTTCT GCCATTTTGG
34451  ACCACATGGG ACCAAGGTGA CTTTGAATCC AGGGTGACAC CAGATTTATT
34501  CTCCGGGGGA GCTGAAGTCA TAAGAAGTAA CTAGTCGTTT TGATTACCAG
34551  GAGCTCTGAG CCTTAGTCTT CCTTCTGATG TGGGGGTCAA GATTTGTTAG
34601  GCTGTAAGAA GATCCCAGTT TATTACCTTT CTACACCACA CCATCTCTAG
34651  TTTGTCTCTT AAAGCTGGTG TGCTCAAATG CAAAATGAAA TAGTTTGAAC
34701  CTTCCAGCAG GTATTCTAAT ACATGTAAAA GAGATTAAGA GTTTTCTGGC
34751  TTTCAAATCA CCCAATCTAA GTTGAATCCA GGCTCTGCTA CCTTCTAGCT
34801  ATGTGACCTT GGGTAAATGT AATCTTTCTG AGGCTCAATT CCCTCAACTG
34851  TAAAATGAAG AGAATAATAG TACCCATTCC TATGATAATA TGTTAATGCC
34901  TGTAAAGCAC AGTTATTAGC ACACAAGACA TATTAAGTGA TCAACTTTTA
34951  AATACAGATG CTCCACATCT TACAATGGGA CTATATCCTG ATCAATCCAT
```

FIGURE 7M

```
35001  CATAAGTTGA AAATGCACTT TCATATTATC CAGATATAAC TCCATCGTAA
35051  ATCGAGAAGC ATACTAAGTG CGTATCACAT TCATGTCATC GTAAAGTTGA
35101  AAAATCATTA AGTCAAACCA TCATAAGTGG AGACTATTAC AAAAAAATTT
35151  AAATATTATC AAATGTATTA TGTTTATTAT TATTAGAAGT GACTCTGTTC
35201  TGCTTTTCTT TGCTTCCATA TTCTGTGAGT ATATTCATTG TTGCATTTTC
35251  TAATCCTCAA AATTGCTTTC TAGGAGGTTG AGGAAATACC TGGAGGATGA
35301  GGCAGAGGTG TCAGGAAGTG ATGTGGGAAG CGAAGATGAG TATGATGGGG
35351  AAGAAATTGA TGAATATGAA GAGGACGTAA TTGATGAAGT ACTTCCTTCT
35401  GATGAGGAAC TGCAGAGTCA AATCAAGAAA ATACACATGT CAGTATCCCA
35451  ATAAGCCCTT CTGAGTAATA GGGTACATCT TAAGACAAGC CCTGTAACCA
35501  GCCAGAATGG TCCTTGTTTT GAACACCTTA TTTCTCCTGT TGCAGGAAAA
35551  CTATGTTGGA TGATGATAAG CGACAGCTAC GTTTATACCA AGAGAGGTAC
35601  CTTGCTGATG GGATCTGCA CAGCGATGGT CCTGGGCGAA TGAGGAAGTT
35651  TCGATGGAAA AACATAGGTA TCTTGGTTGT TGTCTTTAAA AGCAATCAGT
35701  TACGGGCTGA GCATGGTGGC TCACGCCTGT AATCCCAACA CTTTGGGAGG
35751  CAGAGGCAGG TGGATCACAA GGTCAGGAGT TCAGGACCAG CCTGAACAAC
35801  ATGGTGAAAC CCCGTCCCTA CTAAAAGTTC AAAAATTAGC AGGCTGTGAT
35851  GGCACGCGCC TGTAATCCCA GCTACTCAGG AGGCTGAGGC AGGAGAATTG
35901  CGTGAACCCG GGAGACGGAG GTTGCAGTGA GCAGAGATCA TGCCATTGCA
35951  CTCCAGCCTG GGCGACAGAG CGAGACTCCA TCTCAAAAAA AAAAAAAAA
36001  AAGCAAACAG TTACAATGCA TATTTGTCGA GTTTCAGATG GCAAATGGCA
36051  AGCAAAACTA TAACAGGCTA TGTGAAGACC TAGTTGTAAC TGTTTTCTGT
36101  TAATGGATGG GAAAAGTTTA CATCATTATA TAGTAAATGA TAAGGGTTTA
36151  TTTTTTGTCT GTCCAAGCAC CCTCTCCTGT GAGGACTGCC GAATGCTGAT
36201  TACCTTCACT CTTTGTTTAG ATGATGCTTC CCAGATGGAC TTGTTCCACA
36251  GAGACTCTGA TGATGATCAG ACTGAAGAAC AGCTTGATGA GTCAGAAGCC
36301  AGGTGGAGGA AGGAGCGAAT TGAACGAGAG CAGTGGCTTC GGGACATGGT
36351  AGGAGTTCAC CTACTCTGAC CCTAGTTTAT GAGACTGTCC CTTAGCTTGT
36401  CATGATAGTT TCAAAATCTT AGCTTGTCAT GATAGTTTCA AAATCTTAGG
36451  CAACATATTG CTATCTCTTT TAATCCTTGA GCTATCTTTT GTGTTTTGAG
36501  AAGGCTATAC CATAGACAGT TCTCTTCATG TTTGTCTAAG ATTAATTTTT
36551  TTTTGTCTAA GCAGCAAAG GCTGCAAAAA GGAAAACAAA TACCCCAGGA
36601  ACTCTAGTTT CACAATCCAG GCCATGCTAA CTATTTAGGA AGGTTATAGA
36651  CTTTTAATGC TGTATATATA TATATATATA TATATATATT TTTTTTTTTT
36701  TTCAGGCACA GCAGGGAAA ATTACAGCTG AAGAAGAAGA AGAAATTGGG
36751  GAGGACAGTC AGTTTATGAT ACTGGCCAAG AAAGTTACAG CCAAAGCACT
36801  GCAGAAGAAT GGTGAGCTCT TGTTTCTCCT TAGGGTCTAG CCCCCTGGAT
36851  TGTTAGTGGT AGAGCTTGG AGGTGACTCT AACCTTCAGG AGCTGTTGCA
36901  GCTTAATCAT AAGCTTGTGT CTAATACTGT CTTAAAGAGG CTTCACAGAG
36951  GTGGTGGGAG ACAGTGTACT TAGATCTTAG ACTATTGGGC AGTAGAGACT
37001  GTATTCATGA GTATATGTGG CTGGTTTTAC TTTATGTTCT AAGGCTCAGA
37051  GTAGTTAATT CTGGCTTTCT CTAGTTGCCC AGGATTGTAT ACCTAAGTGT
37101  TAGAGGTAGG ATTTGAATCC AGGAATATTT AACTCCAGAA ATGAAGCTCT
37151  TCACTATTCC CTACACTGAC CACTTCTGTT TTTCTTAAAT GATTACTGTT
37201  CAACTTAGTT GTGTCTCTTC TTGGAGCCAA TTATTATAGT TTGAAAGTCA
37251  CCATTATATA GAACAGAGTT CCCATGGCTT TAGCATATTG ATTTAGTTAC
37301  AAGATTTCTT AGCTTGTTTA GATTTAAAAG TAATTCTAAT CAGCTTTTCC
37351  CAGAATAGGC CTCTCTGTCT TTTCTTTCCA GCCAGTCGCC CTATGGTTAT
37401  TCAGGAATCA AAGTCTTTGC TCAGAAATCC TTTTGAAGCC ATCAGACCAG
37451  GAAGTGCTCA ACAGGTTGGT TGGGAACCTT GTTAATCTGA CATCATAGTC
37501  TACAGGTTAT AAAGGCCCAG GTCCAGCTTA GAGAATAGTC TCTGTCATTA
37551  GAGGAAGGAG GTGGCTGCAG GGAAAAAGTT AATGTCAAAG GAGTCTGCTA
37601  TTTCTTTTCT ATTTGAATAG GGTAGGCATA TGTACCCTCA ATATCTAGGG
37651  GGAAGCAGGG AGGGAAGGAC TTTTCATTCT TTAGTTGGCA CTTGGGATTT
```

FIGURE 7N

```
37701  GATACCAGAT GACTCTTCTT TCCTCAGGTG AAGACAGGCT CACTGCTAAA
37751  CCAGCCCAAA GCTGTGCTTC AGAAACTGGC TGCTCTCTCT GACCATAACC
37801  CCAGTGCTCC TCGAAATTCA AGAAACTTTG TCTTTCATAC ACTTTCTCCT
37851  GTCAAGGCTG AGGCGGCAAA GGAATCGTCT AAGTCTCAGG TATGGAATTT
37901  GAGAACTAAT ATGGTGGCTT CCCAAACCAG AATTTATTCA TTTATTTAAA
37951  TTTAAAAACA AAAATTCTGG CTTAACCTCT ATGCTGCAAT GTTGAAATCT
38001  TGCACTCCCC GATAAGGTAC AAGAGAATTG CTACCCCAGT CGGTAATCAA
38051  CTTTTAAACT TGCCGAGAAA GTTTATCTTT CTTTCTTTTT TTCTGTTGTT
38101  AATCATCCAC AATTTATGAG TTGCTTGAGA GCTAATTGAA GGTAAATACT
38151  TGTATGAAGG TCTTTAGCTG GCCCTGACTC CCTCTCTGCT CTCTAGGTAA
38201  AGAAAGGGG TCCATCTTTC ATGACTTCTC CTTCACCTAA GCACCTCAAA
38251  ACAGATGATA GCACTTCAGG ATTGACGCGA AGCATCTTCA AATATTTGGA
38301  GAGCTAACAC CATCAAAGGT GCCAAAATCT ACATTGAGAC TGCTTTGAGA
38351  AGTTTCTAGC ACTGAAAGTT GGAATTGACA CTCCAGCCAA TGATCCTTCC
38401  TTCTTTCATA ATCAATGCAA TAAGATTGCA GACAGAAATT CCAGTGATTT
38451  CTACTGCACA GCTCTGGACA TCTCTTTTCC TAGTATTATT CCCTGAATTG
38501  GCCACTGATT TCAATTCTGC AGTATTTACA ACATCAACAA CTCATGGAAT
38551  ACTTGGGTGA GGTTTCCTTT TTTTTTTTTT TTTTAAGATG GGAGTCTCAC
38601  TCTGTTGCCC AGCTTGGAGT GCAGTGGCGT GATCTCGGCT CACCACAATC
38651  TCTGCCTCCC AGGTTCAAGC GATTCTCCTC CTTCAGCCTC CCGAGTAGCT
38701  GGGATTACAG GCATGTGCCA ATACGCCCAG CTAATTTTTG TATTTTTAGT
38751  AGAGACGGGG TTTCACCATG TTGGCCAGGC TGGTCTTGAA CTCCTGACCT
38801  CAAATGATCC ATCCACCTCG GCCCCACAAA GTGCTGGTCA CATGCATGAG
38851  TCACTGCACC TGGCCTTGGG TTAGGTTTCA CTTCCTCCAT TAGACATTTG
38901  ACATTTTATT GTAGCAGCTT TCTGGGTTAA TATCTCTTTG TGATTGATAG
38951  AAGTGGTTGG AAGAGGAAGA GTAGGGAAAA GTGTGACATT ACAGATTAAA
39001  CAGTGAAAAT CAGTACCATA ATGACTCCTT TACACCCATG AGATACGTAC
39051  CATGATGACC AGGGCTCGGT GAAAGAAAGA TTTCTTTTTT TTTTTTTGAG
39101  ATAGTCTCAC TTTGTTGCCC AGTCTGGAGT GCAGTGGCGC AATCTCGGCT
39151  CACGGCAACC TCTGCCTCCC GGGTTCAAGT GATTCTCCTG TCTCAGCCTC
39201  CCAAGTAGCT GGGACTACAG GTGCATGCCA CCACACCTGG CTAATTTTTG
39251  TATTTTTAGT GGAGACAGGG AGTCACCATG TTGGCCAGGC TGGTCTCGAT
39301  CTCCTGACCT CAAGTGATCC AGCTGCCTCA GCCTCCCAAA GTGCTGAGAT
39351  TACAGGCGTG AGCCACTGTG CCCAGCCAAA AGAACGATTT CTTAGATGGA
39401  GGACCTAGGA ACCAACAGAT GGGCTGCTGT ATTACTCTTA CCCCTTTCAT
39451  TTTCCTGTAT GCTTCTTCCC AAGGCAGCAT CAAATTTTGA ATTAATTTTT
39501  GCTGCTTAAT AAGGACTTAA ACTGGTACCC AAGTCAGAAA GACTCTGCCT
39551  CTAATTTTCT GGGGCTTGGG GATGAAGATA AAGTGTTACA CCCAGTGTTT
39601  GTCCACCACA GTCTGTGGGG CAGAGAGACC CTTCCTGGGA CTGAATTCTC
39651  AATTTGAAGC ACTGTTGTTC AAAGATCTCC CTTCTGGGTC TGACAAGAAG
39701  AAACATAACC CTTATTTATT GCATTCTTCT GGCTTACATA CATTGCCCTC
39751  ACTAATCAAT GGACATTTCA GCATTTCATT ACTAATTTTG AGAGAAGGCC
39801  ACCATGGAAT TTAATAAAAA TATTATTGAA GAGAATTGCC ATCATTCTCC
39851  ATTTTCCCTG AACTACCACA AGCTTCTCAG AATTTTAGAC AAATGTTTTT
39901  CCCCTCAGAA CTGAGCATCA GTGCTGCTTT GGAAAAACAT TCCATGTGAA
39951  TACTGTGGTT TCAGTGTCAG GACCTGTACT TGGGCAGTTG GAAGAGAGTG
40001  TGCCAGTTTT TTACTGGGAG ATGGGAACAC CAATTTAATT GATGCAATTA
40051  GGTTGTAGGT TTTTTACAGT TTTTCTTTTC TTTTCTTTTT CTTTTTCTTT
40101  TCTTTTCTTT TCTTTTTTTT TTTTGAGAC ATAGGCTGGC TCTGTCACCT
40151  AGGCTGGAAT ACAATGGCAT GATCTCGGCT TACTGCAACC TCCGCCTCCT
40201  AGGTTCAAGC AATTCTGCCT CGGCCTCCCA AATAGCAGGG ATTACAGGCA
40251  CCTGCCACCA CTCCCAGCTA ATTTTTTGTA TTTTTATTAG AGATGAGGTT
40301  TCGCCATGTT GGCCAGGCTG GTCTTGAACT CCTGACCTGA GGTGATCCAC
40351  CCGTCTCGGC CTCCCAAAGT GCTGGGATTA TAGGCATGAG CCACCGCACC
```

FIGURE 70

```
40401  CGGCCGGTTT TCTACAGTTT TCTAATACTC AAGATGTTGA CTTTGACAAT
40451  ACTTATGTTT GTATACTTGT AATCTTATAA TGGGGAAAAT GTGTATAAAG
40501  ATGTTTTAAT ATGTATGTAG TTTTTCAATA AATCTTAATG CCTTGAAGGG
40551  AAGATTTGCT GTCCAGCTTG AATGCTCATT CTTGGGTCAG TGCCTGTCTA
40601  ACCTTGAGGA GCATTTCATT TTCAGGTTAT CTCCATCCCA GGGAAACCCT
40651  CTGGGTCTAA ACTGAGAAGC TGCTGCAATT GTCCCCTCAC TGGCTTCTCA
40701  GTCCTAGTGA ATTGATCAAG TTAACTTACC AAGTGGTTTG GGTTCAGCTC
40751  AGGTGAAGAG GATAATTGAG TTTACATAAA TGGTACCTTC TATTATAGCT
40801  CTTTGTTTAA AAAACTTATT TTTTAGAGAC AGTCTCATTC TGTTGCCCAG
40851  GTTAGAGTGC AGTGGCACAA TCATAGCTCA CTGTACCCTT GAACTCCTGG
40901  GCTTCAGCAT CCTCCTTCCT CAACCTTTGG AATAGCTGGG CCACATTACA
40951  GGCATATGCC ACCATGCCCA GCTAATTATT TTATTTTAGT AGAGACAGGG
41001  TCTTGCTGTG TTGCCCCAGC TGATCTTGAA CTCCTGGCCT CAAGTAATCC
41051  TCCCACCTTG GCCTCCCAAA ATGCTGGGGT CACAGGCTCA GCCACCATGC
41101  CCAGCCTGTT ACAGCTTTGA TTGGCCTTTC TCTTTAGCTA AGTTTGTATG
41151  TACTTCATTT TATCCATGGG TTCAAGATAC ATGTTTTTGC CTCTTTCTTT
41201  GAACTCTCTA AACAGTTCCC AAGGCAAAGT AGCCCTTGCT GGGCAAAAGA
41251  GAACTGAGCA GGAAGGCTAG ATATTTCTTC CCTCTTGTTT CCCTACATGT
41301  CTTTTGAGGA GAGATAGAAA AGACAATTGG AATTGACAAC TGAGGATAAG
41351  AAAATTCAGC CAGGTCCGGT GGCTCACGCC AGCACTTTAG GAGACTGAGG
41401  TGGGTGCATT GCTTGAACTC AGGAGTTCGA GACCAGCCTG GGAAACATGG
41451  TGAAATCCCA ACTCTAAAAA AAAAAAAAAA AAGAAAAAAA AAAGAAAATT
41501  AGTGCCTGAG AAATCCAGGG AGAAAATGGT TTCTGGGCTG GGCGTGGTGG
41551  CTTATGCCTG TAATCTCAGC ACTTTGGGAG GCTGAGGCAG CTGGATCACC
41601  TAAGGTCAGG AGTTGGAGAC CAGACTGACC AACAAGGTGA AACCCCGTCT
41651  CTACTAAAAA TACAAAAATC AGCCAGGCTT GGTGGTGGCA GGTGCCTGTA
41701  GTCCCAGCTA CTTGGGAGGC TGAGACAAGA GAATTGCTTG AACCTGGGAG
41751  GCAGAGGTTG CAGTGAGCCG AGATCACGCC ACTGCTCTCC AGCATGGGCG
41801  ACAGAGTGAG ACTCCCTCTC AAAAAAAAAA AGAAAGAAAG AAAATGGTTT
41851  CTGATTGAGG CTCCTGGGAG AAAGCACTCT TTGGAGAAAG AAAACTTGAG
41901  TCAAACTCTG GGTTACTTTT CCTTATGCCA GGATGGCTGC TATAAAGTAA
41951  GCTAAGCCTT GATCTTGGTA ACAGGATTGA CATGGACAGT TTCAATCTGA
42001  CCCATATGCC CTTTGCCCAA AGCACTGAGC CAGCAGCATC AGTTATGTTT
42051  TAATGAAATT GAAGCCCCAG GACCTGCCAC TATGGCTCTG AGGAGGACTC
42101  AGCTTACTA GCTTGGAAAT TACATATTTG GAGGGATGAG AGCCCATGAG
42151  TGTGGGAGAT AGGGTAGGCT CAGTGTCAGT GTTTTGTTT CTTCCTTGTT
42201  CCATACACTT GAGTAGGGAT ACATGGTATT AACCTCTTTA AACAGGTCTC
42251  TAATTTCATC TCATTAATTC ACAGTTGCAC AGCCATACTA GGGTCTCTTC
42301  CATAAACCAT AAGATTTTAT TCACCAAAGC TCTAGAGACA AGGTACTCAG
42351  ATCTCTGTGG CATCCCTCAT TTTCTCAACT GCTTCTCTAC AAACTTCTCC
42401  TCACTTTGAG AGTTTCTAAT GCTCAGGCTG GGAGACTTTT TAGGGGGTGT
42451  TTTTGGTTTT TATCTCCTAG GGTTATGTCT AATCACTCTT GTGGCATCCT
42501  GTCCTGGGAT TTGTGCTCCT AAGGATAGAG GAGAGTATTT CTGGGAGGAG
42551  TGTTCCCATG ATACTATTTG ATTATGTCAT CCTTGAGATG GTATTGTATC
42601  TTCTACCCTT ATATCCTACT CATCGCCTGG CACACAGCTT GGAATGTAGT
42651  GGTGCCTACC ACAGTTTGAA TAAATAACAC TACACCTTTC AGAGCCTCTG
42701  TTTATAAAAT GAGGATACTA AGTCATGGCT GTCTCAGAGT TGCTGGGGGG
42751  CTTCAGTTGG AAAATGTATG TCAGTGCATT ATGTCAAGTG CCACTCTGTA
42801  AGCATAAGAA ATTGCCAGTA GCTCCCAGAA AAAAGAAATT CACCTCCTTT
42851  GAGAATGAAA GAAATTACCA GTATCACAAT TATATCATAT ATTGTAGGCC
42901  ACTTCTGAAA GGCCCATTGT TTCTCAAATA TCTCAAACTT AAAATGAAAA
42951  TGTGATCTTC TCTAAAAACC TGCTCTTCCT CCTGTATTTG CCATTTCAGT
43001  AAAAGGTACC TCCATATATC CAGTCACTCA GACTGGAAAT CTGGAGAGCA
43051  TTCTTGACCT GTTCTTTAAT CCTGTAATCA GACAATTTCC AAGTTCTGTT
```

FIGURE 7P

```
43101  ATTTCTACTT CCAAATTGCA TCTGGAATCA GCTCATTTCT TCCAGCTCTA
43151  TGGCCAGCCC CCTGGTCCAA GATTCCACAA TTTCTTTCTA GGGTCCTACC
43201  GTAGCCTCCT GACCCCCCCA CTTCTGTTTT TGCTTCCTTT TCATCCAATC
43251  TGCACAGCAG CCAGAGGCGA CCTTTATGTA AATATAATTT GGAGGATGAC
43301  ACTTCACTAC TTAAAATCTT TTAATGTCTT CCGCTGCACT CAAAGTTCAA
43351  ACTTCTCATG GCCGATGCAT GACATAGCTC TGCCTCCCAA CCTGCTGTCT
43401  ACTCTTCTTT CTCATGACAT GCAGCCTCAG GAGCATCTAA AGTGTCCTCT
43451  TTCCCTGGAA TGCCCTCCCC TACATCCATC CTCCTTCTTT GTCTGACTAA
43501  TGCATAATTC TCAAGGTGTT AGCTTAAGCC TAATTCCTC AGAGAAGCCT
43551  TCTCTGACCA TTAACACCCC TTTCTTTTTT CTTTCTTTCT TTTTTTTTT
43601  TTTGAGACAG AGTCTCGCCC TGTCGCCCAG GCTGGAATGC AGTGGTACGA
43651  TCTCGGCTCA CTGCAACCTC TGCCTCCCGG GTTCAGGCGA TTCTCCTGCC
43701  CCAGCCTCCC AAGTAGCTGG GATTACAGGC ATGCGCCACT ACACCCAGCT
43751  AATTTTTGTA TTTTCAGTAG AGACGGGGTT TCACTATGTT GGTCAGGCTG
43801  GTCTCGAACT CTTGACCTCG TGATCCGCCC GCCTTGGCCT CCCACAGTGC
43851  TGGGATTACA GGCATGAGCC ACCAAGTCCA GCCTAACACC CCTTTCTTAA
43901  TTAGGTTACC TTTGTATAAG TTTCCTATTC TTTTTTTTTG AGATGGATTC
43951  TCGCTCTGTC GCCCCGGCTG GAGTGAGTGC AGTAGCACGA TCTCAGCTCA
44001  CTGCAACCTT TGTCTCCCCC GTTCAAGCAA TTCTGCCTCA GCCTCCCAAG
44051  GGGCTGGGGT TACAGGCACG CACCACCACA CCCGGCTAAT TTTTGTATTT
44101  TTGATAGAGA CGGGGAAGGT GTTAGCTTAA GCCTAACTTC TTCAGAGAAG
44151  CCTTCTCTGA CCATTACCAC TCCTTTCTTA ATTAGGTTAC CTCTGTTTGA
44201  GTTTCTTGTT CTTTTTTTTT TTTTTTTTTT TTTTAATAT GGATTCTTAC
44251  TCTGTCACCC AGGCTGGAGT GCAGTGACGT GATCTTGGCT CACTGCAACC
44301  TCGGCCTCCC GGGCAATCAA TTCTCCTGCC TCAGCCTCCC AAGTAGCTGG
44351  GGTTACAGGT GTGCACCACC ACATCTGGCT AATTTTTGTG TTTTTAGTGC
44401  CCAGCTAATT TTTGTATTTT TAGTAGAGAC GGGGTTTCAC CATGTTGGCC
44451  AGGCTGATCT CGAACTCCTG ACCTCAAGTG ATCCAGCTAC CTCAGGCTCC
44501  CAAAGTGCTG GGATTATAGG CATGAGCCAC CACACCCAGC CTTAGGTTTC
44551  CCATTCTTTT GGGTCTGTCA TCATGATGTG TTACTTTAAT GTTCGTTGAG
44601  GCTTGCTTTC CCTACTAGAC TGTAAGTGCT GTGAAAACAG AGCATATCCG
44651  TTTTGTTGAA AAATGTATGC TTTGGGTAGC ACCATGCCTG GCACATAAAA
44701  TAATTCAATG AATTTTTTGA GCAATGAGTG ATGGGAGGCC TGGAAGAGCT
44751  AATGGTGAAA AGCATAGAGC TGAATTATAT ACAGAGGAGC TTTCTAGTGC
44801  AGGACAGAAT AGAGGTGTAG AGCTTAGTC CTTGCTCTTT CTGCAGCTTG
44851  TAAGCATCAT GACTTTGGGT AAGTCAGTCT CTTTTTTCCT CAACTGGAAA
44901  ATGGGGCTCA TGTGAAATGA CTTGGTTTAG CTCACAGGGT ATGGTTAGGA
44951  TCAAAGGTAC AAATTAATGT GAAGTGAATG TACATATTTA AGAGGCTGCA
45001  CTAATGCAGG CTAACTCACT GCTGAGGAAT GGGTAGAGCT GAGTGGGAAG
45051  GAGAAGCCAA GCCCAACAA AGCTCCATAG TCCACCATTG GTGGCTAGCT
45101  ATGTGCTGAG ACTTGTTATA GCAGTAGAAA TGGAGGCCTG TGTGTATGCC
45151  TGGACTCCAG TGAACTGGGG AGATAGACGT GGCTTGTGTA TGGCTGGTGT
45201  CACCTCAGAT TTTACCTTTT GAGACCAAGG TGCCTGGTTT CTGTCCCCAG
45251  TAGTTTTATT GTCTTGGTCT GTACCATCCA CGTCCTTCCC ATCCCCTCTT
45301  TTTGTCCTCT CTCCTCTCAC CTTAAAGGTT TTTCATTTC AGTTTATTGA
45351  TTTAGTTCTA CCCTGTGGTG GGATTCATAA TGGGAAAAGG GAGTTTGAAG
45401  TAGCTACAGC CTAAGGGTGA TTGGAAGGAG TTGGGGTGGA CACCTGAGTT
45451  CCTTCCCTTC ATTTTAGAGA GAACCGTAGT CCGCGGAATT CTTGATGGCT
45501  GGTGGGCTAG ATGTAGGGTT GAAGAGGCAG CTCCCAGCTC AGGCTGGAG
45551  AATTATTGCC TAGTCCAAGG GGTAGAAAGT GCTGAGGCAG GGTTGGGAGT
45601  GAGCCGTGGT TTGGGTTTTT TGGCCCTCAT CTCTTTTCT CAGAGGCTGA
45651  AGGAAGGAAA AAGGCTGACT GCCCACCCTT CTGTTTGTTT GTCTTGTCTA
45701  ATTTAACTTA CGTTATTTAT CAAAAAGACA GGTTATTTGG AAAACCAGAT
45751  GGACCTAGGC AAAAATCATC TGGGTTTTCC AAACGTGAAA AATTAGGTTC
```

FIGURE 7Q

```
45801  TGGGGGCCCA GCAGGAAAGG CGTGTGTGTG TGTGTGTGTG TGTGTGTGTG
45851  TGTGTGTGTG TGTGTGTGTG TGTGTGTGTG TTTGAGGGGA GGGTGAGGTT
45901  GAGTGAATGT CTCTGTAGTT AGACCCAGAA ATTGTTCCAT GACTTCCAAG
45951  CATACTCCCT CCTTCATTTT CCTTCAAGTT CTTTATGATT AGAATCTAAA
46001  TGAGAAAATT AAAATCTTCA TGTTGGTTGC TGGATGTCTT AATTGACCAA
46051  GGATTAGAAC CCATCAGGGC TATAGAAGAA CAGCAGCTGA CAGTTTTCTC
46101  TATCTTTCCA GCCCTCAGTC CCTTACACAG AGTGGGCAGG TTAGTGAGAG
46151  GTGCAGGGTA CTGAGAGTTT TCTGAAACAG AAACCTGTGC TTCTTGTCCC
46201  TTCAATGTTA TTGTTCCAAA GAGTTGCAGC AAATATGGAG GTTAGACATT
46251  AGGGAAGAAC TTATCATCAA CTTTCTGATG ATCAAATGGC TAAAAGAACA
46301  CTGAGGATCC AGGGCTGTCT CTCCATTGAC TATCCAGGGA AGGAGCTAGC
46351  CCAGTTTTCT TTTGGGCAAT GGTGGCTTGC TCTGTAGCTA CAACCAGGAA
46401  TTTGTAAAAC TTGTGGTTTT GGGCCAGGCA TGGTGGCACA TGCCTGTAAT
46451  CCCAGCACTT TGGGAGGTTG AGGTGGGGGG TTTGCTTGAA CTCAGGGGTT
46501  TGAGACCAGC CTGGGCAAAA TGGCGAAACC CCATCTCTAC AAAAAATACA
46551  AAAATTAGCT GTGCATGGTG GCATGCACCT GTGGTTCCAA CTACTTGGGA
46601  GGCTGAGGTA GGAAATCACT TGAGCCTGGA GGTTGTGGCT GCAATGAGCC
46651  AAAACTGCAG CATTGCATTC CAGTCTGGGT GACAGAGTGA GACTGCCTCA
46701  AAAGAAAAAA AAAAAAAAAA AAAAAGCTTG TGGTTTTGTT ACCTTGAGCA
46751  GCAACATTTT TAGGAAGGAA TTAAAGCAGG AGGCTATTGA GGCATAGCTC
46801  TTGGCTGCCA TAGAGGAAAT GTTCTGGCTG AAAGCAGAAA GCAAGCCATC
46851  CAGTTCATAC ACATATGCAC ACACACAGAA GACAGCCAAG ACCCTTTCTG
46901  GCCTGAGAAA TCTTTGGCGG CAGCAATAGC ACTTGTCCCA TTGTGAGTGG
46951  CATTTTTTTC AAAGTGTCAT TGGACTGTGA AAGCTACTTA ATAACTTGAT
47001  CTCATCTGAA TAATCTGAGT TAATACTAGC TTCACAGTTG TGAGGATTAA
47051  ATAAAAAAAA ATTGTAAAGT GTCTGCCTCA AGGCCTGGCA CAGAGTAAAT
47101  CTCAACAAAT GCTCGTTGAA TGAATGAATC CATGAATCTG AGCATTAAGG
47151  CCCCCCTCAC CGTTTCCAAG GATCAGTGCA TAACAGCCCC GGTAACTGAG
47201  ACTTGTAGAC TGTCCCAACT GAGCCTGCAG CCTGAGGCAT GATCTAAACC
47251  TGCTGTTCCT TTGACAAATA TTTGATGAGT TATGGTGTGG AGGGTGGACC
47301  CTTCCATGAA GGCCTTGTTG GCCTAGCTGT TGGAAGCACT ATGCAGACAG
47351  TCTTCCAGGG TGGGAATTGC CTCAGAGAGC ACCTTGCCCA AGGTCAAGGA
47401  TAGCCCACAT TCAATGGCAA CAGGTGTGTA ACGGCCTGGC CTTCTTAGCT
47451  TATTTTGGGT CAACTCTGAA GGGCCATTCT AGCTTCAGAG CTCCCTGTGG
47501  GGTTGGCTGA GGCTGTCACT GGCTTGTCTT GTAGATCAGC CTCTTCCTCT
47551  GGCCACTCCT GCTCATTCTC ATTCTTCCAC AGCTGTTGAT CCCAAAGGAG
47601  GTTCTTAATA AACATCCAGC ACATTAAACA GTCTCAGAGT TGGCTTCCTG
47651  GGAAATCCAA GCTATGAATG CACTAGTCCT GGTGGCCAAG CCTTTAGAAC
47701  AACAAGAAC GGAGACTCCT TTGCAATGGA TTTCCAGCGT TGGAGGTGTG
47751  GATACTGTCT CTTTATGCCC ACCAGAGGGC AGCAGCATCC TAGCCACCTG
47801  CCCTTCTGAG GCTCCAGGAG TGGGCTTGAA GCCTTTTCCC CGGCAACTTC
47851  ACGCCCCACA CCAGTATTGG GCAGGATCAC CTCCCTTAGG GTGTTCACCC
47901  TCCTGACTAA AACAACAAAA CTTTCTTAAA CTGTCCAGGC CTTAGTTTTG
47951  TTAGTCTCAA GCTCCTGTAC CACCATCACT GAAGGCCAAT CAGTCTTCCT
48001  ACTGTGCCCC TTCCCCTGCT CCTCGTCCGG CAAGCTCCGT GCCTGGGATC
48051  CCCCACCTCT CACACTTACC ACCCACAATA GATTTGTTTT CTGTGTGACA
48101  AGGTAATTAC AAGCTTGGGG CCAGTAGGCC CAGGGGCCAG TCTGAGGATG
48151  GTCACTTCAT TCTGGCTCTC CCTGTTCTGC TAACGGTATT GATTTTCAGT
48201  TTTATTTATT ATGATGATGT GTGTGTGTGA TCTGGCCCTG GTGACATGAC
48251  ATATGGAGGC AAGAGGGCGA GAGCAAATTT CCTTTTGTCA CAATTTGACT
48301  TCTTGAAACC GCACCCCCAC CACCACCACC CAGCATTGTT TATTTACAGG
48351  TTTTAGCATC TTTGCTTACC TGTCTTCATT CTGTCCCCTC ATCCCCAAAG
48401  ATTTCTAAGA GATTCTTCTG GGAATTGGAG CCAGATGGAT GTGACTACAA
48451  GAAGGAGGAA AGGGTCTGGG AAGAGGAGTG ACAGCAGCAA GCATACTACC
```

FIGURE 7R

```
48501  TTTTGTTAGC AGCCATTAAC TCATCCAGCA AACATTTACT ACATTCCCAT
48551  CACCTGTCAG TTACTTCTAG GCTAAGCTCC CCAACTCCCT GCTGGGGGCC
48601  ATCCTGGAGA CAGGTTTTGC TATGCGCTTT TTTTTTTTTT TTTTTTTTTT
48651  GTCTGCATCT GTTTCTATGG GTGTGTGAGG AAAACCTGGC CAGAAAGCTT
48701  TGAGAGAGTG AGATTGAGTT TGGGTGCAAC CAACTCAAAG AACGATGCTT
48751  GCCTGAATTT AAGGCTACTT AAGGCCTCCC GTAATGTAGT CTACTTCCTT
48801  ACGAGGAAGA GGAAGGGCAA GCTTGAGGCA AACATTACA AGTGGGAGGG
48851  GGCACTCTGA ACTGCAATGA TTGCCGTGGG AATCAGCTGA GGCTGAGGGC
48901  GATTTGTGGG GCCATGTTTC CCCAGCCTGT CTTCTCTGTG CGTGCCAGGA
48951  GAATGAATAA ATCATTGTTC AGGGGCGGGA TGCAGCTGCC GAGCTCCTCC
49001  CCTCGGCACA TGCCCCAACT CCAGCTCCTC CATTGAGGGC TGCTGGAGCA
49051  GAGCGGTTTA TACACCCAGC TCCCCAAATC CTATTGAGGC CTCCCCCTCC
49101  GCACGAGCCA CCGGCTCCAA GCCCATTCAG GCTGGCCCTT TGTGCTGGGG
49151  GTTAAGTGGT TACATGTGGG GGGCACCCAG AAAGGAACTG TCAGGCCTTG
49201  AAAGGCTGTG CTGATACAGT GCCCTCCTAC TGATGAATGG GGTGGGTGGA
49251  GGAGAGGTGG GCGGCCGGAG GGTGGGGTGG GGGAGAGGGC ATGGGGATTA
49301  TGGAGCCCAC AGAGGCAGCT GCTAGGAAGG GGGTGGAACA GGCACCCCCT
49351  TCTCTCTTTC CTCCTTCACT TCAGCTTCTC CGTCTAGCTT ACTCCCTCTG
49401  TTGTGGGCAC TGGATGATCA AGAGCCTTGG GACCTTGGAT TTGGCTTTTC
49451  TGATGTCCTG GTGACCGCTT GAGTGCACTG GAGAGAAAGA ATTTATATTA
49501  CCTTTCATTC TTCCAGCAGC TCCGAAAAGA CCTGTTTCTC CCTTTTCCCT
49551  TGGAAGGGGT GGGTGAGAAG GGAACAGTG TTGGGGACAG GGGGAGGATT
49601  CATTTCCTAG GTTCATCTGG TGCAGTGGAT TTGCAGCTGT GCCCTGCCGA
49651  ACTTTTAAAA GCTTCTCTGA AGTTCCCTCG GAGCCCTTAG GTGGAGGGTT
49701  TAGGGGAAGA CAGATCTCAA ACTGGATATA TTGGAAAGAT TTTGTTGAGG
49751  AAAAAGAAAT TACTTCAAGG CTCTAAAAAT GCTTTAAAAC TTCTAATTGA
49801  ATGTACCGCC TTGTCATTTT ACAGCTGGGA AAACAGCCAA AATGGAAGAT
49851  AGGGGAATGG GCATATTTTA CCTAAGGTAA ACACATAGTA ATTTCTTGAT
49901  AGACTAAAGA GGCACTTTAC CTTTAAGAAG CAGTAGAGAA ATGGATGAAC
49951  AAAACAAGTA GGTCATCAGC TTCCTAGGCC TTCCTTTCCC AAGATGAACC
50001  AATTCTGGGG AATAATGTTC GTTCCAATCT GCCTTAATGG CTCTTTGGCA
50051  TGTCAAAGGT CCTCTGGGGT TGTGCCTGGT CTTGGGAGCC CAAGTGACAA
50101  TGTTCACCAC TATGTTATTG AACAATTTTT AAGGCATATT ATTTTATTTA
50151  GCCCAAAAAG GTTAAAATGA TTTGATTTGC CTAAGTTCCC AAAGCCATGT
50201  GGGGAAGTTG ACAGATGATG TGACCTCAGG AAGAGAGAAG AAAGCAGGTT
50251  AGCAACGTAG TTTGTAATCC AGGATCGTGC TTTGTTCTGA TATGGAAACT
50301  CTGAGGGCTT CCTCAGTTAC TTCCCTGCTG TCCCCAGGAT GGAGCCCAAG
50351  CTCCTTGGGA TGGTGTCAAG AACTTTCACA ACTGGGCCAA CTTTATCTTC
50401  TAGCCTCACC TTACCTCCAT TTCCCACCGA GCTCCAGCCA CACTGGCCTA
50451  CGGGGTGTTT CCTGAACTCA CTCTGAAAAT GCAGTCTCCT ATGCCTTCTC
50501  TTGCTTTCTC TTGGTGAGCT CTTATTCATC CCTCAAGGCC TGGCTCAAAT
50551  ATCACCTCTG TGCTAGCTGG GTTTAGTGGG TCATGCCTGT AATCCCAGAA
50601  TGTTGGGAGG CCAAGGTGGG AGGATCACTT AAGGTTGGGA GTTCGAGACC
50651  AGCCTGGGTA ACATAGCAAG ACTCCCATCT CTTAAAATAA AAAAAATCAC
50701  CTCTGTGAAG CCTTTCCTTA CCCTTTTCTG GGCTTACTAC TTTTGCCTCC
50751  TGGCTCTGTT GCAGGGCCCA TTACATTGTT ATAGCCCACT CTTCTGTCTA
50801  TTCCTTTTCT TTGAGACAGG GTCTGGCTCT GTCACCCAGG CTAGAGTGCC
50851  GTGGTGTGAT CTTGGCTCAC TGCAACCTCT GCCTCCCAAG TTCAAGCAGT
50901  TCTCGTGCCT CAGCCTCCCA AGTAGCTGGG ATTACAGGCG TGTGCCACCA
50951  TGCCCGGCTA ATTTTTGTAT TTTTAGTAGA GACGGGGTTT CACCATGTTG
51001  ATCAGGCTGG TCTCAAACTC CTAGCCTCCA GTGATCTGTC CGCTTCGGCC
51051  TCCCAAAGTG CTGGAATTAC AGGCATGAGC CAACACACCA TGACTTCTGT
51101  TTCCCTTTCT AAACAAGGAG CTCCCCAAGA CCACGACCAG TTCTGATTCT
51151  GCTCTGAATT CCCAACACAG TACCTGGCAC AAAGTAAGCA CTCTGTAACT
```

FIGURE 7S

```
51201   GTATGATACA TGTAAATGAA TGGGTGGGAA GGGACAAGGT CTTTGAAGCT
51251   GAAACACCTT GATCTTACCC ACCCCTTTCT TCCTGAGAAT ACTGATATTG
51301   AGAAATTATC CACCTATGAA TAACCCTTAG GCCTGTCCTA TTTCCTGGAT
51351   GAGAAATTCC TCTCATCTTC TCTGGTCTCC TTGCCTGACA CCCCAGGCCC
51401   TGGGACCTGG ATCTGGCTAC TCACTGCTAG CCTCTCTTGG CTCTGACATC
51451   TGTTTGCCAA GAGGCTTACC CGCTGTCCAT CATTGGGTCT TGATGGCATG
51501   GCCTTTTGCA AAGCCCTGTT CAGGCTGATA CTGGCCATCT CTGGAGGTTT
51551   CTGTGTCCTT GCCACTTAAG TTCCTGGCAT ATATGTGGGT AGGTGAACCC
51601   AGCCACAGAT ACCCTTTCAC TTGGGGGTGA ATTATTCTCT GGTGTCCTCA
51651   CTGGAAAAGC CTCTGGCAAA TGAATAACAG GCATCTCTAT AGCTGCTTTT
51701   TTGTCTTCCT GTGGACATGG ACATCCCTGC ATTTGGAGCT TTTTTTTCTT
51751   CAGGTTTTGA GCTCTGAAAA TTATGGAGTG ACCAGGACTG CTGTGTGAGC
51801   ACTGACTGTA TTAATTATAC AGTGCTAGAA TATTCCATAC AACACTGCCC
51851   TTGATTAACA AAACTGGCTA CAGGCTGGGT GTGGTGGTTC ACGCCTGTAA
51901   TCCCAACACT TTGGGAGGCC GAGGTGGGCA GATCACTTGA GGCCAGGAAT
51951   TTGAGACCAG CCTGGGCAAC ATAGTGAAAC CCTGTCTCTA TTAGAAATAC
52001   AAAAATTAGC CGGTGCAGTG GCACACGCCT GTAGTCTCAG CTACTCAGGA
52051   GGCTGAGGCA TGAGAATCGC TTGATCCTGG GAGGCGGACG TTGCAATGAA
52101   TGGAGATTGC ACCACTGTAC TCCAGCCTGG GCAACAGAGT AAGACTCCGT
52151   CTCAGGGAAA AAAAAAAGAA AGAGAGAGAC TACAATCTGA TTTCCTTTAA
52201   ATGAATTCAC TTGACTTAGC AGGTATTGTA TTATTTAGGA ATAACTAGCT
52251   TTAGGCCAGG TGTGGTGGCT CACGCCTGAA ATCCTAGCAC TTTGGGAGGC
52301   CAAGGCAGGC AGATCACCTG ATGTCAGGAG TTTGAGACCA GCCTGGTCAA
52351   CATGGTGAAA TCCTGCCTCT ACTAAAAATA CAAACATTCA CCAGGTGGCG
52401   GGCACCTGTA GTCCCAGCTA CTCAGGAGGT TGAGGCAGGA GAATTGCTTG
52451   AACCCAGGAC GTGGAGGTTG TAGTGAGCCA AGACTATGCC ACTGCACTCT
52501   AGCCTGGGTG ACAGAGAGAG ACTCCATCTC AAAAAAAAAA AAAAAAAAG
52551   GAATAACTAG CTTTTTAGAA CAATGGAATT GATGACTCAG CTATTCCAGG
52601   CTGGGGTGCT GCCCTGCAGA GCACGATATA GGCTTTATTT ATTTTATTTT
52651   AATTTTTTTT TTTTGAGACA GGGTCTTACT CTATCGCCCA GGCTGGAGTG
52701   CAGTGGCACG ATCTTGGCTC ACTGCAATCT CTGCCTCTTG GGTTCAAGCG
52751   ATTCTCCTGC TTCAGCCTCC TGAATAGCTG GGATTACAGA CGCGCACCAC
52801   CATGCCTGTC TAATTTTTGT ATTTTTAGTA GAAACGGGGT TTCATCATGT
52851   TGGCCAAGCT TGTCTCGAAT TCCCAGCCTC AAGTGATCCG CCTGCCTCGG
52901   CCTCCCAAAG TGCTGGGATT ACAGGTGTGA GCCACCACAC CAGGCCCAAT
52951   ATAGGCTTTA AATCAATGTA TATAATGCTT TGTCCTTTGT GGCCAGAATG
53001   CATAACAAGA AGAGGTAGCG GTGGTTGTGG CACCTTATAT GATTTACCTA
53051   AGGACTAAGA GTTTTCTTCC TGTCTCTGAG ATTCTGGGTA TTGCAGGTCA
53101   GAAGGTGATA GCATCGGCCA GGCACAGTGG CTCACACCTG TAATCCCAGC
53151   ACTTTGGGAG GTCAAGGCGG GCAGATCATT TGAGGTCAGG AATTTGAAAT
53201   CAGCCTGACC AACATGGTGA AACCCTGTCT CTACTAAAAA TACAAAAATT
53251   AGCCGGGTGT GGTGGCACGC GCCTGTAACC CCAGCTACTC GGGAGGCTGA
53301   GGCAGGAGAA TGACTTGAAC CTGGGAGGCG GAGGTTGCAG TGAGCTGAGA
53351   TCGCGCCACT GCACTCCAGC CTGGGTGACA GTGAAACTCT GTCTTGGGAA
53401   AAAAACAAAA CAAAACATGG TGATAGCATC ATGGGAGGAA TGTTTCTTCT
53451   AACCAAGAAA CACAAGATG ATTCCCTGGG ATTTCGGCTC CTGGTAGCAC
53501   TAGAGGAATA GGAGAAGGGG GTGGTCTCAG TGTAGACTGG ACTGATCATG
53551   GCTACCAAGG AGAAGGGAG TTACTGTTAC CTAATAAGTG TTGAGAGGTG
53601   CGTGAATGGA ACCCAGAGAC CCTGGGGTCA CCACCTTGTG CTATTGTAGT
53651   AATCAGCATT CTTTCAATTG TCGGTGAAAG AAATTCCACT CAAGTTAGGC
53701   TTGGCAAAAT AAGGCATACA AAACTATAAG TTTAGATGCA GGAAACAGGG
53751   TCTGCAACAT TATCAGAACT ATCTCTCATC TCTGTTTCTT CCCTGCCTCG
53801   TCTTCCTTTA ATTTCGTTTC AGAAGATCCC AGAGAAGGAC TCTGACTGGC
53851   TCACCTGGAG TGGAGCTCCT ATCCCTGGAT TCTTCAGGCT TTCATTTGAC
```

FIGURE 7T

```
53901  CCACATGGTT AAGCTGGGAG AGACAGAGTC CAAAGAGAGG CGGAGAAGGG
53951  CTATTCTGGG CAGAACAAAC AATTGATGAC TTTATGGCTC TGTGGTCTGG
54001  GCAGAACTGC ATAACCCTAG ATCACCAAAG CTGAGAGCCT TTAGGAGTGA
54051  GGATTTGGGC CAGGCATGGT GGCTCACGCC TGTAATCCCA GCACTTTGGG
54101  AGGCCGAGGT GGGTGGATCA CAAGGTCAGG AGATCAAGAC CAACCTGACC
54151  AACATGGTGA AACCCATCT CTACTAAAAA TACAAAAATT AGCTGACGTG
54201  ATGCATGCAC CTGTAATCCC AGCTACTCAG GAGGCTGAGG CAGGAGAATC
54251  GCTTGAACCC GGGAGGTGGA GGTTGCGGTG AGCCGAGATT GCGCCACTGC
54301  ACTCCAGCCT AGGCGACAGA GCGAGACTCC ATCTCAAAAA AAAAAAAAAA
54351  AAAAAAAAAA GTGAGGATTT GGGTCACCCC AGGCTGAAGG CCAGGGGAAC
54401  CTGAAGTGGA TAAGGGAAGG GAGAAGACTT AGGCCACAGG ATCTGATGTA
54451  GAAATGGGGC TGACGTCTCC ACCTGTATTT TCTTAGCTGG AGGAGTGTGC
54501  AAAGTTTGAA TTACTTCTGC CTTCTCCTTC TTATTTCCTT TTCCCTTTTA
54551  AAATAGTCAT CATAATCATA AAAATTTCTT TTCCATTTTC CCTGTTTTTG
54601  CATATAGGAT TTCTTGGTGT GATTTAATTT GCCAATTAGT CTCTAGGTTG
54651  CAGAATGGTG ACTTGGAATC AAATTGAAAC TGGAAGAGGG CACCTCATAT
54701  ATTAGGGTCA GCAATTACTG AACTCTGTTC TCTTTATTC CAAACAGGGC
54751  CCCCAACTTC ACATTTCCCC AGGGTGCAAA AGAGTGAGGG GGGTCAAGCT
54801  TCAGTAGAGT GGAGCTCTGA GAAGAATCCA CTGGAGTTTG GAACCCAAGA
54851  CCCTTTTTTA TCACGCTGTT CCTCCTCACC TGGGCAAAAG CACTGGTACC
54901  CACTTCACAG GCATCATGGG TGGGCTCTGT GTCCTGCGGA GAGCCCCGT
54951  CCCGGGTACA GGACATCAGC CCTGAGCCCT GTCCCAGGCT GGATCTTCT
55001  TTCTCTCTCT CTCTTTTTTT TTTTTTTTT TTTTTTTTT TTGAGACGGA
55051  GTCCCACTCT GTTGCCCAGA CTGGAGTGCA GTGGTGCAGT CTTGGCTCAC
55101  TGCAACCTCC ACCTCCCAGG TTCAAGCGAT TCTCCTGCCT CAGCCTCCCA
55151  AGTAGCTGGG ATTACAGGCG CCCGCCACCA AGCCCGGCTA ATTTTTGTAT
55201  TTTTAGTAGA GATGGGGTTT CACCATGTTG GCCAGGCTGG TCTCAAACTC
55251  CTGACCTCAG GTTATCTGCC CGCCTCGGCC TCCCAAAGTG CTGGGGTTAC
55301  AGGCGTGAGC CACCGCACCC GGCCTCAGTG ACTTTAGTCA AGTAAGCACA
55351  AAAAGGAATA TATAATTCCA AATTGTGATA AATGCTATGA AGAAAAGGAA
55401  TGTGCTCTGA CATAAAGGGG GGAACGAACG TGATCTAGGG AGTCAGAGAT
55451  CTCTCCGAGA AGAGATCTGA AATAGGAGTA AGTCGAGAGG GGGAAGAGAA
55501  TGCTAGACCG AGGGAACAGT GCGTGCCAAA GCCGCGTGGC GGAAAGGGGC
55551  GTGTGGGAGG GTAACTGCGG AGAGGGAGGG TAGAGGACGA AGCCGGAGAG
55601  GCAGACGAAG GGCAGGACGC ACAGAGCCCC GCGGCTACCG CCTTAGGGGT
55651  TGTCCCGGCG GTGGGGAAGC CATTGAGGAG TTTAACGCCG GAAGGTGGTG
55701  ACTAATCAGA TTTCACTTGA AAATGGCACG GTGTCTGCAG CGAGGCTAAC
55751  TGATGGGAAG GGCCCAGCGA ATGCCAATAG GAGAGAGCAC CGGACCTGGA
55801  AGGCCTGGGT CAACGCGGCC CCGCGCGGGG GCGAAGCGGT TCCGGCGCAG
55851  GGGCCTGGCG CGGGGCTCCG CGGAAAACCG AACCGGCCCA CGTGGGACCG
55901  GTCGCTCCGC CCTGCTGCGC AGACGCCGCC TGACTCCGCA GTCCGGGACT
55951  GGGGCTGGGC GCGCTGCCCG GGAGCCCCGC ACCACGCCT GGACCGCGGA
56001  GACGCCCAGG CCGAGGAACC CCCAGCCCAG GGACTAGACA CCACCAGGGC
56051  CGGGCGGAGC CAGAGCCAGA CGCGCCGGAG CGGGCGCCTC TACGCCGTGA
56101  GTCCGAGTCT GGGGCCCGAG GCGGGGTGGG GCTTGGGGCT CAGCCGCGGG
56151  AAGCGGGGAG TCACAGTGGC CTCCTTCGAG GAGACTAGGG AAGGATGGTC
56201  TCTGTCTCCT GGGGTGGTCT CCCACTCCCG CAAGGCCAGA AAAGGAGGCT
56251  GCCTCCTGTT TGGGCGGAGA CCTAGTCCTG GCGTGTCGGG GTTCTCATTT
56301  TACTATCTCT GAGAACCCTG TGATCCCTAG CGCCACCCCC ACCCCATCCC
56351  AGCTTCCTTC ACGGCCCCAT CCAAGTATAG GAAAAATAAA AAATTGGGGC
56401  GAGGGGAGAT CTCTAGGCAC CTTCCCACAA GCCTTGCTTA GAGGGCGATT
56451  AGAAACGAAC TGTTCCTACA CCCTTCTCCC CAGGACTTCT CTGCCCATTG
56501  CTGGGGGTGG GGAGGGTCCA TGCCACCTAT GGAGCGCCTT CCAGTGCCGG
56551  CTCCACTTAC AATACCCTTC CTCTTCATGC TCTTCAATTG TTCTAATCCC
```

FIGURE 7U

```
56601  AGTGCTGTTT  GGTCAGTAGA  ATCCCTTTGT  CAGTTCAAAT  CCTAATTTTG
56651  GTTAGAAGCA  GGTTATGGAG  GAGAGAAGAG  TGGTGTGGTA  TGCCCTCCCT
56701  CCAGGGCCTC  AGAATGGAGC  AAGCTAGGGA  CGGGGACCGC  AAGATAGTGG
56751  CTGTGTTCCA  GAGGCATTGG  GAGGGAAGGG  GGCAGGCTCA  GAAGAAAAGC
56801  TTGTCACTGG  GGAAGGCGGG  GCTCCCTGGC  TGGGGTAGGA  AAGGGAACCA
56851  AACCCAGCTC  TTCCAGAACC  CAGCTCTTCC  AGCCCTGGGG  AGTCAAGAGT
56901  GGATTCCTGA  GCATGGAAAT  TCACTGCAGT  CTCTTCTCCC  ATTCACTCAC
56951  TTAGCAAGTA  CCTGTATGCA  CAGACAGCCT  GGTTCAGGGC  TCTATGCTGG
57001  CTGACTCTGG  GGAATATGAT  GGAGGATATA  TACAGGAGGT  CCAAGCCAGA
57051  TTACAAACTG  CTATTACAAG  ATCATTACCA  CAAACCAAAA  ATGCCAGTTG
57101  AATAGACATT  CACTGATCGT  CGACCATGTA  TGCCAGGGAC  GGATGCAAAG
57151  TTGGATAAGA  CAGTGTATAC  CCAGCGCAGT  GGGGACCCAG  AGGAAGGCAT
57201  AACTAACCGT  GCTTGTTTAT  GTAATATTGA  TTGGGGCAGT  ATCAAGACGG
57251  CTTCAGAGAC  ATGGGGACAT  GGAAACATGG  GGATATTACA  GCTAATTTTG
57301  AAGTACAAAA  AGGAATTTGC  TGGGTGGAGA  AGGGAGGAGC  TTTGAGGGGA
57351  GGGGAGAGGA  AGGATATTGT  AGGCCAAAGG  AATACTGTAA  GAAAAACAAT
57401  GGTGTGTTTT  GAGATCTCTG  GGCAGTTTGC  TATGATGGGA  GGGGCAGAGT
57451  GGCAAGAGGC  AGGTATGGAG  GGGTGAGCAG  GGGCCAGATC  AAACAGGGTG
57501  TTGTAGGCCA  GGTAGAGGTT  TAGCAGGAAT  TCAGGGAGGG  CATTAGGAGT
57551  GGTGACAAGT  GAAATTTACA  TTTTTAACTG  GAGGCAGAGA  GATCAGTGAA
57601  AAGGCCGAGG  CAATAATCCA  GGTCAGAAAT  GGCCTGGAAG  AGGAAGAATG
57651  GTCAGAATGT  GGTTATTAAT  GAGATGGGAG  AAGGAAGGAT  AGTGAGGACC
57701  CCAGGATGCT  CTCAGCTTTC  TGGATGGAGT  ACAGAGCCAT  CTTGCTGAGG
57751  ATACTGAAGG  AGAGCTTGTT  TGGTTATGTA  GAATTTTGGC  GGGGGGCGGT
57801  GGTGGAGGGG  GATGATGTCA  CTCTGTCACC  CAGGCTGGAG  TGCAGTGGCG
57851  CAATCTCGGC  TCACTGAAAC  CTCTGCCTCC  TGGGTTCAAG  TGATTCCCCT
57901  GCCTCAGCCT  CCCAAATAGC  TGGGATTACA  GGTGCCTGTC  ACCATGCCTG
57951  GCTAATTTTT  GTATTTTTAG  TAGAGATGGG  GTTTCACCAT  GTTGGCCAGT
58001  CTAGTCTCGA  ACTCCTGACC  TCAGGTGATC  TGCCTGCCTC  GGCCTCCCAA
58051  AGTGCTGGGA  TTACAGGTAT  GAGCCACCAT  GCCTGGACTG  GTTATGTAGA
58101  ATTTGAGGAG  ACTATGGTTG  GTTGCAGGGT  TGGATAGCAG  TTGGATCTGG
58151  GCTGAAGACA  GATCTGAGAG  TCACCAGCAT  ATGATGGTCT  TTGAAGCTAC
58201  AGCAGAGAAT  GAGGTCCTCT  GGAGAGAAAT  GCACAAAATC  AGAAGACAGC
58251  CTGGCTCTGA  GGACGGAGGA  AAAACCCTTT  GCAGGAGACT  GAGAATGAAC
58301  AGGTAGACAG  GGAGGACGAA  AACCACGAAG  GAAGTGTTA   CCAGAGTCAA
58351  GAGAAAGGGC  TTGACAGGGA  GTGGCCAGGC  TCTTGCTTGC  AGCCTTGTCC
58401  CTGCAGCTAA  GTTGCCCTGA  CTTCAGGCAC  CCCACCCTGT  CCTACTGTGA
58451  CTCGGTCTCC  TGCTTTCCCT  TTACAGGCTA  GATGTTCGCC  ATCCAGCCAG
58501  GGCTAGCTGA  GGGGGGCCAA  TTCCTGGGGG  ACCCACCTCC  TGGATTATGT
58551  CAGCCCGAGC  TCCAACCAGA  CAGCAACTCC  AACTTCATGG  CAAGTGCCAA
58601  GGATGCTAAC  GAGAATTGGC  ATGGGATGCC  AGGCAGAGTG  GAACCTATCC
58651  TGAGGAGGAG  CTCCTCTGAG  TCACCCTCTG  ACAACCAAGC  CTTCCAGGCC
58701  CCTGGATCCC  CTGAGGAAGG  GGTGCGCAGC  CCCCCAGAGG  GGGCAGAGAT
58751  TCCCGGGGCT  GAGCCTGAGA  AGATGGGTGG  TGCTGGCACA  GTCTGCTCCC
58801  CTCTGGAGGA  CAACGGCTAT  GCCAGCAGTT  CCCTGAG
```

FIGURE 7V

CLASPIN PROTEINS AND METHODS OF USE THEREOF

RELATED APPLICATIONS

This application claims the benefit of priority under 35 U.S.C. § 119(e) of U.S. Provisional Application No. 60/241,246, filed Oct. 17, 2000, incorporated herein in its entirety.

ACKNOWLEDGEMENT OF GOVERNMENT SUPPORT

This invention was made with Government support under Grant Number GM-43974, awarded by the National Institutes of Health. The Government has certain rights in this invention.

FIELD OF THE INVENTION

The present invention relates generally to cell cycle progression and more specifically to molecules involved in regulating DNA replication checkpoints.

BACKGROUND OF THE INVENTION

Growth and division of cells require a cell cycle, that is, a regular sequence of processes. Two processes of the cell cycle are the accurate replication of DNA and the segregation of chromosomes to the two daughter cells during mitosis. When mitosis is not taking place, the cell is in an interphase period. Interphase is subdivided into three phases; a synthetic phase known as S-phase, when DNA synthesis takes place, and G1 and G2, gap phases that separate S-phase from mitosis. G1 is the gap after mitosis before DNA synthesis starts, and G2 is the gap after DNA synthesis is complete before mitosis and cell division. The mechanisms that insure alteration between S-phase and G-phases are critical to achieving cells of correct size and chromosome number. Most cells divide after replication of their chromosomes, and most cells replicate their chromosomes after completing cell division. Cells rely on checkpoints that link cell division processes and chromosome replication processes.

Checkpoint mechanisms guarantee that eukaryotic cells maintain genomic integrity during cell division by monitoring damaged or incompletely replicated. Such mechanisms ensure that cell cycle progression is stalled until aberrant DNA structures or replication intermediates can be eliminated. An ultimate target of these control mechanisms is the Cdc2-cyclin B complex, also known as maturation or M-phase promoting factor (MPF). During interphase, the Cdc2 subunit of MPF is down-regulated by inhibitory phosphorylations on its Thr-14 and Tyr-15 residues. A regulatory system containing two inhibitory kinases, Myt1 and Wee1, and a stimulatory phosphatase, Cdc25C, controls the activity of Cdc2 through reversible phosphorylation of these residues. Checkpoint mechanisms prevent the activating dephosphorylation of Cdc2 at the G2/M transition unless two accurate copies of the genome are available for transmission to daughter cells.

Genetic studies in yeast have identified proteins that are involved in sensing information damaged and/or incompletely replicated DNA and transmitting this information to effector molecules that interact directly with the cell cycle control machinery. In fission yeast, the sensor proteins are currently thought to include Rad1, Rad3, Rad9, Rad17, Rad26, Hus1, and Crb2/Rhp9. Effector proteins include the kinases Chk1 and Cds1 as well as 14-3-3 proteins such as Rad24. Similar pathways are found in budding yeast, and homologues of many of these proteins have been identified in higher eukaryotes, including humans, *Xenopus*, *Drosophila*, and mice. The most well established function of Chk1 in yeast and vertebrates is mediation of the binding of 14-3-3 proteins to Cdc25, which results in its cytoplasmic localization.

Phosphoinositide kinase relatives in fission yeast (Rad3), budding yeast (Mec1), and vertebrates (Atm and Atr) play an essential role in signaling the presence of damaged and/or unreplicated DNA to downstream regulators. For example, in fission yeast, Chk1 and Cds1 cannot function normally in the absence of Rad3. Similarly, Mec1 is a critical regulator of Rad53. a Cds1 homologue in budding yeast. In vertebrates, Atm is an upstream regulator of Chk2/Cds1. Atr is essential for genomic stability and early embryonic viability.

Despite these insights about certain components of checkpoint mechanisms, relatively little is known about how the Cds1 and Chk1 families respond to checkpoint signals. For example, in budding yeast, Rad53, a presumed target of Mec1, must bind to Rad9 to undergo phosphorylation and activation. Chk1 also becomes phosphorylated during checkpoint responses in various organisms. Although it is widely assumed that this phosphorylation leads to activation of Chk1, experimental proof of this possibility has not been provided. In fission yeast, both the phosphorylation of Chk1 and the ability of Chk1 to function in checkpoint control depend upon Crb2/Rhp9, a relative of budding yeast Rad9. Genetic and two-hybrid experiments have established a close relationship between Chk1 and Crb2/Rhp9, but a direct interaction between these proteins has not been reported.

In view of the importance of cell division and development, there is a need for determining further biochemical components of checkpoint mechanisms. This invention meets that need and provides methods of using such components.

SUMMARY OF THE INVENTION

The present invention provides a family of proteins involved in regulating progression of the cell cycle. Specifically, the present invention is based on the discovery that a novel family of proteins, the Claspin proteins, plays a significant role in the activation of kinases important in regulating the cell cycle.

In one embodiment of the invention there is provided a substantially pure Claspin polypeptide characterized as (a) specifically interacting with a Chk1 protein; (b) having SQ/TQ motifs; (c) having an isoelectric point of about 4.5; and (d) having at least one nuclear localization signal. In an illustrative example, there is provided a substantially pure polypeptide having an amino acid sequence as set forth in SEQ ID NO:2 or SEQ ID NO:4, or conservative variants.

In yet another embodiment of the invention, there is provided a substantially pure polypeptide having the contiguous amino acid sequences LAAVSDLNPNAPR (SEQ ID NO:6) or YLADGDLHSDGPGR (SEQ ID NO:7).

In still another embodiment of the invention, there is provided an isolated polynucleotide. The polynucleotide can be (a) a polynucleotide encoding a polypeptide having an amino acid sequence as set forth in SEQ ID NO:2 or SEQ ID NO:4; (b) a polynucleotide of (a), where T can be U; (c) a polynucleotide complementary to (a) or (b); (d) a polynucleotide having a nucleotide sequence as set forth in SEQ ID NO:1 or SEQ ID NO:3; or (d) degenerate variants of (a), (b), (c) or (d). The polynucleotide can be DNA or RNA. Also included in the present invention are isolated nucleotide fragments that hybridize to the polynucleotides of (a), (b), (c), or (d) and having as least 15 continuous bases.

Also included in the present invention is a method for identifying a compound that modulates cell cycle progression. The method includes incubating a compound and a cell expressing a Claspin protein and a chk1 protein under conditions sufficient to permit the compound to interact with the components. The cell cycle progression in a cell incubated with the compound is compared with the cell cycle progression of a cell not incubated with the compound. A difference in progression through the cell cycle between the cells is indicative of a compound that modulates cell cycle progression.

Also provided by the present invention is a method for modulating cell cycle progression in a cell providing to the cell a reagent that affects the activity or expression of a Claspin polypeptide, thereby modulating cell cycle progression.

In yet another embodiment of the invention, there is provided a method for modulating cell cycle progression in a cell. The method comprises providing to the cell a reagent that modulates the activity or expression of a chk1 polypeptide, thereby modulating the cell cycle progression. The chk1 polypeptide is human Chk1 and the reagent is a human Claspin polypeptide.

In still another embodiment of the invention there is provided a method of treating a subject having a disorder associated with increased cell cycle progression as compared to a subject not having a cell cycle disorder. The method includes administering to a subject in need of treatment a therapeutically effective amount of a compound that increases a Claspin polypeptide activity, thereby treating the disorder.

In yet another embodiment of the invention, there is provided a method of treating a subject having a disorder associated with a Claspin-associated protein activity. The method includes administering to a subject in need thereof a therapeutically effective amount of a reagent that modulates Claspin activity.

In a further embodiment of the invention, there is provided a method of diagnosing a disorder associated with cell cycle progression in a subject. The method includes determining the level of Claspin mRNA or protein expression in a sample obtained from the subject. A low level of claspin mRNA or protein expression in the subject compared to the level in a subject not having a claspin-associated disorder is indicative of a disorder associated with cell cycle progression.

BRIEF DESCRIPTION OF THE DRAWINGS

FIGS. 1A and 1B show the nucleotide sequence of *Xenopus* Claspin (SEQ ID NO:1; Accession Number AF297867). FIG. 1C shows the amino acid sequence of *Xenopus* Claspin (SEQ ID NO:2).

FIGS. 2A and 2B show the nucleotide sequence of human Claspin (SEQ ID NO:3; Accession Number AF297866). FIG. 2C shows the amino acid sequence of human Claspin (SEQ ID NO:4)

FIGS. 7A–V show the genomic sequence of human Claspin (SEQ ID NO:5).

DETAILED DESCRIPTION OF THE INVENTION

Figure 3:
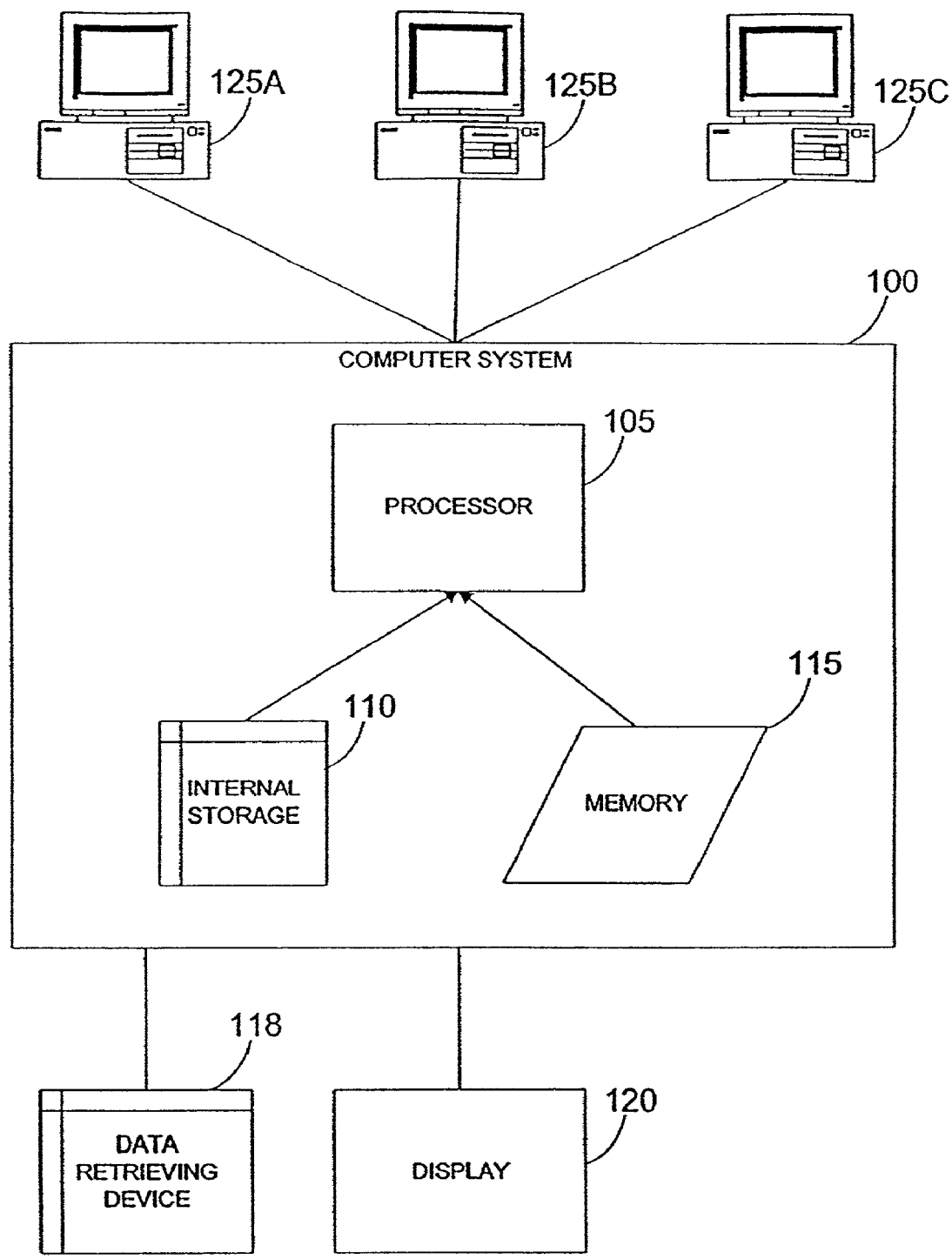
FIG. 3 is a flow diagram illustrating a computer system, data retrieving device and display.

Checkpoint mechanisms during the cell cycle, critically important for appropriate cellular development, involve numerous components. In the absence of a key component, cell division can proceed despite incomplete or erroneous DNA replication. One novel component, identified through phylogeny, is Claspin, a protein that is required for the activation of another key component, Chk1, during a replication checkpoint mechanism. Claspin binds to Chk1 allowing Chk1 to be phosphorylated and activated, and providing an arrest of the cell cycle.

Accordingly, in one embodiment of the invention, there is provided a substantially pure Claspin polypeptide characterized as specifically interacting with a Chk1 protein, as having SQ/TQ motifs, an isoelectric point of about 4.5 and at least one nuclear localization signal Claspin polypeptides specifically interact with a chk1 protein. For example, *Xenopus* Claspin polypeptide interacts with Xchk1, a *Xenopus* chk1. *Xenopus* Chk1 (Xchk1) is required for the checkpoint-associated delay of the cell cycle in frog egg extracts containing unreplicated or DNA or DNA damaged by UV radiation. Mammalian homologues of Xchk1 have been identified and Chk1 proteins share similar biochemical functions. Chk1 proteins are effector kinases that receive signals from checkpoint sensors located upstream of Chk1 in the response pathway to DNA damage. Chk1 proteins phosphorylate and inhibit the function of Cdc25, the protein phosphatase that dephosphorylates tyrosine-15 of the cyclin-dependent kinase (cdk) Cdc2.

Claspin polypeptides have SQ/TQ motifs. *Xenopus* and mammalian Claspin contain a relatively large number of SQ/TQ motifs. The *Xenopus* protein has eight SQ and four TQ motifs, and human Claspin contains nine SQ and three TQ motifs. Serine (S) and threonine (T) residues, each adjacent to a glutamine (Q) residue in this type of motif, are potential substrates for kinases such as ATM, ATR, and DNA-PK that are involved in checkpoint pathways (Kim et al., (1999) *J. Biol. Chem.* 274, 37538–37543).

Claspin polypeptides are further characterized by having an isoelectric point of about 4.5. The proteins are acidic, and therefore may exhibit anomalous migration, i.e., migration inconsistent with the actual molecular mass of the protein when subjected to a gel electrophoretic technique, for example, SDS-PAGE.

Claspin polypeptides have at least one nuclear localization signal. *Xenopus* Claspin and human Claspin have three conserved nuclear localization signals. In *Xenopus* Claspin (SEQ ID NO:2) the nuclear localization signal sites are located at amino acids 158–174, 312–316, and 1078–1084. In Human Claspin (SEQ ID NO:4) the nuclear localization signal sites are located at amino acids 152–170, 319–323 and 1132–1138. A nuclear localization signal is a motif involved in importing cytosolic proteins into the nucleus.

There is no apparent conservation of sequence in nuclear localization signals amongst different protein families, although the shape and a predominance of basic amino acids are important features. The motifs are generally short in length, may contain a proline residue to break alpha-helix formation upstream of the basic residues. Hydrophobic residues are not usually included in the motif (see *Genes VII*, ed. B. Lewin, Oxford University Press, 2000).

Exemplary Claspin polypeptides are set forth in SEQ ID NO:2, SEQ ID NO:4 and conservative variants thereof. The terms "conservative variation" and "substantially similar" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic acid for aspartic acid, or glutamine for asparagine, and the like. The terms "conservative variation" and "substantially similar" also include the use of a substituted amino acid in place of an unsubstituted parent amino acid provided that antibodies raised to the substituted polypeptide also immunoreact with the unsubstituted polypeptide.

In one embodiment of the invention, the polypeptide is identical with or homologous to a Claspin polypeptide, such as a mammalian Claspin represented by SEQ ID NO:4, or a *Xenopus* Claspin represented by SEQ ID NO:2. For instance, the Claspin polypeptide preferably has an amino acid sequence at least 60% homologous to a polypeptide represented by SEQ ID Nos:2 or 4, although polypeptides with higher sequence homologies of, for example, 70%, 80%, 90% or 95% are also included in the present invention. The Claspin polypeptides can comprise a full length protein, such as represented in the sequence listings, or it can comprise a fragment of, for instance, at least 5, 10, 20, 50, 100, 150 or 200 amino acids in length.

As is well known, genes encoding a particular polypeptide may exist in single or multiple copies within the genome of an individual. Such duplicate genes may be identical or may have certain modifications, including nucleotide substitutions, additions or deletions, which all still code for polypeptides having substantially the same activity. The term "nucleic acid sequence encoding a Claspin polypeptide" may thus refer to one or more genes within a particular individual. Moreover, individual organisms may bear different nucleotide sequences, called alleles, which code for substantially the same polypeptide. Such allelic differences may or may not result in differences in amino acid sequence of the encoded polypeptide yet still encode a protein with the same biological activity.

Also provided by the invention is a substantially pure polypeptide having the contiguous amino acid sequences LAAVSDLNPNAPR (SEQ ID NO:6) or YLADGDLHSDG-PGR (SEQ ID NO:7).

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40 percent identity, though preferably less than 25 percent identity, with one of the Claspin sequences of the present invention.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject Claspin polypeptides preferably includes no more than 10 kilobases (kb) of nucleic acid sequence which naturally immediately flanks the Claspin gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Exemplary polynucleotides encoding Claspin protein are set forth in SEQ ID NO:1 and SEQ ID NO:3. The term "polynucleotide", "nucleic acid", "nucleic acid sequence", or "nucleic acid molecule" refers to a polymeric form of nucleotides at least 10 bases in length. As used herein, "isolated polynucleotide" refers to a polynucleotide that is not immediately contiguous with both of the coding sequences in the naturally occurring genome of the organism from which it is derived with which it is immediately contiguous (one on the 5' end and one on the 3' end. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or genomic DNA) independent of other sequences. It also includes cDNA, RNA, antisense nucleic acid, and nucleic acid sequences complementary to invention polynucleotides. It also includes genomic DNA which refers to a contiguous sequence of nucleotide that includes one or more protein coding regions, introns, upstream and downstream regulatory sequences, i.e., non-coding 5'- and 3'- regulatory sequences. Thus, the term "polynucleotide encoding a polypeptide" encompasses a polynucleotide that includes coding sequence for the polypeptide as well as a polynucleotide that includes additional coding and/or non-coding sequence.

Exemplary polynucleotides encoding a polypeptide include the nucleotide sequences set forth in SEQ ID NO:1, SEQ ID NO:3 and SEQ ID NO:5. For example, a nucleic acid sequence encoding a human Claspin genomic sequence includes a region encoding human claspin protein (nucleotides 4933 to 53909) as well as regions encoding regulatory sequences (nucleotides 1–4932), regions encoding one or more start sites (nucleotides 4933–10537), regions encoding introns, and regions encoding exons. Nucleotides located at intron-exon and exon-intron borders are potential splice sites. Such intron-exon and exon-intron sites include exonintron 4956–4957; intron-exon 9476–9477; exon-intron 9585–9586; intron-exon 10088–10089; exon-intron 10537–10538; intron-exon 11481–11482; exon-intron 11647–11648; intron-exon 12325–12326; exon-intron 12399–12400; intron-exon 12732–12733; exon-intron 12805–12806; intron-exon 13598–13599; exon-intron 13707–13708; intron-exon 13886–13887; exon-intron 14461–14462; intron-exon 20866–20867; exon-intron 21058–21059; intron-exon 23296–23297; exon-intron 23553–23554; intron-exon 24991–24992; exon-intron 25170–25171; intron-exon 25271–25272; exon-intron 25336–25337; intron-exon 26198–26199; exon-intron 26398–26399; intron-exon 26741–26742; exon-intron 26896–26897; intron-exon 27810–27811; exon-intron 28037–28038; intron-exon 29240–29241; exon-intron 29352–29353; intron-exon 31272–31273; exon-intron 31348–31349; intron-exon 31561–31562; exon-intron 31662–31663; intron-exon 35273–35274; exon-intron 35438–35439; intron-exon 35545–35546; exon-intron 35667–35668; intron-exon 36220–36221; exon-intron 36348–36349; intron-exon 36705–36706; exon-intron 36811–36812; intron-exon 37381–37382; exon-intron 37464–37465; and intron-exon 37727–37728.

The nucleotides of the invention can be deoxyribonucleotides, ribonucleotides in which uracil (U) is present in place of thymine (T), or modified forms of either nucleotide. The nucleotides of the invention can be complementary to the deoxynucleotides or to the ribonucleotides. A polynucleotide encoding a Claspin protein includes "degenerate variants", sequences that are degenerate as a result of the genetic code. There are 20 natural amino acids, most of which are specified by more than one codon. Therefore, all degenerate nucleotide sequences are included in the invention as long as the amino acid sequence of a polypeptide encoded by the nucleotide sequence of SEQ ID NO: 1 or SEQ ID NO:3 is functionally unchanged.

A nucleic acid molecule encoding a Claspin protein includes sequences encoding functional Claspin polypeptides as well as functional fragments thereof. As used herein, the term "functional polypeptide" refers to a polypeptide which possesses biological function or activity which is identified through a defined functional assay (see Examples), and which is associated with a particular biologic, morphologic, or phenotypic alteration in the cell, for example an alteration in the timing of the cell cycle. The term "functional fragments of Claspin protein" refers to fragments of a Claspin protein that retain a Claspin activity, e.g., the ability to interact with Chk1 proteins, and the like. Additionally, functional Claspin fragments may act as competitive inhibitors of Claspin binding, for example, biologically functional fragments varying in size from a polypeptide fragment as small as an epitope capable of binding an antibody molecule to a large polypeptide can participate in the characteristic induction or programming of biological changes within a cell.

An alternative embodiment of the invention provides nucleotide fragments having at least 15 base pairs and that hybridizes to a polynucleotide as set forth in nucleotides 1–331, 799–903, 1232–1543, 2147–2486 and 2964–4756 of SEQ ID NO:3.

Yet another embodiment of the invention provides an isolated polynucleotide, wherein the nucleotide is at least 15 base pairs in length which hybridizes under moderately to highly stringent conditions to DNA encoding a polypeptide as set forth in SEQ ID NO:2 or SEQ ID NO:4. In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderately stringent conditions); and 0.1×SSC at about 68° C. (highly stringent conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

A polynucleotide agent can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes a peptide, for expressing the encoded peptide in a particular cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51–64, 1994; Flotte, *J. Bioenerg. Biomemb.* 25:37–42, 1993; Kirshenbaum et al., *J. Clin. Invest.* 92:381–387, 1993; each of which is incorporated herein by reference).

A polynucleotide useful in a method of the invention also can be operatively linked to tissue specific regulatory element, for example, a neuron specific regulatory element, such that expression of an encoded peptide agent is restricted to neurons in an individual, or to neurons in a mixed population of cells in culture, for example, an organ culture. For example, neuronal promoters such as the myelin basic protein promoter and other neuronal-specific promotes known to those of skill in the art may be used. Muscle-regulatory elements including, for example, the muscle creatine kinase promoter (Sternberg et al., *Mol. Cell. Biol.* 8:2896–2909, 1988, which is incorporated herein by reference) and the myosin light chain enhancer/promoter (Donoghue et al., *Proc. Natl. Acad. Sci., USA* 88:5847–5851, 1991, which is incorporated herein by reference) are well known in the art. A variety of other promoters have been identified which are suitable for up regulating expression in cardiac tissue. Included, for example, are the cardiac I-myosin heavy chain (AMHC) promoter and the cardiac I-actin promoter. Other examples of tissue-specific regulatory elements include, tissue-specific promoters, pancreatic (insulin or elastase), and actin promoter in smooth muscle cells.

Through the use of promoters, such as milk-specific promoters, recombinant retroviruses may be isolated directly from the biological fluid of the progeny.

A Claspin polynucleotide of the invention can be inserted into a vector, which can be a cloning vector or a recombinant expression vector. The term "expression vector" refers to a plasmid, virus or other vehicle known in the art that has been manipulated by insertion or incorporation of a polynucleotide, particularly, with respect to the present invention, a polynucleotide encoding all or a peptide portion of a Claspin protein. Such expression vectors contain a promoter sequence, which facilitates the efficient transcription of the inserted genetic sequence of the host. The expression vector generally contains an origin of replication, a promoter, as well as specific genes which allow phenotypic selection of the transformed cells. Vectors suitable for use in the present invention include, but are not limited to, the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter, which can be a T7 promoter, metallothionein I promoter, polyhedrin promoter, or other promoter as desired, particularly tissue specific promoters or inducible promoters.

Viral expression vectors can be particularly useful for introducing a polynucleotide useful in a method of the invention into a cell, particularly a cell in a subject. Viral vectors provide the advantage that they can infect host cells with relatively high efficiency and can infect specific cell types. For example, a polynucleotide encoding a Claspin protein or functional peptide portion thereof can be cloned into a baculovirus vector, which then can be used to infect an insect host cell, thereby providing a means to produce large amounts of the encoded protein or peptide portion. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpes virus vectors, vaccinia virus vectors, and the like (see Miller and Rosman, *BioTechniques* 7:980–990, 1992; Anderson et al., *Nature* 392:25–30 Suppl., 1998; Verma and Somia, *Nature* 389:239–242, 1997; Wilson, *New Engl. J. Med.* 334:1185–1187 (1996), each of which is incorporated herein by reference).

When retroviruses, for example, are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

A polynucleotide, which can be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events.

A polynucleotide sequence encoding a Claspin protein can be expressed in either prokaryotes or eukaryotes. Hosts can include microbial, yeast, insect and mammalian organisms. Methods of expressing polynucleotides having eukaryotic or viral sequences in prokaryotes are well known in the art, as are biologically functional viral and plasmid DNA vectors capable of expression and replication in a host. Methods for constructing an expression vector containing a polynucleotide of the invention are well known, as are factors to be considered in selecting transcriptional or translational control signals, including, for example, whether the polynucleotide is to be expressed preferentially in a particular cell type or under particular conditions (see, for example, Sambrook et al., supra, 1989).

A variety of host cell/expression vector systems can be utilized to express a Claspin polypeptide coding sequence, including, but not limited to, microorganisms such as bacteria transformed with recombinant bacteriophage DNA, plasmid DNA or cosmid DNA expression vectors; yeast cells transformed with recombinant yeast expression vectors; plant cell systems infected with recombinant virus expression vectors such as a cauliflower mosaic virus or tobacco mosaic virus, or transformed with recombinant plasmid expression vector such as a Ti plasmid; insect cells infected with recombinant virus expression vectors such as a baculovirus; animal cell systems infected with recombinant virus expression vectors such as a retrovirus, adenovirus or vaccinia virus vector; and transformed animal cell systems genetically engineered for stable expression. Where the expressed Claspin protein is post-translationally modified, for example, by glycosylation, it can be particularly advantageous to select a host cell/expression vector system that can effect the desired modification, for example, a mammalian host cell/expression vector system.

Depending on the host cell/vector system utilized, any of a number of suitable transcription and translation elements, including constitutive and inducible promoters, transcription enhancer elements, transcription terminators, and the like can be used in the expression vector (Bitter et al., *Meth. Enzymol.* 153:516–544, 1987). For example, when cloning in bacterial systems, inducible promoters such as pL of bacteriophage λ, plac, ptrp, ptac (ptrp-lac hybrid promoter) and the like can be used. When cloning in mammalian cell systems, promoters derived from the genome of mammalian cells, for example, a human or mouse metallothionein promoter, or from mammalian viruses, for example, a retrovirus long terminal repeat, an adenovirus late promoter or a vaccinia virus 7.5K promoter, can be used. Promoters produced by recombinant DNA or synthetic techniques can also be used to provide for transcription of the inserted GDF receptors coding sequence.

In yeast cells, a number of vectors containing constitutive or inducible promoters can be used (see Ausubel et al., supra, 1987, see chapter 13; Grant et al., *Meth. Enzymol.* 153:516–544, 1987; Glover, *DNA Cloning* Vol. II (IRL Press, 1986), see chapter 3; Bitter, *Meth. Enzymol.* 152: 673–684, 1987; see, also, *The Molecular Biology of the Yeast Saccharomyces* (Eds., Strathern et al., Cold Spring Harbor Laboratory Press, 1982), Vols. I and II). A constitutive yeast promoter such as ADH or LEU2 or an inducible promoter such as GAL can be used (Rothstein, *DNA Cloning* Vol. II (supra, 1986), chapter 3). Alternatively, vectors can be used which promote integration of foreign DNA sequences into the yeast chromosome.

Eukaryotic systems, particularly mammalian expression systems, allow for proper post-translational modifications of expressed mammalian proteins. Eukaryotic cells which possess the cellular machinery for proper processing of the primary transcript, glycosylation, phosphorylation, and advantageously, plasma membrane insertion of the gene product can be used as host cells for the expression of a Claspin protein, or functional peptide portion thereof.

Mammalian cell systems which utilize recombinant viruses or viral elements to direct expression can be engineered. For example, when using adenovirus expression vectors, the Claspin polypeptide coding sequence can be ligated to an adenovirus transcription/translation control complex, e.g., the late promoter and tripartite leader sequence. Alternatively, the vaccinia virus 7.5K promoter can be used (Mackett et al., *Proc. Natl. Acad. Sci., USA* 79:7415–7419, 1982; Mackett et al., *J. Virol.* 49:857–864, 1984; Panicali et al., *Proc. Natl. Acad. Sci., USA* 79:4927–4931, 1982). Particularly useful are bovine papilloma virus vectors, which can replicate as extrachromosomal elements (Sarver et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host cell chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the Claspin protein gene in host cells (Cone and Mulligan, *Proc. Natl. Acad. Sci., USA* 81:6349–6353, 1984). High level expression can also be achieved using inducible promoters, including, but not limited to, the metallothionein IIA promoter and heat shock promoters.

For long term, high yield production of recombinant proteins, stable expression is preferred. Rather than using expression vectors which contain viral origins of replication, host cells can be transformed with Claspin protein cDNA controlled by appropriate expression control elements such as promoter, enhancer, sequences, transcription terminators, and polyadenylation sites, and a selectable marker. The selectable marker in the recombinant plasmid can confer resistance to the selection, and allows cells to stably integrate the plasmid into their chromosomes and grow to form foci, which, in turn can be cloned and expanded into cell lines. For example, following the introduction of foreign DNA, engineered cells can be allowed to grow for 1 to 2 days in an enriched media, and then are switched to a selective media. A number of selection systems can be used, including, but not limited to, the herpes simplex virus thymidine kinase (Wigler et al., *Cell* 11:223, 1977), hypoxanthine-guanine phosphoribosyltransferase (Szybalska and Szybalski, *Proc. Natl. Acad. Sci., USA* 48:2026, 1982), and adenine phosphoribosyltransferase (Lowy, et al., *Cell* 22:817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Proc. Natl. Acad. Sci. USA* 77:3567, 1980; O'Hare et al., *Proc. Natl. Acad. Sci., USA* 78: 1527, 1981); gpt, which confers resistance to mycophenolic acid (Mulligan and Berg, *Proc. Natl. Acad. Sci., USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1984) genes. Additional selectable genes, including trpB, which allows cells to utilize indole in place of tryptophan; hisD, which allows cells to utilize histinol in place of histidine (Hartman and Mulligan, *Proc. Natl. Acad. Sci., USA* 85:8047, 1988); and ODC (ornithine decarboxylase) which confers resistance to the ornithine decarboxylase inhibitor, 2-(difluoromethyl)-DL-ornithine, DFMO (McConlogue, *Curr. Comm. Mol. Biol.* (Cold Spring Harbor Laboratory Press, 1987), also have been described.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be cotransformed with DNA sequences encoding the Claspin proteins of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Gluzman, *Eukaryotic Viral Vectors* (Cold Spring Harbor Laboratory Press, 1982)).

The invention provides a method for producing a polypeptide encoded by the nucleotide sequence of SEQ ID NO:1 or SEQ ID NO:3 or fragments thereof, including culturing the host cell under conditions suitable for the expression of the polypeptide and recovering the polypeptide from the host cell culture.

A Claspin polypeptide or a fragment thereof, can be encoded by a recombinant or non-recombinant nucleic acid molecule and expressed in a cell. Preparation of a Claspin polypeptide by recombinant methods provides several advantages. In particular, the nucleic acid sequence encoding the Claspin polypeptide can include additional nucleotide sequences encoding, for example, peptides useful for recovering the Claspin polypeptide from the host cell. A Claspin polypeptide can be recovered using well known methods, including, for example, precipitation, gel filtration, ion exchange, reverse-phase, or affinity chromatography (see, for example, Deutscher et al., Guide to Protein Purification in Meth. Enzymol., Vol. 182, (Academic Press, 1990)). Such methods also can be used to purify a fragment of a Claspin polypeptide, for example, a particular binding sequence, from a cell in which it is naturally expressed.

A recombinant nucleic acid molecule encoding a Claspin polypeptide or a fragment thereof can include, for example, a protease site, which can facilitate cleavage of the Claspin polypeptide from a non-Claspin polypeptide sequence, for example, a tag peptide, secretory peptide, or the like. As such, the recombinant nucleic acid molecule also can encode a tag peptide such as a polyhistidine sequence, a FLAG peptide (Hopp et al., Biotechnoloy 6:1204 (1988)), a glutathione S-transferase polypeptide or the like, which can be bound by divalent metal ions, a specific antibody (U.S. Pat. No. 5,011,912), or glutathione, respectively, thus facilitating recovery and purification of the Claspin polypeptide comprising the peptide tag. Such tag peptides also can facilitate identification of the Claspin polypeptide through stages of synthesis, chemical or enzymatic modification, linkage, or the like. Methods for purifying polypeptides comprising such tags are well known in the art and the reagents for performing such methods are commercially available.

A nucleic acid molecule encoding a Claspin polypeptide can be engineered to contain one or more restriction endonuclease recognition and cleavage sites, which can facilitate, for example, substitution of an element of the Claspin polypeptide such as the selective recognition domain or, where present, a spacer element. As such, related Claspin polypeptides can be prepared, each having a similar activity, but having specificity for different function-forming contexts. A restriction endonuclease site also can be engineered into (or out of) the sequence coding a peptide portion of the Claspin polypeptide, and can, but need not change one or more amino acids encoded by the particular sequence. Such a site can provide a simple means to identify the nucleic acid sequence, based on cleavage (or lack of cleavage) following contact with the relevant restriction endonuclease, and, where introduction of the site changes an amino acid, can further provide advantages based on the substitution.

Antibodies of the invention may bind to Claspin polypeptides provided by the invention to prevent normal interactions of Claspin proteins. Binding of antibodies to Claspin proteins can interfere with, for example, cell cycle progression. Binding of antibodies can interfere with Claspin protein binding to intracellular proteins, for example, to a Chk1 protein and the like.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immmunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "antibody" as used in this invention includes intact molecules as well as fragments thereof, such as Fab, F(ab')2, and Fv which are capable of binding to an epitopic determinant present in an invention polypeptide. Such antibody fragments retain some ability to selectively bind with its antigen or receptor.

Methods of making these fragments are known in the art. (See for example, Harlow and Lane, Antibodies: A Laboratory Manual, Cold Spring Harbor Laboratory, New York (1988), incorporated herein by reference). Monoclonal antibodies are made from antigen containing fragments of the protein by methods well known to those skilled in the art (Kohler & Milstein, Nature 256:495 (1975); Coligan et al., sections 2.5.1–2.6.7; and Harlow et al., Antibodies: A Laboratory Manual, page 726 (Cold Spring Harbor Pub. 1988), which are hereby incorporated by reference. Briefly, monoclonal antibodies can be obtained by injecting mice with a composition comprising an antigen/ligand, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., "Purification of Immunoglobulin G (IgG)" in Methods In Molecular Biology, Vol. 10, pages 79–104 (Humana Press 1992).

Antibodies that bind to an invention polypeptide can be prepared using an intact polypeptide or fragments containing small peptides of interest as the immunizing antigen. For example, it may be desirable to produce antibodies that specifically bind to the amino- or carboxyl-terminal domains of an invention polypeptide. For the preparation of polyclonal antibodies, the polypeptide or peptide used to immunize an animal is derived from translated cDNA or chemically synthesized and can be conjugated to a carrier protein, if desired. Commonly used carrier proteins which may be chemically coupled to the immunizing peptide include keyhole limpet hemocyanin (KLH), thyroglobulin, bovine serum albumin (BSA), tetanus toxoid, and the like.

Invention polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See, for example, Coligan, et al., Unit 9, Current Protocols in Immunology, Wiley Interscience, 1994, incorporated herein by reference).

The antibodies of the invention can be bound to many different carriers and used to detect the presence of an antigen comprising the polypeptides of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal and polyclonal antibodies of the invention for the in vivo detection of antigen, e.g., a Claspin protein, the detectably labeled antibody is given a dose which is diagnostically effective. The term "diagnostically effective" means that the amount of detectably labeled antibody is administered in sufficient quantity to enable detection of the site having the antigen comprising a polypeptide of the invention for which the antibodies are specific.

The concentration of detectably labeled antibody which is administered should be sufficient such that the binding to those cells having the polypeptide is detectable compared to the background. Further, it is desirable that the detectably labeled antibody be rapidly cleared from the circulatory system in order to give the best target-to-background signal ratio.

As a rule, the dosage of detectably labeled antibody for in vivo treatment or diagnosis will vary depending on such factors as age, sex, and extent of disease of the individual. Such dosages may vary, for example, depending on whether multiple injections are given, antigenic burden, and other factors known to those of skill in the art.

In another series of embodiments, the present invention provides transgenic animal models diseases or disorders associated with mutations in the Claspin protein genes. The animal may be essentially any amphibian, reptile, fish, mammal, and the like. Preferably, the transgenic animal is mammalian including rats, mice, hamsters, guinea pigs, rabbits, dogs, cats, goats, sheep, pigs, and non-human primates. In addition, invertebrate models, including nematodes and insects, may be used for certain applications. The animal models are produced by standard transgenic methods including microinjection, transfection, or by other forms of transformation of embryonic stem cells, zygotes, gametes, and germ line cells with vectors including genomic or cDNA fragments, minigenes, homologous recombination vectors, viral insertion vectors and the like. Suitable vectors include vaccinia virus, adenovirus, adeno associated virus, retrovirus, liposome transport, neurotropic viruses, herpes simplex virus, and the like. The animal models may include transgenic sequences comprising or derived from Claspin proteins including normal and mutant sequences, intronic, exonic and untranslated sequences, and sequences encoding subsets of Claspin proteins such as functional domains.

The major types of animal models provided include: (1) Animals in which a normal Claspin gene has been recombinantly introduced into the genome of the animal as an additional gene, under the regulation of either an exogenous or an endogenous promoter element, and as either a minigene or a large genomic fragment; in which a normal Claspin gene has been recombinantly substituted for one or both copies of the animal's homologous Claspin gene by homologous recombination or gene targeting; and/or in which one or both copies of one of the animal's homologous Claspin genes have been recombinantly "humanized" by the partial substitution of sequences encoding the human homologue by homologous recombination or gene targeting. (2) Animals in which a mutant Claspin gene has been recombinantly introduced into the genome of the animal as an additional gene, under the regulation of either an exogenous or an endogenous promoter element, and as either a minigene or a large genomic fragment; in which a mutant Claspin gene has been recombinantly substituted for one or both copies of the animal's homologous Claspin gene by homologous recombination or gene targeting; and/or in which one or both copies of one of the animal's homologous Claspin genes have been recombinantly "humanized" by the partial substitution of sequences encoding a mutant human homologue by homologous recombination or gene targeting. (3) Animals in which a mutant version of one of that animal's Claspin genes has been recombinantly introduced into the genome of the animal as an additional gene, under the regulation of either an exogenous or an endogenous promoter element, and as either a minigene or a large genomic fragment; and/or in which a mutant version of one of that animal's claspin genes has been recombinantly substituted for one or both copies of the animal's homologous Claspin gene by homologous recombination or gene targeting. (4) "Knock-out" animals in which one or both copies of one of the animal's Claspin genes have been partially or completely deleted by homologous recombination or gene targeting, or have been inactivated by the insertion or substitution by homologous recombination or gene targeting of exogenous sequences.

In a preferred embodiment of the invention, there is provided a transgenic non-human animal having a transgene that expresses a Claspin-encoding polynucleotide chromosomally integrated into the germ cells of the animal. Animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, Jan. 12, 1994) can be utilized whereby the embryo is obtained from a sacrificed hen approximately two and one-half h after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The non-human animals of the invention are murine typically (e.g., mouse). The transgenic non-human animals of the invention are produced by introducing "transgenes" into the germline of the non-human animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., Proc. Natl. Acad. Sci. USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionine, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, (1976) Proc. Natl. Acad. Sci USA 73:1260–1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al, (1985) Proc. Natl. Acad. Sci. USA 82:6927–6931; Van der Putten, et al., (1985) Proc. Natl. Acad. Sci USA 82:6148–6152, ). Transfection is easily and efficiently obtained by culturing the blastomeres on a monolayer of virus-producing cells (Van der Putten, supra; Stewart, et al., (1987) EMBO J. 6:383–388). Alternatively, infection can be performed at a later stage. Virus or virus-producing cells can be injected into the blastocoel (Jahner et al. (1982) Nature 298:623–628). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (Jahner et al., supra).

A third type of target cell for transgene introduction is the embryonal stem cell (ES). ES cells are obtained from pre-implantation embryos cultured in vitro and fused with embryos (M. J. Evans et al. Nature 292:154–156, 1981; M. O. Bradley et al., Nature 309: 255–258, 1984; Gossler, et al., Proc. Natl. Acad. Sci USA 83: 9065–9069, 1986; and Robertson et al., Nature 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode Claspin polypeptide-sense and antisense polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. As used herein, The term "transgenic" includes any transgenic technology familiar to those in the art which can produce an organism carrying an introduced transgene or one in which an endogenous gene has been rendered non-functional or "knocked out".

Various methods of amplifying target sequences can be used to prepare DNA encoding a polynucleotide or nucleotide fragment according to the sequence set forth in SEQ ID NO:3. Polymerase chain reaction (PCR) technology is used to amplify such nucleic acid sequences directly from mRNA, from cDNA, from genomic libaries or cDNA libraries. Isolated sequences encoding a human Claspin protein may also be used as templates for PCR amplification. PCR techniques require the synthesis of oligonucleotide primers complementary to the two 3' borders of the DNA region to be amplified. The polymerase chain reaction is then performed using two primers. (see *PCR Protocols: A Guide to Methods and Applications*, Innis, Gelfand, Sninsky, and White, eds., Academic Press, San Diego (1990).) Primers can be selected to amplify the entire region or regions that encode the full-length sequence of interest or to amplify smaller DNA segments.

Various method of screening and detecting nucleic acid mutations and polymorphisms are known in the art including hybridization with allele-specific oligonucleotide probes, including immobilized oligonucleotides and oligonucleotide arrays, allele-specific PCR (Newton et al. (1989) *Nucl. Acids, Res.* 17:2503–2516), mismatch-repair detection (Faham and Cox (1995) *Genome Res.* 5:474–482); restriction fragment length polymorphism detection based on allele-specific restriction endonuclease cleavage (Kan and Dozy (1978) *Lancet* 2: 910–912), hybridization with allele-specific oligonucleotide probes (Wallace et al. (1978) *Nucl Acids Res* 6: 3543–3557), including immobilized oligonucleotides (Saiki et al. (1989) *Proc. Natl. Acad. Sci. U.S.A.* 86: 6230–6234) or oligonucleotide arrays (Maskos and Southern (1993) *Nucl Acids Res* 21: 2269–2270), binding of MutS protein (Wagner et al. (1995) *Nucl Acids Res* 23: 3944–3948, denaturing-gradient gel electrophoresis (DGGE) (Fisher and Lerman et al. (1983) *Proc. Natl. Acad. Sci. U.S.A.* 80: 1579–1583), single-strand-conformation-polymorphism detection (Orita et al. (1983) *Genomics* 5: 874–879), RNAase cleavage at mismatched base-pairs (Myers et al. (1985) *Science* 230: 1242), chemical (Cotton et al (1988). *Proc. Natl. Acad. Sci. U.S.A.* 85: 4397–4401) or enzymatic (Youil et al. (1995) *Proc. Natl. Acad. Sci. U.S.A.* 92: 87–91) cleavage of heteroduplex DNA, methods based on allele specific primer extension (Syvanen et al., (1990) *Genomics* 8: 684–692), genetic bit analysis (GBA) (Nikiforov et al. (1994) *Nucl Acids Res* 22: 4167–4175), the oligonucleotide-ligation assay (OLA) (Landegren et al. (1988) *Science* 241: 1077), the allele-specific ligation chain reaction (LCR) (Barrany (1991) Proc. *Natl. Acad. Sci. U.S.A.* 88: 189–193), gap-LCR (Abravaya et al. (1995) *Nucl Acids Res* 23: 675–682), and radioactive and/or fluorescent DNA sequencing using standard procedures well known in the art.

A method is provided for identifying a compound that modulates cell cycle progression. The method includes incubating the compound and a cell expressing a Claspin protein under conditions sufficient to permit the compound to interact with the cell and comparing the cell cycle progression in the cell incubated with the compound with cell cycle progression of a cell not incubated with the compounds. A suitable control includes, but is not limited to, a cell cycle progression of a cell not contacted with the compound.

Modulation of cell cycle progression may be a speeding up of the cell cycle or it may be a slowing down of the cell cycle. A slowing down of the cell cycle can include an increase in the time a cell is in a gap phase, e.g., G0, the pause after mitosis, G1, the gap after mitosis before DNA synthesis starts or G2, the gap after DNA synthesis is complete and before mitosis and cell division begins. The gap phases allow for checkpoints, stopping points in the cell cycle where progress can be halted. During this time, cellular mechanisms insure that DNA is not damaged, or incompletely or incorrectly replicated. Speeding up the cell cycle could allow rounds of mitosis to proceed in a shorter period of time. This may result in damaged DNA which, following mitosis, could have serious or fatal effects for the daughter cells.

Any Claspin protein may be employed in invention methods. The Claspin protein can be an un-phosphorylated form or a phosphorylated form, wherein one or more phosphate groups are chemically linked to a Claspin protein. In certain embodiments a Claspin protein according to the amino acid sequence set forth in SEQ ID NO:2 or SEQ ID NO:4 is used.

The cell may be any cell of interest, including but not limited to neuronal cells, glial cells, cardiac cells, bronchial cells, uterine cells, testicular cells, liver cells, renal cells, intestinal cells, cells from the thymus and spleen, placental cells, endothelial cells, endocrine cells including thyroid, parathyroid, pituitary and the like, smooth muscle cells and skeletal muscle cells. The term "incubating" includes conditions which allow contact between the test compound and the cell of interest. "Contacting" may include in solution or in solid phase.

Compounds that modulate a cellular response can include peptides, peptidomimetics, polypeptides, pharmaceuticals, chemical compounds and biological agents, for example. Antibodies, neurotropic agents, anti-epileptic compounds and combinatorial compound libraries can also be tested using the method of the invention. One class of organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

The test agent may also be a combinatorial library for screening a plurality of compounds. Compounds such as peptides identified in the method of the invention can be further cloned, sequenced, and the like, either in solution of after binding to a solid support, by any method usually applied to the isolation of a specific DNA sequence Molecular techniques for DNA analysis (Landegren et al., *Science* 242:229–237, 1988) and cloning have been reviewed (Sambrook et al., *Molecular Cloning: a Laboratory Manual*, 2nd Ed.; Cold Spring Harbor Laboratory Press, Plainview, N.Y., 1998, herein incorporated by reference).

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including, but not limited to: peptides, saccharides, fatty acids, steroids, purines, pyrimidines, derivatives, structural analogs or combinations thereof.

A variety of other agents may be included in the screening/identification assay. These include agents like salts, neutral proteins, e.g., albumin, detergents, etc. that are used to facilitate optimal protein-protein binding and/or reduce nonspecific or background interactions. Reagents that improve the efficiency of the assay, such as protease inhibitors, nuclease inhibitors, antimicrobial agents and the like may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 10 h will be sufficient.

In another aspect of the invention, there is provided a method of modulating cell cycle progression by providing to the cell a reagent that affects the activity or expression of a Claspin polypeptide.

Claspin expression and activity are required for the proper operation of the DNA replication checkpoint in the cell cycle. Phosphorylation and activation of Chk1 proteins, preferably Xchk1, is dependent on Claspin activity. Detection of altered (decreased or increased) levels of Claspin protein activity can be accomplished by performing assays to assess cell cycle progression and, phosphorylation and activation of Chk1 proteins (see Examples section). Detection of altered (decrease or increased) levels of Claspin expression can be accomplished by numerous methods, e.g., hybridization of nucleic acids isolated from a cell of interest with a Claspin polynucleotide of the invention. Analyses, such as Northern Blot analysis, are utilized to measure expression of Claspin, by assessing the level of Claspin transcript. Other standard nucleic acid detection techniques will be known to those of skill in the art. Detection of altered levels of Claspin can also accomplished using assays designed to detect Claspin polypeptide. For example, antibodies or peptides that specifically bind a Claspin polypeptide can be utilized. Analyses, such as a radioimmune assay or an enzyme-linked immunosorbant assay (ELISA) are then used to measure Claspin, such as to measure protein concentration qualitatively or quantitatively. Immunohistochemical methods can also be used to assess expression of Claspin protein.

The term "modulating the cell cycle progression" refers to altering the cell cycle by inhibiting its progress or by stimulating its progress. For example, inhibition of the cell cycle can be accomplished by inducing a gap phase that would not have occurred in the absence of modulation or increasing the duration of a gap phase relative to the duration in the absence of modulation. Stimulation of the cell cycle can be accomplished by eliminating a gap phase that would have occurred in the absence of modulation or decreasing the duration of a gap phase relative to the duration in the absence of modulation.

The term "reagent" as used herein describes any molecule, e.g., protein, nucleic acid, or pharmaceutical, with the capability of altering the expression of Claspin polynucleotide or activity of Claspin polypeptide. Candidate reagents include nucleic acids encoding a Claspin polypeptide, or that interfere with expression of a Claspin polypeptide, such as an antisense nucleic acid, ribozymes, and the like. Candidate reagents further include antibodies that specifically recognize Claspin polypeptides. Candidate reagents also encompass numerous chemical classes wherein the agent modulates Claspin expression or activity. One exemplary reagent is caffeine.

In another embodiment of the invention, there is provided a method for modulating a cell cycle progression. The method includes providing to the cell a reagent that modulates the activity or expression of a Chk1 polypeptide. The Chk1 polypeptide can be, for example, human Chk1, and the reagent can be a human Claspin polypeptide. One exemplary human Claspin polypeptide has the amino acid sequence set forth in SEQ ID NO:4.

In still another embodiment of the invention, there is provided a method for identifying a compound that can block the interaction of a Claspin protein with a Chk1 protein. The method includes incubating a candidate compound with a cell expressing a Claspin protein and a Chk1 protein under conditions that allow the compound to interact with the cell. The interaction of the Claspin protein with the Chk1 protein is compared to the interaction of the Claspin protein with a Chk1 protein in a cell not incubated with the compound. A difference in interaction, in particular, an interaction is completely or partially blocked, is indicative of a compound that can block the interaction of a Claspin protein with a Chk1 protein. In another embodiment, the method includes incubating the candidate compound in an egg extract with a Claspin protein and a Chk1 protein under conditions that allow the compound to interact with the Claspin protein or the Chk1 protein. A difference in interaction, i.e., binding of Claspin to Chk1 between the extract containing the compound and an extract without the compound is indicative of a compound that can block the interaction of a Claspin protein with a Chk1 protein.

In yet another embodiment of the invention, there is provided a method of treating a subject having a disorder associated with cell cycle progression. The method includes administering to a subject in need thereof a therapeutically effective amount of a compound that modulates a Claspin polypeptide activity.

A method is further provided for treating a disorder associated with a Claspin protein activity. The method includes administering to a subject in need thereof a therapeutically effective amount of a reagent that modulates a Claspin protein activity.

Treatment of a disorder associated with cell cycle progression may influence Claspin binding to Chk1 proteins, Claspin binding to kinases or phosphatases, phosphorylation of a Chk1 protein, cell number, rounds of mitosis, DNA repair, functional properties of Claspin proteins, and the like.

Modulation of a Claspin polypeptide activity envisions the suppression of Claspin activity or expression when Claspin is overexpressed or has an increased activity as compared to a control. The term "modulate" also includes the augmentation of the expression of Claspin polypeptide when it is underexpressed or has a decreased activity as compared to a control.

The disorder can be a cell proliferative disorder. A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumor that is noncancerous, e.g. its cells do not invade surrounding tissues or metastasize to distant sites. The term "malignant" refers to a tumor that is metastastic, invades contiguous tissue or no longer under normal cellular growth control. Neoplasms are generally derived from cells that normally maintain a proliferative capacity; almost every cell and tissue type can give rise to a neoplasm.

Where a disorder is associated with the increased expression of a Claspin polypeptide, nucleic acid sequences that interfere with the expression of a Claspin polypeptide can be used (see Kushner and Silverman (2000) *Curr. Oncol. Reports*, 2:23–30, herein incorporated by reference). In this manner, binding to a Chk1 protein, phosphorylation of a Chk1 protein, cell cycle progression, and the like can be modulated. This approach also utilizes, for example, antisense nucleic acid, ribozymes, or triplex agents to block transcription or translation of a Claspin mRNA, either by masking that mRNA with an antisense nucleic acid or triplex agent, or by cleaving it with a ribozyme in disorders associated with increased Claspin expression. Alternatively, a dominant negative form of a Claspin polypeptide could be administered.

When Claspin is overexpressed, candidate agents include antisense nucleic acid sequences. Antisense nucleic acids are DNA or RNA molecules that are complementary to at least a portion of a specific mRNA molecule (Weintraub (1990) *Scientific American*, 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, (1988) *Anal. Biochem.*, 172:289).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher et al., (1991) *Antisense Res. and Dev.*, 1:227; Helene, (1991) *Anticancer Drug Design*, 6:569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, *J. Amer. Med. Assn.*, 260:3030). A major advantage of this approach is that, because they are sequence-specific, only mRNAs with particular sequences are inactivated.

There are two basic types of ribozymes namely, tetrahymena-type (Hasselhoff (1988) *Nature*, 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

When a disorder is associated with the decreased expression of a Claspin polypeptide, nucleic acid sequences that encode a Claspin polypeptide can be used. An agent which modulates claspin expression includes a polynucleotide encoding a polypeptide of SEQ ID NO:2, SEQ ID NO:4, or a conservative variant thereof. Alternatively, an agent of use with the subject invention includes reagents that increase the expression of a polynucleotide encoding Claspin or a reagent that increases the activity of a Claspin polypeptide. Another embodiment of the invention provides a computer readable medium having store thereon a nucleic acid sequence selected from the group consisting of SEQ ID NO:1, SEQ ID NO:3, and sequences substantially identical thereto, or a polypeptide sequence selected from the group consisting of SEQ ID NO:2, SEQ ID NO:4, and sequences substantially identical thereto.

In another embodiment of the invention, there is provided a kit for diagnosing a claspin-associated disorder. The kit includes a nucleic acid composition for measuring in a cell sample from a subject a level of nucleic acid encoding a human Claspin.

A further embodiment of the invention provides a computer system comprising a processor and a data storage device wherein said date storage device has stored thereon a nucleic acid sequence selected from the group consisting of SEQ ID NO:1, SEQ ID NO:3, and sequences substantially identical thereto, or a polypeptide sequence selected from the group consisting of SEQ ID NO:2, SEQ ID NO:4, and sequences substantially identical thereto. The computer system, additionally can contain a sequence comparison algorithm and a data storage device having at least one reference sequence stored on it. The sequence comparison algorithm comprises a computer program which indicates polymorphisms. The term "polymorphism", as used herein, refers to the existence of multiple alleles at a single locus. Polymorphism can be are several types including, for example, those that change DNA sequence but do not change protein sequence, those that change protein sequence without changing function, those that create proteins with a different activity, and those that create proteins that are non-functional.

Embodiments of the invention include systems (e.g., internet based systems), particularly computer systems which store and manipulate the coordinate and sequence information described herein. One example of a computer system 100 is illustrated in block diagram form in FIG. 3. As used herein, "a computer system" refers to the hardware components, software components, and data storage components used to analyze invention sequences. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a–c in a network or wide area network to provide centralized access to the computer system 100.

Figure 4:
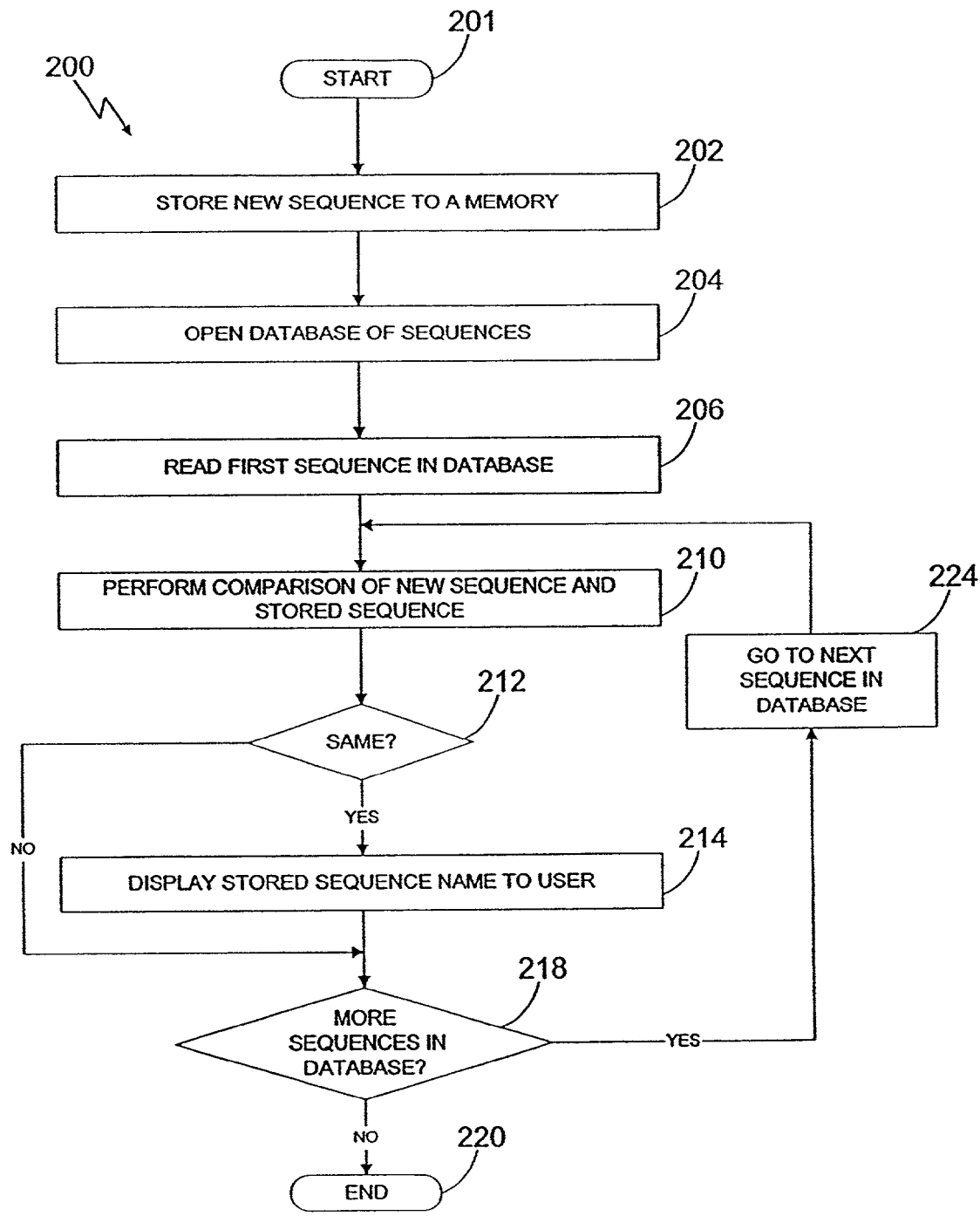
FIG. 4 is a flow diagram illustrating one embodiment of process 200 for comparing a new nucleotide or protein sequence with a database of sequences in order to determine the homology levels between the new sequence and the sequences in the database.

FIG. 4 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Figure 5:
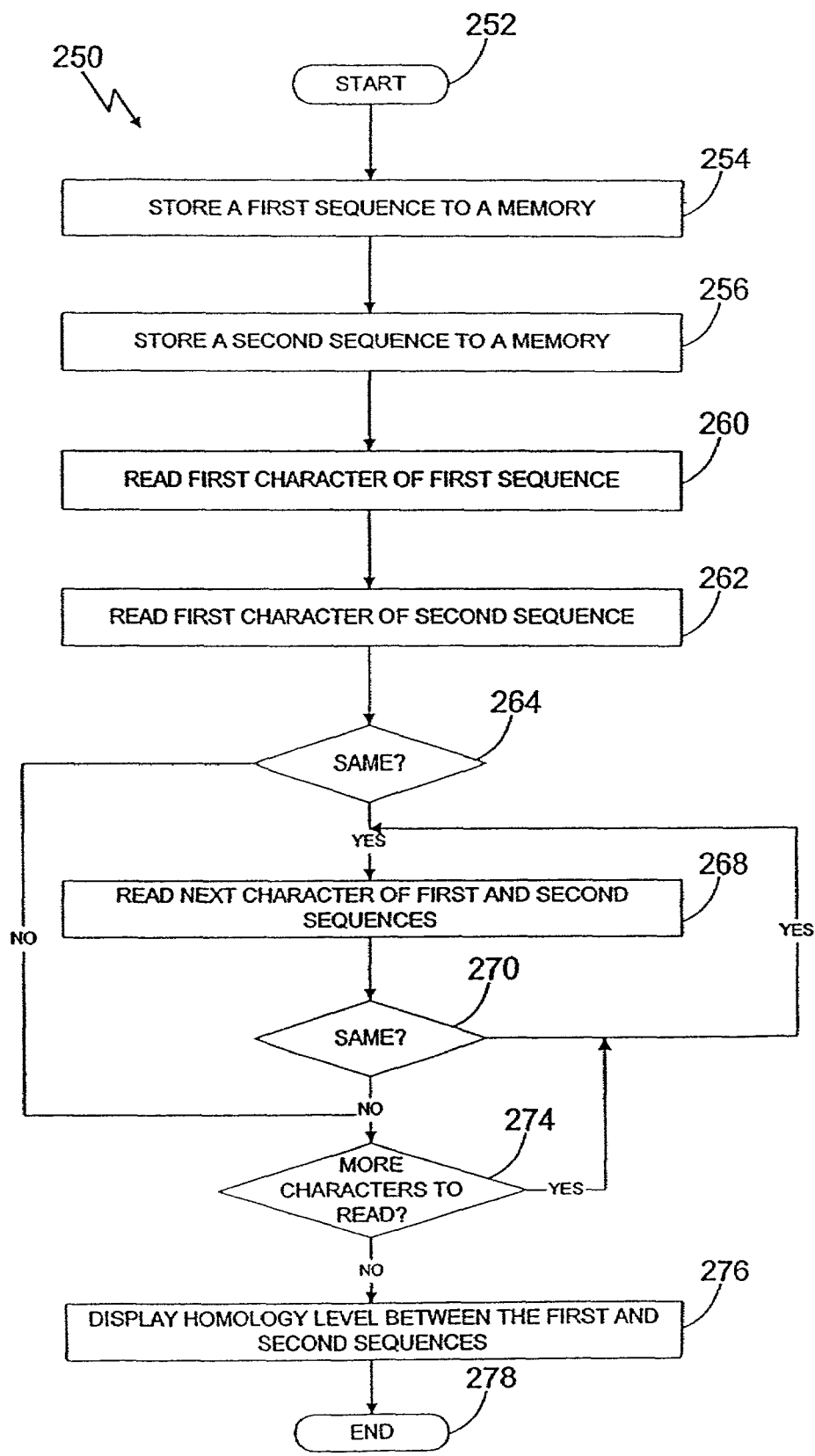
FIG. 5 is a flow diagram illustrating one embodiment of a process 250 in a computer for determining whether two sequences are homologous.
Figure 6:
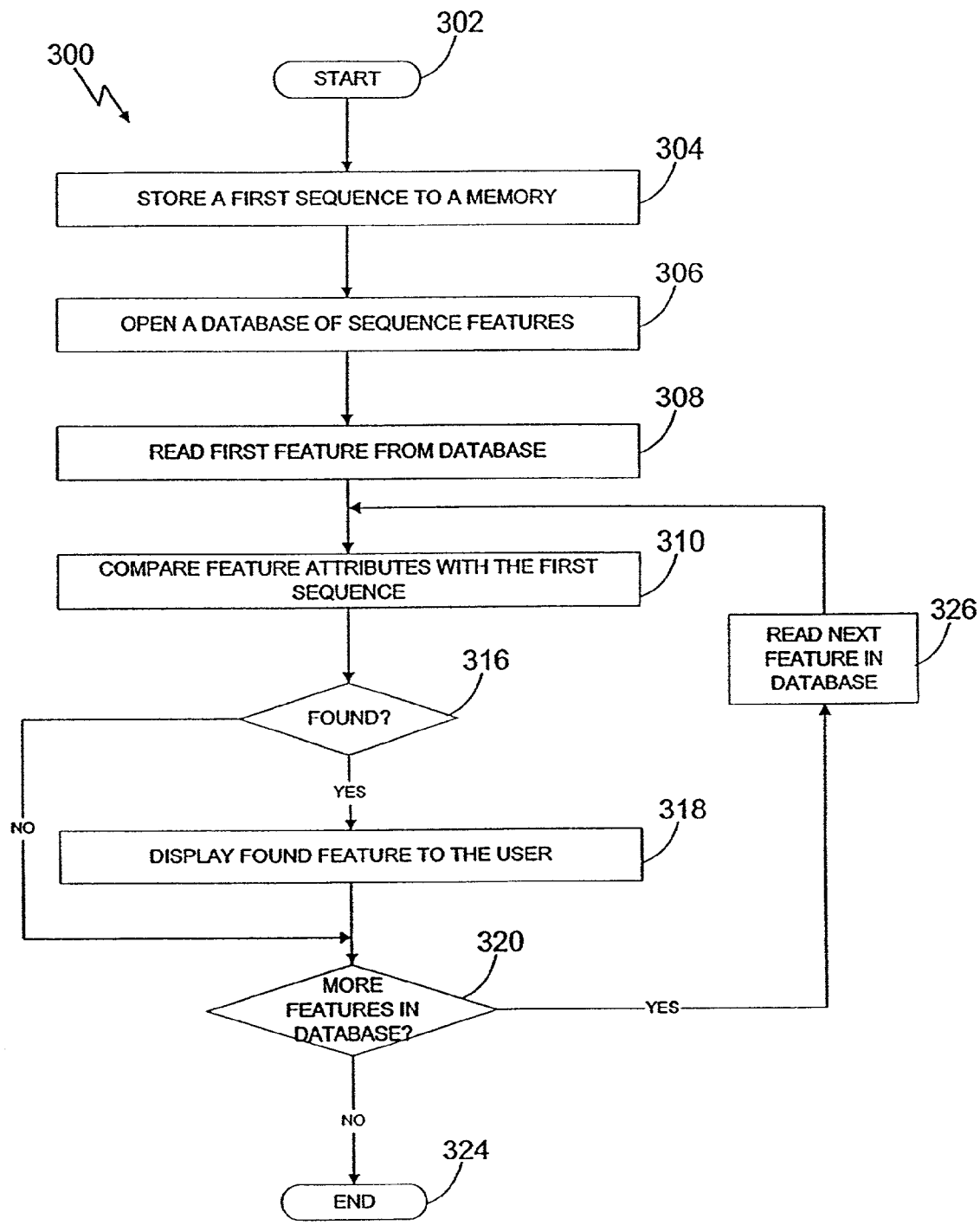
FIG. 6 is a flow diagram illustrating one embodiment of a process 300 for comparing features in polynucleotide and polypeptide sequences.

FIG. 5 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (see J. Roach, at the uniform resource locator (url) weber.u.Washington.edu/~roach/human_genome_progress 2.html) (Gibbs, 1995). At least twenty-one other genomes have already been sequenced, including, for example, *M. genitalium* (Fraser et al., 1995), M. jannaschii (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Several databases containing genomic information annotated with some functional information are maintained by different organization, and are accessible via the internet, for example, world wide web addresses: .tigr.org/tdb; .genetics.wisc.edu; .stanford.edu/~ball; .hiv-web.lanl.gov;.ncbi.nlm.nih.gov;.ebi.ac.uk; Pasteur.fr/other/biology; and .genome.wi.mit.edu.

One example of a useful algorithm is BLAST and BLAST 2.0 algorithms, which are described in Altschul et al., Nuc. Acids Res. 25:3389–3402, 1977, and Altschul et al., J. Mol. Biol. 215:403–410, 1990, respectively. Software for performing BLAST analyses is publicly available through the National Center for Biotechnology Information (http://www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., *Science* 256:1443–1445, 1992; Henikoff and Henikoff, *Proteins* 17:49–61, 1993). Less preferably, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine site on the world wide web, for example The parameters used with the above algorithms may be adapted depending on the sequence length and degree of homology studied. In some embodiments, the parameters may be the default parameters used by the algorithms in the absence of instructions from the user.

The following examples are intended to illustrate but not limit the invention.

EXAMPLE 1

Tautomycin Stabilizes the Phosphorylation of Xchk1 in *Xenopus* Egg Extracts

In the presence of incompletely replicated or UV-damaged chromosomal DNA, only a small portion of the Xchk1 in whole *Xenopus* egg extracts undergoes phosphorylation (see Kumagai et al., (1998) *J. Cell Biol.* 142, 1359–1569). The phosphorylated form of Xchk1 is highly enriched in the nuclear fraction of the extracts. To study the properties of phosphorylated Xchk1 more readily, a system was developed in which Xchk1 could undergo efficient phosphorylation in whole egg extracts in the presence of synthetic oligonucleotides. The establishment of this system was facilitated by the use of a phosphatase inhibitor, tautomycin, that stabilizes the phosphorylation of Xchk1 in egg extracts.

Production of $^{35}$S-Labeled Proteins $^{35}$S-Labeled full-length Claspin, Claspin-N (amino acids 1–743), and Claspin-C (amino acids 776–1285) were synthesized using pBS-Claspin, pBS-Claspin-N, and pBS-Claspin-C, respectively, as templates in the TNT in vitro transcription/translation system (Promega) in the presence of [$^{35}$S]Translabel (ICN Biomedicals). $^{35}$S-Labeled-Xchk1 proteins were synthesized as described (Kumagai et al., 1998.

3 µM tautomycin was added to egg extracts containing *Xenopus* sperm chromatin and aphidicolin, a DNA polymerase inhibitor that induces DNA replication blocks and thereby inhibits cell cycle progression. $^{35}$S-Labeled Xchk1 was incubated for 30 min in interphase egg extracts containing no sperm nuclei, 3000 nuclei/µl, 3000 nuclei/µl and 100 µl/ml aphidicolin, or 3000 UV-irradiated nuclei/µl in the presence or absence of 5 mM caffeine. The extracts were dividied, and the incubation was continued for 70 min in the absence or presence of 3 µM tautomycin. Aliquots (2 µl) were removed for SDS-PAGE and autoradiography.

Tautomycin caused a significant accumulation of phosphorylated Xchk1. Likewise, treatment with tautomycin also resulted in an increase in the amount of phosphorylated Xchk1 that appeared in response to UV-damaged sperm chromatin. Significantly, tautomycin did not have any effect on the phosphorylation of Xchk1 in extracts lacking aphidicolin or UV-damaged DNA. Furthermore, caffeine, an agent that inhibits the checkpoint-dependent phosphorylation of Xchk1 and overrides checkpoint controls in *Xenopus* egg extracts as well as other systems (see Kumagai et al., 1998), blocked the tautomycin-stimulated phosphorylation of Xchk1 in extracts containing aphidicolin or UV-damaged DNA.

It is necessary to add tautomycin to egg extracts at least 30 min after the addition of *Xenopus* sperm chromatin and aphidicolin. In fact, the addition of tautomycin, sperm chromatin, and aphidicolin together at the start of the incubation actually prevents the phosphorylation of Xchk1. Removal of protein phosphatase 2A (PP2A) from egg extracts prevents the initiation of DNA replication but not elongation at existing replication forks (Lin et al. (1998) *Proc. Nat. Acad. Sci. USA* 95, 14693–14698). Tautomycin is an inhibitor of PP2A, among other phosphatases. Furthermore, a period of about 30 min is required for the formation of pre-replication complexes and initiation of replication in egg extracts (Coleman et al. (1996) Cell 87, 53–63). Thus, premature addition of tautomycin most probably blocks the formation of DNA replication forks, which are required for activation of the DNA replication checkpoint (Li and Deshaies, (1993) Cell 74, 223–226).

EXAMPLE 2

Phosphorylation of Xchk1 in the Presence of Synthetic Oligonucleotides

Previous studies have demonstrated that various defined DNA templates, including linearized plasmids, double-stranded oligonucleotides, partially-nicked M13 DNA, and poly(dT)$_{40}$, all trigger the phosphorylation of Xcds1 but not Xchk1 in *Xenopus* egg extracts (Guo and Dunphy, (2000) *Mol. Biol. Cell* 11, 1535–1546). These templates either contain double-stranded DNA ends or undergo replication to a double-stranded form, in the case of M13 and poly(dT)$_{40}$, indicating that double-stranded DNA ends trigger the phosphorylation of Xcds1. Nonetheless, one intriguing aspect of these studies was that, even though M13 DNA and poly(dT)$_{40}$, must be replicated to a double-stranded form to induce phosphorylation of Xcds1, these templates did not elicit the phosphorylation of Xchk1. One rationale suggests that, since these templates are not incorporated into a nuclear structure, any phosphorylated Xchk1 that could potentially be generated as a result of their presence might be more susceptible to dephosphorylation in whole egg extracts.

To test this rationale a number of different DNA templates were incubated in *Xenopus* extracts in the presence or absence of the phosphatase inhibitor tautomycin. In one set of experiments, various DNA homopolymers, e.g., poly(dA)$_{70}$, poly(dT)$_{70}$, poly(dC)$_{70}$ and poly(dG)$_{70}$, were added to extracts containing $^{35}$S-labeled Xchk1 and subsequently, the phosphorylation of Xchk1 was examined. $^5$S-Labeled Xchk1 was added to egg extracts containing 50 µg/ml poly(dA)$_{70}$, 50 µg/ml poly(dT)$_{70}$, 50 µg/ml poly(dA)$_{70}$–poly(dT)$_{70}$, 50 µg/ml poly(dC)$_{70}$, 50 µg/ml poly(dG)$_{70}$, or 50 µg/ml poly(dC)$_{70}$–poly(dG)$_{70}$ in the presence or absence of 5 mM caffeine. The extracts were incubated for 100 min in the absence or presence of 3 µM tautomycin. Aliquots (2 µl) were removed for SDS-PAGE and autoradiography. pA, pT, pC, and pG refer to poly(dA)$_{70}$, poly(dT)$_{70}$, poly(dC)$_{70}$, and poly(dG)$_{70}$, respectively. In other experiments, $^{35}$S-Labeled wild-type Xchk1 and Xchk1-4AQ proteins were incubated for 100 min in interphase extracts containing either poly(dA)$_{70}$, or poly(dA)$_{70}$–poly(dT)$_{70}$ in the presence or absence of 5 mM caffeine. All samples contained 3 µM tautomycin.

None of these individual homopolymers had any effect on the phosphorylation of Xchk1 in the absence of tautomycin. Poly(dT)$_{70}$, induced a modest phosphorylation of Xchk1 in the presence of tautomycin. When a pre-annealed mixture of poly(dA)$_{70}$–poly(dT)$_{70}$ was added to tautomycin-containing extracts, however, there was a pronounced phosphorylation of Xchk1. Without tautomycin, this modification was significantly diminished. Pre-annealed poly(dC)$_{70}$–poly(dG)$_{70}$ was significantly less effective than poly(dA)–poly(dT)$_{70}$. There appears to be a strict requirement with regard to the length of the homopolymers. In particular, a preannealed mixture of shorter homopolymers, such as poly(dA)$_{40}$–poly(dT)$_{40}$, was not able to induce the modification of Xchk1 efficiently.

Further characterization indicated that the phosphorylation of Xchk1 in the presence of the annealed homopolymers and tautomycin has similar properties to the modification of Xchk1 that occurs in nuclei containing unreplicated or UV-damaged DNA. For example, this phosphorylation was strongly reduced by treatment with caffeine. Furthermore, the phosphorylation that was induced by poly(dA)$_{70}$–poly(dT)$_{70}$ was largely abolished in the Xchk1-4AQ mutant. In this mutant, the phosphorylatable residues of Xchk1 in its four conserved SQ/TQ motifs (Thr-314, Ser-344, Ser356, and Ser-365) have all been mutated to alanine. In addition, poly(dA)$_{70}$–poly(dT)$_{70}$ but not poly(dA)$_{70}$, induced a cell cycle arrest efficiently in egg extracts.

EXAMPLE 3

Production of His6-GST, Xchk1-WT-GST-His6, and Xchk1-N135A-GST-His6 Proteins in Insect Cells A KasI-NcoI fragment encoding glutathione S-transferase (GST) was created by PCR (polymerase chain reaction) using Pfu Turbo polymerase (Stratagene) with the appropriate primers and pGEX-2T as template. The fragment was digested with KasI and NcoI and cloned into pFastBacHTa (GIBCO BRL) to yield a baculovirus vector with tandem six histidine and GST tags (pFastBacHT-GST). pFastBac encoding C-terminally tagged Xchk1 (Xchk1-WT-GST-His6) was created by the following procedure. The coding sequence of Xchk1 was amplified in a PCR reaction, digested with RsrII and KasI, and cloned into pFastBacHT-GST. This plasmid was treated with BamHI and XbaI, and two annealed oligonucleotides encoding a six histidine tag were ligated into the vector to yield pFastBac-Xchk1-WT-GST-His6. pFastBac-Xchk1-N135A-GST-His6 and pFast-Bac-Xchk1-4AQ-GST-His6 were created by inserting the SacI-BstEII fragments of pBS-Xchk1-N135A (Kumagai et al., 1998) and pBS-Xchk1-4AQ, respectively, into pFast-Bac-Xchk1-WT-GST-His6. The Xchk1-WT-GST-His6 protein contains a thrombin recognition sequence both between Xchk1 and GST and between GST and the six histidine tag. Recombinant baculoviruses were produced using the Bac-to-Bac system (GIBCO BRL). Recombinant proteins were isolated using nickel iminodiacetic acid (Ni-IDA) agarose as described (Kumagai and Dunphy, (1995) *Mol. Biol. Cell* 6,199–213).

Ni-IDA beads (10 µl) containing Xchk1-WT-GST-His6 protein (5 µg) were incubated for 100 min at 23° C. in 100 µl of interphase egg extract containing 3 µM tautomycin, 100 µg/ml cycloheximide, and either 50 µg/ml poly(dA)$_{70}$ or 50 µg/ml poly(dA)$_{70}$–poly(dT)$_{70}$ in the presence or absence of 5 mM caffeine. The beads were isolated by centrifugation and washed four times in 10 mM Hepes-KOH (pH 7.5) containing 150 mM NaCl, 0.5% NP-40, 2.5 mM EGTA, and 20 mM β-glycerolphosphate. Bound proteins were eluted with 150 mM imidazole in the same buffer. The eluate was diluted to 500 µl and incubated with 10 µl Glutathione Sepharose 4 Fast Flow (Amersham Pharmacia Biotech) for 30 min at 4° C. The beads were washed three times in the same buffer and then subjected to SDS-PAGE. For protein sequencing, 30 ml of interphase egg extract and 1.5 mg of Xchk1-WT-GST-His6 protein were used to isolate Claspin. Proteins were eluted from glutathione agarose with 0.1% SDS, concentrated with a Microsep, 30K device (Filtron Technology), treated with dithiothreitol, alkylated, and subjected to SDS-PAGE. The gel was stained with SYPRO Red (Molecular Probes). Tryptic peptides from Claspin were separated on a Vydac C18 column and sequenced in the Caltech facility.

EXAMPLE 4

Identification of an Xchk1-Binding Protein

Isolation of an Xchk1-binding protein Nickel agarose beads (10 µl) containing 5 µg of either Xchk1-WT-GST-His6 protein or a control His6-GST protein were incubated in interphase egg extracts (100 µl) containing 3 µM tautomycin and either poly(dA)$_{70}$ or poly(dA)$_{70}$–poly(dT)$_{70}$ in the absence or presence of 5 mM caffeine. The beads were re-isolated and bound proteins were eluted with imidazole. The eluted proteins were purified further on glutathione agarose as described herein. The samples were subjected to SDS-PAGE and silver-staining. The control His6-GST protein was electrophoresed through the bottom of the gel in this experiment. Xchk1-WT-GST-His6 becomes only partially phosphorylated in the presence of poly(dA)$_{70}$–poly(dT)$_{70}$ in this case because it was added at a 25-fold molar excess over endogenous Xchk1.

Isolation of Claspin, an Xchk1-Binding Protein As one approach to understand the regulation of Xchk1, a search for proteins that bind to Xchk1 was conducted. A recombinant form of Xchk1 (Xchk1-WT-GST-His6) was incubated in *Xenopus* egg extracts under various conditions and the protein was subsequently re-isolated by sequential chromatography on nickel and glutathione agarose, respectively. A 215 kD protein was identified that had associated with Xchk1 in the presence of poly(dA)$_{70}$–poly(dT)$_{70}$. The binding of this protein was significantly reduced if either 5 mM caffeine was included in the incubation or if poly(dA))$_{70}$, was used as the template. The 215 kD protein was not isolated from mock incubations containing no recombinant Xchk1. In these experiments, no other polypeptide was observed with an abundance comparable to that of the 215 kD protein, but additional proteins may be involved in the interaction with Xchk1.

A large-scale purification was performed to obtain a sufficient quantity of the 215 kD protein for peptide sequencing analysis. Two peptide sequences that did not belong to a previously cloned protein were identified. One combination of degenerate PCR primers based on these peptides was used to amplify a 450-bp DNA fragment, which in turn was employed to isolate a 4.8-kb *Xenopus* oocyte cDNA (GenBank accession number AF297867). This cDNA encodes a 1285 amino acid polypeptide (calculated molecular mass, 145 kD) that contains amino acid sequences (LAAVSDLN-PNAPR (SEQ ID NO:6) and YLADGDLHSDGPGR (SEQ ID NO:7)) that are consistent with the peptide sequencing analysis. A BLAST search with the cDNA sequence indicated that it encodes a novel protein, which has been named Claspin.

Cloning of *Xenopus* Claspin Sets of degenerate oligonucleotides corresponding to the two peptide sequences [(L/D)AAVXDLNPNAPX (SEQ ID NO:8) and YLADGDLHSDGPGR (SEQ ID NO:7); X denotes an ambiguous amino acid] obtained from Claspin were designed. A PCR reaction with GGIGC(A/G)TTIGG(A/G)TTIA(G/A)(G/A)TCI(G/C)(A/T)IACIGCIGC (SEQ ID NO:9) and GCIGA(T/C)GGIGA(T/C)(T/C)TICA(T/C)(T/A)(G/C)IGA(T/C)GGICCIGG (SEQ ID NO:10) Ampli-Taq DNA polymerase (Perkin-Elmer), and *Xenopus* oocyte cDNA yielded a 450-bp fragment that encodes a segment of Claspin. The sequence of this fragment was used to design primers to isolate a 4.7 kb cDNA from a *Xenopus* oocyte library (Mueller et al., (1995) *Mol. Biol. Cell* 6, 119–134) with the ClonCapture kit (Clontech). A 2.3 kb ApaI-XhoI fragment encoding the N-terminal half of the protein and a 2.4 kb XhoI-XhoI fragment encoding the C-terminal half of the protein were cloned into pBluescript SK- to yield pBS-Claspin-N and pBS-Claspin-C, respectively. The XhoI-XhoI fragment of pBS-Claspin-C was cloned into pBS-Claspin-N to yield a vector encoding fill-length Claspin (pBS-Claspin). Nested deletions were sequenced at the Caltech DNA Sequencing Core Facility.

EXAMPLE 5

Cloning of Human Claspin

A BLAST analysis was conducted by using the sequence of *Xenopus* Claspin to search the human EST database. Several sequences with a strong homology to *Xenopus* Claspin sequence were found. Based on these sequences, two primers (CCACGGCTAGGTGCTGATGAAGATTCC (SEQ ID NO:11) and AACAGTGCTTGGCGCTTCTG-GCG (SEQ ID NO:12)) were designed to isolate cDNAs by RACE (Rapid Amplification of cDNA Ends) from a human fetal Marathon-Ready-cDNA library (Clontech).

To obtain further insight into the structure of Claspin, a human homologue (Hu-Claspin) was identified using PCR primers based on sequences related to *Xenopus* Claspin in the human EST database. cDNA fragments from a human library were isolated and used to establish the full-length cDNA sequence of Hu-Claspin (GenBank accession number AF297866). Conceptual translation of the cDNA encoding Hu-Claspin yielded a 1332 amino acid polypeptide that is 49% identical to *Xenopus* Claspin. The gene for Hu-Claspin is located at p34.1–34.3 on chromosome 1 according to the GenBank entry for its genomic sequence (AL139143). Although the *Xenopus* cDNA does not contain an in-frame termination codon upstream of the putative initiation codon, it most likely represents the full-length sequence. The human cDNA contains two in-frame stop codons upstream of an initiation codon that has a position almost identical to that of the putative start codon in *Xenopus* Claspin. Furthermore, endogenous Claspin in *Xenopus* egg extracts is just slightly smaller than recombinant His6-Claspin. It should be noted that *Xenopus* and human Claspin are quite acidic proteins (pI=4.5), which may lead to anormalous migration during SDS-PAGE.

Claspin does not appear to possess any strictly defined sequence motifs that offer insight into its biochemical function. Both the *Xenopus* and human proteins have three conserved potential nuclear localization signals (amino acids 158–174,312–316, and 1078–1084 in the *Xenopus* protein). Likewise, both proteins contain a relatively large number of SQ/TQ motifs (the *Xenopus* protein has eight SQ and four TQ motifs, while Hu-Claspin contains nine SQ and three TQ motifs). The serines and threonines in this type of motif are potential substrates for kinases such as ATM, ATR, and DNX-PK that are involved in checkpoint pathways (Kim et al., (1999) *J. Biol. Chem.* 274, 37538–37543). BLAST searches of the *Saccharomyces cerevisiae* and *Schizosaccharomyces pombe* databases did not reveal any obvious homologue of Claspin. However, a PSI-BLAST search identified a weak homology to the *Drosophila* CG1326 gene product (AAF47885), which is 28% identical to *Xenopus* Claspin.

EXAMPLE 6

Phosphorylation of Claspin is Required for Binding to Xchk1

In order to characterize the interaction of Claspin with Xchk1, $^{35}$S-labeled versions of full-length Claspin, its N-terminal domain (Claspin-N, amino acids 1–743), and a C-terminal fragment (Claspin-C, amino acids 776–1285) were prepared.

Modification of Claspin. $^{35}$S-Labeled full-length Claspin, Claspin-N, and Claspin-C were incubated for 100 min in egg extracts containing poly(dA)$_{70}$ (lane 1), poly(dA)$_{70}$–poly(dT)$_{70}$, or poly(dA)$_{70}$–poly(dT)$_{70}$ and 5 mM caffeine. Aliquots were subjected to SDS-PAGE and autoradiography. In another set of experiments, egg extracts containing $^{35}$S-labeled full-length Claspin, Claspin-N, and Claspin-C and poly(dA)$_{70}$, poly(dA)$_{70}$–poly(dT)$_{70}$, or poly(dA)$_{70}$–poly(dT)$_{70}$ and 5 mM caffeine were incubated in the presence of nickel agarose containing either Xchk1-WT-GST-His6 or a control His6-GST protein. The beads were isolated, washed, and subjected to SDS-PAGE and autoradiography.

Phosphorylated Claspin associates with Xchk1. Claspin-GST-His6 was incubated in egg extracts containing either poly(dA)$_{70}$ or poly(dA)$_{70}$–poly(dT)$_{70}$ and 3 µM tautomycin and subsequently re-isolated with nickel agarose. The GST-His6 tag was then removed with thrombin. Portions of some samples were incubated with PP2A in either the presence or absence of 3 µM okadaic acid. The samples were subjected to SDS-PAGE directly or assayed for binding to Xchk1. For binding assays, samples were incubated at 4° C. for 30 min with nickel agarose containing either Xchk1-WT-GST-His6 or control His6-GST. After washing, the beads were subjected to SDS-PAGE. All samples were immunoblotted with anti-Claspin antibodies.

Interaction of endogenous Claspin and Xchk1 in extracts containing unreplicated or UV-damaged *Xenopus* sperm chromatin. Interphase extracts containing 100 µg/ml cycloheximide and no sperm nuclei, 3000 nuclei/µl , 3000 nuclei/µl and 100 µg/ml aphidicolin, or 3000 UV-damaged nuclei/µl were incubated for 100 min at 23° C. in the absence or presence of 5 mM caffeine. Extracts were immunoprecipitated with control IgG or anti-Xchk1 antibodies. The immunoprecipitates were subjected to SDS-PAGE and immunoblotted with anti-Claspin antibodies.

Labeled proteins were added to egg extracts in the presence of poly(dA)$_{70}$, poly(dA)$_{70}$–poly(dT)$_{70}$, or both poly (dA)$_{70}$–poly(dT)$_{70}$, and caffeine. Full-length Claspin became modified in the presence of poly(dA)$_{70}$–poly(dT)$_{70}$, but not poly(dA)$_{70}$, and this modification was reversed by caffeine. This modification appears to be restricted largely, if not exclusively, to the C-terminal domain of Claspin, since Claspin-C, but not Claspin-N, underwent a substantial, caffeine-sensitive upshift in electrophoretic mobility in the presence of poly(dA)$_{70}$–poly(dT)$_{70}$,.

The interaction of full-length Claspin, Claspin-N, and Claspin-C with Xchk1 was examined. $^{35}$S-labeled versions of these proteins were incubated in egg extracts containing Xchk1-WT-GST-His6 and subsequently re-isolated the recombinant Xchk1 with nickel agarose. Both full-length Claspin and Claspin-C, but not Claspin-N, bound to Xchk1. Moreover, this interaction occurred in the presence of poly (dA)$_{70}$–poly(dT)$_{70}$, but not poly(dA)$_{70}$, and was sensitive to caffeine.

To determine whether the modification of Claspin represented phosphorylation, the up-shifted form of Claspin was treated with PP2A. Recombinant Claspin-GST-His6 was incubated in egg extracts containing poly(dA)$_{70}$ or poly(dA)$_{70}$–poly(dT)$_{70}$. Subsequently, recombinant Claspin was re-isolated with nickel agarose. The modified form of Claspin that had appeared in response to poly(dA)$_{70}$–poly (dT)$_{70}$ was treated with PP2A in the absence or presence of okadaic acid, an inhibitor of PP2A. The modification of Claspin was reversed substantially by PP2A, and this reversal was sensitive to okadaic acid.

The binding of Claspin to Xchk1 is important for phosphorylation. Various modified forms of Claspin without the tags (removed using thrombin) was incubated with Xchk1-WT-GST-His6 or, in some cases, a control His6-GST protein, both of which were bound to nickel agarose beads. After re-isolating and washing the beads, immunoblotting with anti-Claspin antibodies showed that only the phosphorylated form of Claspin interacted specifically with Xchk1.

The physiological significance of the binding between Claspin and Xchk1 was further explored in egg extracts containing incompletely replicated or UV-damaged nuclear DNA. Demembranated *Xenopus* sperm chromatin was added to egg extracts to allow the formation of reconstituted nuclei (see Murray, (1991) *Methods Cell Biol.* 36, 581–605). To induce the formation of DNA replication blocks in the nuclear chromatin, the DNA polymerase inhibitor aphidicolin was added to these extracts (Dasso and Newport (1990). *Cell* 61, 811–823). Alternatively, UV-treated sperm chromatin can be used as a source of damaged DNA (Kumagai et al., 1998). Egg extracts were incubated either in the presence of no chromatin, chromatin and aphidicolin, or UV-damaged chromatin. In some cases, caffeine was also included in the incubation. The extracts were immunoprecipitated with anti-Xchk1 or control antibodies and the immunoprecipitates were examined by immunoblotting with anti-Claspin antibodies. The interaction between endogenous Claspin and Xchk1 was increased in the presence of aphidicolin or UV-damaged DNA. Moreover, the binding between Claspin and Xchk1 was significantly reduced in the presence of caffeine.

EXAMPLE 6

Phosphorylation of Xchk1 Results in its Activation

Chk1 undergoes phosphorylation during a checkpoint response in various experimental systems (Walworth and Bernards, (1996) *Science* 271, 353–356.; Sanchez et al. (1997) *Science* 277, 1497–1501; Kumagai et al., 1998), but the functional consequence of this phosphorylation has not been established. In the case of *Xenopus* egg extracts, it had been difficult to isolate the phosphorylated form of Xchk1 efficiently to address this issue conclusively. Using the technical improvements described herein for the preparation of phosphorylated Xchk1 to investigate whether this modification affects the kinase activity of Xchk1. Recombinant Xchk1-WT-GST-His6 was added to *Xenopus* egg extracts containing tautomycin and either poly(dA)$_{70}$ or poly(dA)$_{70}$–poly(dT)$_{70}$. After a 100-min incubation, recombinant Xchk1 was reisolated with glutathione agarose and assayed kinase activity toward Cdc25 with the model substrate GST-Cdc25(254–316)-WT.

The hyperphosphorylated form of Xchk1-WT-GST-His6 that was isolated from extracts containing poly(dA)$_{70}$–poly (dT)$_{70}$ was approximately 3-fold more active than the hypophosphorylated version of the protein from extracts that contained poly(dA)$_{70}$ This increase may be an underestimate of the maximum possible degree of activation because the recovery of hyperphosphorylated Xchk1 is consistently somewhat lower than that of the hypophosphorylated form. Akinase-inactive mutant of Xchk1 (Xchk1-N135A-GST-His6) and a mutant (Xchk1-4-AQ-GST-His6) that cannot undergo phosphorylation of the four conserved SQ/TQ motifs of Xchk1 was also examined. The kinase-inactive mutant of Xchk1 that was isolated from either type of extract was not able to phosphorylate the Cdc25 substrate in these assays. Also, consistent with previous results (Kumagai et al., 1998), kinase-inactive Xchk1 became only partially phosphorylated in the presence of poly(dA)$_{70}$–poly(dT)$_{70}$, due to its incapacity for autophosphorylation. Finally, the Xchk1-4AQ mutant did not undergo phosphorylation or an increase in kinase activity in the presence of poly(dA)$_{70}$–poly(dT)$_{70}$, indicating that phosphorylation of the SQ/TQ domain is required for the activation of Xchk1.

The kinase activity of hyperphosphorylated Xchk1 that appeared in response to aphidicolin-induced replication blocks in nuclei that had formed around sperm chromatin in egg extracts was examined. Recombinant Xchk1-WT-GST-His6 was added to egg extracts containing 3 μM tautomycin and either no nuclei or 3000 nuclei/μl and 100 μg/ml aphidicolin. After re-isolating the added Xchk1 with glutathione agarose, Xchk1 was activated three-fold when DNA replication blocks were present. Thus, both incompletely replicated chromatin and poly(dA)$_{70}$–poly(dT)$_{70}$ elicit a similar activation of Xchk1.

EXAMPLE 7

Immunodepletion of Claspin Blocks Phosphorylation and Activation of Xchk1

Production of His6-Claspin, His6-Claspin-N, and Claspin-GST-His6 in Insect cells pFastBacIIT-Claspin was created by cloning the NcoI-NheI and NheI-XhoI fragments of pBS-Claspin together into pFastBacHTa, thereby generating a baculovirus vector encoding a six-histidine tagged, full-length Claspin. pFastBacHT-Claspin(1–464) encoding a six-histidine tagged N-terminal fragment of Claspin (amino acids 1–464) was created by amplifying the 1.4 kb NcoI-EcoRI fragment from pBS-Claspin-N by PCR and cloning it into pFastBacHTa that had been digested with NcoI and EcoRI. A baculovirus vector encoding Claspin with GST and six histidine tags at the C-terminal end (pFastBac-Claspin-GST-His6) was prepared as follows. pBS-Claspin was used in a PCR reaction with the appropriate primers to introduce an SpeI site at the termination codon of Claspin. The PCR product was digested with NheI and SpeI and ligated to the appropriate pFastBac fragment. Baculovirus-expressed His6-Claspin, His6-Claspin(1–464), and Claspin-GST-His6 were produced as described above.

Example 8

In vitro Claspin-Xchk1 Binding Assays

Claspin-GST-His6 protein (5 g) bound to 10 µl of Ni-IDA beads was incubated for 100 min in interphase extracts (100 µl) containing 100 µg/ml cycloheximide, 3 µM tautomycin, and 50 µg/ml of either poly(dA)$_{70}$ or poly(dA)$_{70}$–poly(dT)$_{70}$. The beads were isolated by centrifugation and washed twice with buffer A (10 mM Hepes-KOH [pH 7.5], 150 mM NaCl, 0.1% CHAPS, 2.5 mM EGTA, and 20 mM β-glycerolphosphate), once with Hepes-buffered saline (HBS, 10 mM Hepes-KOH [pH 7.5], 150 mM NaCl), and eluted with 150 mM imidazole in HBS. Eluted proteins were treated with 0.06 U thrombin in HBS containing 2.5 mM CaCl$_2$ for 2 hrs at 4° C. during dialysis against HBS to remove imidazole. Digestion was stopped by adding 1 mM PMSF and 5 mM EGTA. Undigested protein and thrombin were removed by incubating with 10 µl Ni-IDA agarose and 5 µl aminobenzamidine agarose for 30 min at 4° C. In some cases, recombinant Claspin from extracts containing both poly(dA)$_{70}$- poly(dT)$_{70}$ and tautomycin was treated with 0.5 U protein phosphatase 2A (Upstate Biotechnology) in the presence or absence of 3 µM okadaic acid for 30 min at 23° C. The various preparations of Claspin were then incubated with either His6-GST or Xchk1-WT-GST-His6 bound to Ni-IDA beads in buffer A containing 1 mg/ml ovalbumin for 30 min at 4° C. The beads were washed three times in buffer A and bound proteins were analyzed by immunoblotting with anti-Claspin antibodies.

Isolation and Assay of Xchk1 from Egg Extracts Xchk1-WT-GST-His6, Xchk1-N135A-GST-His6, and Xchk1-4AQ-GST-His6 proteins (final concentration, 6 µg/ml) were incubated for 100 min in egg extracts (100 µl) containing 100 µg/ml cycloheximide, 3 µM tautomycin, and 50 µg/ml of either poly(dA)$_{70}$ or poly(dA)$_{70}$–poly(dT)$_{70}$. Extracts were diluted to 300 µl with buffer A and centrifuged in a 1 ml Sephadex G-25 column that had been pre-equilibrated with the same buffer to remove endogenous glutathione in the extracts. Glutathione agarose (10 µl) was incubated with the flow-through fraction for 30 min at 4° C. The glutathione beads were washed three times with buffer A, once with HBS, and incubated in kinase assays with GST-Cdc25 (254–316)-WT as the substrate as described (Kumagai et al., 1998).

Depletion of Claspin from Egg Extracts Interphase egg extracts (170 µl) that had been activated for 15 min at 23° C. by the addition of CaCl$_2$ were mixed with 30 µg of either affinity-purified anti-Claspin antibodies or control rabbit IgG bound to 30 µl of Affiprep-protein A beads (Bio-Rad) and incubated while rocking at 4° C. for 1 hr. At the end of incubation, the beads were removed by centrifugation and the immunodepletion procedure was repeated.

In order to investigate the role of Claspin in the regulation of Xchk1, endogenous Claspin was immunodepleted from Xenopus egg extracts using polyclonal antibodies that were raised against an N-terminal fragment of the protein. The level of Claspin was not diminished in a mock-depleted extract that was treated with control IgG. The endogenous concentration of Claspin in egg extracts is estimated to be approximately 33 µg/ml (170 µM). As shown by immunoblotting with anti-Claspin antibodies, the addition of 35 µg/ml His6-Claspin to Claspin-depleted extracts restored the protein to its normal level.

The state of phosphorylation of Xchk1 under various conditions was studied by adding recombinant Xchk1-WT-GST-His6 to extracts (mock-depleted; Claspin-depleted, and Clasp-indepleted containing 35 µg/ml His6-Claspin) in the presence of either poly(dA)$_{70}$ or poly(dA)$_{70}$–poly(dT)$_{70}$. Recombinant Xchk1 was then re-isolated from each extract with glutathione agarose and its state of phosphorylation was examined. The checkpoint-dependent phosphorylation of Xchk1 in Claspin-depleted extracts was almost completely abolished in comparison with mock-depleted extracts. Significantly, the addition of recombinant His6-Claspin to Claspin-depleted extracts completely restored the phosphorylation of Xchk1, indicating that the defect in phosphorylation of Xchk1 in the depleted extracts is due to the absence of Claspin.

The kinase activity of recombinant Xchk1 that was isolated from the extracts that underwent the immunodepletion procedure was also examined. Consistent with the results described above, recombinant Xchk1 was activated about 4-fold in extracts containing poly(dA)$_{70}$–poly(dT)$_{70}$. This activation was strongly reduced in Claspin-depleted extracts, and was completely restored by the addition of recombinant His6-Claspin to these extracts. Taken together, these findings indicate that Claspin is required both for the checkpoint-dependent phosphorylation of Xchk1 and for the resulting increase in its kinase activity.

EXAMPLE 9

Claspin is Necessary for the Delay of the Cell Cycle in Response to Incompletely Replicated DNA In order to investigate the biological role of Claspin in the Xenopus system, cell cycle progression in Claspin-depleted egg extracts containing incompletely replicated DNA was examined. Claspin was removed from egg extracts with anti-Claspin antibodies and aphidicolin and demembranated Xenopus sperm chromatin was added to induce the formation of DNA replication blocks. Entry into mitosis was examined by monitoring the timing of nuclear envelope breakdown (NEB). Mmock-depleted extracts that had been treated with a control IgG or Claspin-depleted extracts to which recombinant His6-Claspin was added were treated in the same manner. Claspin-depleted extracts containing aphidicolin inappropriately entered mitosis (half-maximal NEB at 150 min), indicating that the DNA replication checkpoint had been compromised. In contrast, mock-depleted extracts arrested well in interphase in the presence of aphidicolin. Likewise, aphidicolin-treated, Claspin-depleted extracts that were supplemented with His6-Claspin remained in interphase, indicating that the defect in the extracts lacking Claspin is due to the absence of this protein. Immunodepletion of Claspin had no effect on chromosomal DNA replication in egg extracts, as measured by incorporation of [α-$^{32}$P]dATP (Coleman et al. (1996) Cell 87, 53–63). Thus, the compromised cell cycle delay in aphidicolin-treated extracts lacking Claspin cannot be attributed to a defect in the formation of DNA replication blocks (see Li and Deshaies, (1993) Cell 74, 223–226).

Significantly, the Claspin-depleted extracts containing aphidicolin entered mitosis slower than control extracts lacking aphidicolin. A similar phenomenon was observed in Xchk1-depleted extracts suggesting that the aphidicolin-induced checkpoint in this system involves Xchk1-dependent and Xchk1-independent mechanisms (Kumagai et al., (1998)). Overall, these findings indicate that removal of Claspin strongly compromises but does not completely eliminate the cell cycle delay that is triggered by DNA replication blocks. The response to aphidicolin is very similar in Xchk1-depleted extracts, which would be consistent with the interpretation that Claspin and Xchk1 act in the same pathway.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polynucleotide encoding a polypeptide characterized as:
   (a) specifically interacting with a chK1 protein;
   (b) having SQ/TQ motifs;
   (c) having an isoelectric point of about 4.5;
   (d) having at least one nuclear localization signal; and
   (e) having the amino acid sequence as set forth in SEQ ID NO: 2.

2. An isolated polynucleotide selected from the group consisting of:
   (a) a polynucleotide encoding a polypeptide having the amino acid sequence as set forth in SEQ ID NO: 2;
   (b) a polynucleotide of (a), wherein T can be U;
   (c) the polynucleotide complement to (a) or (b); and
   (d) a polynucleotide having the nucleotide sequence as set forth in SEQ ID NO: 1.

3. An expression vector comprising polynucleotide (a), (b), (c), or (d) as set forth in claim 2.

4. The expression vector of claim 3, wherein the vector is a viral vector.

5. The expression vector of claim 3, wherein the vector is a plasmid vector.

6. A host cell comprising a vector of claim 3.

7. A method for producing a polypeptide comprising the steps of:
   (a) culturing a host of claim 6 under conditions suitable for the expression of the polypeptide; and
   (b) recovering the polypeptide from the host cell culture.

8. The isolated polynucleotide of claim 2, wherein the polynucleotide encodes a polypeptide consisting of the amino acid sequence as set forth in SEQ ID NO:2.

* * * * *

SEQUENCE LISTING

<160> NUMBER OF SEQ ID NOS: 12

<210> SEQ ID NO 1
<211> LENGTH: 4754
<212> TYPE: DNA
<213> ORGANISM: Xenopus laevis

<400> SEQUENCE: 1

```
acgcataggg cgcgaattcc aaggcggcag tagtgaggat tggcgggagc tgtcatcacc      60
gggtagcacc atgccgcgc tttgcgaaga agagcaggta tttttggaac cagaagacat     120
cagtctgaaa attgtggaga ctgattctga cagtggtcaa ggcagctgtg aaatggctga    180
tcagaataaa ttattgggtt gtgtggagga taaagataca gatgatgaaa tcttggttcg    240
taaaaaatct aaaaagaagg aagtattggt ggatagtgac agtgacgaag aattggaaat    300
gcgtaatttt gcagataatg taaggggca ctctgataat gaggagaatg aggagactat    360
gtctgcttat agagaaaaac caagaaagat ccgttcagct gtattggaca gtgacaatag    420
tgatcatgag cttgatgttc aaataagtac aagtcaaaat gcagctgaaa tacctgagtc    480
agaacatgat agcttggaga aggaaactca tactgtgaag cctaaaacaa gcaagtcctt    540
gaaaaaacaa actgacacta ataagagga aatcgtgaag aataaatcaa agcgcaaaat    600
tccgaaagag aagattaaaa ggaggacaaa acagaagtca aaagcagttg ctgaagctag    660
gccaaattta aatgacagtg gctgcttact cacagatgga gatcttttg acaatggggt    720
ggaaaatgag atggattcta atgaagaaga ggattctctt gaagctatcc gggcaaaaat    780
gaaaagcaaa ctgaatagtc attctgctga aaattttgaa gactttgaac ttgatactga    840
aggcaatcaa gaatccccag aaaaagaaa ggaacgaaaa gctgcgcgac ttggtaaaga    900
agccatgaaa caaatgcaca gtgagaccca aagactaata cgtgaatctt ctgtatcttt    960
accatatcat ctacctgaac caaaaacaat ccatgatttt ttcaaaaggc gtccaaggcc   1020
tctttgtcaa ggaaatgcaa tgcagcttat aaagtcaaca aaataccagc cctgcactga   1080
agagaaaaaa aaacccaatg aggaaatatg tgctgaagtt ccagagtttg attatgtttc   1140
aaaggaagat ttagaaatca gtccagagca acctttacta aatactcagt gttcacatgc   1200
tgcagtccta tgtgttgtgc aaaatgatgc tcggactgag gggttaagta aatccacaga   1260
ggcagttgtg actggtcaaa tgaatgacca tgaggatgct ttcagtgatt caaacattgt   1320
tcatgaacaa gaaacagttg gattaataac cgtaactgaa accttcaga cacccttat   1380
tccccaacca gagagcgtag tatgtgaaca aatccagaat gatgtagtag agatgcaacg   1440
tatgcctgaa caacccacgc ataaacccaa gttatccaag cttgaaaagc tgaaagctct   1500
tggagtggac ttgtctataa aacctcgcct ttgccctgat gatggttctt ttgtcaactt   1560
ggatgaacca aagccgaata aagaatttga agctttgaag gagcgtttcc tgaagcacac   1620
tctgcaaaag tccaaaccca gaactgagcg gaaagtcaat cttaatatta tccgcaagga   1680
gaccactgct gatggaaaag aagaactaaa agcagacgtt gtgccaatag ttatggctac   1740
```

-continued

```
agaaaaacca gacaagagca tttatcaaaa gccaggtgag aagctgcagg tattgaaagt   1800
caaactgcag gaagcaatga aaatccgtcg cagtgaggag cgcctgaagc ggcaagcctt   1860
gtataagctt gacaatgaag atggctttga agatgatgaa gaggaggaag aaatgacaga   1920
ggagtctgaa gatgatgggg atggaaatgc tgagactgca gattatcctg gaggggaaga   1980 tgaggaaagag gttggtgatg ctgaagatga caatgatgag gatgatactg taaatgatag   2040
attgttggga aatgtgcctg aaattgttat cccactgccg agaccagtaa ctactgattc   2100
tagcctcatg ctgttcaagg acaattcttc aaagctagga gattcgctac ctgatgaaag   2160
tggatgcaag agaagcagca ggctagaata tgaagaagac tccctgttgc cacaattaaa   2220
agaaaacagc cataatagta gcttTGAACT tattagttca atgataccat cataccagcc   2280
atgtaataaa acaactcgag ttgtgatcaa ctccaataac cttggctttc gctcaccatc   2340
tccggttcat ttcaaaacaa gttttctcag ctctgcatca aagagttctg caagatgtc    2400 tgaaccatcc cttcccgtgg aagactcaca ggatctatat aatgcttccc cagagcccaa   2460
agcctcatat ctctgtgctg gaagaaactc tcaatttcaa ttttcgttgg aggatgacac   2520
ccagagccaa ctgcttgatg ctgatggggtt tctgaatgtt ggtcgccata aatctagctc   2580
tgccaaacac aggctagctt tggatacaat ggacgagaat gctatggatg ccaatatgga   2640
tgaactacta gacctttgct caggacagtt caaagaatct ctttcaggca catcacaggc   2700
agctgaaagt gatgctaaga acaaccaat ggatgaattg cttgaattgt gttctggcaa    2760
atttgtatct caagctgact gctccacaca agattcttct gcttcagcta aggaccgttc   2820
tacagctgta aaaaggaca tttctgatga agtggcaacg gtttcaagtt cattccttac    2880
tgagagagaa caggaagaag atgaggaaga agaatttggt gaattcaagc tcttaccctg   2940
tgatgattcg gagagcgaaa cgaagaacaa aaatgaagag gaagaagaag aaggatgc     3000 taaggatgat gaagatgagg aagaaatttt gcagaagcag caaaaagagaa aattgaggct   3060 gaatgacttc atggaagatg aagccgaatt gtctggaagt gatgtaggta gcggagatga   3120
gtatgaagga gatgatgatg agtatgagga agaagccata gatgaagatc tcccatctga   3180
tgaggaactg caggatcaag tcaataaaat tcatatgaaa gttaccatgg atgaagacca   3240
gcgacagctt cgtttctatc aggagcggta cctggctgat ggggatctcc atagtgacgg   3300
accagggaga acaagaaagt tcagatggaa acatcttgat gatgcctcac aggtggacat   3360
gttccgccga gactctgaat tggaagaggt ggacggagag aatgaggaaa ctgaggaaac   3420
cgaacttaaa tggaggaaag agcggttcga aagggaacaa tggctgcgag aacagccaca   3480
aggtagtaga gataacaatg aggaggagga ggaggatatt ggagaagaca gccagttat    3540 gaaattggca agaaggtca ctgcaaaagc cctacagaga aaagtgagta cagagactaa    3600
tgaaccaaag aaacctgggc ctagaaatcc atatgaagtg atcaggcctt tcagcctccc   3660
caagttgcgt actggttcgc tgttaagcaa accaaaagaa gttttacaga agctggcagc   3720
tgtgtcagac ctgaatccaa atgcacctcg aaactcaaga aactttgtct tccaaactgt   3780
ctcacccgga aagaaagaag aaactacaga caagccaaga tcaaaggtac gaaagaatat   3840
agctgttgcc atgccttccc ctaaacgttt taaagggac agcacccta ctgttaaaag     3900 ccgcagtata tttcagttgt tggagtaggt ttctgcgaat attccactaa atcagtaatt   3960
tgtttttgtg tccagttac agcaaattct atattttaat gtagctgtgc ttacatgcta   4020
cagttctcgc tttactgaaa tttgtcagat acttgaacta agtgttttc atcatgaaat    4080
```

-continued

```
tagttgtgct gcatgttatt catacagagg catgtgaaat acactgtgta tttctattgc    4140
cttgtgtcaa atgttctaca cttgttttgt tcaaaattac acaaaccgta tcacctaatg    4200
taaatctacc tcatagagat acagataccc tacaaaaata cagtaatttt gtttacaacc    4260
acccatatat tttgtacttt gcattcttat tctattctct aaatgtactc catttacaag    4320
tgctgattta taaaggggca ttgtacctat ttgttcaaca caagttcaat tacgtcatgt    4380
gctgaacatg ctctccccccc catcttaaaa tatgttttc ttatgaattg cattaaacag    4440
ggcaaacact gaaactataa gtttatggga gtgctggtaa aaacaacaac ctattagtgc    4500
tttataatat aaaaaattag gttattatat ggattgtttt taattaaaac aataagcaga    4560
acaaatttaa aacaagtcct atttattttg ctcatgttaa ataaaagtgt atatatccat    4620
atactacccg tttaaactgt gtaatgaatg tgtttcttgt aatatatttt attgtacatt    4680
gttataaatg tttgtgagat ttgttaataa atacattttt ttaaaaaaaa aaaaaaaaaa    4740
aaaaaaaaaa aaaa    4754
```

<210> SEQ ID NO 2
<211> LENGTH: 1285
<212> TYPE: PRT
<213> ORGANISM: Xenopus laevis

<400> SEQUENCE: 2

```
Met Ala Ala Leu Cys Glu Glu Glu Gln Val Phe Leu Glu Pro Glu Asp
1               5                   10                  15

Ile Ser Leu Lys Ile Val Glu Thr Asp Ser Asp Ser Gly Gln Gly Ser
            20                  25                  30

Cys Glu Met Ala Asp Gln Asn Lys Leu Leu Gly Cys Val Glu Asp Lys
        35                  40                  45

Asp Thr Asp Asp Glu Ile Leu Val Arg Lys Ser Lys Lys Lys Glu
    50                  55                  60

Val Leu Val Asp Ser Asp Ser Asp Glu Glu Leu Glu Met Arg Asn Phe
65                  70                  75                  80

Ala Asp Asn Val Lys Gly His Ser Asp Asn Glu Glu Asn Glu Glu Thr
                85                  90                  95

Met Ser Ala Tyr Arg Glu Lys Pro Arg Lys Ile Arg Ser Ala Val Leu
            100                 105                 110

Asp Ser Asp Asn Ser Asp His Glu Leu Asp Val Gln Ile Ser Thr Ser
        115                 120                 125

Gln Asn Ala Ala Glu Ile Pro Gly Ser Glu His Asp Ser Leu Glu Lys
    130                 135                 140

Glu Thr His Thr Val Lys Pro Lys Thr Ser Lys Ser Leu Lys Lys Gln
145                 150                 155                 160

Thr Asp Thr Asn Lys Glu Glu Ile Val Lys Asn Lys Ser Lys Arg Lys
                165                 170                 175

Ile Pro Lys Glu Lys Ile Lys Arg Arg Thr Lys Gln Lys Ser Lys Ala
            180                 185                 190

Val Ala Glu Ala Arg Pro Asn Leu Asn Asp Ser Gly Cys Leu Leu Thr
        195                 200                 205

Asp Gly Asp Leu Phe Asp Asn Gly Val Glu Asn Glu Met Asp Ser Asn
    210                 215                 220

Glu Glu Glu Asp Ser Leu Glu Ala Ile Arg Ala Lys Met Lys Ser Lys
225                 230                 235                 240

Leu Asn Ser His Ser Ala Glu Asn Phe Glu Asp Phe Glu Leu Asp Thr
                245                 250                 255
```

```
Glu Gly Asn Gln Glu Ser Pro Glu Lys Arg Lys Glu Arg Lys Ala Ala
            260                 265                 270

Arg Leu Gly Lys Glu Ala Met Lys Gln Met His Ser Glu Thr Gln Arg
            275                 280                 285

Leu Ile Arg Glu Ser Ser Val Ser Leu Pro Tyr His Leu Pro Glu Pro
            290                 295                 300

Lys Thr Ile His Asp Phe Phe Lys Arg Pro Arg Pro Leu Cys Gln
305                 310                 315                 320

Gly Asn Ala Met Gln Leu Ile Lys Ser Thr Lys Tyr Gln Pro Cys Thr
                325                 330                 335

Glu Glu Lys Lys Lys Pro Asn Glu Glu Ile Cys Ala Glu Val Pro Glu
            340                 345                 350

Phe Asp Tyr Val Ser Lys Glu Asp Leu Glu Ile Ser Pro Glu Gln Pro
            355                 360                 365

Leu Leu Asn Thr Gln Cys Ser His Ala Ala Val Leu Cys Val Val Gln
            370                 375                 380

Asn Asp Ala Arg Thr Glu Gly Leu Ser Lys Ser Thr Glu Ala Val Val
385                 390                 395                 400

Thr Gly Gln Met Asn Asp His Glu Asp Ala Phe Ser Asp Ser Asn Ile
                405                 410                 415

Val His Glu Gln Glu Thr Val Gly Leu Ile Thr Val Thr Glu Thr Phe
            420                 425                 430

Gln Thr Pro Phe Ile Pro Gln Pro Glu Ser Val Val Cys Glu Gln Ile
            435                 440                 445

Gln Asn Asp Val Val Glu Met Gln Arg Met Pro Glu Gln Pro Thr His
            450                 455                 460

Lys Pro Lys Leu Ser Lys Leu Glu Lys Leu Lys Ala Leu Gly Val Asp
465                 470                 475                 480

Leu Ser Ile Lys Pro Arg Leu Cys Pro Asp Asp Gly Ser Phe Val Asn
                485                 490                 495

Leu Asp Glu Pro Lys Pro Asn Lys Glu Phe Glu Ala Leu Lys Glu Arg
            500                 505                 510

Phe Leu Lys His Thr Leu Gln Lys Ser Lys Pro Arg Thr Glu Arg Lys
            515                 520                 525

Val Asn Leu Asn Ile Ile Arg Lys Glu Thr Thr Ala Asp Gly Lys Glu
            530                 535                 540

Glu Leu Lys Ala Asp Val Val Pro Ile Val Met Ala Thr Glu Lys Pro
545                 550                 555                 560

Asp Lys Ser Ile Tyr Gln Lys Pro Gly Glu Lys Leu Gln Val Leu Lys
                565                 570                 575

Val Lys Leu Gln Glu Ala Met Lys Ile Arg Arg Ser Glu Glu Arg Leu
            580                 585                 590

Lys Arg Gln Ala Leu Tyr Lys Leu Asp Asn Glu Asp Gly Phe Glu Asp
            595                 600                 605

Asp Glu Glu Glu Glu Met Thr Glu Glu Ser Glu Asp Asp Gly Asp
            610                 615                 620

Gly Asn Ala Glu Thr Ala Asp Tyr Pro Gly Gly Asp Glu Glu Glu
625                 630                 635                 640

Val Gly Asp Ala Glu Asp Asp Asn Asp Glu Asp Thr Val Asn Asp
                645                 650                 655

Arg Leu Leu Gly Asn Val Pro Glu Ile Val Ile Pro Leu Pro Arg Pro
            660                 665                 670
```

-continued

Val Thr Thr Asp Ser Ser Leu Met Leu Phe Lys Asp Asn Ser Ser Lys
        675                 680                 685

Leu Gly Asp Ser Leu Pro Asp Glu Ser Gly Cys Lys Arg Ser Ser Arg
690                 695                 700

Leu Glu Tyr Glu Glu Asp Ser Leu Leu Pro Gln Leu Lys Glu Asn Ser
705                 710                 715                 720

His Asn Ser Ser Phe Glu Leu Ile Ser Ser Met Ile Pro Ser Tyr Gln
                725                 730                 735

Pro Cys Asn Lys Thr Thr Arg Val Val Ile Asn Ser Asn Asn Leu Gly
            740                 745                 750

Phe Arg Ser Pro Ser Pro Val His Phe Lys Thr Ser Phe Leu Ser Ser
        755                 760                 765

Ala Ser Lys Ser Ser Gly Lys Met Ser Glu Pro Ser Leu Pro Val Glu
770                 775                 780

Asp Ser Gln Asp Leu Tyr Asn Ala Ser Pro Glu Pro Lys Ala Ser Tyr
785                 790                 795                 800

Leu Cys Ala Gly Arg Asn Ser Gln Phe Gln Phe Ser Leu Glu Asp Asp
                805                 810                 815

Thr Gln Ser Gln Leu Leu Asp Ala Asp Gly Phe Leu Asn Val Gly Arg
            820                 825                 830

His Lys Ser Ser Ser Ala Lys His Arg Leu Ala Leu Asp Thr Met Asp
        835                 840                 845

Glu Asn Ala Met Asp Ala Asn Met Asp Glu Leu Leu Asp Leu Cys Ser
850                 855                 860

Gly Gln Phe Lys Glu Ser Leu Ser Gly Thr Ser Gln Ala Ala Glu Ser
865                 870                 875                 880

Asp Ala Lys Lys Gln Pro Met Asp Glu Leu Leu Glu Leu Cys Ser Gly
                885                 890                 895

Lys Phe Val Ser Gln Ala Asp Cys Ser Thr Gln Asp Ser Ser Ala Ser
            900                 905                 910

Ala Lys Asp Arg Ser Thr Ala Val Lys Lys Asp Ile Ser Asp Glu Val
        915                 920                 925

Ala Thr Val Ser Ser Ser Phe Leu Thr Glu Arg Glu Gln Glu Glu Asp
930                 935                 940

Glu Glu Glu Glu Phe Gly Glu Phe Lys Leu Leu Pro Cys Asp Asp Ser
945                 950                 955                 960

Glu Ser Glu Asn Glu Glu Gln Asn Glu Glu Glu Glu Glu Glu Glu Asp
                965                 970                 975

Ala Lys Asp Asp Glu Asp Glu Glu Ile Leu Gln Lys Gln Gln Lys
            980                 985                 990

Arg Lys Leu Arg Leu Asn Asp Phe Met Glu Asp Glu Ala Glu Leu Ser
        995                 1000                1005

Gly Ser Asp Val Gly Ser Gly Asp Glu Tyr Gly Asp Asp Asp
1010                1015                1020

Glu Tyr Glu Glu Glu Ala Ile Asp Glu Asp Leu Pro Ser Asp Glu
    1025                1030                1035

Glu Leu Gln Asp Gln Val Asn Lys Ile His Met Lys Val Thr Met
    1040                1045                1050

Asp Glu Asp Gln Arg Gln Leu Arg Phe Tyr Gln Glu Arg Tyr Leu
    1055                1060                1065

Ala Asp Gly Asp Leu His Ser Asp Gly Pro Gly Arg Thr Arg Lys
    1070                1075                1080

Phe Arg Trp Lys His Leu Asp Asp Ala Ser Gln Val Asp Met Phe

-continued

```
                    1085                1090                1095
Arg Arg Asp Ser Glu Leu Glu Glu Val Asp Gly Glu Asn Glu Glu
    1100                1105                1110

Thr Glu Glu Thr Glu Leu Lys Trp Arg Lys Glu Arg Phe Glu Arg
    1115                1120                1125

Glu Gln Trp Leu Arg Glu Gln Pro Gln Gly Ser Arg Asp Asn Asn
    1130                1135                1140

Glu Glu Glu Glu Glu Asp Ile Gly Glu Asp Ser Gln Phe Met Lys
    1145                1150                1155

Leu Ala Lys Lys Val Thr Ala Lys Ala Leu Gln Arg Lys Val Ser
    1160                1165                1170

Thr Glu Thr Asn Glu Pro Lys Lys Pro Gly Pro Arg Asn Pro Tyr
    1175                1180                1185

Glu Val Ile Arg Pro Phe Ser Leu Pro Lys Leu Arg Thr Gly Ser
    1190                1195                1200

Leu Leu Ser Lys Pro Lys Glu Val Leu Gln Lys Leu Ala Ala Val
    1205                1210                1215

Ser Asp Leu Asn Pro Asn Ala Pro Arg Asn Ser Arg Asn Phe Val
    1220                1225                1230

Phe Gln Thr Val Ser Pro Gly Lys Lys Glu Glu Thr Thr Asp Lys
    1235                1240                1245

Pro Arg Ser Lys Val Arg Lys Asn Ile Ala Val Ala Met Pro Ser
    1250                1255                1260

Pro Lys Arg Phe Lys Arg Asp Ser Thr Pro Thr Val Lys Ser Arg
    1265                1270                1275

Ser Ile Phe Gln Leu Leu Glu
    1280                1285
```

<210> SEQ ID NO 3
<211> LENGTH: 4756
<212> TYPE: DNA
<213> ORGANISM: Homo sapiens

<400> SEQUENCE: 3

```
gacggcggga gccgctgctc tccggctgag ggaatcagag acagctccgt ccctagtgga    60
gcgcagggga ggcagaagtc atgacaggcg aggtgggttc tgaggttcac ctagaaatca   120
atgacccaaa cgtcatttca caagaggaag cagatagtcc ttcagatagt ggacagggca   180
gctatgaaac aattggaccc ttgagtgaag gagattcaga tgaagagata tttgtaagta   240
agaagttgaa aaacaggaag gttctacaag acagtgattc cgaaacagag gacacaaatg   300
cctctccaga gaaactaccc tatgacagtc cgaggaggaa aaataaagag aatttatatg   360
ctgggaaaaa tacaaaaatc aaaaggattt acaaaactgt ggcagacagt gatgaaagtt   420
acatggaaaa gtctttgtat caggaaaatc ttgaagcgca agtgaaacct tgcttagagc   480
tgagtcttca gtctggaaac tctacagact ttaccactga cagaaagagt tccaaaaagc   540
acatacatga taagaagga actgcaggaa agcaaaagt aaaatcaaaa agaagacttg   600
agaaagagga gagaaaaatg gaaaaaatta cagctaaa aagaaggaa acaaaaaacc   660 aggaagatga tgtagaacag ccatttaatg acagtggctg tcttcttgtg ataaagacc   720 tttttgaaac tgggttggag gatgaaaata actctccatt ggaagatgaa gagtcattag   780
aatcaataag agcagctgta aaaacaaag taaaaagca caagaaaaaa gaaccatctt   840
tggagagtgg ggtccattca tttgaggaag gaagtgagtt atcaaaagga accacgagga   900
```

-continued

```
aggaaagaaa ggcagccaga ttaagtaaag aagcattaaa acaactgcat agtgagactc      960
agcgccttat tcgagagtct gcactgaacc ttccatatca tatgcctgag aataaaacca     1020
ttcatgattt cttcaaacgt aaaccccggc ccacttgcca cggaaatgcc atggcactat     1080
tgaagtcatc taaatatcag tcaagccatc acaaagaaat catagacact gcaaatacta     1140
ctgaaatgaa cagtgatcac catagtaaag gttctgagca gacaacaggt gcagaaaatg     1200
aagtggaaac taatgcactc cctgtagttt caaaggaaac ccagatcatt actggatcag     1260
atgagtcttg caggaaggat ttggtaaaaa atgaagagct agaaattcag gagaaacaga     1320
agcagagtga cattagacct tcacctgggg acagctcagt gttgcaacag gaatccaact     1380
tcctcgggaa caatcacagt gaggaatgtc aggttggagg gcttgtagca tttgaacctc     1440
atgccctgga gggtgaaggc ccccaaaatc cagaagaaac agatgagaaa gtggaagagc     1500
ctgagcagca aaataaatca tcagcagttg gccacctgaa aaagtgaga cggtttactc      1560
tggatagact taagcaactg ggagtagatg tttccattaa accacggcta ggtgctgatg     1620
aagattcctt tgtgatactt gaacctgaaa ccaacagaga actggaagcc ttgaagcagc     1680
gtttctggaa gcatgctaat ccagcagcca aacccagggc tggtcagaca gtgaatgtga     1740
acgtcatagt gaaagacatg ggcactgatg aaaggaagaa gctaaaagca gatgtggtac     1800
ctgtgacttt agcacctaag aagttggatg agcaagcca cacaaaacca ggtgaaaagc      1860
ttcaggtgtt aaaagctaaa ctgcaagaag caatgaaact ccgaaggttt gaggagcgcc     1920
agaagcgcca agcactgttt aaattagata atgaagatgg gtctgaggaa gaggaggagg     1980
aagaggaaga aatgacagat gagtctgagg aagatggaga agagaaggta gagaaagaag     2040
agaaagagga agaactagag gaagaggagg ggaaagaaga ggaggaggaa gaagaggaa      2100
atcaggagac tgcagaattc cttcttagta gtgaagaaat agaaacaaaa gatgaaaaag     2160
aaatggataa agaaaataat gatggcagta gtgaaattgg caaggcagtt ggcttcctct     2220
ctgttcccaa gtctctctca tcagattcta ctttacttct gtttaaggac agctcttcca     2280
agatgggtta ctctcctact gaagaaaaat cagaaacaga tgaaaactca ggcaagcagc     2340
ctagcaaaact ggatgaggat gattcatgtt cattgctaac aaaggagagc agccacaata     2400
gcagctttga gctgattggc tccacgattc catcctatca gccttgcaac agacaaacag     2460
gccgtgggac cagttttttc cctacagcag gaggattcag atctccttcc cctgggctat     2520
ttcgagccag tttggtcagc tcagcttcta agagttcagg gaaactgtct gagccttcac     2580
ttcccataga ggattcccag gatctgtata acgcctcccc agagcctaag acacttttcc     2640
taggagcagg agacttccag ttctgtttag aagatgacac tcagagccaa ctgttggatg     2700
cagatgggtt cttaaatgtt agaaaccaca ggaatcagta ccaagctttg aagcctcgat     2760
tgccattggc cagtatggat gagaatgcca tggatgccaa catggatgag ctgttggatt     2820
tgtgtactgg aaagttcaca tctcaggctg aaaaacatct acccaggaag agtgacaaga     2880
aagagaacat ggaggaactt ctgaacctt gttcaggaaa attcacttct caggatgcct      2940
ccactccagc ctcatcagag ttaaataaac aggagaagga gagcagcatg ggtgatccaa     3000
tggaagaagc acttgctctt tgctcaggct cttttcccac agacaaggaa gaggaagacg     3060
aggaggagga atttggagac tttcggcttt tttcaaatga taatgagttt gatagtgatg     3120
aggatgaaca cagtgactct ggtaatgatc tggcactgga agaccatgaa gatgatgatg     3180
aagaagaact cctgaagcga tctgagaagt tgaaaaggca aatgaggttg aggaaatacc     3240
tggaggatga ggcagaggtg tcaggaagtg atgtgggaag cgaagatgag tatgatgggg     3300
```

-continued

```
aagaaattga tgaatatgaa gaggacgtaa ttgatgaagt acttccttct gatgaggaac    3360
tgcagagtca aatcaagaaa atacacatga aaactatgtt ggatgatgat aagcgacagc    3420
tacgtttata ccaagagagg taccttgctg atggggatct gcacagcgat ggtcctgggc    3480
gaatgaggaa gtttcgatgg aaaaacatag atgatgcttc ccagatggac ttgttccaca    3540
gagactctga tgatgatcag actgaagaac agcttgatga gtcagaagcc aggtggagga    3600
aggagcgaat tgaacgagag cagtggcttc gggacatggc acagcagggg aaaattacag    3660
ctgaagaaga agaagaaatt ggggaggaca gtcagtttat gatactggcc aagaaagtta    3720
cagccaaagc actgcagaag aatgccagtc gccctatggt tattcaggaa tcaaagtctt    3780
tgctcagaaa tccttttgaa gccatcagac caggaagtgc tcaacaggtg aagacaggct    3840
cactgctaaa ccagcccaaa gctgtgcttc agaaactggc tgctctctct gaccataacc    3900
ccagtgctcc tcgaaattca agaaactttg tctttcatac actttctcct gtcaaggctg    3960
aggcggcaaa ggaatcgtct aagtctcaga agatcccaga aaggactct gactggctca    4020 cctggagtgg agctcctatc cctggattct tcaggctttc atttgaccca catggttaag    4080
ctgggagaga cagagtccaa agagaggcgg agaagggcta ttctgggcag aacaaacaat    4140
tgatgacttt atggctctgt ggtctgggca gaactgcata ccctagatc accaaagctg    4200 agagccttta ggagtgagga tttgggccgg gcatggtggc tcacgcctgt aatcccagca    4260
ctttgggagg ccgaggtggg tggatcacaa ggtcaggaga tcaagaccaa cctgaccaac    4320
atggtgaggc cccatctcta ctaaaaatac aaaaattagc tgacgtgatg catgcacctg    4380
taatcccagc tactcgggag gctgaggcgg gagaatcgct tgaacccggg aggttggagg    4440
ttgcggtggg ccgagattgc gccactgcac tccagcctgg gcgacagagc gggactccat    4500
ctcaaaaaaa aaaaaaaaaa agtgaggatt tgggtcaccc caggctgaag gccaggggaa    4560
cctgaatgat aagggaaggg aaaacttagg ccacagtctg attagaaatg gggctgaatt    4620
ccaccctgtt tttcctttac tggagattca atttgaatta ctctgcctcc cttcttattc    4680
cttttccctt ttaaaatagt catcataatc ataaaaattt cttttccaaa aaaaaaaaa    4740 aaaaaaaaaa aaaaaa                                                    4756
```

<210> SEQ ID NO 4
<211> LENGTH: 1332
<212> TYPE: PRT
<213> ORGANISM: Homo sapiens

<400> SEQUENCE: 4

```
Met Thr Gly Glu Val Gly Ser Glu Val His Leu Glu Ile Asn Asp Pro
1               5                   10                  15

Asn Val Ile Ser Gln Glu Glu Ala Asp Ser Pro Ser Asp Ser Gly Gln
            20                  25                  30

Gly Ser Tyr Glu Thr Ile Gly Pro Leu Ser Glu Gly Asp Ser Asp Glu
        35                  40                  45

Glu Ile Phe Val Ser Lys Lys Leu Lys Asn Arg Lys Val Leu Gln Asp
    50                  55                  60

Ser Asp Ser Glu Thr Glu Asp Thr Asn Ala Ser Pro Glu Lys Thr Thr
65                  70                  75                  80

Tyr Asp Ser Ala Glu Glu Glu Asn Lys Glu Asn Leu Tyr Ala Gly Lys
                85                  90                  95

Asn Thr Lys Ile Lys Arg Ile Tyr Lys Thr Val Ala Asp Ser Asp Glu
            100                 105                 110
```

-continued

Ser Tyr Met Glu Lys Ser Leu Tyr Gln Glu Asn Leu Glu Ala Gln Val
            115                 120                 125

Lys Pro Cys Leu Glu Leu Ser Leu Gln Ser Gly Asn Ser Thr Asp Phe
130                 135                 140

Thr Thr Asp Arg Lys Ser Ser Lys Lys His Ile His Asp Lys Glu Gly
145                 150                 155                 160

Thr Ala Gly Lys Ala Lys Val Lys Ser Lys Arg Arg Leu Glu Lys Glu
            165                 170                 175

Glu Arg Lys Met Glu Lys Ile Arg Gln Leu Lys Lys Glu Thr Lys
                180                 185                 190

Asn Gln Glu Asp Asp Val Glu Gln Pro Phe Asn Asp Ser Gly Cys Leu
            195                 200                 205

Leu Val Asp Lys Asp Leu Phe Glu Thr Gly Leu Glu Asp Glu Asn Asn
            210                 215                 220

Ser Pro Leu Glu Asp Glu Ser Leu Glu Ser Ile Arg Ala Ala Val
225                 230                 235                 240

Lys Asn Lys Val Lys Lys His Lys Lys Glu Pro Ser Leu Glu Ser
            245                 250                 255

Gly Val His Ser Phe Glu Glu Gly Ser Glu Leu Ser Lys Gly Thr Thr
            260                 265                 270

Arg Lys Glu Arg Lys Ala Ala Arg Leu Ser Lys Glu Ala Leu Lys Gln
            275                 280                 285

Leu His Ser Glu Thr Gln Arg Leu Ile Arg Glu Ser Ala Leu Asn Leu
            290                 295                 300

Pro Tyr His Met Pro Glu Asn Lys Thr Ile His Asp Phe Phe Lys Arg
305                 310                 315                 320

Lys Pro Arg Pro Thr Cys His Gly Asn Ala Met Ala Leu Leu Lys Ser
                325                 330                 335

Ser Lys Tyr Gln Ser Ser His His Lys Glu Ile Ile Asp Thr Ala Asn
            340                 345                 350

Thr Thr Glu Met Asn Ser Asp His His Ser Lys Gly Ser Glu Gln Thr
            355                 360                 365

Thr Gly Ala Glu Asn Glu Val Glu Thr Asn Ala Leu Pro Val Val Ser
370                 375                 380

Lys Glu Thr Gln Ile Ile Thr Gly Ser Asp Glu Ser Cys Arg Lys Asp
385                 390                 395                 400

Leu Val Lys Asn Glu Glu Leu Glu Ile Gln Glu Lys Gln Lys Gln Ser
                405                 410                 415

Asp Ile Arg Pro Ser Pro Gly Asp Ser Ser Val Leu Gln Gln Glu Ser
            420                 425                 430

Asn Phe Leu Gly Asn Asn His Ser Glu Glu Cys Gln Val Gly Gly Leu
            435                 440                 445

Val Ala Phe Glu Pro His Ala Leu Glu Gly Gly Pro Gln Asn Pro
450                 455                 460

Glu Glu Thr Asp Glu Lys Val Glu Glu Pro Glu Gln Gln Asn Lys Ser
465                 470                 475                 480

Ser Ala Val Gly Pro Pro Glu Lys Val Arg Arg Phe Thr Leu Asp Arg
            485                 490                 495

Leu Lys Gln Leu Gly Val Asp Val Ser Ile Lys Pro Arg Leu Gly Ala
            500                 505                 510

Asp Glu Asp Ser Phe Val Ile Leu Glu Pro Glu Thr Asn Arg Glu Leu
515                 520                 525

-continued

```
Glu Ala Leu Lys Gln Arg Phe Trp Lys His Ala Asn Pro Ala Ala Lys
            530                 535                 540

Pro Arg Ala Gly Gln Thr Val Asn Val Asn Val Ile Val Lys Asp Met
545                 550                 555                 560

Gly Thr Asp Gly Lys Glu Glu Leu Lys Ala Asp Val Val Pro Val Thr
                565                 570                 575

Leu Ala Pro Lys Lys Leu Asp Gly Ala Ser His Thr Lys Pro Gly Glu
            580                 585                 590

Lys Leu Gln Val Leu Lys Ala Lys Leu Gln Glu Ala Met Lys Leu Arg
                595                 600                 605

Arg Phe Glu Glu Arg Gln Lys Arg Gln Ala Leu Phe Lys Leu Asp Asn
610                 615                 620

Glu Asp Gly Ser Glu Glu Glu Glu Glu Glu Glu Glu Met Thr Asp
625                 630                 635                 640

Glu Ser Glu Glu Asp Gly Glu Glu Lys Val Glu Lys Glu Glu Lys Glu
                645                 650                 655

Glu Glu Leu Glu Glu Glu Gly Lys Glu Glu Glu Glu Glu Glu
            660                 665                 670

Gly Asn Gln Glu Thr Ala Glu Phe Leu Leu Ser Ser Glu Glu Ile Glu
            675                 680                 685

Thr Lys Asp Glu Lys Glu Met Asp Lys Glu Asn Asn Asp Gly Ser Ser
690                 695                 700

Glu Ile Gly Lys Ala Val Gly Phe Leu Ser Val Pro Lys Ser Leu Ser
705                 710                 715                 720

Ser Asp Ser Thr Leu Leu Phe Lys Asp Ser Ser Lys Met Gly
                725                 730                 735

Tyr Ser Pro Thr Glu Glu Lys Ser Glu Thr Asp Glu Asn Ser Gly Lys
                740                 745                 750

Gln Pro Ser Lys Leu Asp Glu Asp Ser Cys Ser Leu Leu Thr Lys
            755                 760                 765

Glu Ser Ser His Asn Ser Ser Phe Glu Leu Ile Gly Ser Thr Ile Pro
770                 775                 780

Ser Tyr Gln Pro Cys Asn Arg Gln Thr Gly Arg Gly Thr Ser Phe Phe
785                 790                 795                 800

Pro Thr Ala Gly Gly Phe Arg Ser Pro Ser Pro Gly Leu Phe Arg Ala
                805                 810                 815

Ser Leu Val Ser Ser Ala Ser Lys Ser Ser Gly Lys Leu Ser Glu Pro
            820                 825                 830

Ser Leu Pro Ile Glu Asp Ser Gln Asp Leu Tyr Asn Ala Ser Pro Glu
            835                 840                 845

Pro Lys Thr Leu Phe Leu Gly Ala Gly Asp Phe Gln Phe Cys Leu Glu
    850                 855                 860

Asp Asp Thr Gln Ser Gln Leu Leu Asp Ala Asp Gly Phe Leu Asn Val
865                 870                 875                 880

Arg Asn His Arg Asn Gln Tyr Gln Ala Leu Lys Pro Arg Leu Pro Leu
            885                 890                 895

Ala Ser Met Asp Glu Asn Ala Met Ala Asn Met Asp Glu Leu Leu
            900                 905                 910

Asp Leu Cys Thr Gly Lys Phe Thr Ser Gln Ala Glu Lys His Leu Pro
    915                 920                 925

Arg Lys Ser Asp Lys Lys Glu Asn Met Glu Glu Leu Leu Asn Leu Cys
930                 935                 940

Ser Gly Lys Phe Thr Ser Gln Asp Ala Ser Thr Pro Ala Ser Ser Glu
```

-continued

```
               945                 950                 955                 960
Leu Asn Lys Gln Glu Lys Glu Ser Ser Met Gly Asp Pro Met Glu Glu
                    965                 970                 975
Ala Leu Ala Leu Cys Ser Gly Ser Phe Pro Thr Asp Lys Glu Glu Glu
                    980                 985                 990
Asp Glu Glu Glu Glu Phe Gly Asp Phe Arg Leu Val Ser Asn Asp Asn
           995                 1000                1005
Glu Phe Asp Ser Asp Glu Asp Glu His Ser Asp Ser Gly Asn Asp
       1010                1015                1020
Leu Ala Leu Glu Asp His Glu Asp Asp Glu Glu Leu Leu
       1025                1030                1035
Lys Arg Ser Glu Lys Leu Lys Arg Gln Met Arg Leu Arg Lys Tyr
       1040                1045                1050
Leu Glu Asp Glu Ala Glu Val Ser Gly Ser Asp Val Gly Ser Glu
       1055                1060                1065
Asp Glu Tyr Asp Gly Glu Glu Ile Asp Glu Tyr Glu Glu Asp Val
       1070                1075                1080
Ile Asp Glu Val Leu Pro Ser Asp Glu Glu Leu Gln Ser Gln Ile
       1085                1090                1095
Lys Lys Ile His Met Lys Thr Met Leu Asp Asp Asp Lys Arg Gln
       1100                1105                1110
Leu Arg Leu Tyr Gln Glu Arg Tyr Leu Ala Asp Gly Asp Leu His
       1115                1120                1125
Ser Asp Gly Pro Gly Arg Met Arg Lys Phe Arg Trp Lys Asn Ile
       1130                1135                1140
Asp Asp Ala Ser Gln Met Asp Leu Phe His Arg Asp Ser Asp Asp
       1145                1150                1155
Asp Gln Thr Glu Glu Gln Leu Asp Glu Ser Glu Ala Arg Trp Arg
       1160                1165                1170
Lys Glu Arg Ile Glu Arg Glu Gln Trp Leu Arg Asp Met Ala Gln
       1175                1180                1185
Gln Gly Lys Ile Thr Ala Glu Glu Glu Glu Ile Gly Glu Asp
       1190                1195                1200
Ser Gln Phe Met Ile Leu Ala Lys Lys Val Thr Ala Lys Ala Leu
       1205                1210                1215
Gln Lys Asn Ala Ser Arg Pro Met Val Ile Gln Glu Ser Lys Ser
       1220                1225                1230
Leu Leu Arg Asn Pro Phe Glu Ala Ile Arg Pro Gly Ser Ala Gln
       1235                1240                1245
Gln Val Lys Thr Gly Ser Leu Leu Asn Gln Pro Lys Ala Val Leu
       1250                1255                1260
Gln Lys Leu Ala Ala Leu Ser Asp His Asn Pro Ser Ala Pro Arg
       1265                1270                1275
Asn Ser Arg Asn Phe Val Phe His Thr Leu Ser Pro Val Lys Ala
       1280                1285                1290
Glu Ala Ala Lys Glu Ser Ser Lys Ser Gln Lys Ile Pro Glu Lys
       1295                1300                1305
Asp Ser Asp Trp Leu Thr Trp Ser Gly Ala Pro Ile Pro Gly Phe
       1310                1315                1320
Phe Arg Leu Ser Phe Asp Pro His Gly
       1325                1330
```

<210> SEQ ID NO 5

<211> LENGTH: 58837
<212> TYPE: DNA
<213> ORGANISM: Homo sapiens

<400> SEQUENCE: 5

```
aagcaggtag ttttaaactt tactccagag aatagcagt actaaaaatg taacatggta     60
atcttcctca atttgcagaa aagaaataa aagacataat tcagtcaatt atcttcctcc    120
aaactttctt aagcctttgg tttctgcttt tgtctgccaa ggagcacaat ataaatagag    180
cacttttaga actggctgag catgttaagt tccatggctg attttttccc agacttgtaa    240
tgtcagaatt gcttttaaa tattttttg tgatataata atatatccta ctagttaaaa    300
tgtttccgca ttcaaatgac cagattaaca gcatcagtac tgcaaaatgc ttcctatgaa    360
gtgctatact ttcgggtgcc ctactcatta aacctatttg agaatcatga tctcatccag    420
tgttttctag ttacaaaaaa gaacaagttt cttttctttt tttgaaatgg agtcttgctc    480
tgtcacccag gctggagtgc agtggtgcac gatctcagct caccacaatc tccgcctccc    540
aggttcaagc aattctcctg cctcagcctc ccaagtagct gggactacag gtgcccgcca    600
ccacgcccgg ctaattttg tgttttagt agagtcaggg tttcaccatg ttggccaggc    660
tggtctcaaa ctcctggcct caagtgatct gactgcctca gcctcccaaa attctgggat    720
tacaggcatg acccactgca cccaacctcc aaaaagaac acatttctga gaaactaaat    780
tagttaccta agtttatgaa gccctctatg ggacaggttc agactaatcc ctgtaaagtg    840
agcactccag atgtttcctt tgttgccatt tatcaacttg ataaacaagg attgttggat    900
gactacaaca atgaagggac agagaggtca aggtgattca caggtttcta aactggtgag    960
tggatatggt tccactcacc aaaattgaga atacaggttg ctaattctaa atacagactc   1020
actttatctt ggcacaagtt aatgtgtaaa ataaaagttt cctggggatg ggaggagtat   1080
gaagttgttg cttaatgggc atagagtttc agttttgcaa gatgaaagga ttctaggcc    1140
aggcccgttg ggtcacacct gtaatcccag cgctttggga ggccgaggtg catgggtcac   1200
ttgaggtcag gagttcaaga ctagcctggc caacatggtg aaaccccgtc tctcctaaga   1260
atacatacaa aaaagtagcc aggcgtggtg gcaggtgcct gtaatcccag ctacttggga   1320
ggctgaggca ggagaattgc ttgaacccgg gaggcagagg ttgcagtgag ccaagatagc   1380
accattgcat tccagcctag gcaacaagag caaaactcca tttcaaaaaa aaaaaagaag   1440
agaaaagaa aagaattctg aagattggta gattggttac ataacaattt gaatgtactt   1500
ctgaactgca tactttaaaa tggttaagat ggtaaatttc atgttatata tgttttacca   1560
caataaaaat tgaatgaaag gttttccttt cctagcttac ccatgtccac ccattgttca   1620
aattggagct ttctctctta gcttctgtga tgagtgaaaa ggtgctcccc aaagatattt   1680
taaaatacta atataaggaa tattatttca ctcattcatt ttcagaggga gctcaagaag   1740
ttgtcaagtg aatgaattaa ttagttcaac aaatatttat cagttttcct accttgaacc   1800
tgggatgttc taagtccttt gttctcaaag tgtggtctcc agatcagcaa cactagcatc   1860
accagggaat tgttagtaa tatacattcc tgtgggcac ggtggttcat gcccgtaatc    1920
ccagcacttt gcgaggccga gatgtgcagg ttgcttgagt ccaggagttt gagaccagct   1980
tgggcaacat ggtgacaccc cgtctctaca aaataaaaaa ttagctgggc atggtggtgc   2040
acacctgtag tcccagccac ttgggaggct gaggtggaag ggttgcttga gcctgggagg   2100
ttgaggctgc agtgagctgt gatcatgcca ctgcactcag ggagaaaaag aaaaaaagga   2160
aagaaagaag tatacatctc tggaccccac ttcagacata ctgaatcaga aactttggca   2220
```

```
ctaggaccca acaatagctg ttttttaccag cctttcagat tattctgatg catgctcaag    2280
tttaagaaag acaattctag gttgcaatga tacagaggcc aagaaaacaa aacgcctgtt    2340
ctcttggagc aacaacagac aaatagatat aaataaaatt tcaggcaaag gaaagtgtta    2400
tcagggaaac cagcatagga taaggaggca gaacacagag gatgctcagg cagggtcttt    2460 ctgagggta tgagctctga agtcacatag agtctgaaaa ttggctccac cagtttctag    2520
ccttttaaaa gtctggtttc ctcatcttct aagaaagaga taataatatt acaagtttac    2580
tctgaagatt aaataagata acacttataa aatccttgca actgtttctg ccactgagta    2640
aggcttcaat aaacgttagc cctccatata tgatggggag tgccatagat gtatacctgg    2700
gaatcgttga tgtagaaatt aatagtaaat ggatgaaaag gtggataaac caagacacaa    2760
aaagagaaga ggatggatga tgggctcttg ttggtgggga cagaagtgga ttgagagatg    2820
gtggggaagt aaagaaatga agatgtggag agggagcttt tttctgaacc cagctaaagg    2880
tggaaacttg gaagaggagg ccagtggatt gggtgaagaa ccaaccattt ggtatacctg    2940
tgactgagga ggttctcagg atgcaggact tttagtgcta aaactaggaa agtcctgggc    3000
aagctgggcc aagctggcca cactggcagt ggatatgacc atggagggtg aagtgagcaa    3060
taaatactct gacctttctt tcctggtggc ctctcatctc cttacagtaa ccttataagg    3120
tgtctttaca ggggcctgac ccaaccagaa gggcaaggga gctgggataa tacagtctag    3180
agaggtcagc cttgccttga cacacaccag ggtaaaggaa ggacagagaa ttgacctgga    3240
gaggcaaaaa ataatggcca gcacagtggc aaaactggga ttagaattgt ctgggatagg    3300
ccaggtgcgg tgactcacac ctgtaatccc agcactttgg gaggctgaga cgggcggatc    3360
acgaggtcag gagttcaaga tcagcctggc caaaatggtg aaatcttgtc tctactaaag    3420
ttacaaaaaa ttatctgagc gtggtggcac atgcctataa tcctagctac tcaggaggct    3480
gaggcaggag aatcgcttga acccgggagg cggaggttgc agtgagccga gatcacgcca    3540
ttgcacccag ccatggtgac agggagagac tctgtctcaa caaaaaaaaa aaaaaaaaaa    3600
aaagaactgt gtctgggata aacctgattt cagagcttca attctttttc cagccttgtt    3660
taaaggtaga atgccctcta ggagtgatga gtgctttcta catcctcaaa ttaactctac    3720
agagaattat aaagattatc caaccatatt ctttggtatc tgagcagccc acaaaacttt    3780
tttctttaga gacaaggtct ccctctatcg cctacgctga agtgcagtgg tgcgatcata    3840
actcactcta acctcaaact cctggactca agcatcctc ccacctcggc ctcccaaagc    3900
gttgagatta caagcgtgag ccatggagcc cggccctctt taaaaaataa aagtgggccg    3960
ggcacagtgg ctcacgcctg tgagggtat gaggcctccc agcactttgg gaggccgagg    4020
cgaggatcat ttgagatcag gagttcgaga ccagcctggc caacatggtg aaaccccgtc    4080
tctactaaaa atacaaaaat tagccagggg ttggtggcgg gtgcctgtaa tcctagctac    4140
tcaggaggct gaggcacgag aatcgcttga acccgggagg cggaggttgc agtgagccga    4200
gatcgcgcca ctgcatttca tcctggctaa cagagggaga ctccatctca aaaaaaaaa    4260 aagtgtgtgt gtatacacat acatgtgtat gtgtatatat gtgtatgtat atatgtgtgt    4320
acatatgtgt gtgtgtgtgt atatatatat atatatatat atatatatat atatatatat    4380
attcagtggt aagtgtcatg tacaagaggc acacaggatc tagctgctcc agaaatgaag    4440
tcagtggaga aaatcccccac gggaaccttg gaattcctct aaaaagttca ggtacaggac    4500 actcccagt gcccaggaac cgtttcccag ctcacttccc cccgaaagac tcaccctctcc    4560
```

```
aatcgcactc gatgctttgg caagtgtcaa aggtcaaaga ccacggctcg cctggtaccg    4620
actgccccgc ccccgtgcac ctccagctcc cccaggctcc gctaccagca gctgcgaccc    4680
gccaactcag cctgggtaat aggagattgg gcggccagag gcgctgcgtg attggtgggt    4740
cggaaggggg cggggactcg ctggaaagcc ccctctggat tggtgcaaac catctgggtg    4800
ggacctccac tctggctggg cgggaaagca agaacagcac tgctgggctg agacgcgcgg    4860
gagccgctgc tctccggctg agggaatcag agacagctcc gtccctagtg gagcgcaggg    4920
gaggcagaag tcatgacagg cgaggtgggt tctgaggtga gtttatgcac acgccccca    4980 cgggggctta gaaggccggg caccgagagg ttaggtgggg ccggggtaga ccccgctgac    5040
ccgaggcgcc cggcgggag gactgcggct cccggcgttc gccgcgccgg ctcccgcggc    5100
ctcgagactc ggccgggatg ggttccgacc gggcatcccg tcccgccgcc gggcttcccg    5160
cgcttcgggc tccgtggccg gagagctcca ggtctctgcg gcgcgcactg ccggcagccc    5220 agccctctt cagccggttc ctgccgccag ccctcccctt tggcgcgttt cctgtcgcgg    5280
aagctcctcc cctcagggtg ctctgaaagc cgggaggctc tagccgaacc cggccgcagc    5340
ggtgcggggg gattctccgc agagagaggg cgagcgaggg tgttagggag ttccacactg    5400
ggcctgggag gggccctgga ggtcatcgcg cgcaggccct ttgcgttttc cgaccgggcc    5460
ccgagtgggg aagtcaccgc tggggctcct ggctggtggc tggcagctcc ctggcgaaat    5520
tgggcataga aaacagatgt tccagagct gtgtcctttc tgggccggat tcgggcaagg    5580
cactcccgcc ttaggagcaa aatttaaagg ggcgccaaaa ccctcaatca aactcatatt    5640
ttaatgcaat attttttaaaa aaccaaaatt aatgcaaaaa cttttttatga tttgatattg    5700 aacaaaatat cagacgttta aacaaagacg agatccgacc agtcatttgc acgaccttgc    5760
ctcaatcacc tcaccctaat tccatccctg tttccaataa actttattta caaaagcggg    5820
catattattt acctcatgag ctgtagatta ttgatttaat ttttaaaaa atattgcatt    5880 aatgttattc attttgatta ctgaattttt tgagacctca ccccaccctg ttactggccc    5940 tgcccttga cgttgctgca aattgcctag aagataatcg tcattcaaag cagccctatt    6000
ccttgagctg tctggttacc taaattcggt ttccacactc acaaacagaa gtaatagttt    6060
tactgctttg gattgttgag aggatcatca gtgcatacat attaattctc agcaatccca    6120
gcacttcggg aggctaaggc cggcagattg cttgagctca agagttcgaa accagcctgc    6180
atagaaaaca tggcaaaacc ccgcctctac aaaaaaaaaa aaattagccg ggcgtcgcct    6240
gtggtcccag ctactcggtc ccagctactc gggtggctga ggtgagagaa tcctttgggc    6300 ctggaggtc aaggctgcag tgagccatga tcctgccact gcactccagc ctaggtgaca    6360
gagtgagaca ctgtatcaaa aaaaaaaa atttgtacct tgcattcaaa tcaatttaat    6420
aatttttttt tttttgagac ggagtctcgc tctgttgccc agactggagt gcagtggcac    6480
aatctcggct cactgcaact tctgtctcct ggattcaagc gattctcctg ccccagcctc    6540
ctgagcagct gggactacag gcacacacca ccacgcccag ctaattttg tattttagt    6600 agatacgggg ttttactgta ttggccaggc tagtctcgaa ctcctgacct tgtgatccac    6660
ccacctcggc ctcccaaagt gctgggatta caggcgtgag ccaccatgcc tgaccaattt    6720 ataattttt tgagaaacca ctcagctgag gccttgtgcc ctgttacatt actgatgttc    6780
atatttctcc ctttattaat aagttgattc agagccctga gaacactaag gaggtagact    6840
tggcatctag ggttagcttt aaggtcacta actgatcaag tcacctaaca cacccctcct    6900
ccttaggttt ttatttgcga ctttttaaac tgtcttattt agaaattttc aaacctatac    6960
```

-continued

```
aaccgtagaa aggatggtat aatgaaccca tcaccttact tcaactacag tttgaatatc    7020
tctcgtctga aatgcttggg accagaagcg ttttgaattt cagattcatt ttggattttg    7080
gaatattcgc atacacataa tgagatatct tggggagggg acccaagtct aaacatgaaa    7140
ttcagttata tttcatatat accttacaca catagtctga aggtaatttt atacagcatt    7200
ttaaaataat ttcgtgcatg aagcaaaggt tttactgcag ctcatcatat gaggtcaggt    7260
gtggaatttt catctagtgg catcatgtca gtgctcaaat attttggaat tgggagcatt    7320
tcagattttc aggttagaga tgttcaacct gtattttcaa gtcatggcca atcttgtttt    7380
attcatacag ctacccattt ttcctctcac aggattattt ggaagaaaat ccaagatatc    7440
atattatttg aaccacaaag attttagtgt gcatatctaa caaacaagag ctttccaaaa    7500
atagatacta cgatattatt accacaccta agaagtatct agtcagtgtt cagatttctt    7560
tgactcagag atatttcatt tattttttata tgccacttta gcataattat ttacattttt    7620
agttttttga atcatcatcc gaagttggca ttttgtaatt gtttatatta tatatgtgta    7680
tatatgcata tatgtatgta ttttaagata tacatacata tataaagcat acatttatgt    7740
atatagaaat atacagggcc ggttgtggtg gcttacgctt gtaattccag cattttggga    7800
ggctgaggca ggcggatcac ctgaggtcaa aagttcgaga ccagcctggc taacattgtg    7860 aaacccgtt tctacaaaaa attagccggg catggtggcc cgcacctgta atcccagcta    7920
ctcgggaggc tgaggctgga gaatcgcttg aacccaggag gcggaggttg tagggagcca    7980
agatcgtgcc attgcactcc agcttgggca ataagagcga aactccgtct caaaaaaaga    8040
aaaaaggaaa tatacatata gccgggcgtg gtggctcacg tctgtaatcc caccactttg    8100
ggaggctgag gcgggcggat cacctgaggt caggagttgg agaccagcct gactaacatg    8160
gagaaacccc atctctacta aaaatacaaa attagccaga cgtggtgaca catgcctgta    8220
atcccagcta ctcgggaggc tgaggcagga gaatcgcttg aacctgggag gcagaggttg    8280
cggtgagccg agatcgcgcc gttgcgctcc atcctgggcg acaacggcaa aactccatct    8340
caaaaaaaaa gaaatataca catagcatat agaaatatac atacatatat aaatatatag    8400
aaatatacat acgtacacac atatatacat tcacttatgt gttaactttc tttataggtt    8460 tctctcccctc tcttttttttt ttctttgcaa tatattgtta aagaaaccgg ccgggtgcag    8520
tggctcatac ctgtaatccc agcattttgg gaggccgagg tgggcggatc acctgaggtc    8580
aggagtttgc aaccggcctg gccagcatgg tgaaaccttg tctctattaa aatagaaaaa    8640
attagctggg tgtgttgatg tgcgcctgta atcccagcta ctcaggaggc tgaggcagga    8700
gaatcgcttg aacccaggag gcagaggttg cagtgagccg agattgcacc actgcactcc    8760
agcctgggtg acagagcgag attctatctc aaaaaaaaa aaaaaaaga gagagagaga    8820 gaaagaaacc acccagtttg acttgtagaa tttcccacgt ctagattgca tatctgtggt    8880
attattcaac atgttcccct attccctcta tttcctataa cttgctagtt agatctagag    8940
acttgatagg attcaaattt gattgttctg tcaggaatac tttatggcta gtattgggta    9000
cttctattag gcagcacata atgtctggtt gtttctcttt tggtgatgtt agcagccatt    9060
aatgataatt gcctaggtct gttatttaat tgagggttga taaaattgtg ataatctaat    9120
tctatcattt attaattcat taggatattt ctctaaatag aaacttcccc tcatcaattg    9180
tatggatata ttggggaaca gttcacacag aaaaggcata taaatgctt gattcttttc    9240 atttttttttt ttaccgttac taaaagagtt ggttctgtta gcatccttca aaggtgaaaa    9300
```

```
atgaactttt gtttgtttgt tgtccagtaa ttctaaatgt catcccttca aggaaccatt    9360
gtatttggtt cttttccttag ttcaggttga tgatcccacg atgatttgtg tgtcattatg    9420
tacttggagc tttcggtcac ctgctggttg atataaagta tattgtcatt ttctaggttc    9480
acctagaaat caatgaccca aacgtcattt cacaagagga agcagatagt ccttcagata    9540
gtggacaggg cagctatgaa acaattggac ccttgagtga aggaggtttg taatagtact    9600
tttattttta ggaataggtt gcgggagcct cagttgtaag tagattggat tgatttcatt    9660
attctcttga tttattacat tattaatgcc ccatccttat tgtttgtttt attataaaag    9720
caaaataaca gtgcttgtac cttttttgaaa ctatgttata ttgttgaatg tctaatagct    9780
accatattgc ctggttaatt gcattcatcc tataataaaa ggaatttttaa cacctgccgg    9840 aggttagaac aactttacac attgtaaata tacgtaaaat tacatttccc agtaagagac    9900
atttttccca gggaaaatgt ttttcaaaat gtatttttag atttgctttg ctacaatcag    9960
ttcttaacag tagtcacgta atttcacaat gttatatatc acttgtataa aaatatattt   10020
ttgaggagta gtgggactag gaggaagatc aaatgatggt ataattaaaa gaaaattgtt   10080
tcctccagat tcagatgaag agatatttgt aagtaagaag ttgaaaaaca ggaaggttct   10140
acaagacagt gattccgaaa cagaggacac aaatgcctct ccagagaaaa ctacctatga   10200
cagtgccgag gaggaaaata aagagaattt atatgctggg aaaaatacaa aaatcaaaag   10260
gatttacaaa actgtggcag acagtgatga agttacatg gaaaagtctt tgtatcagga    10320
aaatcttgaa gcgcaagtga aaccttgctt agagctgagt cttcagtctg gaaactctac   10380
agactttacc actgacagaa agagttccaa aaagcacata catgataaag aaggaactgc   10440
aggaaaagca aaagtaaaat caaaagaag acttgagaaa gaggagagaa aaatggaaaa    10500
aattagacag ctaaaaaaga aggaaacaaa aaaccaggta cattttaaag aataatttgc   10560
tattgcttgg gtaggttaac attttagaaa aggttgctgt tagtacttga ggttgttct    10620 gctctctgac tattgctttg aattgactat tttgtgttga gaattattct caataggtat   10680
gtgatttaaa actaactggt cttggccagg tgcagtggtg catacgtcta atcccagcac   10740
tttgggaggc tgaggccaga gggtcactta agcccaggag ttcgagaaca gcctaggcaa   10800
cagagtgaga tcccatctct acaaaaaatt taaaaattag ttgggtgtgg tggccgtagt   10860
cccagctgta gtcccaacta cttgggaggg tgaggtggga gaatcacttg agcccaggaa   10920
gtcgaggctg caatgaagct gtaattgtac cactgcattc cagcctggat gacagagtga   10980
gaccctgtct caaaaaaaaa aaaacaaaa accaaaaaaa caaaacttat tggtcttatt    11040
ctattttggg tatgcagagg acatttccaa ataaatgggt ttctgatttt ctttatgagc   11100
acatggagta attctttgct gtctctgagc tgatgaaaat taactgaaag aaggcttttt   11160
tatgcatcta tcagtcagta gtcttgtttg ctaactagaa aaaccatcct caaatttata   11220
aactagttgc ttaacaagta ttttacttca aaaaatatt tactgtttat taagttagtt    11280
ttagacagtt gcataaaatc acaacttgga cttcaaagga tacatgtgag ttagaaacca   11340
gtaagaatgt tctagatttt atatgcttgt ctgttgatga aacatgggct ttttctggcc   11400
tgatccaaat tgccatatga tgttgtgaaa tactggattt taaatgatt ggattatgct    11460 ttttgtttat gtattactta ggaagatgat gtagaacagc catttaatga cagtggctgt   11520
cttcttgtgg ataaagacct ttttgaaact gggttggagg atgaaaataa ctctccattg   11580
gaagatgaag agtcattaga atcaataaga gcagctgtaa aaaacaaagt aaaaaagcac   11640
aaggcaagta aagcatgatt gcaataagag ttaatcaact gcttctgacc tttgctatat   11700
```

```
ttttaattta ctgttggaac cttaattttt tttttaactg aagaaaaact tgtgtcagtt    11760
gacttaagtg tttcagctgt taattttgga gacttgcagt acaagtgata gacatgctaa    11820
cttctttgga aactagtgtt ttgttattac ccttttagga atgctgaaaa aaaaaaccac    11880
taagatattt gatggtgtag taagatgcag gtaaataata gggaagagat gtaaattttg    11940
caatcctata gcctttgaga aatgaaccct atagggtttc aggaagggta tcaaagagag    12000
gcatcagtca aaacattgtt gtcccgagtg tttggaagca taattttcct tcctaagatt    12060 ttttttagc ttcctgcgag ttattatccc tctttaggga aagatgtaag cagaggtaaa     12120
agaaataagg gtccagactc catctgaggt atctgttttc taagcataat aggatgctgt    12180
gtgtttaata atttctagtt gatgattatt gatttattaa tgtagcatga tgtggtgttg    12240
gactacaaaa gtagtcttca gctaaagcat cctcttattt gaatttcgtt tttgtcctaa    12300
tcaacctgcc atttctttta gaaaaaagaa ccatctttgg agagtggggt ccattcattt    12360
gaggaaggaa gtgagttatc aaaaggaacc acgaggaagg tgaggtagag ccctgtatat    12420
tagtcacact gatctcttta cacaggagat tatagatttc ttagggataa atattttatt    12480
ttgtctatca tatttttctg ttacccatca tattgctttg tacatagtag gaacaaaata    12540
tggattggat tgaacaaatt ctctgagact tgggaataaa tgaattcctt gagtttatac    12600
tgcatttggg cttactcatg cttactattt cctttcctct tttcttggag agagcaaact    12660
cttgagtgat gaatatctat ctttctggat attcatataa ttaatgtagt ctcacttctt    12720
gttttcttta aggaaagaaa ggcagccaga ttaagtaaag aagcattaaa acaactgcat    12780
agtgagactc agcgccttat tcgaggtaat gcaacccagt aaactttgag gcaaaatcac    12840
aacatttctt tgtaagctca acttggatgt tggggacttt tatttttta acacttctaa     12900 tgtgaactca ggttataata ttaagtttag aattgatctt ggtgaaaggc cattgttcta    12960
aagcccttgg aacattagta taaactgaag aaatttttcag aactgtagtg caggtaagga   13020
ggaaattttt taatggttgt ctatggactg attgtgtcag gattctttgg agaggtagta    13080
atccctccct atttgcagtt ttggttacct gtgtcagcca tggtccatgg aacttaaaaa    13140
tatcatccct ttgtccagag tatcacgctg tatacattac ctgcctgtta gtccgttagt    13200
agccctctca gttatcagat caaaaaaaca ctgcatggtt tagtaccatc tgcagtttca    13260
ggcatccact gcaggtcttg gaatgtgtct gtctggataa gcggggacta ctgtatataa    13320
atgtttaggt cccacagaga ttctgattca gtagattcga aatgggatcc aagaatctgt    13380
atttctaaaa aacttcctgg atcattttga tttcacatct aggtttaaaa gccactggtc    13440
ttcagggagc ttttttgtac ttagctcctc tgccttttgtt aaaggggagt tttctatttc    13500
tagtgatggc tttggttatt atgtttagtt aactgaatat gaagtgacat ttcagaatat    13560
acagtatata tatttgcttg ttttattcca ttttatagag tctgcactga accttccata    13620
tcatatgcct gagaataaaa ccattcatga tttcttcaaa cgtaaacccc ggcccacttg    13680
ccacggaaat gccatggcac tattgaagta agaaccctct ttccttatta taattttcat    13740
gaacatttag ttttgtagca aacatctggc ataaaaagtt cagatttctc actcccttaa    13800
aactgattta actgatatat actaagggat gagaatgttt cacatttagg ataattttca    13860
actccagctc aatttctctt ctctaggtca tctaaatatc agtcaagcca tcacaaagaa    13920
atcatagaca ctgcaaatac tactgaaatg aacagtgatc accatagtaa aggttctgag    13980
cagacaacag gtgcagaaaa tgaagtggaa actaatgcac tccctgtagt ttcaaaggaa    14040
```

```
acccagatca ttactggatc agatgagtct tgcaggaagg atttggtaaa aaatgaagag  14100
ctagaaattc aggagaaaca gaagcagagt gacattagac cttcacctgg ggacagctca  14160
gtgttgcaac aggaatccaa cttcctcggg aacaatcaca gtgaggaatg tcaggttgga  14220
gggcttgtag catttgaacc tcatgccctg gagggtgaag gcccccaaaa tccagaagaa  14280
acagatgaga aagtggaaga gcctgagcag caaaataaat catcagcagt tgggccacct  14340
gaaaaagtga gacggtttac tctggataga cttaagcaac tgggagtaga tgtttccatt  14400
aaaccacggc taggtgctga tgaagattcc tttgtgatac ttgaacctga aaccaacaga  14460
ggtaatcctt tacattgtgg ggagcctccc tggagtgatt atcctggtag cttttgatta  14520
ttgactactg tcgaggacag agaacacagg aggaaccaat aaccactttg atcttatcct  14580
gcagttgttc cagatatggg cagagtcttt tttagagaaa tttggcaggg tatcagaatg  14640
atctaagcca tgtttaaaat ggaagtctgt tggctgggtg cggtggctta cgcctgtaat  14700
cccagcactt tgggaggcca aggcgggcag atcacgaggt caggagtttg agactagcct  14760
ggccaataca gtgaaacccc gtctgtacta aaaatacaaa aattagccgg gcatggtggc  14820
acgcatctgt agtcctagct actcggggagg ctggggcagg agaattactt gaacccagaa  14880
ggcagaggtt gcagtgagcc gagactgcac cattgcactc cagcctgggt gagagagcga  14940
gactctgtct caaaaaaaaa aaaaaaaaaa aaaggttgtt gatagttaat ataaaaagaa  15000
ggtacattgc tactgtgtta tggtatttag gaatttatta tttctgcctt tccaatctga  15060
aattaagttt tttctgtaat cctgagtcaa atcttaagac attgatgaaa acatcattta  15120 gtttttttact gctaaagaga aacatttttgg ttcacttaaa ttatctgtga aaccgaattt  15180 cttttgttttt cactcattca acaaatatta agtatctac tatgagtaag ttgctgtggg  15240
gcataccaag ataaatctga catttaaggt atacttaaga tgcttttact ctaatgggcg  15300
agataagaag tatgcaaata agaagtacaa aggagaaaat ggtaaatgat gtctttgata  15360
atgaatatgt cattgataat tggaaaataa ataacatgaa gaaaaaggaa aagtattttc  15420
ttaaagaaca tttagaataa agtactgtgg gaattcagag aagcataaat ttcttccaat  15480
gaatagttaa aagacagcct gaagaatagg tggattaatt acttgttcac tgccttccct  15540
ttatactgtg agttggtatc ttctgccttg ttccctactc tatccctagt gcttcctcag  15600
tggacgacac attgtaggca cttgtattta tcaaatgaat gaatgatccc tcaacactga  15660
actcaagtat taccacattg aataaatttc ctgactctta gatagagctg gatgctcccc  15720
actctgcctt gaggcagtat ggaatggtgg ttaagagctt agactttgta gcaagaccag  15780
gatttgaatc tgaactagca tagtaattgt ttaacattgt atacgccatt tgacctcttc  15840
aagcatcttt tgtttaaaaa agagaagaaa gccagacaca gtggtgcaca cctgtagttc  15900
cagctactcg ggaggctgag gcacaagagg gtcacttgaa cccaggagtt taaggccatc  15960
ctgggcagca tatgaaatcc tgtctcaaaa aaaaaaaaa agaaaaagaa aaagcacta  16020 tatgacttgt gggctatggt gaagatttgt tgaaataatg catgcaaatg gatagtataa  16080
acaagcactc aaaaagttgt tgctgcttct actattatta gtgaaatggt tcacatcaag  16140
actttttttt tttgagacgg gctttcactt gctcttgcca cctaggctgg agtgcaatgc  16200
tgcgatctcg gctcactgca acctccgcct cctgggttca gcaattctt ctgcctcagg  16260 ctctcaagta gctgggatta caggtacccg ccaccacacc cagctaattt ttgtattttt  16320
agtagagaca gggtttcacc atgttggcca ggctggtctc aaactcctga ccttaggtga  16380
tctgcctgcc tcagcctccc aaagtgctgg gattacaggt gtgagccact acactcagcc  16440
```

```
aagactcttt cattaaacca agcatagtca gtggcttatg cctgtaattc tagcacttta    16500
ggaggctgag gtgggaggat tgcttgagcc caggaggtca aagctgcagt gagttgtgag    16560
ctgaaattgc actcctgcac tccagtctgg gagacagaac gagaccctgt ctcataaaaa    16620
aaaaaaaaac acaaaaaaat tatctttcat taaacatctt attgttggca ggtgctatgt    16680
cagtgactat atctggtgtg taaaatatgc tcagtgagtc tgttaattga atgggttgac    16740
tttggagatg gagaggatag aaagagcacc ttgtctcatt aaaacaaaaa gaaaaacaaa    16800
acacacacaa aaaagattct gtttcattaa acagcttatt gttggcaagt gctatgtcag    16860
ccactgtatc tggtgtgtaa aatatgctta gtgagtctga taattgaatg ggttgacttt    16920
ggagatggag agaaggacag aaagaactct gcatggtggt gcgtattggg aagatgtgaa    16980
agtcactttg accagggctg gaggttcagg tggcagagtt gtataacaga actagcatag    17040
ctccattagc aaagaagcat gagaataagc tgttgtccgg aacactgagg gaaagttttt    17100
gttatatggg actaaaagtt acctaaacag tcctagactg ataggaaagg gagaaacatt    17160
ttttgagtac caactatatt agacactggt acattctttg ttagttgtct ttcttaattc    17220
tcacagtgcc aggtattatt ttgcaaaatg aagagactga ggctcagaga ggttaggtaa    17280
tttttccagc attatacttg gcttataaag ggacctacac agtggctggc atataatgag    17340
cacttatttt ttaacttgga acatgttttc ctttagaaat aattgacacg aaatttgggt    17400
ttccagacca gccataatat acatgaagtt agaatcaaca ttcattcatt cattcatgca    17460
ataaactttt atttagcact gtgttgggtg ctgtgtatac acgtaaaaca ctccctgctc    17520
tcaaagaaat tgaagtgtaa taggagtgat agacaggcaa acagaccatt acaatactgg    17580
atggtaagtg ctgcgatcaa ggtatataat tgagggtgca ttgggaacct agaggaaggg    17640
taccttactt ggagcctaga agtcagggaa gtttctgaaa tgagctcagt agagatacca    17700
aggcagagag gtgaggggagg ctttttttgg tggaggggtt ggacctgcag atgtcagaga    17760
caatggaaag cacagggtga tctccctggc tgaagtgaag atagcaagga cattggtgat    17820
cagagcccag atcattcagg gttttttatgc catgctagga gcttggactt tagctctttg    17880
taagtagagg accactgaaa ggttttcagc aaaggaaatg ttcaatcaga tactcacttt    17940
aggaagttaa atctggtagc tgttgtggtg gatgcattgg aaggggttaa gagtaaaaac    18000
agtgggaaca gctcagtttc tttacctcat atagaataag gtttccatga gaaaatgcat    18060
gtaaatttaa attttgtgat gtcagaaata cattatttct gttgcttgca atagcatatg    18120
gaataatccc tgcctctaat tcctctactt tctggacaag agcaatgtga atgagaacag    18180
ttcttatgct gctgatagag ataagctagg aaagagactt ttcacttaag agaggagatg    18240
agaggtgatg gaggatgaga ggtgatggac taatagagat gaatggaggt agaggaactt    18300
gaacaggggt tttaggatga agacagtgat ggttgcatca tgtaataaag gccaaagaaa    18360
gtggttgctc caatgggttg ggggaggaag agctttgagg atcctagctt tctccagtta    18420
tgaatgaaga tacctcttgc ctgactacta ttttaagtcc caggtaatct tcccaccccaa   18480 ccatttctct taccctagtg gcacccataa taacctgcct atttctgttc ccttttccct    18540
gctaccacct gttgctttca gctttactga accactgcaa aataggaggc agacttacag    18600
cttgtctctc tactctttttg tttgcaatgt aaacatacca tcctttagag ttgggttttt    18660
gctgctaata atgttgggt ttcaggataa aaagatttcc ttcatttttc tcttttcta     18720 gtaagaccgt ctagaggaaa aaaacacatc tagatgctag tcacaaaaac accgaagtat    18780
```

```
gatttgagtg catttttagaa aattagtcaa gtttcatgcc tatagtccca gcactttggg    18840
agactaaggt gggaagttcg ctttgaggcc aggtgtttga gaccagcttg ggcaacatag    18900
cgagttcctg tctttacaaa aaataacaaa gccagatgtg gtgacatgca cctgtagtcc    18960
tagctacttg ggagggtgag gtaggaggaa tgcttaaacc caggaggtca aggttgcagt    19020
gagctgtgat cgcaccactg cactccagcc tgagcaacag agcaagaccc tgtctctaaa    19080
aagacaaatg aaaagtggct gggcacaatg gctcacacct gtaacccag  cactttggga    19140
ggctgaggag ggtggatcat ttcagtccag gagttcaaga ccagcctgga caacatggca    19200
aaaccggtct ctacaaaaaa tacaaaaatc ggccagtcgc agtggctcac tcctgtaatc    19260
tcagcacttt gggaggccga ggtgggtgga tcatctgaga tcaggagttc aagaccagcc    19320
tggccaacat ggtgaaaccc catctctact aaaaataaaa ataaaaaaat tagctgggtg    19380
tggtgacgca tgcctgtaat cccagcttct agggaggctg aggcaggaga attgcttgaa    19440
cccaggaggt ggaggttaca gtgagccgag atcatgccac tgcactttgg cctgggcaac    19500
agagtgagac tccgtctcaa aaaaaaaaa  aaaaaattag ctggatatgg tggtacatgc    19560
ctatagtcct ggctatctca ggaggctgag gtgagaggat cacctctaag cttggggaga    19620
ttgaggctac agtgagagcc aagattgcac cactgcactc cagcctgggc gacaaagcga    19680
gactccattt aaaaataaac cattttatca tggacgagaa ggccgcctga aaatatccag    19740
tgtgcatcaa ctccaaagga actttctcct taaaactgcc agctctcatc acagattcca    19800
ttatgatatg aagtgttaag cagagtgagt agggattggt tccaggtaac agctagctga    19860
gggagaagga aattctaaga tattgcagtg gggaagaggg gtaagtttat atcactattg    19920
gattgctgaa cttactgttc ccagtatata tatatttccg tttgtataca agttgagcat    19980
gtggtactgg ggctgcagta ttttctttct cattgtacca attgtactag tgtaacagtt    20040
ttcaccaaaa aacttttttac agtcctgctg cttagttata tcactgactg gattgtcatt    20100
ttattttccc ttcttgaaaa aaattgactt tgcctatatt tagtaagatt gccaataatg    20160
aaacattcaa aatagggaat ttgatcccag cactttggga ggccaaggtg ggctgatcat    20220
ttgaggtcag gagttcgaga ccagcctggc taacatggtg aaaccctgtc tctactaaaa    20280
atacaaaaaa attagctggg catggtggtg ctcacctgta acctcagcta ctcaggagac    20340
tgaggcagga gaatcgcttg aaccctggag atggaggttg cagtgagctg agatcacatc    20400
actgcactcc agcctgggca atagagtgag actgcatctc aaaacaaaaa caaaaaacag    20460
caataacaaa tagggaattt taaaaggaga ccaaaaccca tgaaaaatta agcccttgaa    20520
tagatgagat tataatcttt tttcctacca gttaatact  tttaaagaat ttttaaagaa    20580
tgttcaaaag aattgcacat atttagaaat ttcaggtata aatttctgtc tgatttttta    20640
aagtctgatt tttgaaacgt tgaggaagaa cagttgtggc agtcaattag tttgggttaa    20700
gttgtatgaa tttgactcag gagttagtag caagggtttt ttggtttctc tgtgtatgtg    20760
tggtttccct cataattgtt gagctaaaaa aaacttagct tataagtctt aaggaaaga    20820
gttttgagca tggcaaactg acacactggt tggcgtttgg gtttagaact ggaagccttg    20880
aagcagcgtt tctggaagca tgctaatcca gcagccaaac ccagggctgg tcagacagtg    20940
aatgtgaacg tcatagtgaa agacatgggc actgatggaa aggaagagct aaaagcagat    21000
gtggtacctg tgactttagc acctaagaag ttggatggag caagccacac aaaaccaggt    21060
atttgagccc acaggttttg tttttttgctt tttgctttgt attctaacag atcttcaagg    21120
ctattgaaaa cctttataatg aaaagttata gaatcttttt ccttggaggc tttgcagagc    21180
```

```
agtatctctg gcatgattca cgtgtagcac acctagaggt gtggggtgga caagctggct    21240
ttattttttt tttagatatc atttgtctta ttataaaaaa ccccattata gacaaatata    21300
tagaataaat gaaaaactta atcttctatc agagacaggt tctataacca tatcgtgtat    21360
ccttttaaac tctcttcttt gcacatatgt atatgtaatt taaacaaaaa caggctgggt    21420
gcagtggcac atgcctgtaa tcctagcact ttggaaggac aaggcaggag gatctgttga    21480
gctcaggagt tggagaccag cctgggcaac atagtgagcc ctcatctcta ccaaaaaaaa    21540
aaaattatcc aggcatggtg gcctgcacct gtggccccag atacttggga ggctgagaca    21600
ggaggatcat ttgagccagg aggttgaggt tgtaatgagt catgattgtg gcactgcact    21660
ccagcctagg cgagagagtg agaccctgtc tcaaaacaaa aaacccaaaa caaaacaacc    21720
cacctataat gtgatcataa catgcattct gctttgtgtt ttagaaatgt attaaggaca    21780
gctctcaccc ctcccttgaa atcacaagta atatatcaca tggaaaacag ttttaaacac    21840
tgaaaaaagg tatcaaatga aaaactagtc ttcccaaaga taactattaa caatttcttg    21900
tatgtcttta taggagtatt tttatccata taccgtattt tgtgaatgtg tgtgacattg    21960
aacatttact ccctgtcagg cattgctcta ggtgctttat atgttttatc tcatttaatc    22020
cttacaaccc tatgaggtaa ataacattag tatccttatt ttgtatatga agaaactgat    22080
atgcagagca cttaagacac ttgctcaagt ttacacagct aataaatggt aggaccagta    22140
gtctaatcca gaccacctaa ctccagagct cagatctact ttatattgct tttgaggctt    22200
tttttttttt tttttttttt cctctaagac agagtcctgc actgtcaccc tggctggagt    22260
gcaatggcac gatcttagct cactgcaacc tctacctcct gggttcaagt gattctcctg    22320
cctcagcctc ccgaatagct gggattacag gtgcctgcca ccatgcctgg ctaattttg    22380
tattttagt agagatgaag tttcgctatg ttggccaggc tggtctcgaa ctcctgacct    22440
cgtgatctgc ccaccttggc cccgcaaagt gctgggatta caggcgtgag tcactgcgcc    22500
cggccttgag gcttttttta aaatggctgc ataatattcc attgaatgaa tacaacatga    22560
ctcattaaac catactcgta ttgacagatg tcttgttgt tccagttgtt gctattgcat    22620
acagtgttat attatagtgc cagatatatg gtggtatatt agatgaaaat tccttacagt    22680
ggaattgtca tgatatatat cacattttga tatatatcat ccagttgtct ttcagaatgg    22740
ttgtaccact ctgaatcaca gtgtatgagt tcctgtttcc tctcaatagg tattatcaaa    22800
ccttctaatt tttgccaggc taacatgtcg aaaatgtatc tcgttatttt gatttgtagc    22860
tcttcaatta gaagtgagat taagcattac ttttaattta ttaacaatat atgtttattt    22920
ttcgtgaact gccagttcat atcattagct cattttactc gagtcgtttc tcttttttct    22980
taatataggt aaatttatca atgttttct tcatggcttt tgagccacag acttgaagct    23040
ctactcccta cccacctttt ctctcttttg aacaattatt ttataatccc tgagtagtat    23100
actatctagg gtgcagaagt tctctttgat acttcaattc ataataatac tcttgtgttc    23160
aaataacaaa aaagcccaga atactagagt ctcagatttt cctttgggga tgtgactaga    23220
atatttctgg agttgcctaa aatgcatacc taattattgt attatgtcta aagcatttct    23280
acatatttct gttcaggtga aaagcttcag gtgttaaaag ctaaactgca agaagcaatg    23340
aaactccgaa ggtttgagga gcgccagaag cgccaagcac tgtttaaatt agataatgaa    23400
gatgggtttg aggaagagga ggaggaagag gaagaaatga cagatgagtc tgaggaagat    23460
ggagaagaga aggtagagaa agaagagaaa gaggaagaac tagaggaaga ggaggagaaa    23520
```

```
gaagaggagg aggaagaaga aggaaatcag gaggtttctg gcaattacgt tgttttgtta    23580
ccttgtcatg gtgaatatga gagaaaaagt cagacttgaa aaagagtata ataagcatgt    23640
tcaattgtat aagaggtttt aggggcatga tgagggtaac tacctcatat atccctaaat    23700
cttaggaact tcagttctgt cagtaccact gaatatctgt agatcatcat tatatatctg    23760
aatacagata ttcagtggta ctgacagaat accattgcct gggcttccac ctgtttatat    23820
attttaatat aataatgcta atattaaaaa tggctttgta ttcgtaggaa attttatctt    23880
tgttgtttat ttaggtttct ctagcagatt aaaaagcagt cctaaccttg gctagattga    23940
ggcctggagt aaattcttag ggaggtagag gcctttctga gttattttcg ttctttgtag    24000
aagaaggcat tgtagaagg gcctcttgcc cttgttccgt agtactgttt tctgcctagg      24060
gaaaacaggt gatgatacga ttgttaagta ttaaaaaact ttccttttg ggccgggcag      24120 ggtggctcat gcctgtaatc ctagcacttt ggaaggctga ggtaggtgga tcacctgagg    24180
tcaggagttt gagaacagcc tagccaacat cgtgaaaatc catctctact aaaaatacaa    24240
aaattagctg tgtgtggtgg cacacacctg taatcccagc tactcaggca ggagaattgc    24300
ttgaacttgg gcagtgaagg ttgcagtgag ccaagattgt gccactatac tctagcctga    24360
gcgacagagc aagactgcat ctcaaaaaaa gaaaaaaaaa aaaaaacttt cctttttgta    24420
tgctgggatc actttatttt atttttatttt atttatttat ttaaattttt ttgagatgag    24480
ggtctcacta tgttgaccag actggtctcg aactcctggc ctcaagtgat cctcccatcg    24540
ttgtggcctc ccaaagtgct gggattacag gcatgagcca ccatgcccag caacttgagt    24600
tattatttaa ttttgggtaa aggagaaaga aagcaatggc tgagctatac agcctgtctc    24660
agtctgtgct tggtttgaga tcagtagtca gcctgcaatc ttagactgat taattaacct    24720
cttactgcct caataaaatg ataatccagt cgtcctttat aatcttagca atttcgggag    24780
ggtagaaggt aaaaaaaaaa aatagaaaaa agttctagaa gtgtcaggga aaattatgtt    24840
gataatggtc atatggaact tccttcaagt ttaccttttt gaatttaaga tgtgatctgt    24900
aaccaatcag ccatatttca ggctaccagt gtatttgctt ttaaatgttt tgacttgtat    24960
tttttgtttt gtggtggcct gattggtaaa gactgcagaa ttccttctta gtagtgaaga    25020
aatagaaaca aaagatgaaa aagaaatgga taaagaaaat aatgatggca gtagtgaaat    25080
tggcaaggca gttggcttcc tctctgttcc caagtctctc tcatcagatt ctactttact    25140
tctgtttaag gacagctctt ccaagatggg gtaagtgatt ctctctaaga aaacttaaaa    25200
ttgccttgga tttgcccctc ctgtaaaaac taggaacaga tactgaacca atttactttc    25260
ttattttgca gttactttcc tactgaagaa aaatcagaaa cagatgaaaa ctcaggcaag    25320
cagcctagca aactgggtaa gtagtgattc ttgtgcagaa cttaacattt cttttgtccc    25380
tcagctttga tatttaagga ctgcagtacg gtaagtttcc atgtttttaa atctggtcac    25440
ttcccagttt catatgtagc tatgaaaagg gtttatgaat tagaatattt tcttggtct     25500 attttttgca gtttatttat agtagaccat ggtacataat gtccttagtg aatgtgtgtt    25560
gattgagtga gcaatgaaat gtttctgtat gtagatcaaa ggaagacgta taattgattg    25620
gacaatgaag agtgtgatca taggcattag gaaggataag agaaagaaga gaactttcgg    25680
ccaggcgcag tgactcacgc ctgtaatccc agcactttgg gaggctgagg caggcggatc    25740
atgaggtcag gagatcgaga ccagcctggc taacatggtg aaaccctgtc tctactaaaa    25800
atataaaaaa ttagccaggt gtggtggcac gcgcctgtag tcccagctac ttgggagggt    25860
gaggcaggag aatcgcttga acctgggagg cggaggttgc agtgagccga attcacgcca    25920
```

```
ctacactcca gctggggtga cagagcgaga ctgtctcaaa aaaaaaaaaa aaaaaaaaa     25980 aagaactttc aagtgtcact tagctcagag taataagccc tgattatata atgctatctt    26040
agtactgtaa tttacccttta acttaatgtt ttggaacata taacttgagg ggtttgccta   26100
tgaattttat ctgacagttt catcctcaac tcttttttcct aaacaaatcc accttatttc   26160
tgtaatcatg tgcttaaaag gtgtttctct ttctttagat gaggatgatt catgttcatt    26220
gctaacaaag gagagcagcc acaatagcag ctttgagctg attggctcca cgattccatc    26280
ctatcagcct tgcaacagac aaacaggccg tgggaccagt ttttcccta cagcaggagg     26340 attcagatct ccttcccctg ggctatttcg agccagtttg gtcagctcag cttctaaggt    26400
aagatggtaa tggttttttct aatctcctcc tctctttgct tcccacattg ctaaataaag   26460
tttgtcccag ccaaccaact cccaccacgt tggtactgag cttatgtgtg ttcagtttaa    26520
aaaatccacc cccttttgtgt attaaaaaca agcttcatcc agtattctta ctttcttgga   26580
ggtatttttc tttatgcttc tcatggctgt gtattgtccc cctcaactac aatttcctga    26640
gagtagctta aatattgcaa atagcaactt ttgtggttgt catgacaatg actgacattt    26700
gtaaaatgtt ttgttattgt ttgttttttgt ttgtgtgcca gagttcaggg aaactgtctg   26760
agccttcact tcccatagag gattcccagg atctgtataa cgcctcccca gagcctaaga    26820
cacttttcct aggagcagga gacttccagt tctgtttaga agatgacact cagagccaac    26880
tgttggatgc agatgggtag gtagttttgt gtttctgtgg gcgggaatgg tgctgggtac    26940
tgcttaattt tgtttaaaaa taagtgagct tctgtcactc catctgtgct ttctcttctg    27000
agaaagagaa ggtgtacaga ccattagtat tacattctat aagtttgaac aaagtctgtc    27060
cagaaaataa acataaatag ctcttgctaa cattctggtc cttcaatttc tgtcttattt    27120
gaaatgcata gatcttgtat tgtaaggtca tcaaatttcc ctgtatccat cctgctatgt    27180
tattattgtt gggtaaggtt gagaattcac agactggtgg cacattacag gacataatgc    27240
caagccctgc tctagcatca tctgaagcta aaagttatcc tttacacttt accttctgag    27300
taacatttta ttctttcaca aaacttttcc ctccctcttt agattaacac aagcctaaag    27360
tttgaatctt ttgctttctg gtttgagatt cagcttttaa ctggtgtagg aaatgaattc    27420
agaggttttt caccccctac tttgccattt tctctgaggaa tttttttta ttttttttt    27480 tgaggcagag tcttgctctg tcgcccaggc tggagtgcag tggcgcgatc tcggctcact    27540
gcaagctcca cctcctgggt tcacgccctt ctcctgcctc agcctcccga atagctggga    27600
ctacaggcgc ccaccaccac gcccggctaa ttttttgtat ttttagtaga cggggtttt    27660 caccatgtta gccaggatgg tcttgatctc ctgacctcgt gatccgcccg cctcggcctc    27720
ccgaagtgct gggattacag gcgtgagcta ccgcacccgg ccctctctga ggaatttttt    27780
acactattcg ttgtgctcat tggttcttag gttcttaaat gttagaaacc acaggaatca    27840
gtaccaagct ttgaagcctc gattgccatt ggccagtatg gatgagaatg ccatggatgc    27900
caacatggat gagctgttgg atttgtgtac tggaaagttc acatctcagg ctgaaaaaca    27960
tctacccagg aagagtgaca agaaagagaa catggaggaa cttctgaacc tttgttcagg    28020
aaaattcact tctcagggta aatatccaac cgagagtatc aagcttacca cacccaagta    28080
tcagtgccct tgaaaagaat tccctgggcg ggtgggtgg ctcatgcctg taatcctaga    28140
actttgggag gctaagttgg atggatcgct tgagctcaga agtttgagac cagcctgggc    28200
aacatggcaa atccccatct ctacgaaaaa aaaaaaaaaa attagccagg catggtggca    28260
```

```
cgtgcctgtg gtcctagcta cttgggaggc tgaggtggga ggatctcttg agcctgggag   28320
atgaaggttg cagtgagctg agatcacacc agtgcactcc agcctgggtg gcagagaccc   28380
tgcataaaaa tagaaaaaaa gaaagaaaga aagaagccc cttaccctca ggtgaaaagt    28440
tcacagaaaa cagggctgtg atggaatctg tgtataaact gaattcactg cttagtgccc   28500
tgatatttag aactcttact ttcttagagt ggtaaagtat caacttaaga ctactttagg   28560
ccgggcgcag tggctcacgc ctgtaatccc agcactttgg gaggccaagg cggggattt    28620 cctgagctca ggagttcgcc accagcctgg gcagcacggt gaaacccgt ctctactaaa    28680 atacaaaaaa ttatctgggc atggtggccc gtgcctgtaa tcgcagctac ttgggaggct   28740
gagacaggag aactgcttga accccggagg tggaggttgc agtgagccga gattgtgcca   28800
ctgcactcca gcctgggcaa cagagagaga ctgtctcaaa aaaaagtct tgaaaaaaa    28860 aaagactgct ttagctttgc ccatatatca tttatgatta atgtatgtac aaagtttaga   28920
acagtgtctg atgtataata aatttcatat aaatgttaac ttacttcctg ttccctgccc   28980
ccaatacaca caactgctag atcgaacata agctctatga gacctgggat agtggtttgt   29040
tcattactgt atccctggtg gcctggcaca tatggcacat agtaagcact aaataaggat   29100
ttgttgaatg aatagatggt aggctcttct tggcaagctt accttagaac tgtatcgagc   29160
tggcatgact ttagatggct gggaaaagag tataaagcta tcattccttg gtgacacatc   29220
ttttccttgt tgtgatgtag atgcctccac tccagcctca tcagagttaa ataaacagga   29280
gaaggagagc agcatgggtg atccaatgga agaagcactt gctctttgct caggctcttt   29340
tcccacagac aagtaagtct cagattgctg ggaatttggg aaggcctggc cttttgataa   29400
aatcaaaata actgatcatc ttaagggctt gcacctttt ctgagaatct tgcagtggat    29460
ttgagtctca tatatgccta gtaagcaaat tataatgctt tggtggagaa cagggtaaaa   29520
aaggcaagaa tatgaaagct atttaatatc attaatagag aaatgccaat caaaaccata   29580
gtgagacacc cattaagatg acttttatca gaaaacccc aagagtgtta gtgagaatgt    29640
ggagaaattg gaaccttgt gtactattgg tgagaatgta aaatagtgca gctgccaggg    29700
aaagtatgat ggctcctcaa aaattaaaaa tagaggccag gcacggtgga tcatctgagg   29760
tcaggagttc gagaccagcc tgaccaacat ggtgaaaccc cgtctctact aaatacaaaa   29820
aattagctgg gcatggtggc gcatgcctgt aatcccagct acttgggagg ctgaggcagg   29880
agaattgctt gaaccgggga ggcagaggtt gtagtgagcc gagatcatgc cattgcactc   29940
caacctgggc aacaagaaca aaactccgtc tcaaaataaa taaataaaaa tagaatgacc   30000
atatgatcca gcaatttcac ttcttagtct gtacccaaa aaagtgaaag caggacttga    30060
acagatattt gcaccccat gttcaaagca gcattattca cagtaagtag tcaaaacatg    30120
aaagcgacct atgttttattg gcaaatgaat gggtaaacaa aatgcggtat atatgcaaag   30180
gaatattcaa cttaaaatgg aaattctggc tgggcatggt ggctcacacg tgtaatccca   30240
acactttggg tggctgaggt gggcgcatca cttgagctca ggagtttgag accagcctgg   30300
ataatatggc aaaaccccat ccctataaaa aaaatactaa aattagctag gcgtgtgccg   30360
gcagtaccag ctattcaggg ggctgaggtg ggagaattgc ttgagcctgg gaggtcaatg   30420
ctgcattgag ccatgattgt gccactgcac tctgggcatc agagcaagac cctgtctcaa   30480
aaaaaaagaa gttctgacac ttgctacaac atggatgaac cttagaatgt tatgctaaaa   30540
gaaataagcc agtcaccaaa agacaaatac tgtatgagtc cacttacatg agatacttag   30600
agtagtcaaa tgcatagaga cagaaggtag aatggtggtt gccagagact gaggttataa   30660
```

```
ggaaatggag agtgtaatgg gtatagagtt ttagttttgc aagctgaaaa gagttctgga    30720
gattgcttaa caatatgaat gtacttaaca ctacagaact atagaaagat cgttaaaaag    30780
gcaaatttta tattatgtgt attttaccac aattgaaaat ttaaaaaatt ttcttcctgt    30840
ttattgaaga gattattggt gataataaaa gttttaaatt tggctgggcg aggtggctca    30900
tacctataat cccagtactt tgggagccca aggcaagcag attgcttgaa tccagaaatt    30960
caagatgaac ctgggcaaca tggtgaaatc tgtctctaca aaatacaaa aattagctga     31020 acatggtggc ttgtatctct agtcccagct actcaggagg ctgatgtggg aggatcactt    31080
gagccctgga ggtggaggtt acagtgagct gagatggtgc cactgtattc caggtggtgt    31140
aagagaccaa gactgtctca gagaaaaaaa aaaattaac acacacaaaa ttttttttaa     31200
ttcataactt ggctgactac ttgtagtttg ctttcaacaa cttatttatt gattcattga    31260
tttacatttt agggaagagg aagacgagga ggaggaattt ggagactttc ggcttgtttc    31320
aaatgataat gagtttgata gtgatgaggt gagtatgaag ggaacaaagt aatcataact    31380
gagctccatg tattgctgcc ctcaagtgtt ttttcccct cagttcttga gaattctaag     31440
tttggcatct tatcagaaac aatttcctag aatgaggtat ttgggcagat gtttataaat    31500 cctttttca ttgaggacgc attttattct gcttaatttg gatatgatgc tgattttgta     31560
ggatgaacac agtgactctg gtaatgatct ggcactggaa gaccatgaag atgatgatga    31620
agaagaactc ctgaagcgat ctgagaagtt gaaaaggcaa atgtacgtgt tattaatatg    31680
tccattcctt caggtgtatt taaaatttgg tcactaggcc aggcatggtg gcttgcgcct    31740
gtaatcccat catttgggga ggctgaagca ggcggatcac ctgaggtcag gagttcaaga    31800
ccagcctggt cttggtgaca caggtcaaga gatcgagacc atcctgacaa acatggtgaa    31860
accctgtctc tactaaaaaa tataaaaatt agccagatgt gatgacaggt gcctgtagtc    31920
ccagctactc aggaagctga ggcagggaga atcgcttgca cccaggaggt ggaggttgca    31980
gtgagccgag atcgcaccac tgcatttcag cctgggtgac agagcgagac tctgtctcaa    32040
aaaaaaaaaa aaaaaaaaag ttgatcactt aatatgtcct gtgtgctaat aactgtgctt    32100
tacaggcatt aacatattat cttatgccag gcacagtggc tcacgcctgt aatcccagca    32160
ctttgggagg ccaaggcagg catattactt gaggtcagga gtttgagacc agcgtgacca    32220
acatggtgaa accctctcta ctaaaaatac aaaatacaaa ataaaataca aaaattagcc    32280
aggcatggtt ctgggcgcct gtagtgccag ctacttggga ggctgaggca ggagaattgc    32340
ttgaatatgg gaggcggagg ttgcagtgag ccaagattgc cccactgcac tccagcctgg    32400
gtgatagagc aagactccat ctcaaaaaaa ttatcttatg agtgggtact attattctcc    32460
tcattttaca gttgaaggaa ctgagcctca gaaagattaa atttacccaa gatcacatag    32520
ctagaaggca gcagaggctg gattcaactt agattaggtg aaatctcccc taacagtcag    32580
ttaatagttt gccactttt aacttaaatc ctcctgcctc agcttcccaa gtagctggga    32640
caacaggcat gtgccaccac acctggctaa ttctttctat ttttttgtaga gatgggcct     32700 tgctttgttc ccaggctggt cttaaactgt tggcctcaag tgatcctcct gcctctgctt    32760
cccaaagtct gggattacag gcatgagcca ccaggcccag cttttttttt ttttttttt    32820 tttttttttg agacggagtc tcgctctgtc gcccaggctg gagggcagtg gcatgatctc    32880
ggctcactgc aacctccgcc tcccgggttc aaagcgattc tcctgcttca gcctcctgag    32940
tagctgggaa tataggcacg tgccaccaca cccagctaat ttttgtatat ttagtagaga    33000
```

```
cggggtttca ccatgttggt caggatggtc tcgatctctt gacctcacga tccacccgcc   33060
ttggccttcc aacatgctgg gattacaggc gtgagccacc ccacctggcc ggcccaactc   33120 attttttttga tatgctgttc tggtcatgaa agtaaaatat ttattttagg atatttaaaa  33180
gaatacaaac tgggtgcagt ggcccacgcc tataatctca gcactttggg aagctgaggc   33240
gggtggatca cctgaggtca ggagttcgag accagcctgg ccaacatggc gagacccgt    33300 ctctactaaa aatacaaaat tagccaagcg tgatggccag tgcctgtaat cccagctact   33360
caggaggcaa agctggagaa tcgcttgaac cgggaggtgg agggtgcagt gagctgagat   33420
tgtgccattg cattccagcc tgggcgacga gagaaactcc attctcccg acccccgcaa    33480 aaaaagaata cagaaagata taaataaaaa cttatccatg tccaccatcc aggatataaa   33540
tgaaagttag tttgttcccc ttaatctttt ttatgcatat atttttatat agttgagatt   33600
tgtacaatct ttctatatgt ataattttgc atcttttttt ttctacttag catatccaga   33660
aacattttcc tatgatgtta aaaaagttt tataaagata attctaatag gtatttaata    33720
ttatattgta tgtgaatgat ttggaattca catataggac atcatattga tccctattag   33780
atttatatgg ttgcttttat cccatcattt cattctatta agattcactt tgggttctaa   33840
tttatcacct atcaaattaa ctctcataca gctttaggtt atccatagat ttttctaagg   33900
tagtggttct tctctgcaga gctctttgtt caaataaaat cttttaaaga atgacagata   33960
aaagttgaac tgttcaaaga tggtaagtgg gaagtttggg aaacttagtg actagtggcc   34020
tctgaaggaa ttttccagga actctaggat ttagaacaac ttagctttaa gaaaatacag   34080
tataggctgg gcgtggtggc tcatgcctgt aatcccagca ctttgggagg ctgagatgga   34140
cagatcccct gaggtcagga gttcaagacc accctggcca acatggtgaa accctatctc   34200
tactaaaaaa acaaaaatta gccaggcatg gtggcacgca cctgtaatcc cagctactcg   34260
ggaggttgag gcatgagaat cacttgaacc caggaggtgg aggttgcagt gagccgagat   34320
ggcatctctg cactccagcc taggcgacag agcgacactt catctcaaaa aaaaaaaaa    34380 agagaaaata cagtataggt cttcgataaa aatcagtttt cagaaagcca ccaaacttct   34440
gccattttgg accacatggg accaaggtga ctttgaatcc agggtgacac cagatttatt   34500
ctccggggga gctgaagtca taagaagtaa ctagtcgttt tgattaccag gagctctgag   34560
ccttagtctt ccttctgatg tgggggtcaa gatttgttag gctgtaagaa gatcccagtt   34620
tattaccttt ctacaccaca ccatctctag tttgtctctt aaagctggtg tgctcaaatg   34680
caaaatgaaa tagtttgaac cttccagcag gtattctaat acatgtaaaa gagattaaga   34740
gttttctggc tttcaaatca cccaatctaa gttgaatcca ggctctgcta ccttctagct   34800 atgtgaccett gggtaaatgt aatctttctg aggctcaatt ccctcaactg taaaatgaag   34860
agaataatag tacccattcc tatgataata tgttaatgcc tgtaaagcac agttattagc   34920
acacaagaca tattaagtga tcaacttta aatacagatg ctccacatct tacaatggga   34980
ctatatcctg atcaatccat cataagttga aaatgcactt tcatattatc cagatataac   35040
tccatcgtaa atcgagaagc atactaagtg cgtatcacat tcatgtcatc gtaaagttga   35100
aaaatcatta agtcaaacca tcataagtgg agactattac aaaaaaattt aaatattatc   35160
aaatgtatta tgtttattat tattagaagt gactctgttc tgcttttctt tgcttccata   35220
ttctgtgagt atattcattg ttgcattttc taatcctcaa aattgctttc taggaggttg   35280
aggaaatacc tggaggatga ggcagaggt tcaggaagtg atgtgggaag cgaagatgag    35340
tatgatgggg aagaaattga tgaatatgaa gaggacgtaa ttgatgaagt acttccttct   35400
```

```
gatgaggaac tgcagagtca aatcaagaaa atacacatgt cagtatccca ataagccctt    35460
ctgagtaata gggtacatct taagacaagc cctgtaacca gccagaatgg tccttgtttt    35520
gaacacctta tttctcctgt tgcaggaaaa ctatgttgga tgatgataag cgacagctac    35580
gtttatacca agagaggtac cttgctgatg gggatctgca cagcgatggt cctgggcgaa    35640
tgaggaagtt tcgatggaaa aacataggta tcttggttgt tgtctttaaa agcaatcagt    35700
tacgggctga gcatggtggc tcacgcctgt aatcccaaca ctttgggagg cagaggcagg    35760
tggatcacaa ggtcaggagt tcaggaccag cctgaacaac atggtgaaac cccgtcccta    35820
ctaaaagttc aaaaattagc aggctgtgat ggcacgcgcc tgtaatccca gctactcagg    35880
aggctgaggc aggagaattg cgtgaacccg ggagacggag gttgcagtga gcagagatca    35940
tgccattgca ctccagcctg ggcgacagag cgagactcca tctcaaaaaa aaaaaaaaa    36000 aagcaaacag ttacaatgca tatttgtcga gtttcagatg gcaaatggca agcaaaacta    36060
taacaggcta tgtgaagacc tagttgtaac tgttttctgt taatggatgg gaaaagttta    36120
catcattata tagtaaatga taagggttta ttttttgtct gtccaagcac cctctcctgt    36180
gaggactgcc gaatgctgat taccttcact ctttgtttag atgatgcttc ccagatggac    36240
ttgttccaca gagactctga tgatgatcag actgaagaac agcttgatga gtcagaagcc    36300
aggtggagga aggagcgaat tgaacgagag cagtggcttc gggacatggt aggagttcac    36360
ctactctgac cctagtttat gagactgtcc cttagcttgt catgatagtt tcaaaatctt    36420
agcttgtcat gatagtttca aaatcttagg caacatattg ctatctcttt taatccttga    36480
gctatctttt gtgttttgag aaggctatac catagacagt tctcttcatg tttgtctaag    36540
attaattttt ttttgtctaa agcagcaaag gctgcaaaaa ggaaaacaaa taccccagga    36600
actctagttt cacaatccag gccatgctaa ctatttagga aggttataga cttttaatgc    36660
tgtatatata tatatatata tatatatatt tttttttttt ttcaggcaca gcaggggaaa    36720
attacagctg aagaagaaga agaaattggg gaggacagtc agtttatgat actggccaag    36780
aaagttacag ccaaagcact gcagaagaat ggtgagctct tgtttctcct tagggtctag    36840 cccctggat tgttagtggt agagctttgg aggtgactct aaccttcagg agctgttgca    36900
gcttaatcat aagcttgtgt ctaatactgt cttaaagagg cttcacagag gtggtgggag    36960
acagtgtact tagatcttag actattgggc agtagagact gtattcatga gtatatgtgg    37020
ctggttttac tttatgttct aaggctcaga gtagttaatt ctggctttct ctagttgccc    37080
aggattgtat acctaagtgt tagaggtagg atttgaatcc aggaatattt aactccagaa    37140
atgaagctct tcactattcc ctacactgac cacttctgtt tttcttaaat gattactgtt    37200
caacttagtt gtgtctcttc ttggagccaa ttattatagt ttgaaagtca ccattatata    37260
gaacagagtt cccatggctt tagcatattg atttagttac aagatttctt agcttgttta    37320
gatttaaaag taattctaat cagcttttcc cagaataggc ctctctgtct tttctttcca    37380
gccagtcgcc ctatggttat tcaggaatca aagtctttgc tcagaaatcc ttttgaagcc    37440
atcagaccag gaagtgctca acaggttggt tgggaacctt gttaatctga catcatagtc    37500
tacaggttat aaaggcccag gtccagctta gagaatagtc tctgtcatta gaggaaggag    37560
gtggctgcag ggaaaaagtt aatgtcaaag gagtctgcta tttcttttct atttgaatag    37620
ggtaggcata tgtaccctca atatctaggg ggaagcaggg agggaaggac ttttcattct    37680
ttagttggca cttgggattt gataccagat gactcttctt tcctcaggtg aagacaggct    37740
```

-continued

| | | | | | |
|---|---|---|---|---|---|
| cactgctaaa | ccagcccaaa | gctgtgcttc | agaaactggc | tgctctctct | gaccataacc | 37800 |
| ccagtgctcc | tcgaaattca | agaaactttg | tctttcatac | actttctcct | gtcaaggctg | 37860 |
| aggcggcaaa | ggaatcgtct | aagtctcagg | tatggaattt | gagaactaat | atggtggctt | 37920 |
| cccaaaccag | aatttattca | tttatttaaa | tttaaaaaca | aaaattctgg | cttaacctct | 37980 |
| atgctgcaat | gttgaaatct | tgcactcccc | gataaggtac | aagagaattg | ctaccccagt | 38040 |
| cggtaatcaa | cttttaaact | tgccgagaaa | gtttatcttt | ctttcttttt | ttctgttgtt | 38100 |
| aatcatccac | aatttatgag | ttgcttgaga | gctaattgaa | ggtaaatact | tgtatgaagg | 38160 |
| tctttagctg | gccctgactc | cctctctgct | ctctaggtaa | agaaaagggg | tccatctttc | 38220 |
| atgacttctc | cttcacctaa | gcacctcaaa | acagatgata | gcacttcagg | attgacgcga | 38280 |
| agcatcttca | aatatttgga | gagctaacac | catcaaaggt | gccaaaatct | acattgagac | 38340 |
| tgctttgaga | agtttctagc | actgaaagtt | ggaattgaca | ctccagccaa | tgatccttcc | 38400 |
| ttctttcata | atcaatgcaa | taagattgca | gacagaaatt | ccagtgattt | ctactgcaca | 38460 |
| gctctggaca | tctcttttcc | tagtattatt | ccctgaattg | gccactgatt | tcaattctgc | 38520 |
| agtatttaca | acatcaacaa | ctcatggaat | acttgggtga | ggtttccttt | ttttttttt | 38580 |
| ttttaagatg | ggagtctcac | tctgttgccc | agcttggagt | gcagtggcgt | gatctcggct | 38640 |
| caccacaatc | tctgcctccc | aggttcaagc | gattctcctc | cttcagcctc | ccgagtagct | 38700 |
| gggattacag | gcatgtgcca | atacgcccag | ctaattttg | tattttagt | agagacgggg | 38760 |
| tttcaccatg | ttggccaggc | tggtcttgaa | ctcctgacct | caaatgatcc | atccacctcg | 38820 |
| gccccacaaa | gtgctggtca | catgcatgag | tcactgcacc | tggccttggg | ttaggtttca | 38880 |
| cttcctccat | tagacatttg | acattttatt | gtagcagctt | tctgggttaa | tatctctttg | 38940 |
| tgattgatag | aagtggttgg | aagaggaaga | gtagggaaaa | gtgtgacatt | acagattaaa | 39000 |
| cagtgaaaat | cagtaccata | atgactcctt | tacacccatg | agatacgtac | catgatgacc | 39060 |
| agggctcggt | gaaagaaaga | tttctttttt | ttttttgag | atagtctcac | tttgttgccc | 39120 |
| agtctggagt | gcagtggcgc | aatctcggct | cacggcaacc | tctgcctccc | gggttcaagt | 39180 |
| gattctcctg | tctcagcctc | ccaagtagct | gggactacag | gtgcatgcca | ccacacctgg | 39240 |
| ctaattttg | tattttagt | ggagacaggg | agtcaccatg | ttggccaggc | tggtctcgat | 39300 |
| ctcctgacct | caagtgatcc | agctgcctca | gcctcccaaa | gtgctgagat | tacaggcgtg | 39360 |
| agccactgtg | cccagccaaa | agaacgattt | cttagatgga | ggacctagga | accaacagat | 39420 |
| gggctgctgt | attactctta | cccctttcat | tttcctgtat | gcttcttccc | aaggcagcat | 39480 |
| caaattttga | attaattttt | gctgcttaat | aaggacttaa | actggtaccc | aagtcagaaa | 39540 |
| gactctgcct | ctaattttct | ggggcttggg | gatgaagata | aagtgttaca | cccagtgttt | 39600 |
| gtccaccaca | gtctgtgggg | cagagagacc | cttcctggga | ctgaattctc | aatttgaagc | 39660 |
| actgttgttc | aaagatctcc | cttctgggtc | tgacaagaag | aaacataacc | cttatttatt | 39720 |
| gcattcttct | ggcttacata | cattgccctc | actaatcaat | ggacatttca | gcatttcatt | 39780 |
| actaattttg | agagaaggcc | accatggaat | ttaataaaaa | tattattgaa | gagaattgcc | 39840 |
| atcattctcc | attttccctg | aactaccaca | agcttctcag | aattttagac | aaatgttttt | 39900 |
| cccctcagaa | ctgagcatca | gtgctgcttt | ggaaaaacat | tccatgtgaa | tactgtggtt | 39960 |
| tcagtgtcag | gacctgtact | tgggcagttg | gaagagagtg | tgccagtttt | ttactgggag | 40020 |
| atgggaacac | caatttaatt | gatgcaatta | ggttgtaggt | tttttacagt | ttttcttttc | 40080 |
| ttttcttttt | cttttctttt | tcttttcttt | tcttttttt | ttttgagac | ataggctggc | 40140 |

```
tctgtcacct aggctggaat acaatggcat gatctcggct tactgcaacc tccgcctcct   40200
aggttcaagc aattctgcct cggcctccca aatagcaggg attacaggca cctgccacca   40260
ctcccagcta ttttttgta tttttattag agatgaggtt tcgccatgtt ggccaggctg   40320
gtcttgaact cctgacctga ggtgatccac ccgtctcggc ctcccaaagt gctgggatta   40380
taggcatgag ccaccgcacc cggccggttt ctacagtttt tctaatactc aagatgttga   40440
ctttgacaat acttatgttt gtatacttgt aatcttataa tggggaaaat gtgtataaag   40500
atgtttaat atgtatgtag tttttcaata aatcttaatg ccttgaaggg aagatttgct    40560
gtccagcttg aatgctcatt cttgggtcag tgcctgtcta accttgagga gcatttcatt   40620
ttcaggttat ctccatccca gggaaaccct ctgggtctaa actgagaagc tgctgcaatt   40680
gtcccctcac tggcttctca gtcctagtga attgatcaag ttaacttacc aagtggtttg   40740
ggttcagctc aggtgaagag gataattgag tttacataaa tggtaccttc tattatagct   40800
ctttgtttaa aaacttatt ttttagagac agtctcattc tgttgcccag gttagagtgc    40860
agtggcacaa tcatagctca ctgtacccctt gaactcctgg gcttcagcat cctccttcct  40920
caacctttgg aatagctggg ccacattaca ggcatatgcc accatgccca gctaattatt   40980
ttattttagt agagacaggg tcttgctgtg ttgccccagc tgatcttgaa ctcctggcct   41040
caagtaatcc tcccaccttg gcctcccaaa atgctggggt cacaggctca gccaccatgc   41100
ccagcctgtt acagctttga ttggcctttc tctttagcta gtttgtatg tacttcattt    41160
tatccatggg ttcaagatac atgttttttgc ctctttcttt gaactctcta aacagttccc  41220
aaggcaaagt agcccttgct gggcaaaaga gaactgagca ggaaggctag atatttcttc   41280
cctcttgttt ccctacatgt cttttgagga gagatagaaa agacaattgg aattgacaac   41340
tgaggataag aaaattcagc caggtccggt ggctcacgcc agcactttag gagactgagg   41400
tgggtgcatt gcttgaactc aggagttcga gaccagcctg ggaaacatgg tgaaatccca   41460
actctaaaaa aaaaaaaaaa aagaaaaaaa aagaaaatt agtgcctgag aaatccaggg    41520
agaaaatggt ttctgggctg ggcgtggtgg cttatgcctg taatctcagc actttgggag   41580
gctgaggcag ctggatcacc taaggtcagg agttggagac cagactgacc aacaaggtga   41640
aaccccgtct ctactaaaaa tacaaaaatc agccaggctt ggtggtggca ggtgcctgta   41700
gtcccagcta cttgggaggc tgagacaaga gaattgcttg aacctgggag gcagaggttg   41760
cagtgagccg agatcacgcc actgctctcc agcatgggcg acagagtgag actccctctc   41820
aaaaaaaaa agaaagaaag aaaatggttt ctgattgagg ctcctgggag aaagcactct    41880
ttggagaaag aaaacttgag tcaaactctg ggttactttt ccttatgcca ggatggctgc   41940
tataaagtaa gctaagcctt gatcttggta acaggattga catggacagt ttcaatctga   42000
cccatatgcc ctttgcccaa agcactgagc cagcagcatc agttatgttt taatgaaatt   42060
gaagcccag gacctgccac tatggctctg aggaggactc agcttcacta gcttggaaat    42120
tacatatttg gagggatgag agcccatgag tgtgggagat agggtaggct cagtgtcagt   42180
gttttttgttt cttccttgtt ccatacactt gagtagggat acatggtatt aacctcttta  42240
aacaggtctc taatttcatc tcattaattc acagttgcac agccatacta gggtctcttc   42300
cataaaccat aagatttat tcaccaaagc tctagagaca aggtactcag atctctgtgg    42360
catccctcat ttctcaact gcttctctac aaacttctcc tcactttgag agtttctaat   42420
gctcaggctg ggagactttt tagggggtgt ttttggtttt tatctcctag ggttatgtct   42480
```

```
aatcactctt gtggcatcct gtcctgggat ttgtgctcct aaggatagag gagagtatt    42540 ctgggaggag tgttcccatg atactatttg attatgtcat ccttgagatg gtattgtatc   42600
ttctaccctt atatcctact catcgcctgg cacacagctt ggaatgtagt ggtgcctacc   42660
acagtttgaa taaataacac tacacctttc agagcctctg tttataaaat gaggatacta   42720
agtcatggct gtctcagagt tgctggggggg cttcagttgg aaaatgtatg tcagtgcatt  42780
atgtcaagtg ccactctgta agcataagaa attgccagta gctcccagaa aaagaaatt   42840 cacctccttt gagaatgaaa gaaattacca gtatcacaat tatatcatat attgtaggcc   42900
acttctgaaa ggcccattgt ttctcaaata tctcaaactt aaaatgaaaa tgtgatcttc   42960
tctaaaaacc tgctcttcct cctgtatttg ccatttcagt aaaaggtacc tccatatatc   43020
cagtcactca gactggaaat ctggagagca ttcttgacct gttctttaat cctgtaatca   43080
gacaatttcc aagttctgtt atttctactt ccaaattgca tctggaatca gctcatttct   43140
tccagctcta tggccagccc cctggtccaa gattccacaa tttctttcta gggtcctacc   43200
gtagcctcct gaccccccca cttctgtttt tgcttccttt tcatccaatc tgcacagcag   43260
ccagaggcga cctttatgta aatataattt ggaggatgac acttcactac ttaaaatctt   43320
ttaatgtctt ccgctgcact caaagttcaa acttctcatg gccgatgcat gacatagctc   43380
tgcctcccaa cctgctgtct actcttcttt ctcatgacat gcagcctcag gagcatctaa   43440
agtgtcctct ttccctggaa tgccctcccc tacatccatc ctccttcttt gtctgactaa   43500
tgcataattc tcaaggtgtt agcttaagcc taatttcctc agagaagcct tctctgacca   43560
ttaacacccc tttctttttt ctttctttct tttttttttt tttgagacag agtctcgccc   43620
tgtcgcccag gctggaatgc agtggtacga tctcggctca ctgcaacctc tgcctccgg    43680 gttcaggcga ttctcctgcc ccagcctccc aagtagctgg gattacaggc atgcgccact   43740
acacccagct aattttttgta ttttcagtag agacggggtt tcactatgtt ggtcaggctg   43800
gtctcgaact cttgacctcg tgatccgccc gccttggcct cccacagtgc tgggattaca   43860
ggcatgagcc accaagtcca gcctaacacc cctttcttaa ttaggttacc tttgtataag   43920
tttcctattc ttttttttttg agatggattc tcgctctgtc gccccggctg gagtgagtgc   43980
agtagcacga tctcagctca ctgcaacctt tgtctccccc gttcaagcaa ttctgcctca   44040
gcctcccaag gggctgggt tacaggcacg caccaccaca cccggctaat ttttgtattt    44100
ttgatagaga cggggaaggt gttagcttaa gcctaacttc ttcagagaag ccttctctga   44160
ccattaccac tcctttctta attaggttac ctctgtttga gtttcttgtt ctttttttt    44220 tttttttttt ttttttaatat ggattcttac tctgtcaccc aggctggagt gcagtgacgt   44280
gatcttggct cactgcaacc tcggcctccc ggcaatcaa ttctcctgcc tcagcctccc    44340
aagtagctgg ggttacaggt gtgcaccacc acatctggct aattttttgtg ttttagtgc   44400 ccagctaatt tttgtatttt tagtagagac ggggtttcac catgttggcc aggctgatct   44460
cgaactcctg acctcaagtg atccagctac ctcaggctcc caaagtgctg ggattatagg   44520
catgagccac cacacccagc cttaggtttc ccattctttt gggtctgtca tcatgatgtg   44580
ttactttaat gttcgttgag gcttgctttc cctactagac tgtaagtgct gtgaaaacag   44640
agcatatccg ttttgttgaa aaatgtatgc tttgggtagc accatgcctg gcacataaaa   44700
taattcaatg aatttttga gcaatgagtg atgggaggcc tggaagagct aatggtgaaa    44760
agcatagagc tgaattatat acagaggagc tttctagtgc aggacagaat agaggtgtag   44820
agctttagtc cttgctcttt ctgcagcttg taagcatcat gactttgggt aagtcagtct   44880
```

-continued

```
cttttttcct caactggaaa atggggctca tgtgaaatga cttggtttag ctcacagggt    44940
atggttagga tcaaaggtac aaattaatgt gaagtgaatg tacatattta agaggctgca    45000
ctaatgcagg ctaactcact gctgaggaat gggtagagct gagtgggaag gagaagccaa    45060
gccccaacaa agctccatag tccaccattg gtggctagct atgtgctgag acttgttata    45120
gcagtagaaa tggaggcctg tgtgtatgcc tggactccag tgaactgggg agatagacgt    45180
ggcttgtgta tggctggtgt cacctcagat tttacctttt gagaccaagg tgcctggttt    45240
ctgtccccag tagttttatt gtcttggtct gtaccatcca cgtccttccc atccctctt     45300 tttgtcctct ctcctctcac cttaaaggtt tttcattttc agtttattga tttagttcta    45360
ccctgtggtg ggattcataa tgggaaaagg gagtttgaag tagctacagc ctaagggtga    45420
ttggaaggag ttggggtgga cacctgagtt ccttcccttc attttagaga gaaccgtagt    45480
ccgcggaatt cttgatggct ggtgggctag atgtagggtt gaagaggcag ctcccagctc    45540
caggctggag aattattgcc tagtccaagg ggtagaaagt gctgaggcag ggttgggagt    45600
gagccgtggt ttgggttttt tggccctcat ctcttttcct cagaggctga aggaaggaaa    45660
aaggctgact gcccacccct ctgtttgttt gtcttgtcta atttaactta cgttatttat    45720
caaaaagaca ggttatttgg aaaccagatg gacctaggc aaaaatcatc tgggttttcc     45780
aaacgtgaaa aattaggttc tgggggccca gcaggaaagg cgtgtgtgtg tgtgtgtgtg    45840
tgtgtgtgtg tgtgtgtgtg tgtgtgtgtg tgtgtgtgtg tttgagggga gggtgaggtt    45900
gagtgaatgt ctctgtagtt agacccagaa attgttccat gacttccaag catactccct    45960
ccttcatttt ccttcaagtt ctttatgatt agaatctaaa tgagaaaatt aaaatcttca    46020
tgttggttgc tggatgtctt aattgaccaa ggattagaac ccatcagggc tatagaagaa    46080
cagcagctga cagttttctc tatctttcca gccctcagtc ccttacacag agtgggcagg    46140
ttagtgagag gtgcagggta ctgagagttt tctgaaacag aaacctgtgc ttcttgtccc    46200
ttcaatgtta ttgttccaaa gagttgcagc aaatatggag gttagacatt agggaagaac    46260
ttatcatcaa ctttctgatg atcaaatggc taaaagaaca ctgaggatcc agggctgtct    46320
ctccattgac tatccaggga aggagctagc ccagttttct tttgggcaat ggtggcttgc    46380
tctgtagcta caaccaggaa tttgtaaaac ttgtggtttt gggccaggca tggtggcaca    46440
tgcctgtaat cccagcactt gggaggttg aggtgggggg tttgcttgaa ctcagggggtt    46500 tgagaccagc ctgggcaaaa tggcgaaacc ccatctctac aaaaaataca aaaattagct    46560
gtgcatggtg gcatgcacct gtggttccaa ctacttggga ggctgaggta ggaaatcact    46620
tgagcctgga ggttgtggct gcaatgagcc aaaactgcag cattgcattc cagtctgggt    46680
gacagagtga gactgcctca aagaaaaaa aaaaaaaaaa aaaagcttg tggttttgtt     46740 accttgagca gcaacatttt taggaaggaa ttaaagcagg aggctattga ggcatagctc    46800
ttggctgcca tagaggaaat gttctggctg aaagcagaaa gcaagccatc cagttcatac    46860
acatatgcac acacacagaa gacagccaag acccttctg gcctgagaaa tctttggcgg     46920
cagcaatagc acttgtccca ttgtgagtgg cattttttc aaagtgtcat ggactgtga     46980 aagctactta ataacttgat ctcatctgaa taatctgagt taatactagc ttcacagttg    47040
tgaggattaa ataaaaaaaa attgtaaagt gtctgcctca aggcctggca cagagtaaat    47100
ctcaacaaat gctcgttgaa tgaatgaatc catgaatctg agcattaagg ccccctcac     47160 cgtttccaag gatcagtgca taacagcccc ggtaactgag acttgtagac tgtcccaact    47220
```

-continued

```
gagcctgcag cctgaggcat gatctaaacc tgctgttcct ttgacaaata tttgatgagt   47280
tatggtgtgg agggtggacc cttccatgaa ggccttgttg gcctagctgt tggaagcact   47340
atgcagacag tcttccaggg tgggaattgc ctcagagagc accttgccca aggtcaagga   47400
tagcccacat tcaatggcaa caggtgtgta acggcctggc cttcttagct tattttgggt   47460
caactctgaa gggccattct agcttcagag ctccctgtgg ggttggctga ggctgtcact   47520
ggcttgtctt gtagatcagc ctcttcctct ggccactcct gctcattctc attcttccac   47580
agctgttgat cccaaaggag gttcttaata acatccagc acattaaaca gtctcagagt   47640
tggcttcctg ggaaatccaa gctatgaatg cactagtcct ggtggccaag cctttagaac   47700
aacaaagaac ggagactcct ttgcaatgga tttccagcgt tggaggtgtg gatactgtct   47760
ctttatgccc accagagggc agcagcatcc tagccacctg cccttctgag gctccaggag   47820
tgggcttgaa gccttttccc cggcaacttc acgccccaca ccagtattgg gcaggatcac   47880
ctcccttagg gtgttcaccc tcctgactaa acaacaaaa ctttcttaaa ctgtccaggc   47940
cttagttttg ttagtctcaa gctcctgtac caccatcact gaaggccaat cagtcttcct   48000
actgtgcccc ttcccctgct cctcgtccgg caagctccgt gcctgggatc ccccacctct   48060
cacacttacc acccacaata gatttgtttt ctgtgtgaca aggtaattac aagcttgggg   48120
ccagtaggcc caggggccag tctgaggatg gtcacttcat tctggctctc cctgttctgc   48180
taacggtatt gattttcagt tttatttatt atgatgatgt gtgtgtgtga tctggccctg   48240
gtgacatgac atatggaggc aagagggcga gagcaaattt cctttgtca caatttgact   48300 tcttgaaacc gcaccccac caccaccacc cagcattgtt tatttacagg ttttagcatc   48360
tttgcttacc tgtcttcatt ctgtcccctc atccccaaag atttctaaga gattcttctg   48420
ggaattggag ccagatggat gtgactacaa gaaggaggaa agggtctggg aagaggagtg   48480
acagcagcaa gctatactacc ttttgttagc agccattaac tcatccagca aacatttact   48540
acattcccat cacctgtcag ttacttctag gctaagctcc ccaactccct gctggggggcc   48600 atcctggaga caggttttgc tatgcgcttt tttttttttt tttttttttt gtctgcatct   48660
gtttctatgg gtgtgtgagg aaaacctggc cagaaagctt tgagagagtg agattgagtt   48720
tgggtgcaac caactcaaag aacgatgctt gcctgaattt aaggctactt aaggcctccc   48780
gtaatgtagt ctacttcctt acgaggaaga ggaagggcaa gcttgaggca aaacattaca   48840
agtgggaggg ggcactctga actgcaatga ttgccgtggg aatcagctga ggctgagggc   48900
gatttgtggg gccatgtttc cccagcctgt cttctctgtg cgtgccagga gaatgaataa   48960
atcattgttc aggggcggga tgcagctgcc gagctcctcc cctcggcaca tgccccaact   49020
ccagctcctc cattgagggc tgctggagca gagcggttta tacacccagc tccccaaatc   49080
ctattgaggc ctcccccctcc gcacgagcca ccggctccaa gcccattcag gctggcccctt   49140 tgtgctgggg gttaagtggt tacatgtggg gggcacccca aaaggaactg tcaggccttg   49200
aaaggctgtg ctgatacagt gccctcctac tgatgaatgg ggtgggtgga ggagaggtgg   49260
gcggccggag ggtgggggtgg gggagagggc atggggatta tggagcccac agaggcagct   49320
gctaggaagg gggtggaaca ggcaccccct tctctctttc ctccttcact tcagcttctc   49380
cgtctagctt actccctctg ttgtgggcac tggatgatca agagcttggg gaccttggat   49440
ttggcttttc tgatgtcctg gtgaccgctt gagtgcactg gagagaaaga atttatatta   49500
cctttcattc ttccagcagc tccgaaaaga cctgttctc ccttttcccct tggaagggggt   49560 gggtgagaag gggaacagtg ttggggacag ggggaggatt catttcctag gttcatctgg   49620
```

```
tgcagtggat tgcagctgt gccctgccga acttttaaaa gcttctctga agttccctcg    49680
gagcccttag gtggagggtt taggggaaga cagatctcaa actggatata ttggaaagat    49740
tttgttgagg aaaagaaat tacttcaagg ctctaaaaat gctttaaaac ttctaattga    49800
atgtaccgcc ttgtcatttt acagctggga aaacagccaa aatggaagat aggggaatgg    49860
gcatatttta cctaaggtaa acacatagta atttcttgat agactaaaga ggcactttac    49920
ctttaagaag cagtagagaa atggatgaac aaaacaagta ggtcatcagc ttcctaggcc    49980
ttcctttccc aagatgaacc aattctgggg aataatgttc gttccaatct gccttaatgg    50040
ctctttggca tgtcaaaggt cctctggggt tgtgcctggt cttgggagcc caagtgacaa    50100
tgttcaccac tatgttattg acaattttt aaggcatatt attttattta gcccaaaaag    50160
gttaaaatga tttgatttgc ctaagttccc aaagccatgt ggggaagttg acagatgatg    50220
tgacctcagg aagagagaag aaagcaggtt agcaacgtag tttgtaatcc aggatcgtgc    50280
tttgttctga tatggaaact ctgagggctt cctcagttac ttccctgctg tccccaggat    50340
ggagcccaag ctccttggga tggtgtcaag aactttcaca actgggccaa ctttatcttc    50400
tagcctcacc ttacctccat ttcccaccga gctccagcca cactgcccta cggggtgttt    50460
cctgaactca ctctgaaaat gcagtctcct atgccttctc ttgctttctc ttggtgagct    50520
cttattcatc cctcaaggcc tggctcaaat atcacctctg tgctagctgg gtttagtggc    50580
tcatgcctgt aatcccagaa tgttgggagg ccaaggtggg aggatcactt aaggttggga    50640
gttcgagacc agcctgggta acatagcaag actcccatct cttaaaataa aaaaaatcac    50700
ctctgtgaag cctttcctta cccttttctg ggcttactac ttttgcctcc tggctctgtt    50760
gcagggccca ttcattgtt atagcccact cttctgtcta ttccttttct ttgagacagg    50820
gtctggctct gtcacccagg ctagagtgcc gtggtgtgat cttggctcac tgcaacctct    50880
gcctcccaag ttcaagcagt tctcgtgcct cagcctccca agtagctggg attacaggcg    50940
tgtgccacca tgcccggcta attttttgtat ttttagtaga cgggggtttt caccatgttg    51000
atcaggctgg tctcaaactc ctagcctcca gtgatctgtc cgcttcggcc tcccaaagtg    51060
ctggaattac aggcatgagc caacacacca tgacttctgt ttccctttct aaacaaggag    51120 ctcccccaaga ccacgaccag ttctgattct gctctgaatt cccaacacag tacctggcac    51180
aaagtaagca ctctgtaact gtatgataca tgtaaatgaa tgggtgggaa gggacaaggt    51240
ctttgaagct gaaacacctt gatcttaccc accccttcct tcctgagaat actgatattg    51300
agaaattatc cacctatgaa taacccttag gcctgtccta tttcctggat gagaaattcc    51360
tctcatcttc tctggtctcc ttgcctgaca ccccaggccc tgggacctgg atctggctac    51420
tcactgctag cctctcttgg ctctgacatc tgtttgccaa gaggcttacc cgctgtccat    51480
cattgggtct tgatggcatg gccttttgca aagccctgtt caggctgata ctggccatct    51540
ctggaggttt ctgtgtcctt gccacttaag ttcctggcat atatgtgggt aggtgaaccc    51600
agccacagat acccttttcac ttgggggtga attattctct ggtgtcctca ctggaaaagc    51660
ctctggcaaa tgaataacag gcatctctat agctgctttt ttgtcttcct gtggacatgg    51720
acatccctgc atttgagct tttttttttctt caggttttga gctctgaaaa ttatggagtg    51780
accaggactg ctgtgtgagc actgactgta ttaattatac agtgctagaa tattccatac    51840
aacactgccc ttgattaaca aaactggcta caggctgggt gtggtggttc acgcctgtaa    51900
tcccaacact ttgggaggcc gaggtgggca gatcacttga ggccaggaat ttgagaccag    51960
```

```
cctgggcaac atagtgaaac cctgtctcta ttagaaatac aaaaattagc cggtgcagtg    52020
gcacacgcct gtagtctcag ctactcagga ggctgaggca tgagaatcgc ttgatcctgg    52080
gaggcggacg ttgcaatgaa tggagattgc accactgtac tccagcctgg gcaacagagt    52140
aagactccgt ctcagggaaa aaaaaaagaa agagagagac tacaatctga tttcctttaa    52200
atgaattcac ttgacttagc aggtattgta ttatttagga ataactagct ttaggccagg    52260
tgtggtggct cacgcctgaa atcctagcac tttgggaggc caaggcaggc agatcacctg    52320
atgtcaggag tttgagacca gcctggtcaa catggtgaaa tcctgcctct actaaaaata    52380
caaacattca ccaggtggcg ggcacctgta gtcccagcta ctcaggaggt tgaggcagga    52440
gaattgcttg aacccaggac gtggaggttg tagtgagcca agactatgcc actgcactct    52500
agcctgggtg acagagagag actccatctc aaaaaaaaaa aaaaaaaaag gaataactag    52560 cttttttagaa caatggaatt gatgactcag ctattccagg ctgggtgct gccctgcaga    52620 gcacgatata ggcttttattt attttatttt aatttttttt ttttgagaca gggtcttact    52680
ctatcgccca ggctggagtg cagtggcacg atcttggctc actgcaatct ctgcctcttg    52740
ggttcaagcg attctcctgc ttcagcctcc tgaatagctg ggattacaga cgcgcaccac    52800
catgcctgtc taattttttgt attttttagta gaaacggggt ttcatcatgt tggccaagct    52860
tgtctcgaat tccagcctc aagtgatccg cctgcctcgg cctcccaaag tgctgggatt    52920
acaggtgtga gccaccacac caggcccaat ataggcttta aatcaatgta tataatgctt    52980
tgtcctttgt ggccagaatg cataacaaga agaggtagcg gtggttgtgg caccttatat    53040
gatttaccta aggactaaga gttttcttcc tgtctctgag attctgggta ttgcaggtca    53100
gaaggtgata gcatcggcca ggcacagtgg ctcacacctg taatcccagc actttgggag    53160
gtcaaggcgg gcagatcatt tgaggtcagg aatttgaaat cagcctgacc aacatggtga    53220
aaccctgtct ctactaaaaa tacaaaaatt agccgggtgt ggtggcacgc gcctgtaacc    53280
ccagctactc gggaggctga ggcaggagaa tgacttgaac ctgggaggcg gaggttgcag    53340
tgagctgaga tcgcgccact gcactccagc ctgggtgaca gtgaaactct gtcttgggaa    53400
aaaaacaaaa caaaacatgg tgatagcatc atgggaggaa tgtttcttct aaccaagaaa    53460
cacaaagatg attccctggg atttcggctc ctggtagcac tagaggaata ggagaagggg    53520
gtggtctcag tgtagactgg actgatcatg gctaccaagg agaaagggag ttactgttac    53580
ctaataagtg ttgagaggtg cgtgaatgga acccagagac cctggggtca ccaccttgtg    53640
ctattgtagt aatcagcatt ctttcaattg tcggtgaaag aaattccact caagttaggc    53700
ttggcaaaat aaggcataca aaactataag tttagatgca ggaaacaggg tctgcaacat    53760
tatcagaact atctctcatc tctgtttctt ccctgcctcg tcttccttta atttcgtttc    53820
agaagatccc agagaaggac tctgactggc tcacctggag tggagctcct atccctggat    53880
tcttcaggct ttcatttgac ccacatggtt aagctgggag agacagagtc caaagagagg    53940
cggagaaggg ctattctggg cagaacaaac aattgatgac tttatggctc tgtggtctgg    54000
gcagaactgc ataaccctag atcaccaaag ctgagagcct ttaggagtga ggatttgggc    54060
caggcatggt ggctcacgcc tgtaatccca gcactttggg aggccgaggt gggtggatca    54120
caaggtcagg agatcaagac caacctgacc aacatggtga acccccatct ctactaaaaa    54180
tacaaaaatt agctgacgtg atgcatgcac ctgtaatccc agctactcag gaggctgagg    54240
caggagaatc gcttgaaccc gggaggtgga ggttgcggtg agccgagatt gcgccactgc    54300
actccagcct aggcgacaga gcgagactcc atctcaaaaa aaaaaaaaaa aaaaaaaaaa    54360
```

```
gtgaggattt gggtcacccc aggctgaagg ccaggggaac ctgaagtgga taagggaagg    54420
gagaagactt aggccacagg atctgatgta gaaatggggc tgacgtctcc acctgtattt    54480
tcttagctgg aggagtgtgc aaagtttgaa ttacttctgc cttctccttc ttatttcctt    54540
ttccctttta aaatagtcat cataatcata aaaatttctt ttccattttc cctgtttttg    54600
catataggat ttcttggtgt gatttaattt gccaattagt ctctaggttg cagaatggtg    54660
acttggaatc aaattgaaac tggaagaggg cacctcatat attagggtca gcaattactg    54720
aactctgttc tcttttattc caaacagggc ccccaacttc acatttcccc agggtgcaaa    54780
agagtgaggg gggtcaagct tcagtagagt ggagctctga aagaatcca ctggagtttg     54840 gaacccaaga cccttttta tcacgctgtt cctcctcacc tgggcaaaag cactggtacc     54900
cacttcacag gcatcatggg tgggctctgt gtcctgcgga gagccccgt cccgggtaca     54960 ggacatcagc cctgagccct gtcccaggct tggatcttct ttctctctct ctctttttt     55020 tttttttttt tttttttttt ttgagacgga gtcccactct gttgcccaga ctggagtgca    55080
gtggtgcagt cttggctcac tgcaacctcc acctcccagg ttcaagcgat tctcctgcct    55140
cagcctccca agtagctggg attacaggcg cccgccacca gcccggcta attttttgtat    55200 ttttagtaga gatggggttt caccatgttg gccaggctgg tctcaaactc ctgacctcag    55260
gttatctgcc cgcctcggcc tcccaaagtg ctggggttac aggcgtgagc caccgcaccc    55320
ggcctcagtg actttagtca agtaagcaca aaaaggaata tataattcca aattgtgata    55380
aatgctatga agaaaaggaa tgtgctctga cataaagggg ggaacgaacg tgatctaggg    55440
agtcagagat ctctccgaga agagatctga aataggagta agtcgagagg gggaagagaa    55500
tgctagaccg agggaacagt gcgtgccaaa gccgcgtggc ggaaagggc gtgtgggagg     55560 gtaactgcgg agagggaggg tagaggacga agccggagag gcagacgaag ggcaggacgc    55620
acagagcccc gcggctaccg ccttaggggt tgtcccggcg gtggggaagc cattgaggag    55680
tttaacgccg gaaggtggtg actaatcaga tttcacttga aaatggcacg gtgtctgcag    55740
cgaggctaac tgatgggaag ggcccagcga atgccaatag gagagagcac cggacctgga    55800
aggcctgggt caacgcggcc ccgcgcgggg gcgaagcggt tccggcgcag gggcctggcg    55860
cggggctccg cggaaaaccg aaccggccca cgtgggaccg gtcgctccgc cctgctgcgc    55920
agacgccgcc tgactccgca gtccgggact ggggctgggc gcgctgcccg ggagcccgc    55980 acccacgcct ggaccgcgga gacgcccagg ccgaggaacc cccagcccag ggactagaca    56040
ccaccagggc cgggcggagc cagagccaga cgcgccggag cgggcgcctc tacgccgtga    56100
gtccgagtct ggggcccgag gcggggtggg gcttgggct cagccgcggg aagcggggag     56160
tcacagtggc ctccttcgag gagactaggg aaggatggtc tctgtctcct ggggtggtct    56220
cccactcccg caaggccaga aaaggaggct gcctcctgtt tgggcggaga cctagtcctg    56280
gcgtgtcggg gttctcattt tactatctct gagaaccctg tgatccctag cgccacccc     56340 acccatccc agcttccttc acggcccat ccaagtatag gaaaaataaa aaattggggc      56400
gaggggagat ctctaggcac cttcccacaa gccttgctta gaggcgatt agaaacgaac     56460 tgttcctaca ccccttctccc caggacttct ctgcccattg ctggggtgg ggagggtcca    56520 tgccacctat ggagcgcctt ccagtgccgg ctccacttac aatacccttc ctcttcatgc    56580
tcttcaattg ttctaatccc agtgctgttt ggtcagtaga atcccttgt cagttcaaat     56640 cctaattttg gttagaagca ggttatggag gagagaagag tggtgtggta tgccctccct    56700
```

-continued

```
ccagggcctc agaatggagc aagctaggga cggggaccgc aagatagtgg ctgtgttcca   56760
gaggcattgg gagggaaggg ggcaggctca gaagaaaagc ttgtcactgg ggaaggcggg   56820
gctccctggc tggggtagga aagggaacca aacccagctc ttccagaacc cagctcttcc   56880
agccctgggg agtcaagagt ggattcctga gcatggaaat tcactgcagt ctcttctccc   56940
attcactcac ttagcaagta cctgtatgca cagacagcct ggttcagggc tctatgctgg   57000
ctgactctgg ggaatatgat ggaggatata tacaggaggc ccaagccaga ttacaaactg   57060
ctattacaag atcattacca caaaccaaaa atgccagttg aatagacatt cactgatcgt   57120
cgaccatgta tgccagggac ggatgcaaag ttggataaga cagtgtatac ccagcgcagt   57180
ggggacccag aggaaggcat aactaaccgt gcttgtttat gtaatattga ttggggcagt   57240
atcaagacgg cttcagagac atggggacat ggaaacatgg ggatattaca gctaattttg   57300
aagtacaaaa aggaatttgc tgggtggaga agggaggagc tttgagggga ggggagagga   57360
aggatattgt aggccaaagg aatactgtaa gaaaaacaat ggtgtgtttt gagatctctg   57420
ggcagtttgc tatgatggga ggggcagagt ggcaagaggc aggtatggag gggtgagcag   57480
gggccagatc aaacagggtg ttgtaggcca gtagaggtt tagcaggaat tcagggaggg   57540
cattaggagt ggtgacaagt gaaatttaca ttttaactg gaggcagaga gatcagtgaa   57600
aaggccgagc aataatcca ggtcagaaat ggcctggaag aggaagaatg gtcagaatgt   57660
ggttattaat gagatgggag aaggaaggat agtgaggacc ccaggatgct ctcagctttc   57720
tggatggagt acagagccat cttgctgagg atactgaagg agagcttgtt tggttatgta   57780
gaattttggc gggggggcggt ggtggagggg gatgatgtca ctctgtcacc caggctggag   57840
tgcagtggcg caatctcggc tcactgaaac ctctgcctcc tgggttcaag tgattcccct   57900
gcctcagcct cccaaatagc tgggattaca ggtgcctgtc accatgcctg gctaattttt   57960
gtattttttag tagagatggg gtttcaccat gttggccagt ctagtctcga actcctgacc   58020
tcaggtgatc tgcctgcctc ggcctcccaa agtgctggga ttacaggtat gagccaccat   58080
gcctggactg gttatgtaga atttgaggag actatggttg gttgcagggt tggatagcag   58140
ttggatctgg gctgaagaca gatctgagag tcaccagcat atgatggtct ttgaagctac   58200
agcagagaat gaggtcctct ggagagaaat gcacaaaatc agaagacagc ctggctctga   58260
ggacggagga aaaccccttt gcaggagact gagaatgaac aggtagacag ggaggacgaa   58320
aaccacgaag ggaagtgtta ccagagtcaa gagaaagggc ttgacaggga gtggccaggc   58380
tcttgcttgc agccttgtcc ctgcagctaa gttgccctga cttcaggcac ccaccctgt   58440
cctactgtga ctcggtctcc tgctttccct ttacaggcta gatgttcgcc atccagccag   58500
ggctagctga gggggggccaa ttcctggggg acccacctcc tggattatgt cagcccgagc   58560
tccaaccaga cagcaactcc aacttcatgg caagtgccaa ggatgctaac gagaattggc   58620
atgggatgcc aggcagagtg gaacctatcc tgaggaggag ctcctctgag tcaccctctg   58680
acaaccaagc cttccaggcc cctggatccc ctgaggaagg ggtgcgcagc cccccagagg   58740
gggcagagat tcccggggct gagcctgaga agatgggtgg tgctggcaca gtctgctccc   58800
ctctggagga caacggctat gccagcagtt ccctgag              58837
```

<210> SEQ ID NO 6
<211> LENGTH: 13
<212> TYPE: PRT
<213> ORGANISM: Xenopus laevis

<400> SEQUENCE: 6

Leu Ala Ala Val Ser Asp Leu Asn Pro Asn Ala Pro Arg
1               5                   10

<210> SEQ ID NO 7
<211> LENGTH: 14
<212> TYPE: PRT
<213> ORGANISM: Xenopus laevis

<400> SEQUENCE: 7

Tyr Leu Ala Asp Gly Asp Leu His Ser Asp Gly Pro Gly Arg
1               5                   10

<210> SEQ ID NO 8
<211> LENGTH: 13
<212> TYPE: PRT
<213> ORGANISM: Artificial sequence
<220> FEATURE:
<223> OTHER INFORMATION: Amino acid sequence encoded by degenerate
      oligonucleotide
<220> FEATURE:
<221> NAME/KEY: MISC_FEATURE
<222> LOCATION: (1)..(1)
<223> OTHER INFORMATION: Xaa is Leu or Asp
<220> FEATURE:
<221> NAME/KEY: MISC_FEATURE
<222> LOCATION: (5)..(13)
<223> OTHER INFORMATION: Xaa is any amino acid

<400> SEQUENCE: 8

Xaa Ala Ala Val Xaa Asp Leu Asn Pro Asn Ala Pro Xaa
1               5                   10

<210> SEQ ID NO 9
<211> LENGTH: 32
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (1)..(32)
<223> OTHER INFORMATION: n is Inosine

<400> SEQUENCE: 9
ggngcrttng grttnarrtc nswnacngcn gc                                  32

<210> SEQ ID NO 10
<211> LENGTH: 32
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (1)..(32)
<223> OTHER INFORMATION: n is Inosine

<400> SEQUENCE: 10
gcngayggng ayytncayws ngayggnccn gg                                  32

<210> SEQ ID NO 11
<211> LENGTH: 27
<212> TYPE: DNA
<213> ORGANISM: Artificial sequence
<220> FEATURE:
<223> OTHER INFORMATION: Amplification primer

<400> SEQUENCE: 11

```
ccacggctag gtgctgatga agattcc                                    27
```

<210> SEQ ID NO 12
<211> LENGTH: 23
<212> TYPE: DNA
<213> ORGANISM: Artificial sequence
<220> FEATURE:
<223> OTHER INFORMATION: Amplification primer

<400> SEQUENCE: 12

```
aacagtgctt ggcgcttctg gcg                                        23
```